United States Patent
Roubos et al.

(10) Patent No.: US 11,149,268 B2
(45) Date of Patent: Oct. 19, 2021

(54) ASSEMBLY SYSTEM FOR A EUKARYOTIC CELL

(71) Applicant: DSM IP ASSETS B.V., Heerlen (NL)

(72) Inventors: Johannes Andries Roubos, Echt (NL); René Verwaal, Echt (NL); Bianca Elisabeth Maria Gielesen, Echt (NL); Brenda Vonk, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/319,746

(22) PCT Filed: Dec. 15, 2016

(86) PCT No.: PCT/EP2016/081240
§ 371 (c)(1),
(2) Date: Jan. 22, 2019

(87) PCT Pub. No.: WO2017/037304
PCT Pub. Date: Mar. 9, 2017

(65) Prior Publication Data
US 2019/0185843 A1    Jun. 20, 2019

(30) Foreign Application Priority Data

Jul. 28, 2016    (EP) .................................... 16181781

(51) Int. Cl.
| C12N 15/09 | (2006.01) |
| C12N 15/10 | (2006.01) |
| C12N 15/11 | (2006.01) |
| C12N 15/90 | (2006.01) |

(52) U.S. Cl.
CPC .......... *C12N 15/102* (2013.01); *C12N 15/111* (2013.01); *C12N 15/902* (2013.01); *C12N 2310/20* (2017.05); *C12Q 2521/301* (2013.01)

(58) Field of Classification Search
CPC .. C12N 15/102; C12N 15/902; C12N 15/111; C12N 2310/20; C12Q 2521/301
See application file for complete search history.

(56) References Cited

U.S. PATENT DOCUMENTS

2015/0184199 A1* 7/2015 Horwitz ................ C12N 15/111
                                                         435/34

FOREIGN PATENT DOCUMENTS

| WO | 2014/099744 A1 | 6/2014 |
| WO | 2016/081923 A2 | 5/2016 |
| WO | 2016/094872 A1 | 6/2016 |
| WO | 2016/110453 A1 | 7/2016 |
| WO | 2016/166340 A1 | 10/2016 |
| WO | 2016/205749 A1 | 12/2016 |

OTHER PUBLICATIONS

DeMarini et al. (BioTechniques (2001) 30:520-523). (Year: 2001).*
International Search Report of International Patent Application No. PCT/EP2018/081240 dated Dec. 15, 2016.
Yoshimi, Kazuto et al., "ssODN-mediated knock-in with CRISPR-Cas for large genomic regions in zygotes", Nature Communications, Jan. 20, 2016, vol. 7.
Zetsche, Bernd et al., "Cpf1 is a Single RNA-Guided Endonuclease of a Class 2 CRISPR-Cas System", Cell, Oct. 1, 2015, pp. 759-771, vol. 163, No. 3.
De Kok, Stefan et al., "Rapid and Reliable DNA Assembly via Ligase Cycling Reaction", ACS Synthetic Biology, Jan. 9, 2014, pp. 97-106, vol. 3, No. 2.
Cong, Le et al., "Multiplex Genome Engineering Using CRISPR/Cas Systems", Science, Jan. 3, 2013, pp. 819-823, vol. 339, No. 6121.
Dicarlo, James E. et al "Genome engineering in *Saccharomyces cerevisiae* using CRISPR-Cas systems", Nucleic Acids Research, Mar. 4, 2013, pp. 1-8, vol. 41, No. 7.
Gaj, Thomas et al., "ZFN, TALEN, and CRISPR/Cas-based methods for genome engineering", Trends in Biotechnology, Jul. 2013, pp. 397-405, vol. 31, No. 7.
Gao, Feng et al., "DNA-guided genome editing using the Natronobacterium gregoryi Argonaute", Nature Biotechnology, Jul. 2016, pp. 768-776, vol. 34, No. 7.
Glaser, A. et al., "GFP to BFP Conversion: A Versatile Assay for the Quantification of CRISPR/Cas9-mediated Genome Editing", Molecular Therapy Nucleic Acids, 2016, pp. 1-4, vol. 5.
Gibson, Daniel G., "Synthesis of DNA fragments in yeast by one-step assembly of overlapping oligonucleotides", Nucleic Acids Research, 2009, pp. 6984-6990, vol. 37, No. 20.
Gibson, Daniel G. et al,, "Enzymatic assembly of DNA molecules up to several hundred kilobases", Nature Methods, May 2009, pp. 343-345, vol. 6, No. 5.
Gietz, R. Daniel et al., "Transformation of Yeast by Lithium Acetate/Single-Stranded Carrier DNA/Polyethylene Glycol Method", Methods Enzymol, 2002, pp. 87-96, vol. 350.
Hur, JK et al., "Targeted mutagenesis in mice by electroporation of Cpf1 ribonucleoproteins", Nature Biotechnology, Aug. 2016, pp. 807-808, vol. 34, No. 8.
Inui, Masafumi et al., "Rapid generation of mouse models with defined point mutations by the CRISPR/Cas9 system", Scientific Reports 4, 2014, article No. 5396.
Jinek, Martin et al., "A Programmable Dual-RNA-Guided DNA Endonuclease in Adaptive Bacterial Immunity", Science, Aug. 7, 2012, pp. 816-821, vol. 337, No. 6096.
Jorgensen, Thomas R. et al., "Fungal Genetics and Biology", Fungal Genetics and Biology, 2011, pp. 544-553, vol. 48.

(Continued)

*Primary Examiner* — J. E. Angell
(74) *Attorney, Agent, or Firm* — McBee Moore & Vanik IP, LLC; Chester G. Moore; Susan E. Shaw McBee

(57) ABSTRACT

The present invention is based on the advantageous use of single-stranded oligonucleotides in the in vivo (within a cell) assembly of double-stranded oligonucleotides into a single double-stranded nucleic acid construct.
The present invention relates to the use of at least a first and a second single-stranded oligonucleotide in the assembly within a cell of at least two double-stranded nucleic acid molecules into a single double-stranded nucleic acid construct of pre-determined sequence, wherein the first and second single-stranded oligonucleotide are essentially complementary to each other.

13 Claims, 36 Drawing Sheets

Specification includes a Sequence Listing.

(56) References Cited

OTHER PUBLICATIONS

Kim, Daesik et al., "Genome-wide analysis reveals specificities of Cpf1 endonucleases in human cells", Nature Biotechnology, Aug. 2016, pp. 863-870, vol. 34, No. 8.
Looke, Marko et al., "Extraction of genomic DNA from yeasts for PCR-based applications", Biotechniques, May 2011, pp. 325-328, vol. 50, No. 5.
Mali, Prashant et al., "RNA-Guided Human Genome Engineering via Cas9", Science, Feb. 15, 2013, pp. 823-826, vol. 339.
Mohanraju, Prarthana et al., "Diverse evolutionary roots and mechanistic variations of the CRISPR-Cas systems", Science, Aug. 5, 2016, vol. 353, No. 6299.
Nagai, Takeharu et al., "A variant of yellow fluorescent protein with fast and efficient maturation for cell-biological applications", Nature Biotechnology, Jan. 2002, pp. 87-90, vol. 20.
Orr-Weaver, Terry L. et al., "Genetic applications of yeast ransformation with linear and gapped plasmids", Methods Enzymol, 1983, pp. 228-245, vol. 101.
Paques, Frederic et al., "Meganucleases and DNA double-strand break-induced recombination: perspectives for gene therapy", Current Gene Therapy, 2007, pp. 49-66, vol. 7.
Port, Fillip et al., "Augmenting CRISPR applications in *Drosophila* with tRNA-flanked sgRNAs", Nature Methods, Oct. 2016, pp. 852-854, vol. 13, No. 10.
Sander, Jeffry D. et al., "CRISPR-Cas systems for editing, regulating and targeting genomes", Nature Biotechnology, Apr. 2014, pp. 347-355, vol. 32, No. 4.
Sikorski, Robert S. et al., "A system of shuttle vectors and yeast host strains designed for efficient manipulation of DNA in *Saccharomyces cerevisiae*", Genetics, May 1989, pp. 19-27, vol. 122.
Singh, Priti et al., "A Mouse Geneticist's Practical Guide to CRISPR Applications", Genetics, Jan. 2015, pp. 1-15, vol. 199.
Stoddard, Barry L., "Homing endonucleases: from microbial genetic invaders to reagents for targeted DNA modification", Structure, Jan. 12, 2011, pp. 7-15, vol. 19.
Van Dijken, J.P. et al., "An interlaboratory comparison of physiological and genetic properties of four *Saccharomyces cerevisiae* strains", Enzyme and Microbial Technology, 2006, pp. 706-714, vol. 26.
Verwaal, Rene et al., "High-level production of beta-carotene in *Saccharomyces cerevisiae* by successive transformation with carotenogenic genes from Xanthophyllomyces dendrorhous", Applied and Environmental Microbiology, Jul. 2007, pp. 4342-4350, vol. 73, No. 13.
Xu, Rongfang et al., "Generation of targeted mutant rice using a CRISPR-Cpf1 system", Journal of Plant Biotechnology, Nov. 22, 2016.
Zhumabayeva, B. et al., "Oligonucleotide-Mediated, PCR-Independent Cloning by Homologous Recombination", BioTechniques, Mar. 2001, pp. 520-523, vol. 30.
Kim, Y. et al., "Generation of knockout mice by Cpf1-mediated gene targeting", Nature Biotechnology, Aug. 2016, pp. 808-810, vol. 34, No. 8.

* cited by examiner

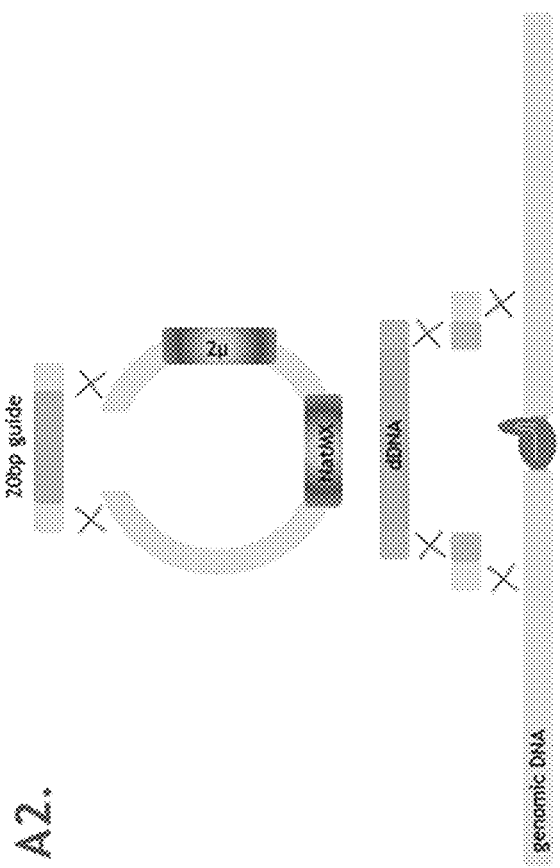
Figure 5 A2
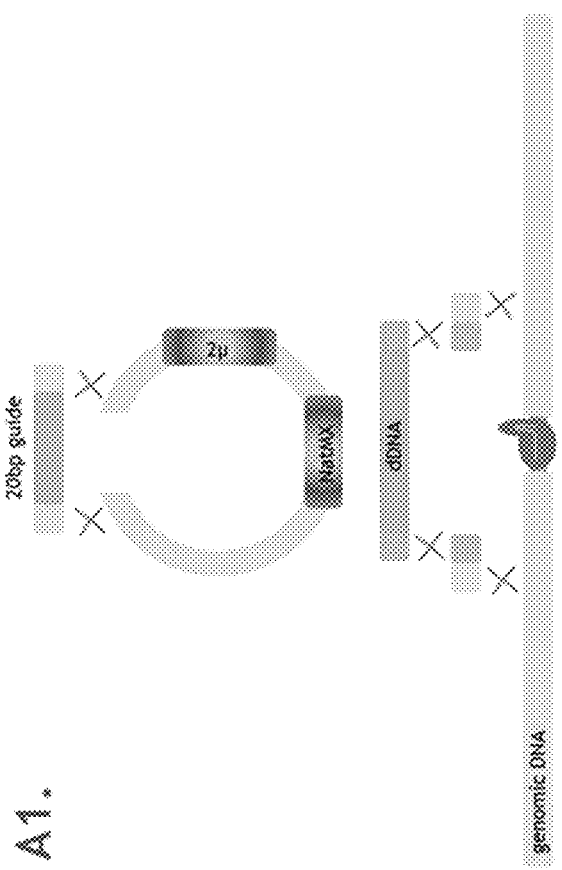
Figure 5 A1

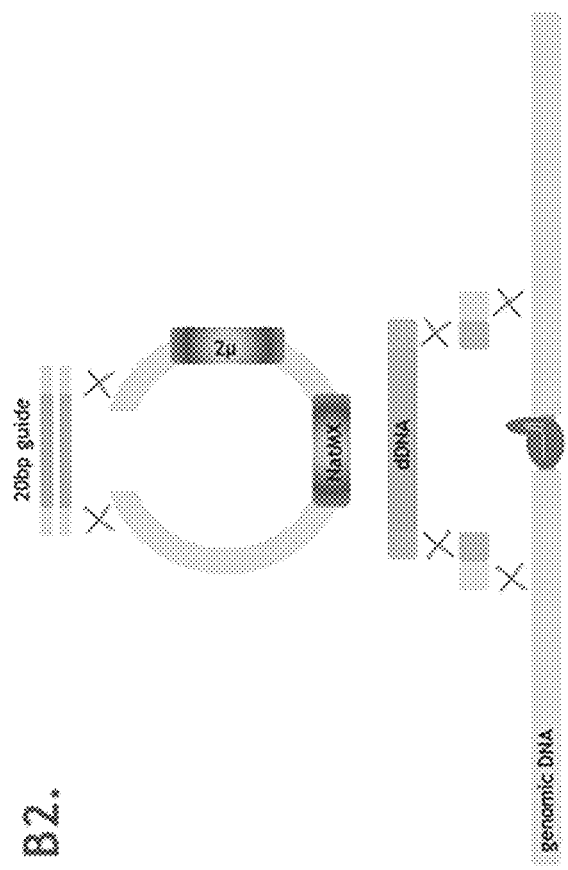
Figure 5 B2
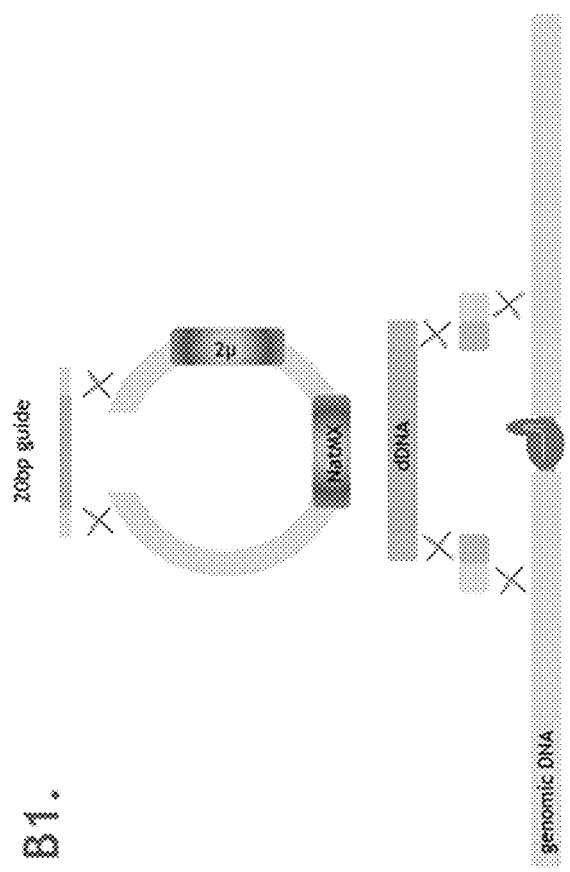
Figure 5 B1

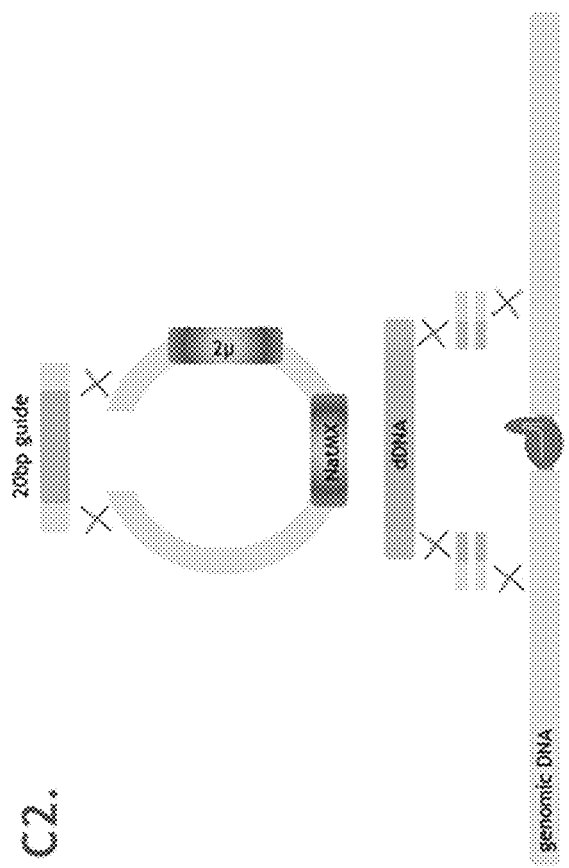
Figure 5 C1
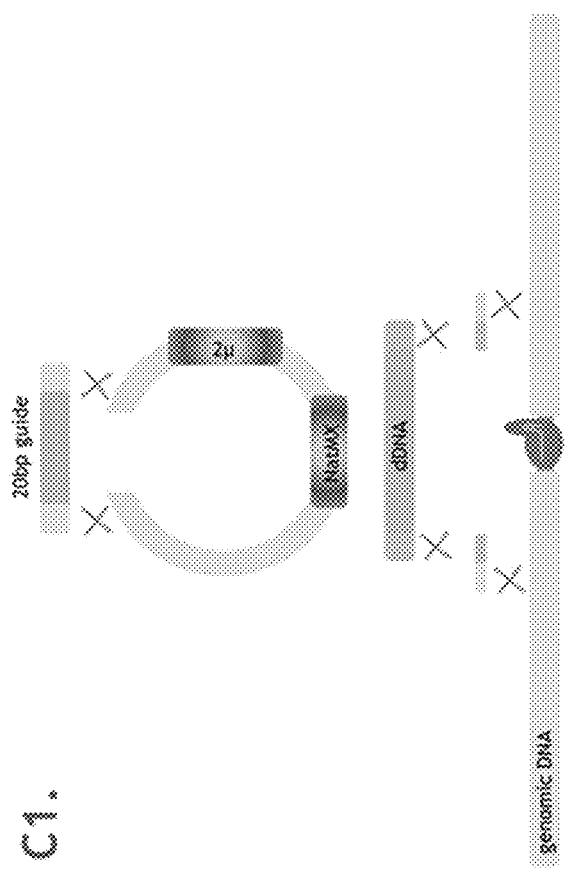
Figure C2

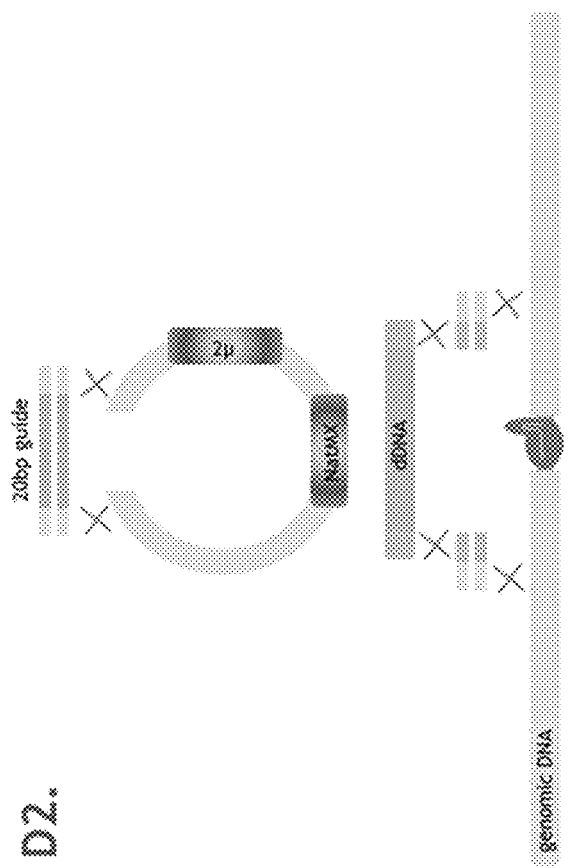
Figure 5 D2
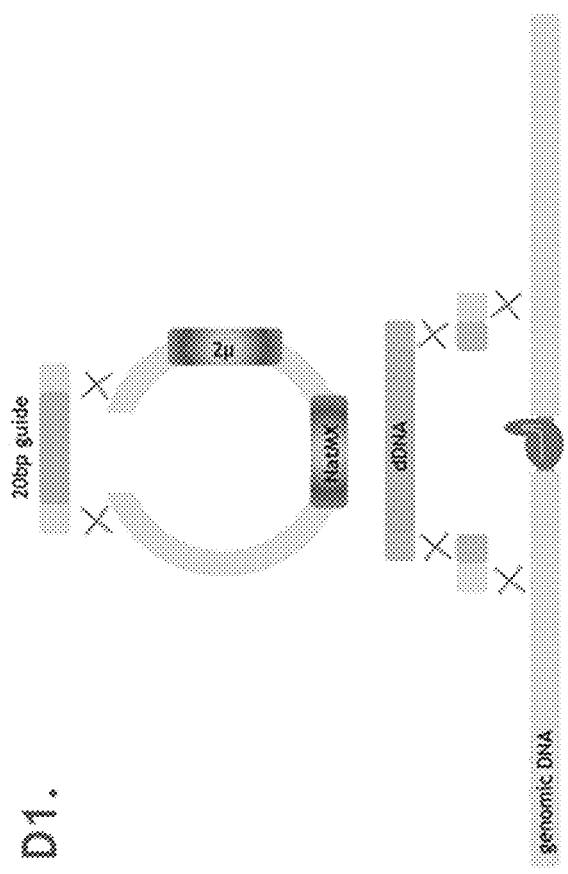
Figure 5 D1

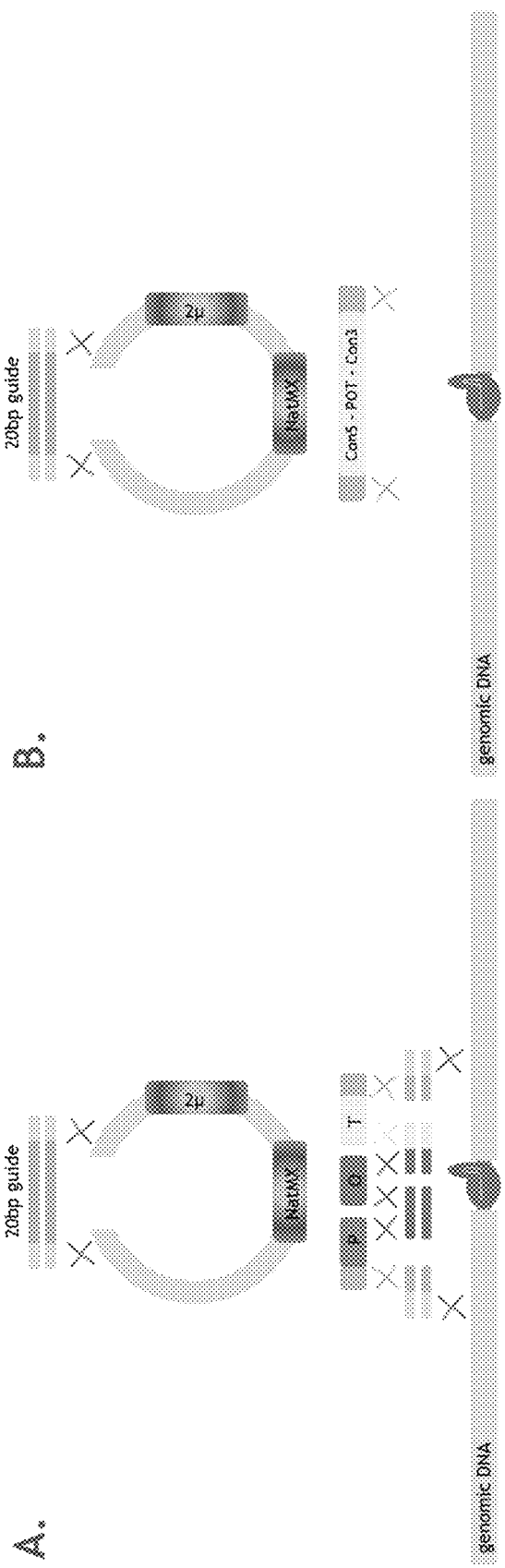

ASSEMBLY SYSTEM FOR A EUKARYOTIC CELL

CROSS-REFERENCE TO RELATED APPLICATIONS

This application is a National Stage entry of International Application No. PCT/EP2016/081240, filed 15 Dec. 2016, which claims priority to European Patent Application No. 16181781.2, filed 28 Jul. 2016.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-496000 ST25_.txt" created on 16 Jan. 2019, and 230,584 bytes in size) is submitted concurrently with the instant application, and the entire contents of the Sequence Listing are incorporated herein by reference.

BACKGROUND

Field of the Invention

The present invention relates to the field of molecular biology and cell biology. More specifically, the present invention relates to an assembly system for in a eukaryotic cell

DESCRIPTION OF RELATED ART

Recent techniques in gene editing such as CRISPR/Cas have revolutionized the field. Since the major leap, this technique has taken over the last years and more recently a lots of fine-tuning and improvements have been made. E.g. in WO2015095804 a technique is described wherein a linear vector comprising a marker gene is co-transfected with a nuclease and a donor nucleic acid to increase efficiency of selection for integration of the donor nucleic acid. In WO2009048885, a technique is described that allows the assembly of multiple nucleic acids cassettes with overlapping (complementary) portions into a single nucleic acid molecule.

Recently, various oligo-mediated methods have been developed to facilitate the efficient assembly of DNA in vitro.

Kok et al. (2014) developed a so-called ligase cycling reaction (LCR) for one-step, scarless DNA assembly. LCR uses single-stranded bridging oligo's complementary to the ends of neighboring DNA parts, a thermostable ligase to join DNA backbones and multiple denaturation-annealing-ligation temperature cycles to assemble complex DNA constructs. Such constructs can then be introduced in a living cell in a subsequent transformation and screening experiment.

Gibson (2009) demonstrated that the yeast *Saccharomyces cerevisiae* can take up and assemble at least 38 overlapping (complementary) single-stranded oligonucleotides. These oligonucleotides can overlap (be complementary) by as few as 20 bp, and can be as long as 200 nucleotides in length. This straightforward scheme for assembling chemically-synthesized oligonucleotides could be a useful tool for building synthetic DNA molecules.

Zhumbayeva et al. (2001) reported on an oligonucleotide-mediated cloning technique based on homologous recombination in *Saccharomyces cerevisiae* that would allow precise DNA sequences to be transferred independent of restriction enzymes and PCR. In this procedure (termed yeast-based, oligonucleotide-mediated gap repair technique (YOGRT), linear DNA sequences are targeted to a chosen site in a yeast vector by DNA linkers, which consist of two annealed, partially overlapping (complementary) oligonucleotides.

Recently single-stranded oligonucleotides have been used as donor templates in CRISPR-CAS9-mediated genome editing experiments.

Glaser et al. (2016) demonstrated that Green Fluorescent Protein (GFP) to Blue Fluorescent Protein (BFP) conversion is a reliable and simple method for the quantification of homology-directed repair (HDR) and Non Homologous End Joining (NHEJ). For this the required and introduced single basepair and three basepair mutations, respectively, in the encoding gene of a fluorescent protein at a genomic locus using a single-stranded donor oligonucleotide (ssODN) of about 120 bp as donor DNA, and a single guide RNA (gRNA) in combination with Cas9 were used. Frequencies of homology-directed repair (HDR) were in the range of 5-25%.

Inui et al (2014) applied the CRISPR/Cas9 system to generate mice with point mutations in their genomes, which led to single amino acid substitutions in proteins of interest by microinjecting gRNA, hCas9 mRNA and 110 bp single-stranded donor oligonucleotides (ssODN) into mouse zygotes.

Singh et al (2015) reviewed CRISPR/Cas methods for editing mouse embryo cells. In FIG. 1 of the Singh paper, the proposed cellular repair pathways operating at CRISPR/Cas9-generated DNA breaks or nicks was shown. Singh made a comparison between ssODN and dsDNA as repair template in the above context. Singh discussed that in many precise genome editing applications, synthetic ssODNs successfully replaced the need for larger gene targeting plasmids and required no additional experimental effort for construction of repair DNA. They also yielded higher editing frequencies than double-stranded DNA (dsDNA) repair templates. Typically ssODNs in length of 60-200 bp were used, centered around the DNA locus cleavage site.

Yoshimi et al (2016) reported the use of a CRISPR-Cas system targeted knock-in (KI) via homologous recombination in rats. Efficient gene knock-in was shown by combining CRISPR-Cas with single-stranded oligodeoxynucleotides (ssODNs). First, a 1-kb ssODN co-injected with gRNA and Cas9 messenger RNA produced a knock-in of a GFP expression cassette at the rat Thy1 locus. Then, using the so-called "two-hit two-oligo with plasmid" method (2H2OP method), two gRNAs with two 80-bp ssODNs directed efficient integration of a 5.5-kb CAG-GFP vector (a vector comprising the synthetic CAG promoter driving expression of Green Fluorescent Protein) into the Rosa26 locus via ssODN-mediated end joining. This protocol also allowed knock-in of a 200-kb Bacterial Artificial Chromosome (BAC) containing the human SIRPA locus, concomitantly knocking out the rat Sirpa gene. Finally, three gRNAs and two ssODNs replaced 58-kb of the rat Cyp2d cluster with a 6.2-kb human CYP2D6 gene. In these protocols, single ssODNs are applied as homology arms centered around the site of the CRISPR-Cas induced break. For knockout of DNA fragments and/or direct replacement, two gRNAs are used. A drawback of the method, as recognised by the authors, is the high rate of indel mutations at ssODN-mediated conjunction sites.

There is thus a continuing urge to simplify and/or improve on the provision, assembly and delivery of donor nucleic acid molecules and/or guide-polynucleotides and especially on the increase of efficiency of integration and of accuracy of integration of donor nucleic acids.

SUMMARY OF THE INVENTION

The present invention addresses above described need and provides such technique. The present invention is based on the use of single-stranded oligonucleotides in the assembly within a cell (in vivo assembly) of double-stranded oligonucleotides into a single double-stranded nucleic acid construct. The addition of these assembly techniques significantly simplify assembly, delivery and/or provision of donor nucleic acid molecules and guide-polynucleotides.

The present invention relates to the use of at least a first and a second single-stranded oligonucleotide in the assembly within a cell of at least two double-stranded nucleic acid molecules into a single double-stranded nucleic acid construct of pre-determined sequence, wherein the first and second single-stranded oligonucleotide are essentially complementary to each other.

The invention further relates to a method for the assembly within a cell (in vivo assembly) of at least two double-stranded nucleic acid molecules into a single double-stranded nucleic acid construct of pre-determined sequence, wherein the assembly is mediated by at least a first and a second single-stranded oligonucleotide, wherein the first and second single-stranded oligonucleotide are essentially complementary to each other, said method comprising contacting the cell with the single-stranded oligonucleotides and at least one of the double-stranded nucleic acid molecules such that the single-stranded oligonucleotides and at least one of the double-stranded nucleic acid molecules are introduced into the cell.

The invention further relates to a composition comprising the at least first and second essentially complementary single-stranded oligonucleotides, the cell and at least one of at least two double-stranded nucleic acid molecules as defined herein.

The invention further relates to a cell comprising an assembled double-stranded nucleic acid construct, obtainable by a method as defined herein.

The invention further relates to a cell obtainable by or produced by a method as defined herein, further comprising a polynucleotide encoding a compound of interest.

The invention further relates to a method for the production of a compound of interest, comprising culturing a cell as defined herein under conditions conducive to the production of the compound of interest, and, optionally, purifying or isolating the compound of interest.

BRIEF DESCRIPTION OF THE DRAWINGS

FIG. 5 A1-B2 depict the first 4 different experimental designs applied in Example 1 and detailed in Table 1 and Table 2: A1, A2, B1, B2.

FIG. 5 C1-D2 depict the second 4 different experimental designs applied in Example 1 and detailed in Table 1 and Table 2: C1, C2, D1, D2.

Figure 9:
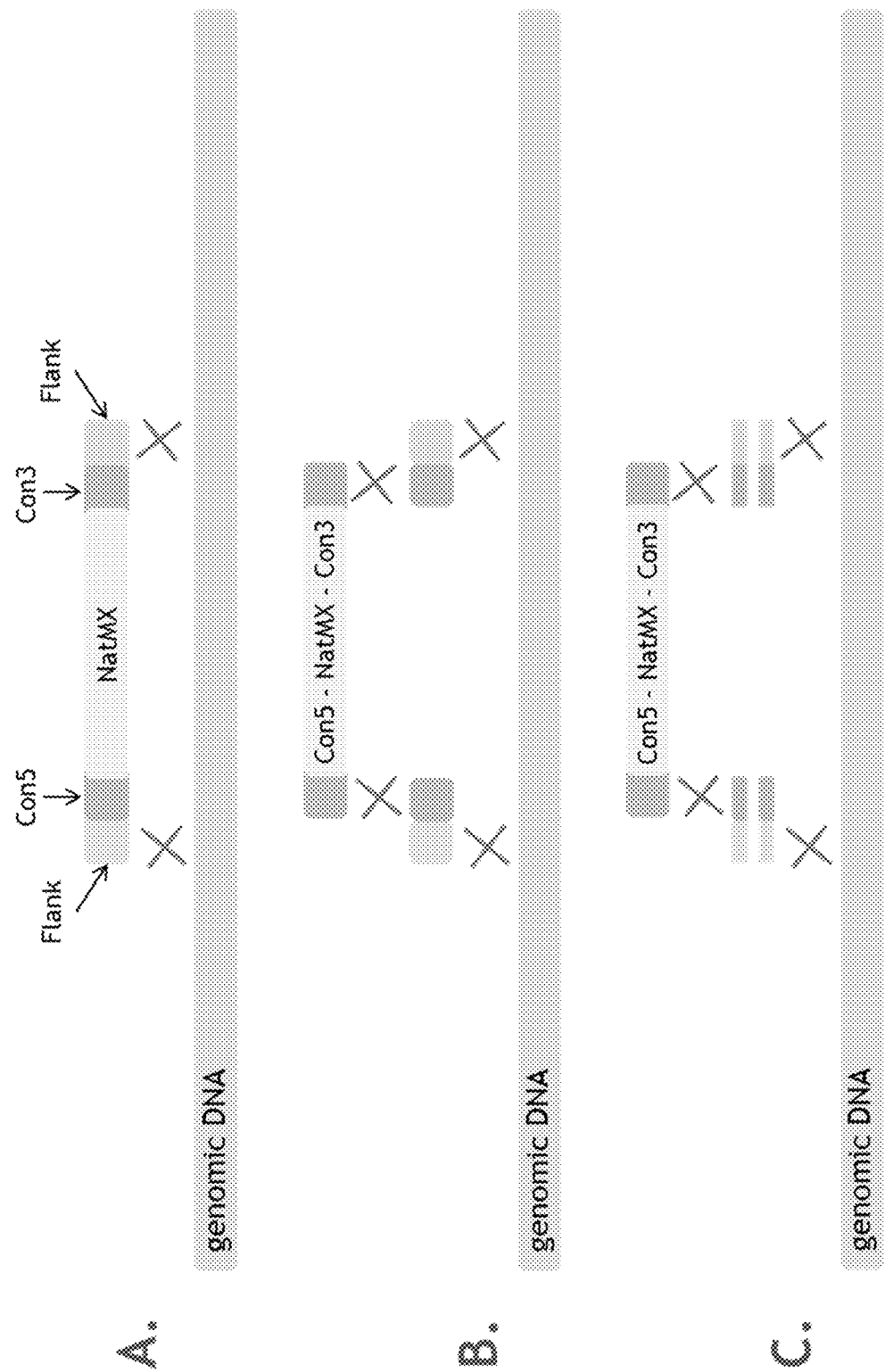

FIG. 9 depicts the experimental set-up of Example 2.

Figure 10:
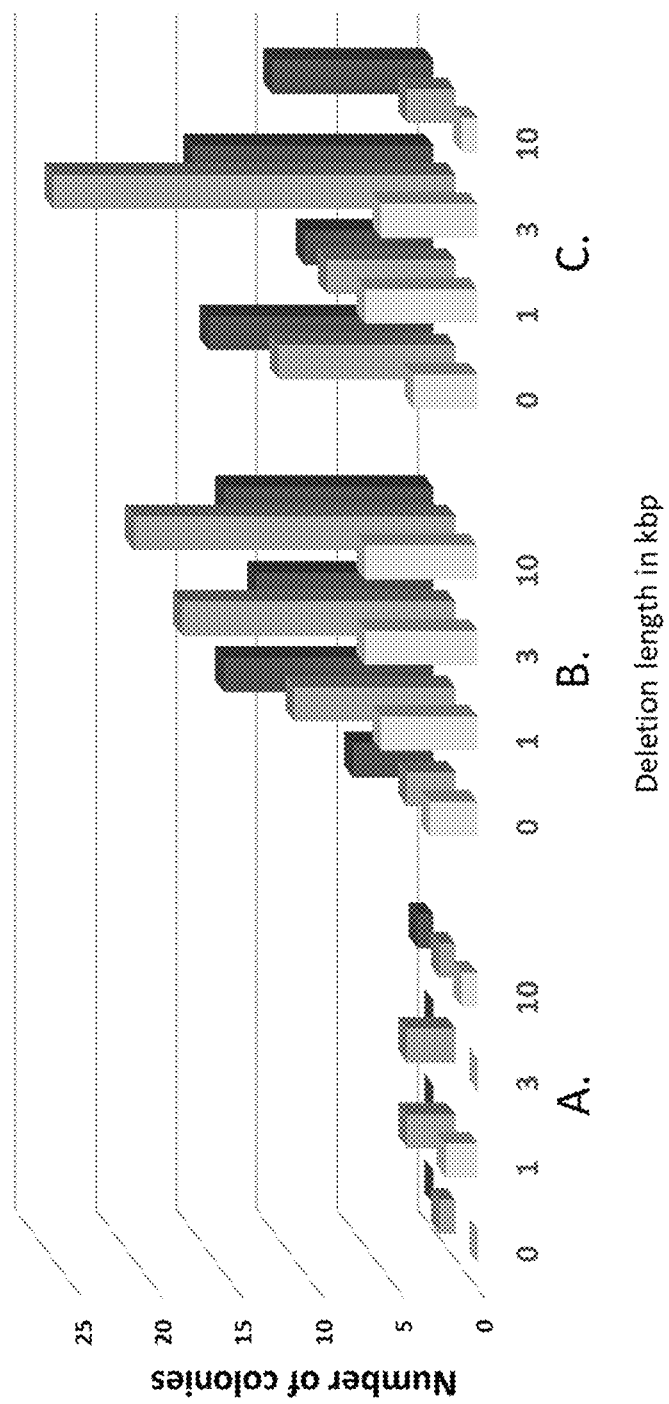

FIG. 10 depicts a stacked bar chart visualizing the number of NatMX resistant transformants that appeared on the transformation plate from a 1:10 (light grey), 1:5 (grey) and 1:3 (dark grey) diluted transformation mixture for 12 transformations outlined in Table 4 and Table 5. Subset A: flanks added to PCR fragment. Subset B: 2× dsDNA flank sequences. Subset C: 4× ssODN (2×2 complementary ssODN) flank sequences FIGS. 11 A-D depict the experimental set-up of Example 3.

Figure 12:
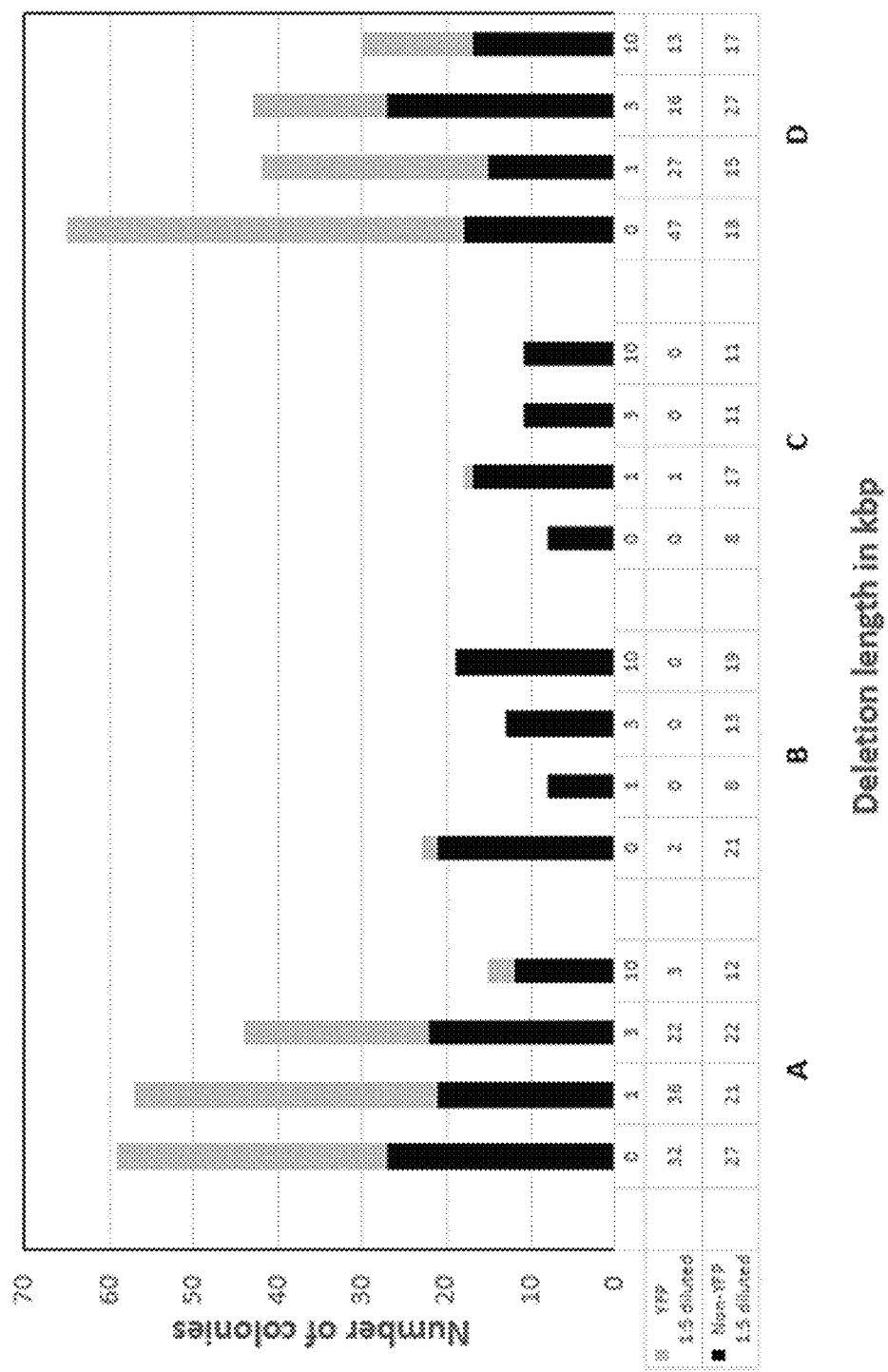

FIG. 12 depicts a stacked bar chart visualizing the number of non-fluorescent (black) and fluorescent (gray) transformants that appeared on the transformation plate from a 1:5 diluted transformation mixture for the 16 transformations outlined in Table 6 and Table 7.

The subsets A to D are detailed in Table 6 and Table 7. The numbers at the X-axis represent designed knock-out stretch in kbp (top row), number of fluorescent YFP (middle row) and number of non-fluorescent transformants (bottom row).

Figure 13:
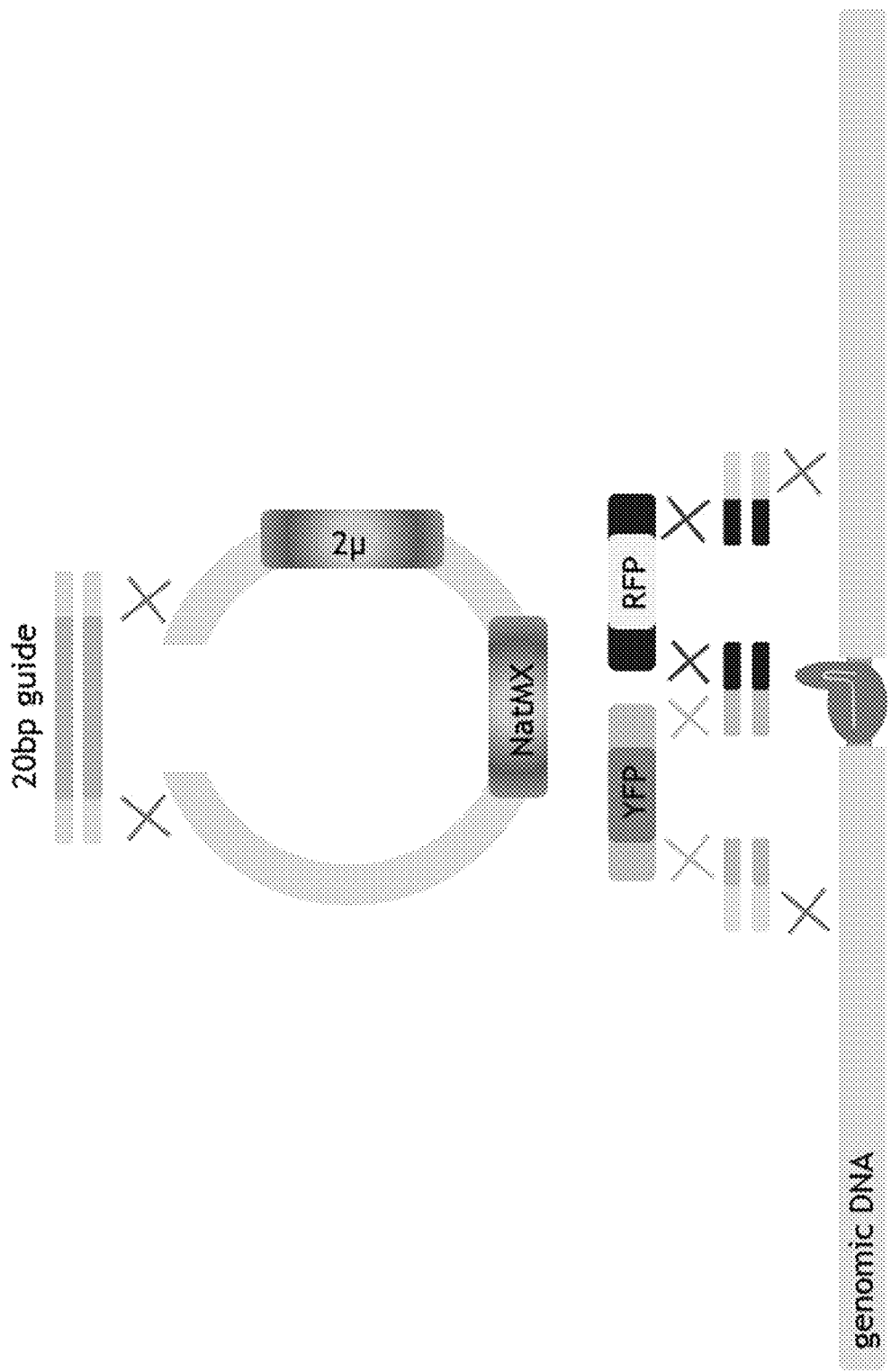

FIG. 13 depicts the experimental set-up of Example 4.

Figure 14:
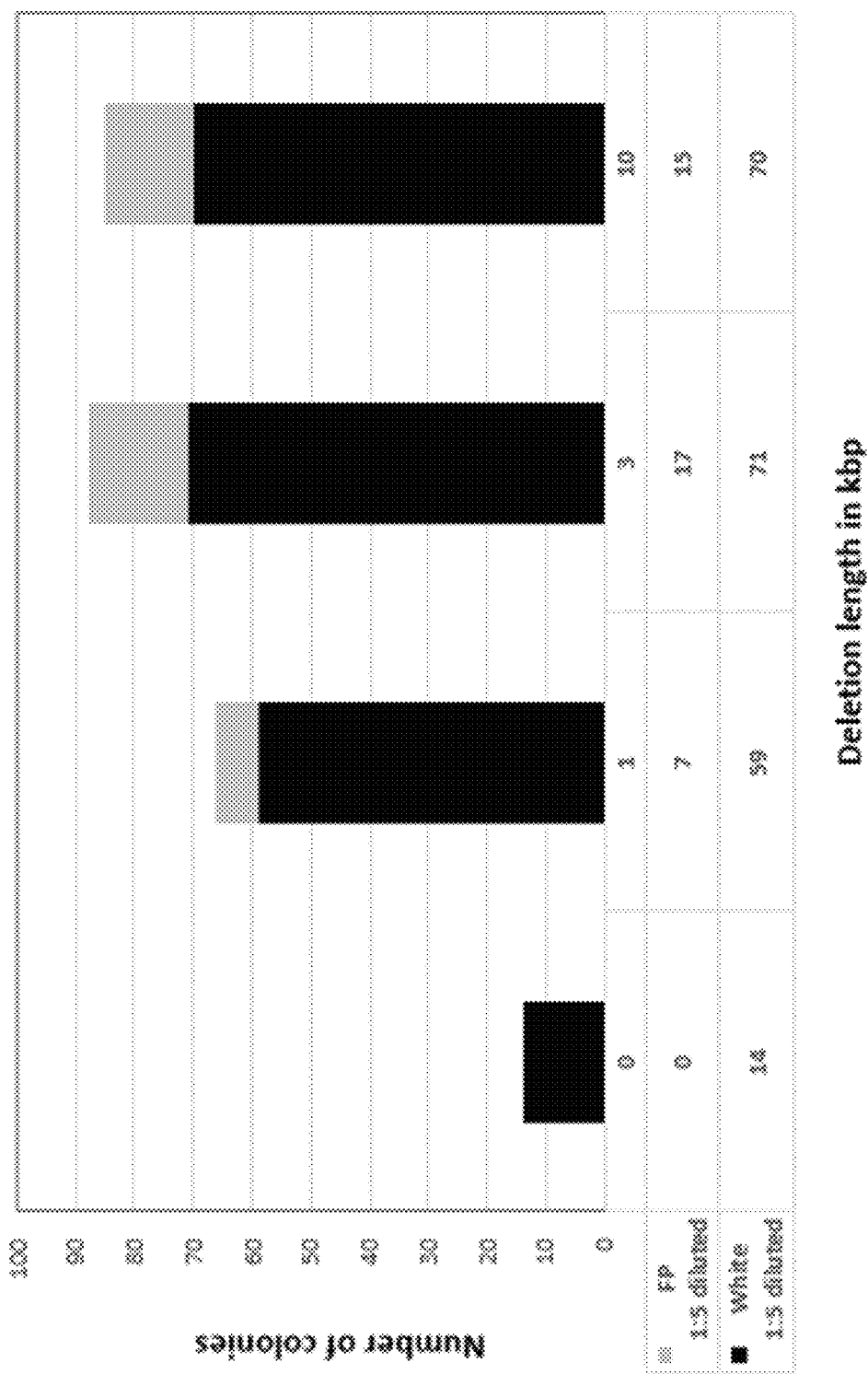

FIG. 14 depicts a stacked bar chart visualizing the number of non-fluorescent (black) and fluorescent (gray) transformants that appeared on the transformation plate from a 1:5 diluted transformation mixture for the 4 transformations outlined in Table 8. The numbers at the X-axis represent designed knock-out stretch in kbp (top row), number of fluorescent trasformants (middle row) and number of non-fluorescent transformants (bottom row).

Figure 15:
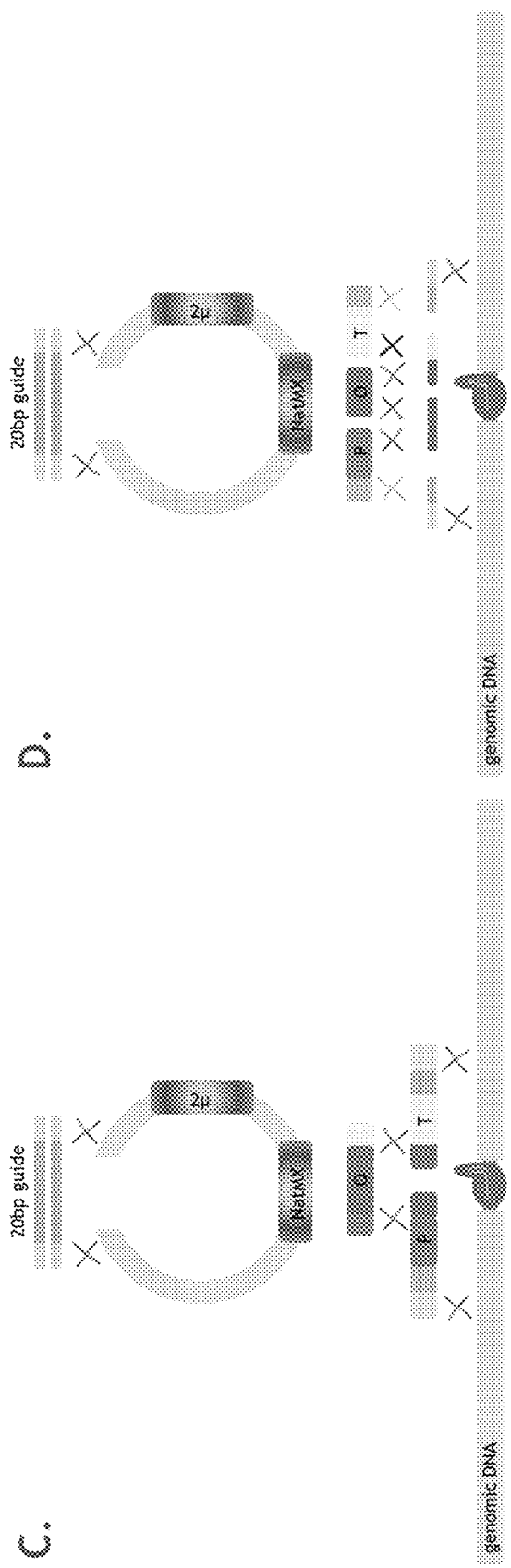
Figure 15:
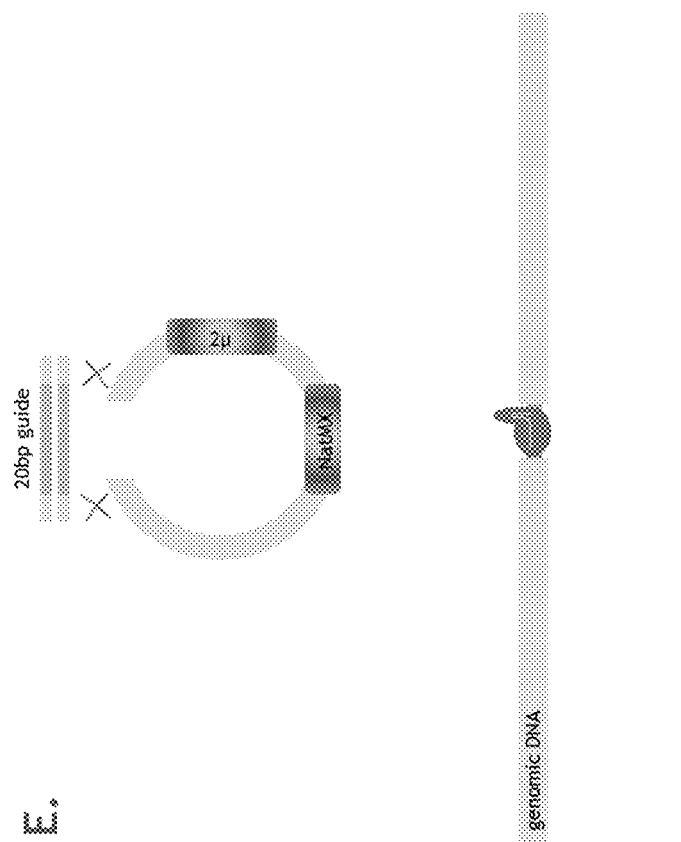

FIGS. 15 A-E depict the experimental set-up of Example 5.

Figure 16:
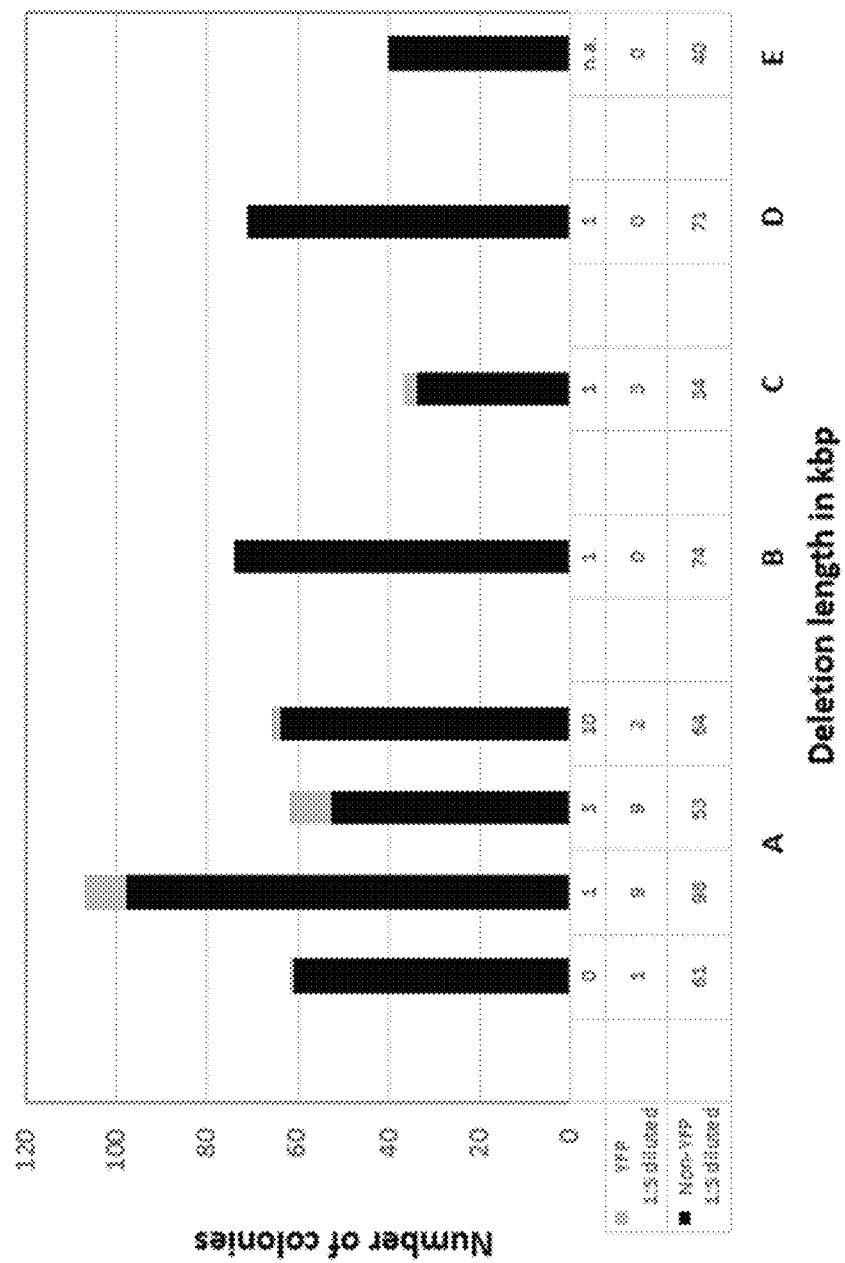

FIG. 16 depicts a stacked bar chart visualizing the number of non-fluorescent (black) and fluorescent (gray) transformants that appeared on the transformation plate from a 1:5 diluted transformation mixture for the 9 transformations outlined in Table 9 and Table 10, including details of subsets A to E. The numbers at the X-axis represent designed knock-out stretch in kbp (top row), number of fluorescent YFP (middle row) and number of non-fluorescent transformants (bottom row).

Figure 17:
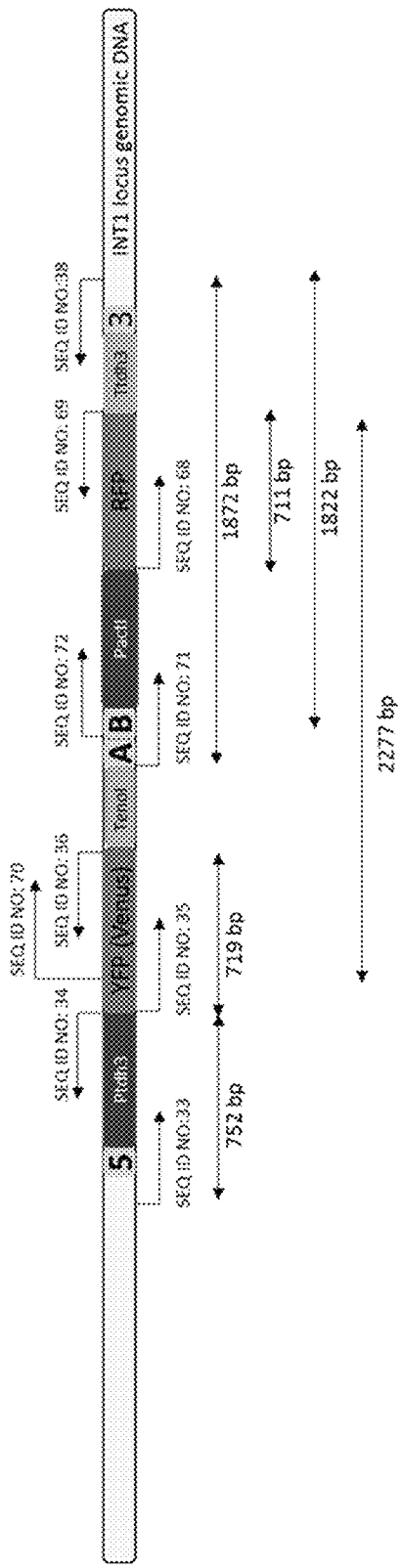

FIG. 17 depicts the PCR approach to confirm correct tandem integration of the YFP and RFP expression cassettes and to confirm deletion of ~1 kB of genomic DNA at the INT1 locus. "5", "3", "A" and "B" represent connector sequences, which are non-coding DNA sequences added to the expression cassette.

Figure 18:
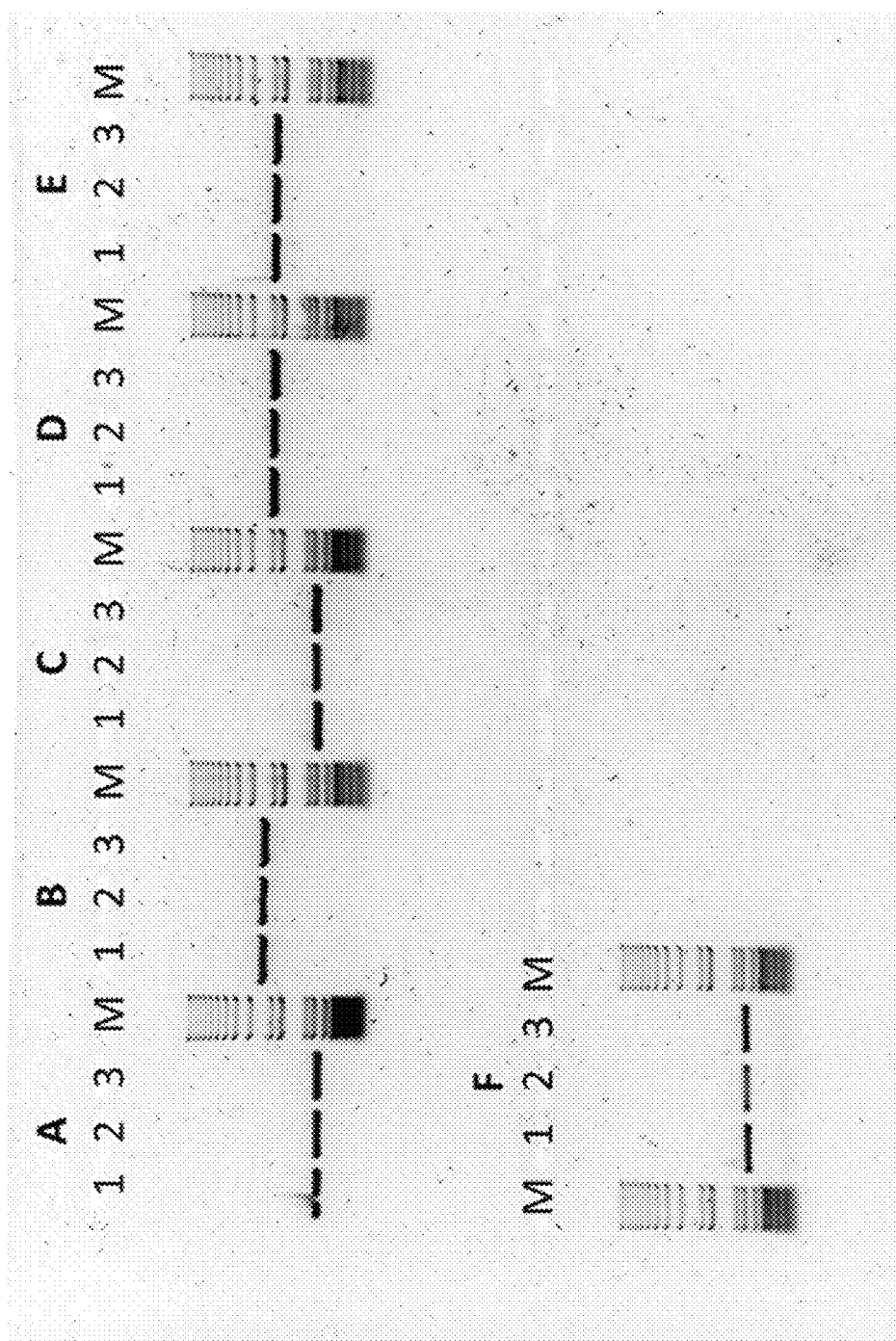

FIG. 18 depicts an agarose gel, used for analysis of PCR products to confirm correct tandem integration of the YFP and RFP expression cassettes in genomic DNA and to confirm deletion of ~1 kB genomic DNA at the INT1 locus.

A. Confirmation integration of the RFP expression cassette (711 bp band, primer SEQ ID NO: 68+SEQ ID NO: 69).

B. Confirmation tandem integration of YFP and RFP expression cassettes into the genome (2277 bp band, primers SEQ ID NO: 70+SEQ ID NO: 69).

C. Confirmation correct deletion of 1 kb genomic DNA at 5' end (752 bp band, primers SEQ ID NO: 33+SEQ ID NO: 34).

D. Confirmation correct deletion of 1 kb genomic DNA at 3' end (1872 bp band, primers SEQ ID NO: 71+SEQ ID NO: 38).

E. Confirmation correct deletion of 1 kb genomic DNA at the 3' end (1822 bp band, primers SEQ ID NO: 72+SEQ ID NO: 38).

F. Confirmation integration of YFP expression cassette (719 bp band, primers SEQ ID NO: 35+SEQ ID NO: 36). Transformants 1 to 3: Fluorescent transformants, RFP and YFP fluorescence confirmed by BioLector® (M2P labs—Germany). Marker: 1 kB+ marker (ThermoFisher, Bleiswijk, the Netherlands, Cat no. 10787018).

Figure 19:
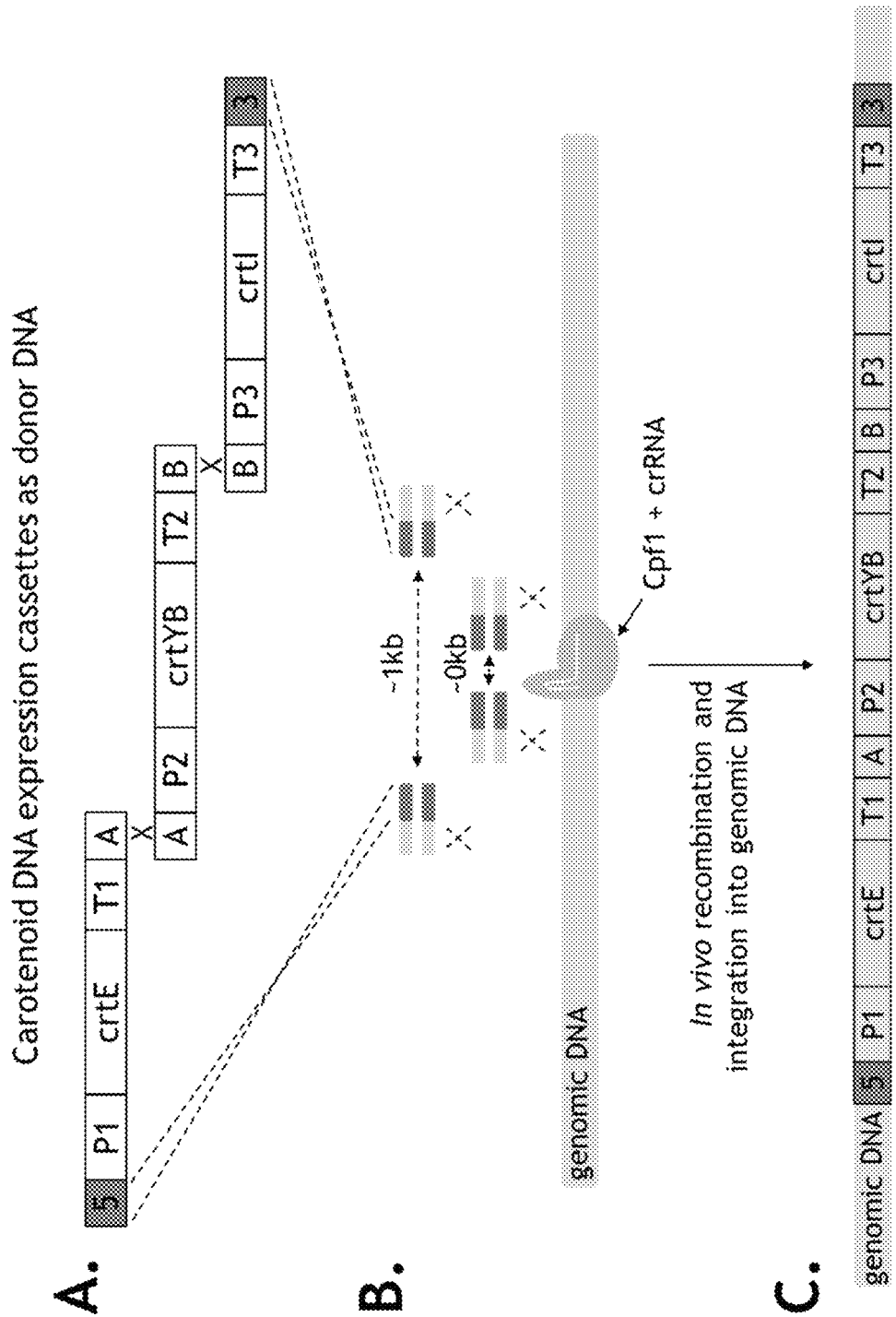

FIG. 19 depicts the knock-out/carotenoid gene expression cassettes knock-in approach of Example 6. (A). depicts the three double-stranded (DS) expression cassette of donor DNA: connector 5 (5)-*K. lactis* (KI)THD2 promoter (P1)-crtE-*S. cerevisiae* (Sc)TDH3 terminator (T1)-connector A (A), connector A (A)-KIYDR2p (P2)-crtYB-ScPDC1t (T2)-connector B (B), connector B (B)-ScPRE3p (P3)-crtI-ScTAL1t (T3)-connector 3 (3); (B) schematically visualizes the ~0 and ~1 knockout using flexible knock-out/knock-in ssODN flanks, here as complementary ssODN pairs. (C). Representation of transformed DNA sequences and integration into genomic DNA by in vivo recombination in yeast using connector sequences with complementarity with genomic DNA. The transformation approach is further depicted and explained in FIG. 24.

Figure 20:
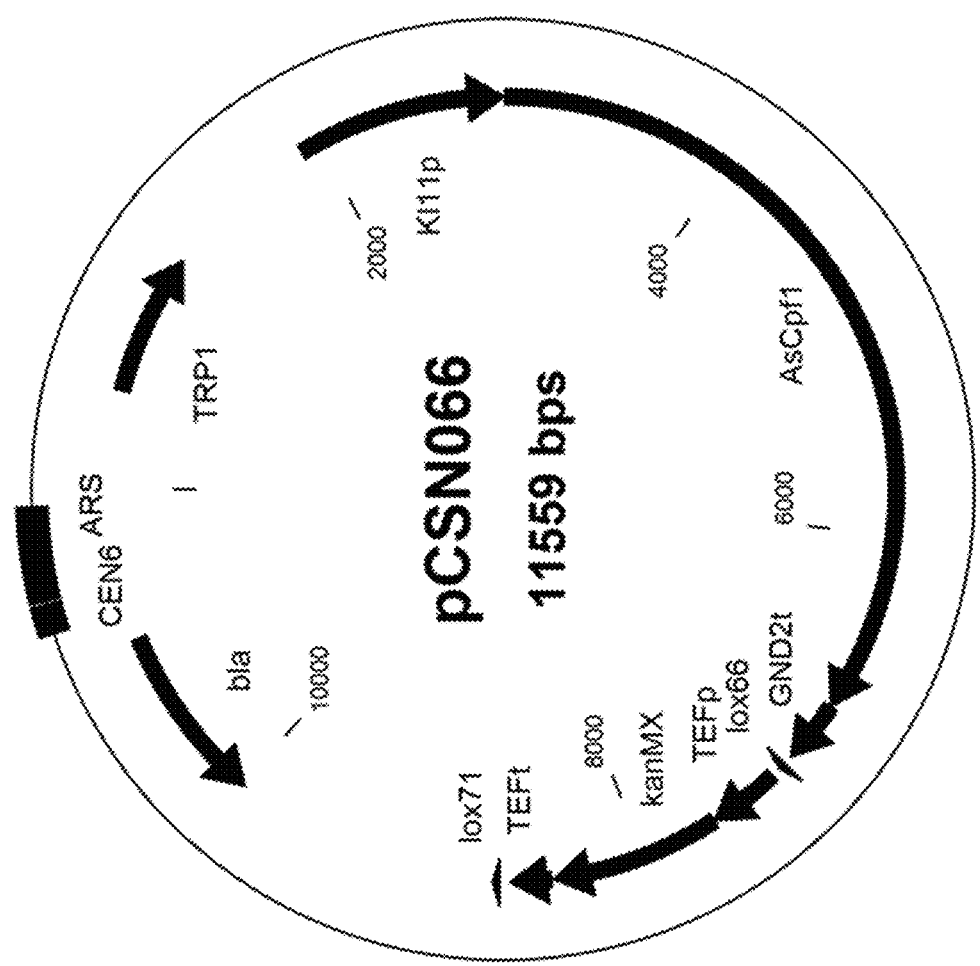

FIG. 20 depicts the vector map of single copy (CEN/ARS) vector pCSN066 expressing AsCpf1 (from *Acidaminococcus* spp. BV3L6). A KanMX marker is present on the vector.

Figure 21:
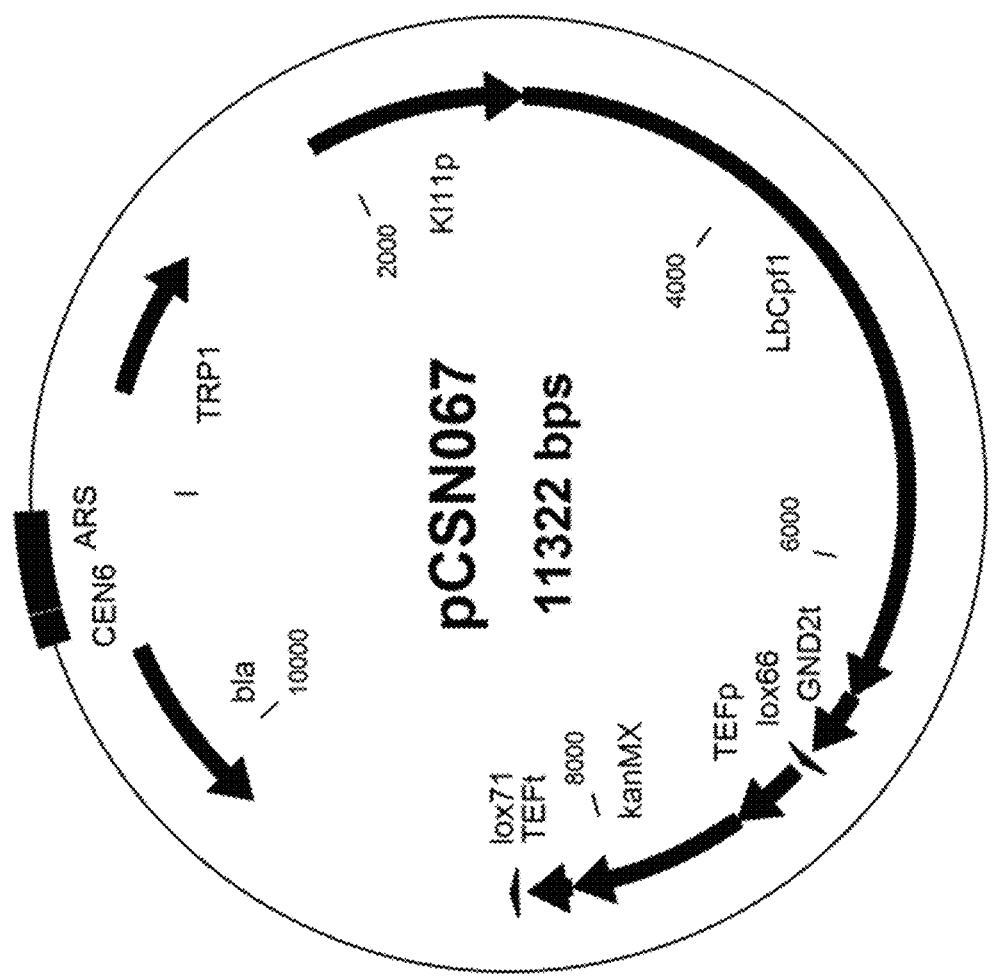

FIG. 21 depicts the vector map of single copy (CEN/ARS) vector pCSN067 expressing LbCpf1 (from *Lachnospiraceae* bacterium ND2006). A KanMX marker is present on the vector.

Figure 22:
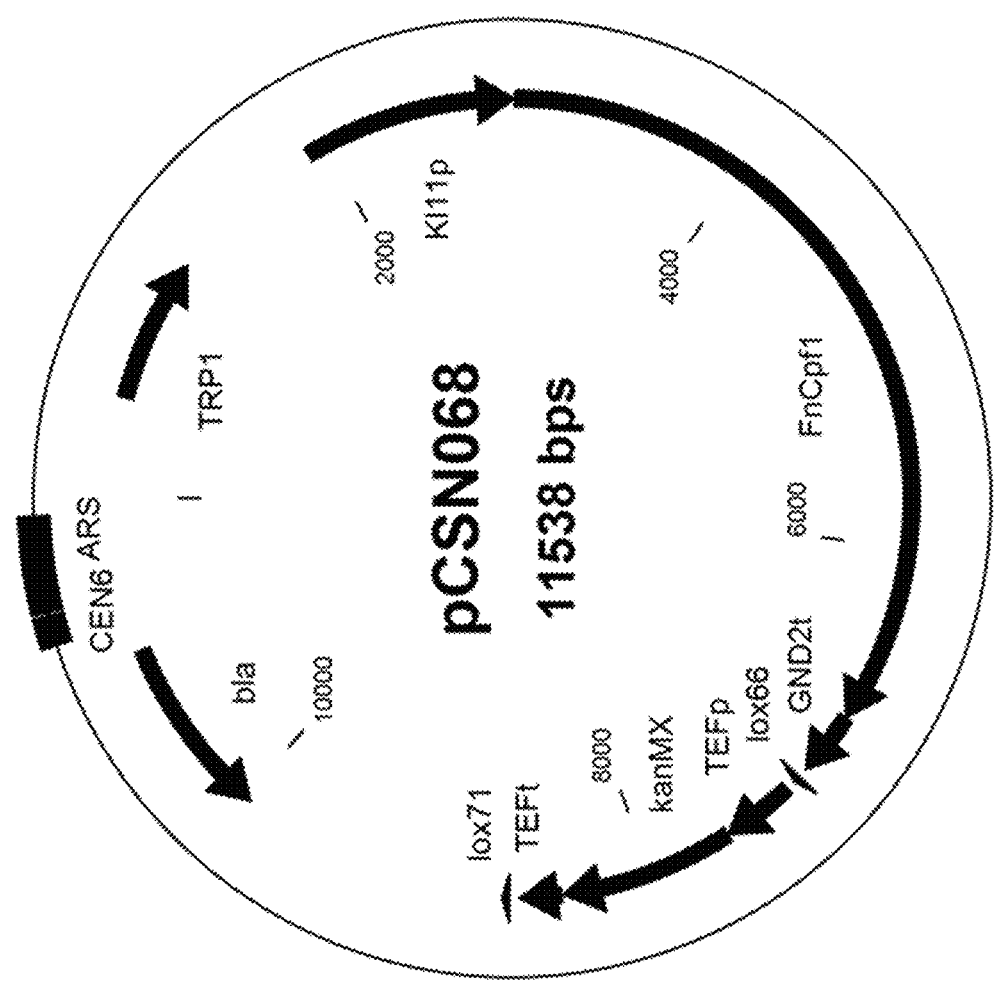

FIG. 22 depicts the vector map of single copy (CEN/ARS) vector pCSN068 expressing FnCpf1 (from *Francisella novicida* U112). A KanMX marker is present on the vector.

Figure 23:
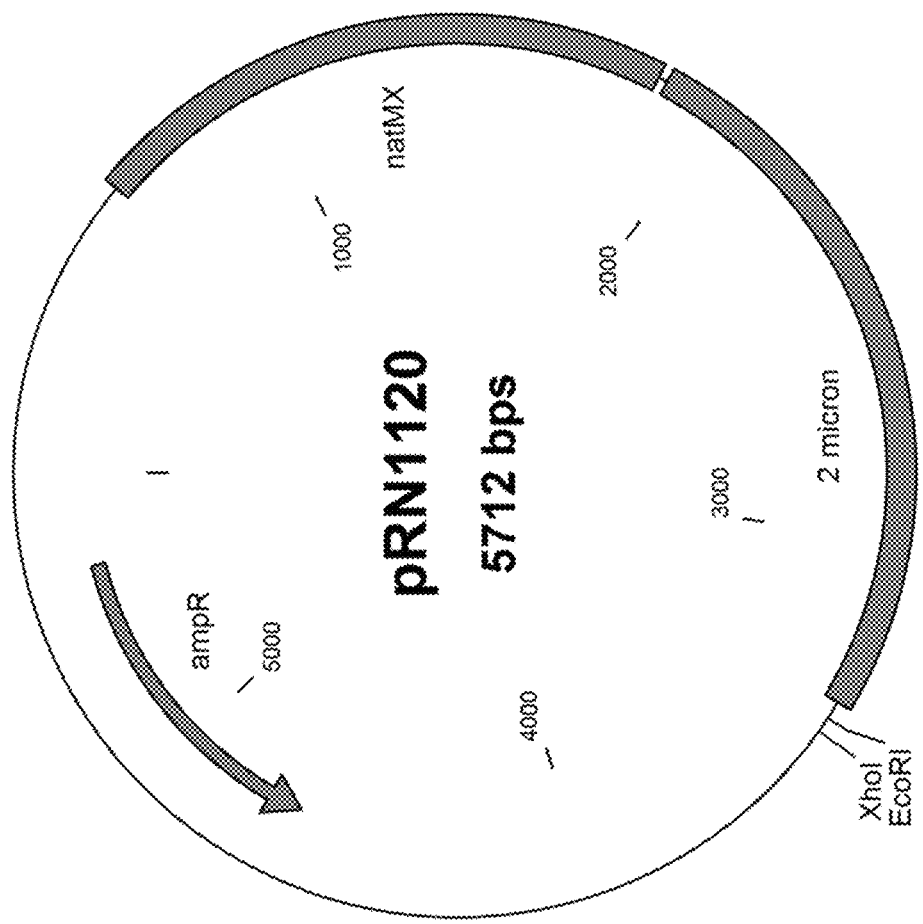

FIG. 23 depicts the vector map of multicopy (2 micron) vector pRN1120. A NatMX marker is present on the vector.

Figure 24:
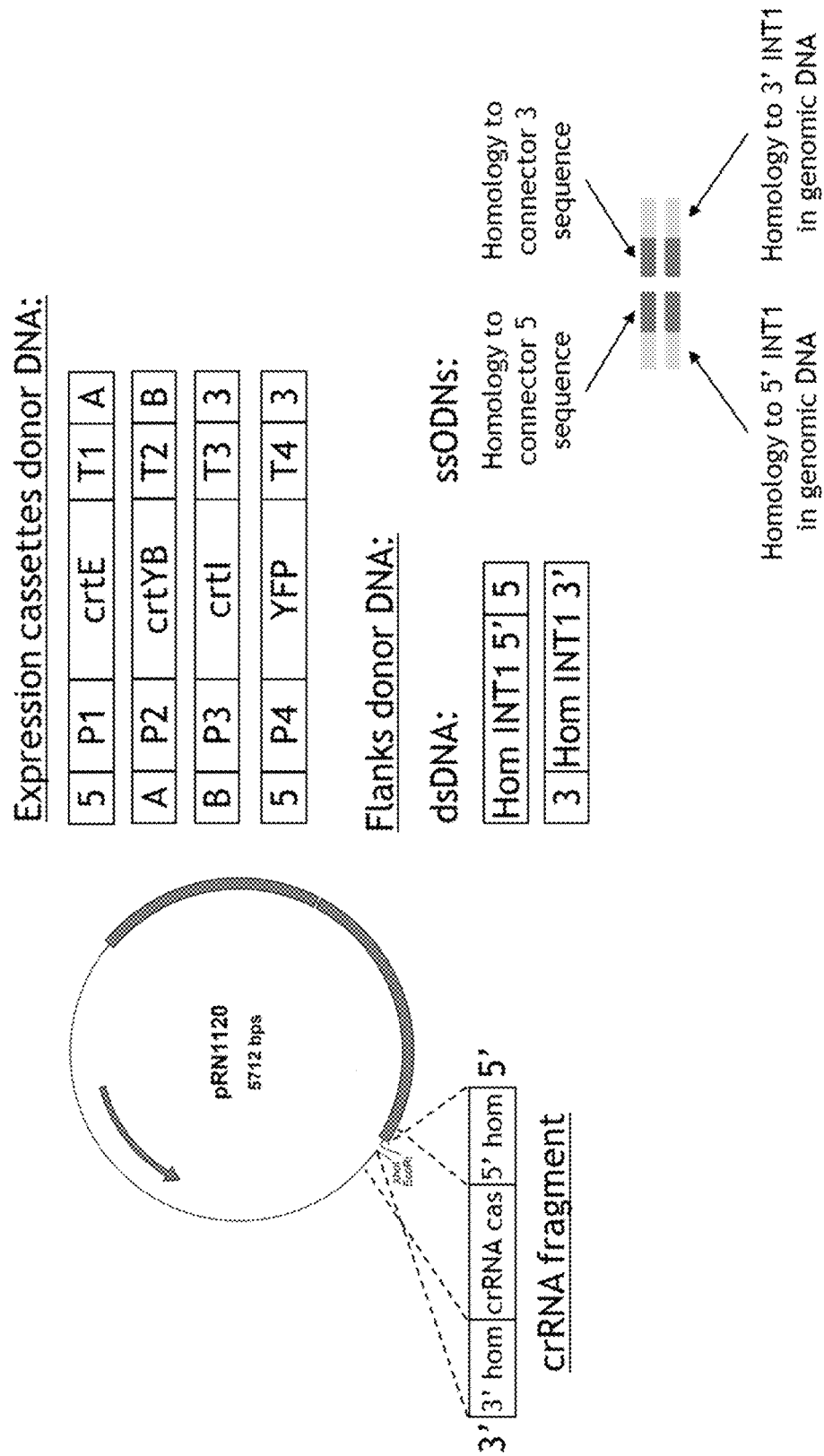

FIG. 24 depicts elements of the transformation approach as described in the following steps. Step 1: Transform cells with pSCN066, pCSN067 or pCSN068 (AsCpf1, LbCpf1, FnCpf1 expression plasmid) or with pCSN061 (SpCas9, i.e. *S. pyogenes* Cas9). Step 2: Transform cells pre-expressing AsCpf1, LbCpf1, FnCpf1 or CAS9 obtained in step 1 with pRN1120 digested with XhoI, EcoRI and with a crRNA expression cassette or guide RNA expression cassette (depicted as crRNA cas in the figure) including complementarity with linearized pRN1120 and donor DNA. The guide RNA fragment (indicated as crRNA fragment in the figure) contains 78 bp at its 5' end (5' hom) and 87 bp at the 3' end (3' hom) with the linearized pRN1120 vector to allow in vivo recombination into linearized pRN1120 to form a circular expression vector. Donor DNA consists of one of following expression cassettes: connector 5 (5)-*K. lactis* (KI)THD2 promoter (P1)-crtE *S. cerevisiae* (Sc)TDH3 terminator (T1)-connector A (A); connector A (A)-KIYDR2p (P2)-crtYB-ScPDC1t (T2)-connector B (B); connector B (B)-ScPRE3p (P3)-crtI-ScTAL1t (T3)-connector 3 (3); connector 5 (5)-ScTDH3p (P4)-YFP-ScENO1t (T)-connector 3 (3) expression cassettes) and flanks. The flanks can be composed of doubled strand DNA (dsDNA) containing connector 5 (5) or connector 3 (3) sequences (Hom INT1 5': homology with 5' INT1 integration site, Hom INT1 3': homology with 3' INT1 integration site) or 100 bp single-stranded oligodeoxynucleotides (ssODNs) sequences composed of 50 bp homology with a connector sequence and 50 bp homology with genomic DNA, as depicted in the figure.

Figure 25:
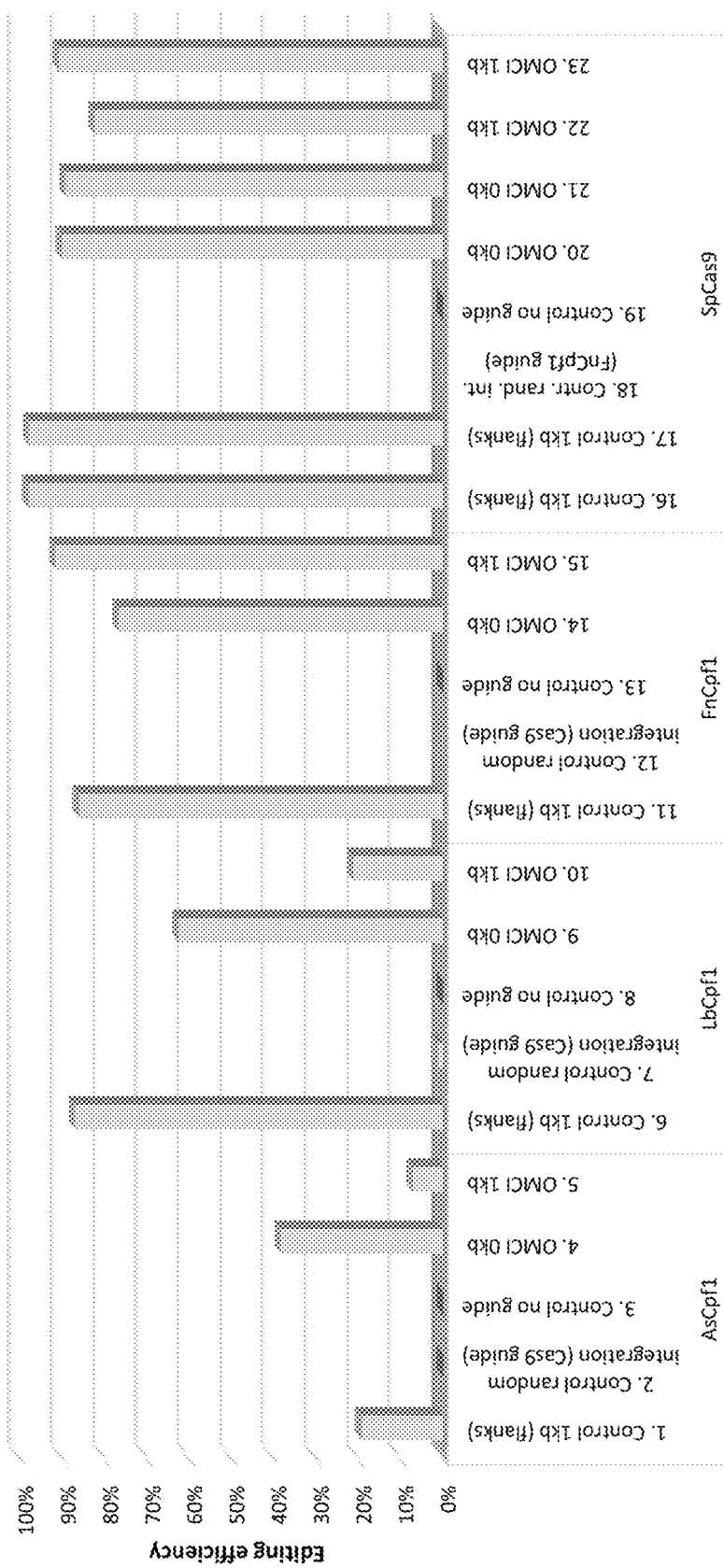

FIG. 25 depicts the results of the carotenoid genes transformation experiments (Table 16 transformations 1-23). The editing efficiency is indicated on the Y-axis.

Figure 26:
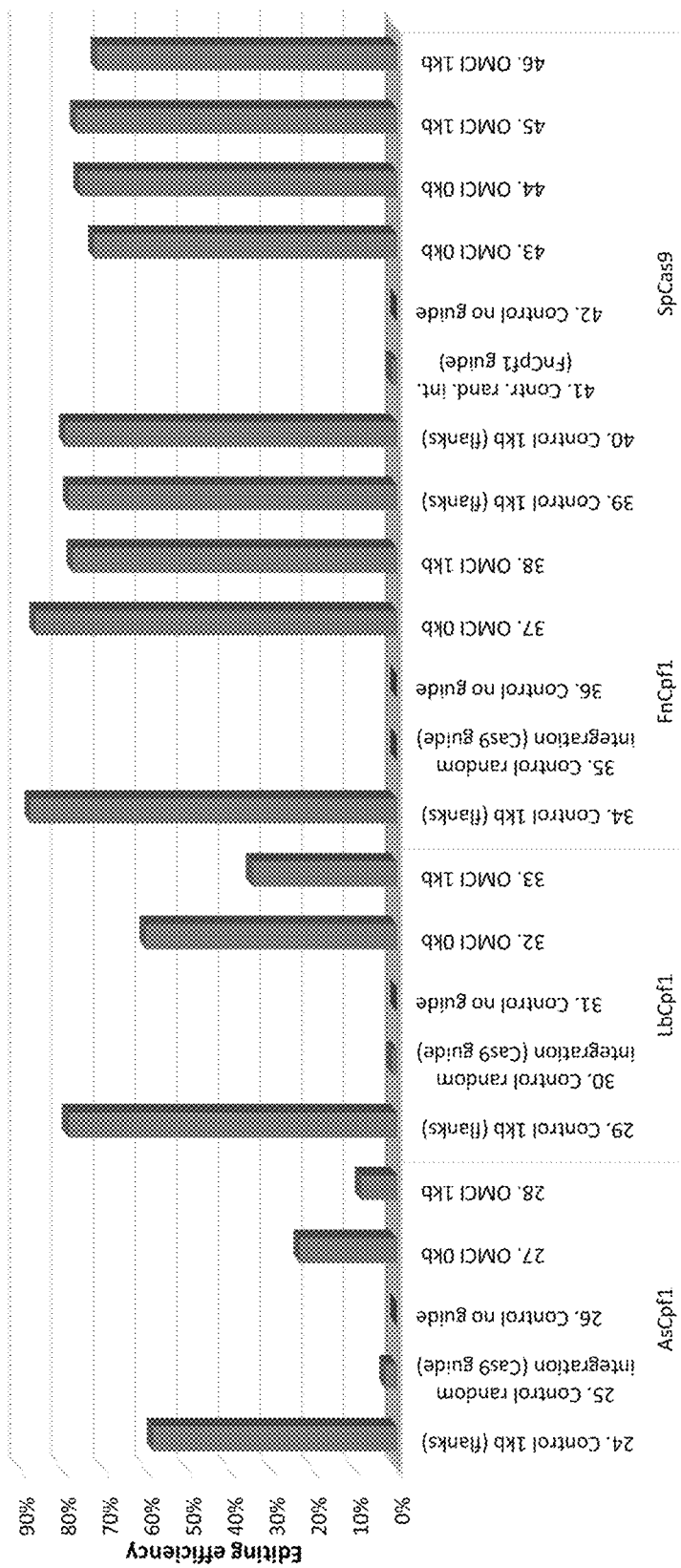

FIG. 26 depicts the results of the YFP transformation experiments (Table 16 transformations 24-46). The editing efficiency is indicated on the Y-axis.

Figure 27:
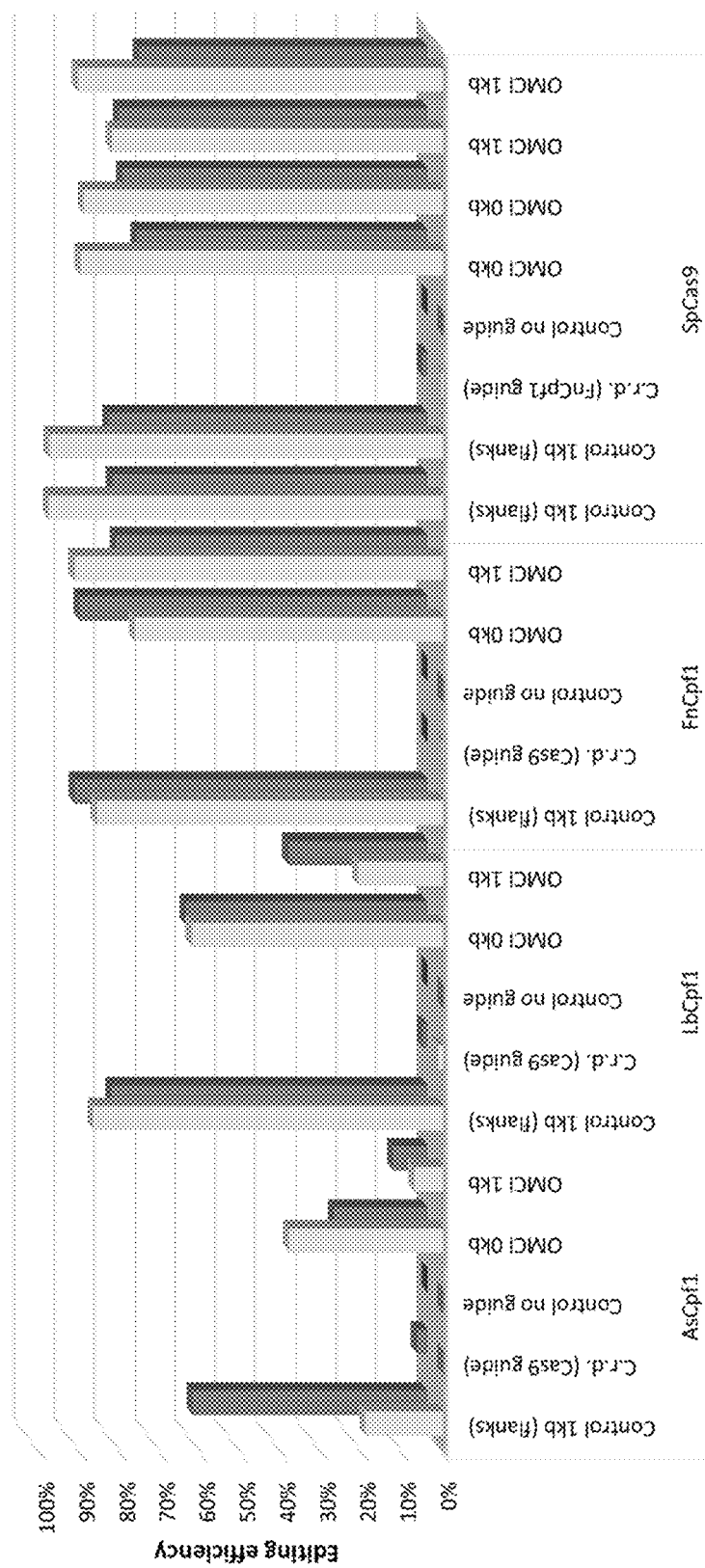

FIG. 27 provides a combination of the results of the carotenoid genes transformation experiments (Table 16 transformations 1-23, light grey bars) and the YFP transformation experiments (Table 16 transformations 24-46, dark grey bars). C.r.d. means control for random integration. The editing efficiency is indicated on the Y-axis.

Figure 28:
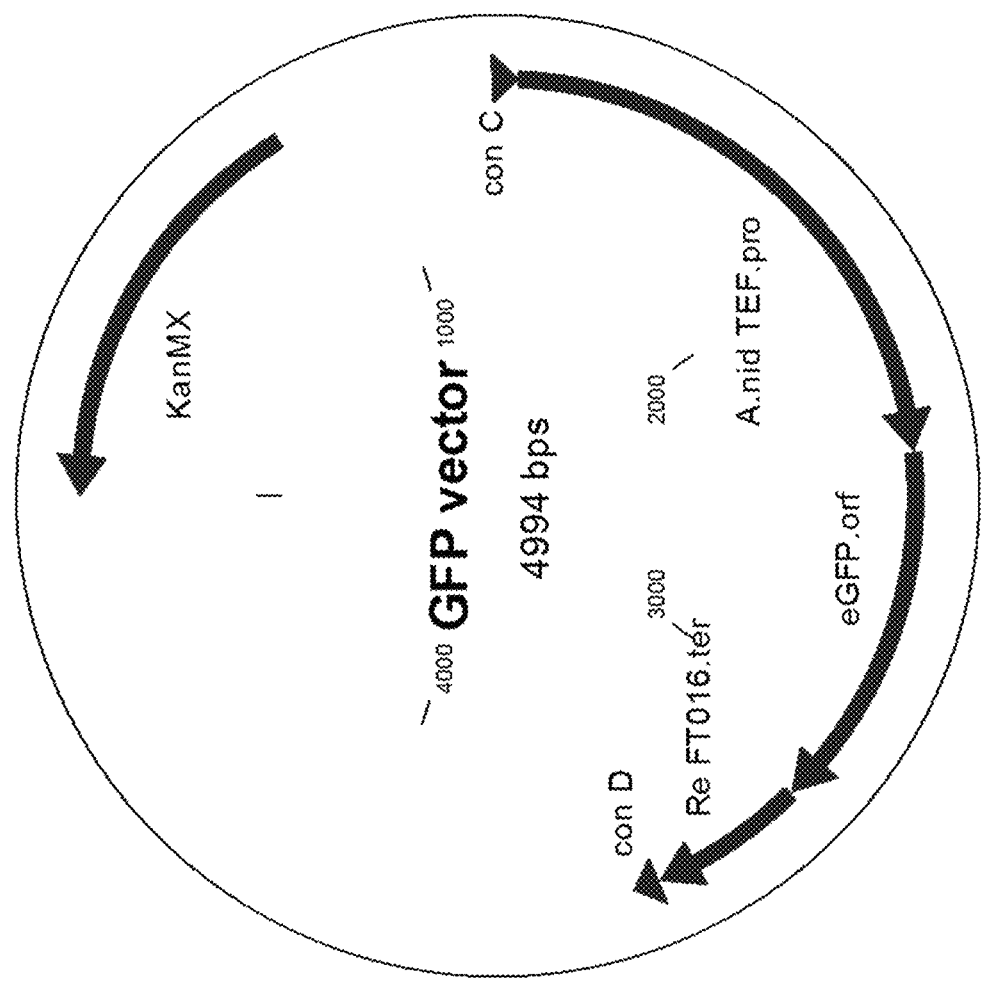

FIG. 28 depicts a vector map of the GFP vector, containing a GFP expression cassette that is functional in *Aspergillus niger*.

Figure 29:
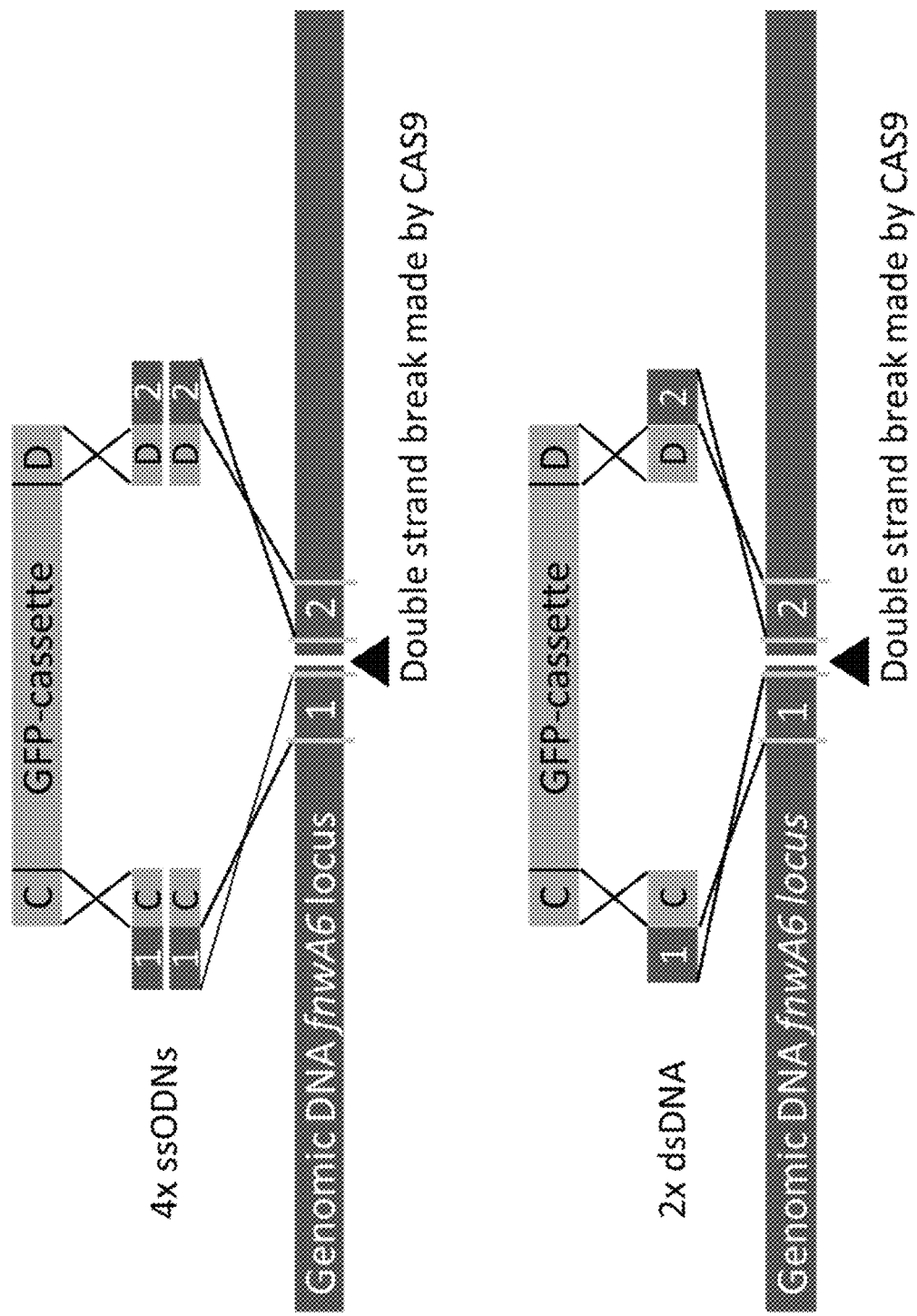

FIG. 29 provides a graphical representation of the approaches to integrate the GFP expression cassette (GFP-cassette), using four ssODNs or two dsDNAs, into the genome of *A. niger* at the fnwA6 locus.

Figure 30:
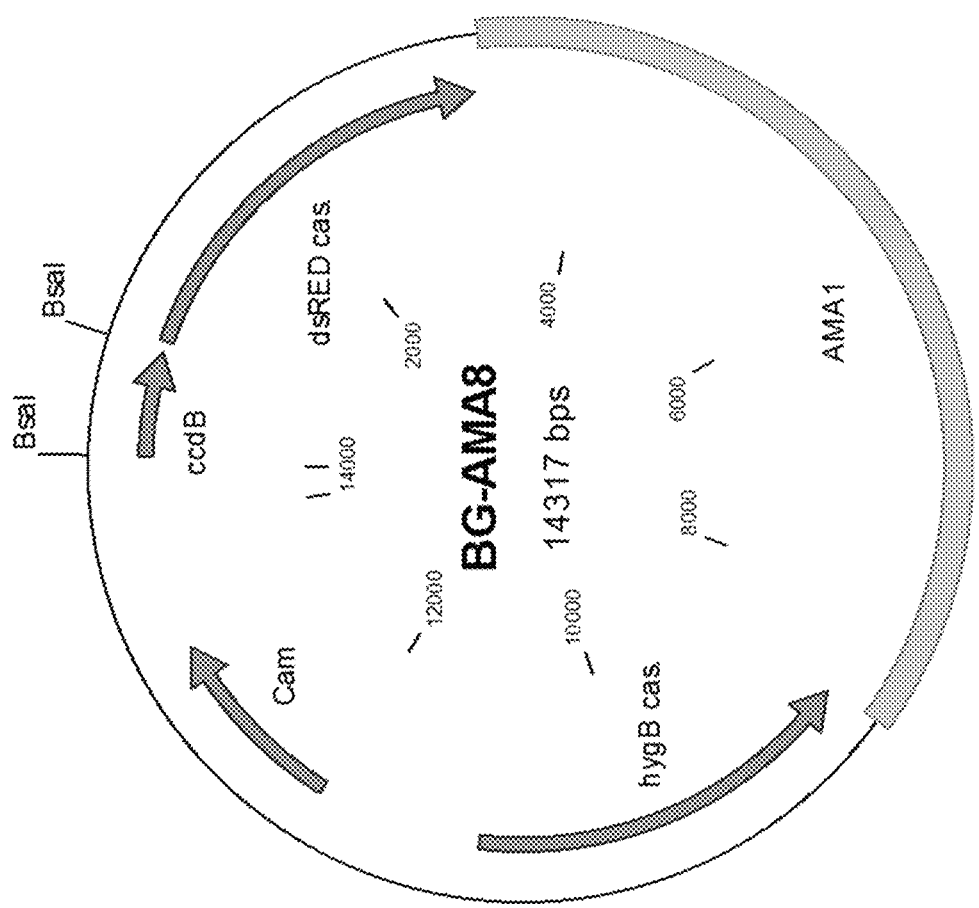

FIG. 30 depicts a vector map of vector BG-AMA8.

DESCRIPTION OF THE SEQUENCES

SEQ ID NO: 1 sets out the nucleotide sequence of vector pRN1120.

SEQ ID NO: 2 sets out the nucleotide sequence of the forward (FW) primer to remove SapI restriction site in pRN1120.

SEQ ID NO: 3 sets out the nucleotide sequence of the reverse (REV) primer to remove SapI restriction site in pRN1120.

SEQ ID NO: 4 sets out the nucleotide sequence of the gBlock allowing direct SapI cloning of genomic target, part of vector pGRN002.

SEQ ID NO: 5 sets out the nucleotide sequence of vector pGRN002.

SEQ ID NO: 6 sets out the nucleotide sequence of the FW primer to obtain the linear recipient PCR fragment (SEQ ID NO: 8)

SEQ ID NO: 7 sets out the nucleotide sequence of the REV primer to obtain the linear recipient PCR fragment (SEQ ID NO: 8).

SEQ ID NO: 8 sets out the nucleotide sequence of the linear recipient PCR fragment used for assembly of a guide sequence in a cell.

SEQ ID NO: 9 sets out the nucleotide sequence of vector pCSN061.

SEQ ID NO: 10 sets out the nucleotide sequence of Yellow Fluorescent Protein (Venus) donor DNA expression cassette: connector 5-THD3p-YFP (Venus)-ENO1t-connector 3.

SEQ ID NO: 11 sets out the nucleotide sequence of FW primer to obtain YFP (Venus) promoter-ORF-terminator.

SEQ ID NO: 12 sets out the nucleotide sequence of REV primer to obtain YFP (Venus) promoter-ORF-terminator.

SEQ ID NO: 13 sets out the nucleotide sequence of FW primer to obtain connector 5-THD3p-YFP (Venus)-ENO1t-connector 3 PCR fragment.

SEQ ID NO: 14 sets out the nucleotide sequence of REV primer to obtain connector 5-THD3p-YFP (Venus)-ENO1t-connector 3 PCR fragment.

SEQ ID NO: 15 sets out the nucleotide sequence of ssODN 50 bp homology pGRN002-guide sequence-50 bp homology pGRN002 upper strand of vector pGRN002.

SEQ ID NO: 16 sets out the nucleotide sequence of ssODN 50 bp homology pGRN002-guide sequence-50 bp homology pGRN002 lower strand of vector pGRN002.

SEQ ID NO: 17 sets out the nucleotide sequence of ssODN 5' flank 10 kb upper strand sequence.

SEQ ID NO: 18 sets out the nucleotide sequence of ssODN 5' flank 10 kb lower strand sequence.

SEQ ID NO: 19 sets out the nucleotide sequence of ssODN 5' flank 3 kb upper strand sequence.

SEQ ID NO: 20 sets out the nucleotide sequence of ssODN 5' flank 3 kb lower strand sequence.

SEQ ID NO: 21 sets out the nucleotide sequence of ssODN 5' flank 1 kb upper strand sequence.

SEQ ID NO: 22 sets out the nucleotide sequence of ssODN 5' flank 1 kb lower strand sequence.

SEQ ID NO: 23 sets out the nucleotide sequence of ssODN 5' INT flank upper strand sequence.

SEQ ID NO: 24 sets out the nucleotide sequence of ssODN 5' INT flank lower strand sequence.

SEQ ID NO: 25 sets out the nucleotide sequence of ssODN 3' flank INT upper strand sequence.

SEQ ID NO: 26 sets out the nucleotide sequence of ssODN 3' flank INT lower strand sequence.

SEQ ID NO: 27 sets out the nucleotide sequence of ssODN 3' flank 1 kb upper strand sequence.

SEQ ID NO: 28 sets out the nucleotide sequence of ssODN 3' flank 1 kb lower strand sequence.

SEQ ID NO: 29 sets out the nucleotide sequence of ssODN 3' flank 3 kb upper strand sequence.

SEQ ID NO: 30 sets out the nucleotide sequence of ssODN 3' flank 3 kb lower strand sequence.

SEQ ID NO: 31 sets out the nucleotide sequence of ssODN 3' flank 10 kb upper strand sequence.

SEQ ID NO: 32 sets out the nucleotide sequence of ssODN 3' flank 10 kb lower strand sequence.

SEQ ID NO: 33 sets out the nucleotide sequence of FW primer to confirm correct deletion of 1 kB genomic DNA at 5' end.

SEQ ID NO: 34 sets out the nucleotide sequence of REV primer to confirm correct deletion of 1 kB genomic DNA at 5' end.

SEQ ID NO: 35 sets out the nucleotide sequence of FW primer to confirm integration of YFP expression cassette.

SEQ ID NO: 36 sets out the nucleotide sequence of REV primer to confirm integration of YFP expression cassette.

SEQ ID NO: 37 sets out the nucleotide sequence of FW primer to confirm correct deletion of 1 kB genomic DNA at 3' end.

SEQ ID NO: 38 sets out the nucleotide sequence of REV primer to confirm correct deletion of 1 kB genomic DNA at 3' end.

SEQ ID NO: 39 sets out the nucleotide sequence of the NatMX donor DNA expression cassette:
connector 5-NatMX expression cassette-connector 3 sequence.

SEQ ID NO: 40 sets out the nucleotide sequence of the FW primer to obtain the connector 5-NatMX expression cassette-connector 3 sequence.

SEQ ID NO: 41 sets out the nucleotide sequence of the REV primer to obtain the connector 5-NatMX expression cassette-connector 3 sequence.

SEQ ID NO: 42 sets out the nucleotide sequence of the FW primer to obtain left flank-connector 5-NatMX expression cassette-connector 3-right flank PCR fragment, 0 bp deletion.

SEQ ID NO: 43 sets out the nucleotide sequence of the REV primer to obtain left flank-connector 5-NatMX expression cassette-connector 3-right flank PCR fragment, 0 bp deletion.

SEQ ID NO: 44 sets out the nucleotide sequence of the FW primer to obtain left flank-connector 5-NatMX expression cassette-connector 3-right flank PCR fragment, 1 kbp deletion.

SEQ ID NO: 45 sets out the nucleotide sequence of the REV primer to obtain left flank-connector 5-NatMX expression cassette-connector 3-right flank PCR fragment, 1 kbp deletion.

SEQ ID NO: 46 sets out the nucleotide sequence of the FW primer to obtain left flank-connector 5-NatMX expression cassette-connector 3-right flank PCR fragment, 3 kbp deletion.

SEQ ID NO: 47 sets out the nucleotide sequence of the REV primer to obtain left flank-connector 5-NatMX expression cassette-connector 3-right flank PCR fragment, 3 kbp deletion.

SEQ ID NO: 48 sets out the nucleotide sequence of the FW primer to obtain left flank-connector 5-NatMX expression cassette-connector 3-right flank PCR fragment, 10 kbp deletion.

SEQ ID NO: 49 sets out the nucleotide sequence of the REV primer to obtain left flank-connector 5-NatMX expression cassette-connector 3-right flank PCR fragment, 10 kbp deletion.

SEQ ID NO: 50 sets out the nucleotide sequence of the gBlock of the guide RNA expression cassette to target CAS9 to the INT1 locus.

SEQ ID NO: 51 sets out the nucleotide sequence of the FW primer to obtain the guide RNA cassette with homology to the linear recipient gRNA-vector PCR fragment.

SEQ ID NO: 52 sets out the nucleotide sequence of the REV primer to obtain the guide RNA cassette with homology to the linear recipient gRNA-vector PCR fragment.

SEQ ID NO: 53 sets out the nucleotide sequence of the guide RNA expression cassette to target CAS9 to the INT1 locus.

SEQ ID NO: 54 sets out the nucleotide sequence of the con5-YFP-conA sequence.

SEQ ID NO: 55 sets out the nucleotide sequence of the conB-RFP-con3 sequence.

SEQ ID NO: 56 sets out the nucleotide sequence of the ssODN conA-conB upper strand sequence.

SEQ ID NO: 57 sets out the nucleotide sequence of the ssODN conA-conB lower strand sequence.

SEQ ID NO: 58 sets out the nucleotide sequence of the con5-TDH3 promoter sequence.

SEQ ID NO: 59 sets out the nucleotide sequence of the YFP ORF sequence.

SEQ ID NO: 60 sets out the nucleotide sequence of the ENO1 terminator-con3 sequence.

SEQ ID NO: 61 sets out the nucleotide sequence of the ssODN TDH3 promoter-YFP upper strand sequence.

SEQ ID NO: 62 sets out the nucleotide sequence of the ssODN TDH3 promoter-YFP lower strand sequence.

SEQ ID NO: 63 sets out the nucleotide sequence of the ssODN YFP-ENO1 terminator upper strand sequence.

SEQ ID NO: 64 sets out the nucleotide sequence of the ssODN YFP-ENO1 terminator lower strand sequence.

SEQ ID NO: 65 sets out the nucleotide sequence of the 1 kb deletion flank genomic DNA (50 bp complementarity (sequence identity))-con5-TDH3p-YFP (100 bp complementarity (sequence identity) in total) sequence.

SEQ ID NO: 66 sets out the nucleotide sequence of the TDH3p (100 bp complementarity (sequence identity) in total)-YFP-ENO1t (100 bp complementarity (sequence identity)) sequence.

SEQ ID NO: 67 sets out the nucleotide sequence of the YFP-ENO1t (100 bp complementarity (sequence identity) in total)-Con3-1 kb deletion flank genomic DNA (50 bp complementarity (sequence identity)) sequence.

SEQ ID NO: 68 sets out the nucleotide sequence of the FW primer to confirm integration of RFP expression cassette.

SEQ ID NO: 69 sets out the nucleotide sequence of the REV primer to confirm integration of RFP expression cassette.

SEQ ID NO: 70 sets out the nucleotide sequence of the FW primer to confirm tandem integration of YFP and RFP expression cassettes.

SEQ ID NO: 71 sets out the nucleotide sequence of the FW primer to confirm correct deletion of 1 kB genomic DNA at the 3' end.

SEQ ID NO: 72 sets out the nucleotide sequence of the REV primer to confirm correct deletion of 1 kB genomic DNA at the 3' end.

SEQ ID NO: 73 sets out the nucleotide sequence of the FW primer to amplify the KI11p-pCSN061 backbone-GND2t PCR fragment.

SEQ ID NO: 74 sets out the nucleotide sequence of the REV primer to amplify the KI11p-pCSN061 backbone-GND2t PCR fragment.

SEQ ID NO: 75 sets out the protein sequence of AsCpf1 (from *Acidaminococcus* spp. BV3L6) including a carboxy (C)-terminal nuclear localization signal (NLS).

SEQ ID NO: 76 sets out the protein sequence of LbCpf1 (from *Lachnospiraceae* bacterium ND2006) including a C-terminal NLS.

SEQ ID NO: 77 sets out the protein sequence of FnCpf1 (from *Francisella novicida* U112) including a C-terminal NLS.

SEQ ID NO: 78 sets out the nucleotide sequence of codon pair optimized (CPO) AsCpf1 including a C-terminal NLS.

SEQ ID NO: 79 sets out the nucleotide sequence of CPO LbCpf1 including a C-terminal NLS.

SEQ ID NO: 80 sets out the nucleotide sequence of CPO FnCpf1 including a C-terminal NLS.

SEQ ID NO: 81 sets out the nucleotide sequence of the FW primer to amplify AsCpf1 expression cassette.

SEQ ID NO: 82 sets out the nucleotide sequence of the REV primer to amplify AsCpf1 expression cassette.

SEQ ID NO: 83 sets out the nucleotide sequence of the FW primer to amplify LbCpf1 expression cassette.

SEQ ID NO: 84 sets out the nucleotide sequence of the REV primer to amplify LbCpf1 expression cassette.

SEQ ID NO: 85 sets out the nucleotide sequence of the FW primer to amplify FnCpf1 expression cassette.

SEQ ID NO: 86 sets out the nucleotide sequence of the REV primer to amplify FnCpf1 expression cassette.

SEQ ID NO: 87 sets out the nucleotide sequence of vector pCSN066 encoding AsCpf1.

SEQ ID NO: 88 sets out the nucleotide sequence of vector pCSN067 encoding LbCpf1.

SEQ ID NO: 89 sets out the nucleotide sequence of vector pCSN068 encoding FnCpf1.

SEQ ID NO: 90 sets out the nucleotide sequence of the crtE expression cassette (con5-KlTDH2p-crtE-ScTDH3t-conA)

SEQ ID NO: 91 sets out the nucleotide sequence of the crtYB expression cassette (conA-KIYDR2p-crtYB-ScPDC1t-conB)

SEQ ID NO: 92 sets out the nucleotide sequence of the crtI expression cassette (conB-ScPRE3p-crtI-ScTAL1t-con3)

SEQ ID NO: 93 sets out the nucleotide sequence of INT1 5' flank-Con5 (connector 5).

SEQ ID NO: 94 sets out the nucleotide sequence of Con3-INT1 3' flank.

SEQ ID NO: 95 sets out the nucleotide sequence of the con5 FW primer.

SEQ ID NO: 96 sets out the nucleotide sequence of the conA REV primer.

SEQ ID NO: 97 sets out the nucleotide sequence of the conA FW primer.

SEQ ID NO: 98 sets out the nucleotide sequence of the conB REV primer.

SEQ ID NO: 99 sets out the nucleotide sequence of the conB FW primer.

SEQ ID NO: 100 sets out the nucleotide sequence of the Con3-ScTAL1t REV primer to include a con3 sequence in the crtI expression cassette.

SEQ ID NO: 101 sets out the nucleotide sequence of 5' flank FW 1 kb deletion.

SEQ ID NO: 102 sets out the nucleotide sequence of 5' flank REV 1 kb deletion-connector 5 tail.

SEQ ID NO: 103 sets out the nucleotide sequence of 3' flank FW 1 kb deletion-connector 3 tail.

SEQ ID NO: 104 sets out the nucleotide sequence of 3' flank REV 1 kb deletion.

SEQ ID NO: 105 sets out the nucleotide sequence of the SNR52 promoter.

SEQ ID NO: 106 sets out the nucleotide sequence of the AsCpf1 crRNA direct repeat.

SEQ ID NO: 107 sets out the nucleotide sequence of the LbCpf1 crRNA direct repeat.

SEQ ID NO: 108 sets out the nucleotide sequence of the FnCpf1 crRNA direct repeat.

SEQ ID NO: 109 sets out the nucleotide sequence of the INT1 genomic DNA position A spacer sequence comprising the guide-sequence or genomic target sequence, specific for Cpf1.

SEQ ID NO: 110 sets out the nucleotide sequence of the INT1 genomic DNA position B spacer sequence comprising the guide-sequence or genomic target sequence, specific for Cpf1.

SEQ ID NO: 111 sets out the nucleotide sequence of the INT1 genomic DNA position C spacer sequence comprising the guide-sequence or genomic target sequence, specific for SpCas9.

SEQ ID NO: 112 sets out the nucleotide sequence of the SUP4 terminator.

SEQ ID NO: 113 sets out the nucleotide sequence of the AsCpf1 crRNA expression cassette, genomic DNA INT1 position A.

SEQ ID NO: 114 sets out the nucleotide sequence of the LbCpf1 crRNA expression cassette, genomic DNA INT1 position B.

SEQ ID NO: 115 sets out the nucleotide sequence of the FnCpf1 crRNA expression cassette, genomic DNA INT1 position A.

SEQ ID NO: 116 sets out the nucleotide sequence of the SpCAS9 gRNA expression cassette, genomic DNA INT1 position C.

SEQ ID NO: 117 sets out the nucleotide sequence of the FW primer to amplify a crRNA (Cpf1) or guide RNA (SpCas9) expression cassette with pRN1120 complementarity (sequence identity).

SEQ ID NO: 118 sets out the nucleotide sequence of the REV primer to amplify a crRNA (Cpf1) or guide RNA (SpCas9) expression cassette with pRN1120 complementarity (sequence identity).

SEQ ID NO: 119 sets out the nucleotide sequence of the Anid_TEF promoter.

SEQ ID NO: 120 sets out the nucleotide sequence of the GFP ORF.

SEQ ID NO: 121 sets out the nucleotide sequence of the RE_FT016 terminator.

SEQ ID NO: 122 sets out the nucleotide sequence of the receiving CD backbone vector used to assemble the GFP expression cassette.

SEQ ID NO: 123 sets out the nucleotide sequence of the GFP expression cassette vector, containing a functional GFP expression cassette.

SEQ ID NO: 124 sets out the nucleotide sequence of the forward primer to amplify the GFP expression cassette.

SEQ ID NO: 125 sets the nucleotide sequence of out the reverse primer to amplify the GFP expression cassette.

SEQ ID NO: 126 sets out the nucleotide sequence of the ssODN 5' end of the fnwA6 locus upper strand.

SEQ ID NO: 127 sets out the nucleotide sequence of the ssODN 5' end of the fnwA6 locus lower strand.

SEQ ID NO: 128 sets out the nucleotide sequence of the ssODN 3' end of the fnwA6 locus upper strand.

SEQ ID NO: 129 sets out the nucleotide sequence of the ssODN 3' end of the fnwA6 locus lower strand.

SEQ ID NO: 130 sets out the nucleotide sequence of the fwnA6 guide-polynucleotide.

SEQ ID NO: 131 sets out the nucleotide sequence of vector BG-AMA8.

SEQ ID NO: 132 sets out the nucleotide sequence of forward primer colony/sequence PCR to determine correct integration of the 5' part of GFP expression cassette at the fwnA6 locus. This primer was also used as forward primer in the sequencing reaction.

SEQ ID NO: 133 sets out the nucleotide sequence of the reverse primer colony/sequence PCR to determine correct integration of the 3' part of GFP expression cassette at the fwnA6 locus.

This primer was also used as reverse primer in the sequencing reaction.

SEQ ID NO: 134 sets out the nucleotide sequence of the reverse primer used in the colony PCR to determine correct integration of the 5' part of GFP expression cassette at the fwnA6 locus.

SEQ ID NO: 135 sets out the nucleotide sequence of the forward primer used in the colony PCR to determine correct integration of the 3' part of GFP expression cassette at the fwnA6 locus.

SEQ ID NO: 136 sets out the guide RNA structural component sequence specific for SpCAS9.

DETAILED DESCRIPTION OF A PREFERRED EMBODIMENT

In a first aspect, the invention relates to the use of single-stranded oligonucleotides in the assembly within a cell (in vivo assembly) of double-stranded nucleic acid molecules into a single double-stranded nucleic acid construct. More specifically the invention provides for the use of a first and second single-stranded oligonucleotide in the assembly within a cell of at least two double-stranded nucleic acid molecules into a single double-stranded nucleic acid construct of pre-determined sequence, wherein the first and second single-stranded oligonucleotide are essentially complementary to each other.

The use, the single-stranded oligonucleotide, the cell, each of the two double-stranded nucleic acid molecules and the single double-stranded nucleic acid construct of predetermined sequence are herein referred to as the use, the single-stranded oligonucleotide, the cell, each of the two double-stranded nucleic acid molecules and the single double-stranded nucleic acid construct of predetermined sequence according to the invention.

For the sake of completeness, since "a" is defined elsewhere herein as "at least one", "a single-stranded oligonucleotide", "a first double-stranded nucleic acid molecule", "a second double-stranded nucleic acid molecule", "a cell", and "a single double-stranded nucleic acid construct of pre-determined sequence" are to be construed as: one, two, three or more "single-stranded oligonucleotides", one, two, three or more "first double-stranded nucleic acid molecules", one, two, three or more "second double-stranded nucleic acid molecules", one, two, three or more "cells", and one, two, three or more "single double-stranded nucleic acid constructs of pre-determined sequence". The invention thus conveniently provides a system wherein one or more double-stranded nucleic acid constructs of pre-determined sequence can be assembled within a single cell or in multiple cells. The invention explicitly refers to the assembly of a double-stranded nucleic acid construct of pre-determined (man-made or engineered) sequence to exclude any process that may occur in nature; only engineered (man-made) processes and products are contemplated to be within the scope of the present invention.

In the context of all embodiments of the invention said at least two-double-stranded nucleic acid molecules are preferably not capable of recombining with each other such as via homology-mediated recombination. Preferably said at least two double-stranded nucleic acids molecules share substantially no region of homology. In the context of the present invention said at least two double-stranded nucleic acids molecules share substantially no region of homology when they share homology within at most 100 consecutive nucleotides, preferably within at most 80, more preferably within at most 50, 40, 30, 20, 10 consecutive nucleotides. Most preferably said at least two double-stranded nucleic acids molecules share homology within at most 9, 8, 7, 6, 5, 4, 3, 2 consecutive nucleotides. In one embodiment said at least two double-stranded nucleic acids molecules share no region of homology.

The single-stranded oligonucleotide according to the invention, the first and second double-stranded nucleic acid molecule according to the invention and the single double-stranded nucleic acid construct all refer in the context of all embodiments of the present invention to a polymeric form of nucleotides of any length or a defined specific length-range or length, of either deoxyribonucleotides or ribonucleotides, or mixes or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, oligonucleotides and primers. A polynucleotide may comprise natural and non-natural nucleotides and may comprise one or more modified nucleotides, such as a methylated nucleotide and a nucleotide analogue or nucleotide equivalent wherein a nucleotide analogue or equivalent is defined as a residue having a modified base, and/or a modified backbone, and/or a non-natural internucleoside linkage, or a combination of these modifications. Preferred nucleotide analogues and equivalents are described in the section "General definitions". As desired, modifications to the nucleotide structure may be introduced before or after assembly of the polynucleotide. A polynucleotide may be further modified after polymerization, such as by conjugation with a labeling compound.

A single-stranded oligonucleotide according to the invention preferably has a length of about 20 nucleotides to about 400 nucleotides, more preferably of about 40 to about 400 nucleotides, more preferably about 40 to about 300 nucleotides, more preferably about 40 to about 200 nucleotides, more preferably about 60 to about 400 nucleotides, more preferably about 60 to about 300 nucleotides, more preferably about 60 to about 200 nucleotides, more preferably about 80 to about 400 nucleotides, more preferably about 80 to about 300 nucleotides, more preferably about 80 to about 200 nucleotides, more preferably about 80 to about 120 nucleotides.

A single-stranded oligonucleotide according to the invention preferably has a length of 20 nucleotides to 400 nucleotides, more preferably of 40 to 400 nucleotides, more preferably 40 to 300 nucleotides, more preferably 40 to 200 nucleotides, more preferably 60 to 400 nucleotides, more preferably 60 to 300 nucleotides, more preferably 60 to 200 nucleotides, more preferably 80 to 400 nucleotides, more preferably 80 to 300 nucleotides, more preferably 80 to 200 nucleotides, more preferably 80 to 120 nucleotides.

A single-stranded oligonucleotide according to the invention preferably has a length of about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, or about 160 nucleotides. A single-stranded oligonucleotide according to the invention more preferably has a length of 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, or 160 nucleotides.

Assembly is herein preferably construed according to the general knowledge in the art. Preferably, assembly is the connection of two (or more) polynucleotides to one another by a chemical bond such as mediated by a nucleic acid polymerase, -ligase, -helicase, -gyrase etc. Assembly as herein construed may involve involve insertion, replacement and/or deletion of a polynucleotide or a part thereof.

Essentially complementary means herein that there is sufficient complementarity (sequence identity) between the first and second single-stranded oligonucleotide for hybridizing under physiological conditions as within a cell according to the invention. Preferably, the complementarity (sequence identity) is at least about 80%, about 85%, about 90%, about 95%, about 97.5%, or at least about 99%; more preferably the complementarity (sequence identity) is at least 80%, 85%, 90%, 95%, 97.5%, or at least 99%; more preferably the sequences are completely complementary. Therefore, most preferably, both the first and second single stranded oligonucleotide have the same length and are complementary to each other over the whole sequence; i.e. hybridization of the first and second single-stranded oligonucleotides and further sets of single-stranded oligonucleotides according to the invention results in a blunt-end double-stranded oligonucleotide. In an embodiment, the first and a second single-stranded oligonucleotide that are essentially complementary does not have to result in a blunt-end double-stranded oligonucleotide; some 5'- and/or 3'-protruding nucleotides in the formed double-stranded oligonucleotide are allowed in this embodiment. In this embodiment, the first and second single-stranded oligonucleotides and further sets of single-stranded oligonucleotides according to the invention have at most 3, 2, or most preferably at most 1 protruding nucleotide(s) when aligned with each other.

In the use according to the invention, the cell may be any cell as defined elsewhere herein. Preferably, the cell is a eukaryotic cell, preferably a fungus, an algae, a microalgae or a marine eukaryote, more preferably a yeast cell, a filamentous fungal cell, a Labyrinthulomycetes host cell as defined elsewhere herein. Preferably, the cell is deficient in an NHEJ (non-homologous end joining) component. Said component associated with NHEJ is preferably a yeast Ku70, Ku80, MRE11, RAD50, RAD51, RAD52, XRS2, SIR4, LIF1, NEJ1 and/or LIG4 or homologue thereof.

In the use according to the invention, preferably a first of the at least two double-stranded nucleic acid molecules integrates into a second of the at least two double-stranded nucleic acid molecules to result into a single double-stranded nucleic acid construct. Preferably, the integration occurs within the proximity of a break in the second of the at least two double-stranded nucleic acid molecules, wherein the break is one selected from the group consisting of a single-stranded break (nick), an induced single-stranded break, a double-stranded break and an induced double-stranded break. Preferably, the break is an induced single-stranded break or an induced double-stranded break. Within the proximity is herein defined as within at least 5 nucleotides of the break, within at least 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000 or at least 100000 nucleotides of the break. In an embodiment, the integration occurs at the site of the break, i.e. the first of the at least two double-stranded nucleic acid molecules integrates into the second of the at least two double-stranded nucleic acid wherein the break is repaired by homologous recombination of the at least first and second single-stranded oligonucleotides and the at least two double-stranded nucleic acid molecules to result into a single double-stranded nucleic acid construct of pre-determined sequence within a cell. In this process, homologous end joining will introduce (or actually reproduce) the corresponding nucleotides of the single-stranded oligonucleotides and of the first stranded nucleic acid molecule around the break in the second double-stranded polynucleotide.

In the use according to the invention, the at least two double-stranded nucleic acid molecules may be any double-stranded nucleic acid molecule. The at least two double-stranded nucleic acid molecules are preferably at least 100, 200, 300, 400, 500, 600, 700, 800, 900, or at least 1000 basepair in length. Preferably, the second double-stranded nucleic acid molecule is a vector or a genome; preferably a genome locus. The second double-stranded nucleic acid molecule may be located anywhere in the cell, such as within the cytoplasm, within a chloroplast, mitochondrion or within the nucleus. A genome may be comprised in a chromosome, may be extra-chromosomal or may be comprised in an artificial chromosome such a Yeast Artificial Chromosome (YAC). The second of the at least two double-stranded nucleic acid molecules may be a chromosomal entity or an extra-chromosomal entity such as an autosomal replicating entity such as an episomal plasmid or vector. The second of the at least two double-stranded nucleic acid molecule to the present invention may be native or foreign to the cell.

Where the second double-stranded polynucleotide is a vector, a preferred vector is a plasmid; said plasmid may be an integrative plasmid or an autonomously replicating plasmid. In this embodiment, the vector is assembled according to the use and method according to the invention. Subsequently, the vector may be integrated into the genome and replicated together with the chromosome(s) into which it has been integrated. An integrative vector may integrate at random or at a predetermined target locus in a chromosome of the host cell. A preferred integrative vector comprises a DNA fragment, which is homologous to a DNA sequence in a predetermined target locus in the genome of the host cell for targeting the integration of the vector to this predetermined locus. In order to promote targeted integration, a vector is preferably linearized prior to transformation of the cell. Linearization is preferably performed such that at least one but preferably either end of the vector is flanked by sequences homologous to the target locus. In the integrative vector, the length of the homologous sequences flanking the target locus in the genome is preferably at least 10, 20, 30 bp, preferably at least 50 bp, preferably at least 0.1 kb, even preferably at least 0.2 kb, more preferably at least 0.5 kb, even more preferably at least 1 kb, most preferably at least 2 kb. Preferably, the efficiency of targeted integration into the genome of the host cell, i.e. integration in a predetermined target locus, is increased by augmented homologous recombination abilities of the host cell. The homologous flanking DNA sequences in the vector (which are homologous to the target locus) may be derived from a highly expressed locus, meaning that they are derived from a gene, which is capable of high expression level in the host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/I (e.g. as described in EP 357 127 B1). In the use according to the invention, at least one of the at least two double-stranded nucleic acid molecules is an exogenous nucleic acid molecule. Herein, an exogenous nucleic acid molecule may also be referred to as a donor nucleic acid molecule. The term "exogenous" is herein to be construed as that an exogenous nucleic acid molecule is not present in the cell at the moment of use according to the invention or at the moment of a method according to the invention; the exogenous nucleic acid molecule is brought from outside into the cell. The exogenous nucleic acid molecule will mostly be foreign to the cell. However in certain embodiments, the exogenous nucleic acid molecule may be native to the cell but has been engineered outside the cell and is brought into the cell; in such case, the exogenous nucleic acid molecule may be considered native to the cell.

In the use according to invention, a part of the first single-stranded oligonucleotide has sequence identity with the first of the at least two double-stranded nucleic acid molecules and a part of the first single-stranded oligonucleotide has sequence identity with the second of the at least two double-stranded nucleic acid molecules, wherein the sequence identity is sufficient for assembly of the double-stranded nucleic acid construct. Preferably, the sequence identity, when optimally aligned using a suitable alignment algorithm, is at least 50%, 60%, 75%, 80%, 85%, 90%, 95%, 97.5%, 99% sequence identity and results in hybridization of complementary strands at physiological conditions in a cell according to the invention. Examples of these embodiments are e.g. depicted in FIGS. 2, 4, 5A1, 5A2, 5B1, 5B2, 5D1, 5D2, 9A, 9B, 9C, 11A, 11B, 11O, 11D, 13, and 15A, 15B, 15C, 15E. The term "hybridization" herein refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence-specific manner. The complex may comprise two strands forming a duplex structure, three or more strands forming a multi stranded complex, a single self-hybridizing strand, or any combination of these. A hybridization reaction may constitute a step in a more extensive process, such as the cleavage of a polynucleotide by an enzyme. Preferred hybridization conditions are physiological conditions as within a cell according to the invention. The part of the first single-strand oligonucleotide that has sequence identity with the first of the at least two double-stranded nucleic acid molecules is preferably about half of the length of the first single-strand oligonucleotide and the part that has sequence identity with the second of the at least two double-stranded nucleic acid molecules is preferably about the other half of the length of the first single-strand oligonucleotide. More preferably, part of the first single-strand oligonucleotide that has sequence identity with the first of the at least two double-stranded nucleic acid molecules is preferably half of the length of the first single-strand oligonucleotide and the part that has sequence identity with the second of the at least two double-stranded nucleic acid molecules is preferably the other half of the length of the first single-strand oligonucleotide. As an example, a single-strand oligonucleotide according to the invention of 80 nucleotides in length may have 40 nucleotides sequence identity with the first of the at least two double-stranded nucleic acid molecules and may have 40 nucleotides sequence identity with the second of the at least two double-stranded nucleic acid molecules (depicted as a 40-40 configuration). Other examples would be a 20-20 configuration, 20-30, 30-20, 30-40, 20-40, 40-40, 50-50, 60-60, 80-80, 50-60, 60-50, 60-80, 80-60 etc. The person skilled in the art knows that hybridization conditions may vary dependent on the sequence and may adapt the parts appropriately. Since the first and second single-stranded oligonucleotides are essentially complementary, the second single-stranded oligonucleotide will also have parts that have sequence identity with the first and second of the at least two double-stranded nucleic acid molecules. The person skilled in the art comprehends that the region in the second of the at least two double-stranded nucleic acid molecules where part of the first single-strand oligonucleotide has sequence identity to, will be at a desired site of assembly. This region may be close to or several nucleotides away from the break (when present) in the second of the at least two double-stranded nucleic acid molecules. The region may be at least 1, 2, 3, 4, 5, 6, 7, 8, 9, 10, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000 or at least 100000 nucleotides away from the break.

It is within the scope of the invention that several single-stranded oligonucleotides are used, such as three single-stranded oligonucleotides wherein the first and second single-stranded oligonucleotide are essentially complementary to each other; or wherein at least a first, second, third and fourth single-stranded oligonucleotide are used, wherein the first and second single-stranded oligonucleotide are essentially complementary to each other and wherein the third and fourth single-stranded oligonucleotide are essentially complementary to each other. Preferably, when at least a first, second, third and fourth single-stranded oligonucleotide are used:

a part of the first and second essentially complementary single-stranded oligonucleotides has sequence identity with the first of the at least two double-stranded nucleic acid molecules and a part of the first and second essentially complementary single-stranded oligonucleotides has sequence identity with the second of the at least two double-stranded nucleic acid molecules; and a part of the third and fourth essentially complementary single-stranded oligonucleotides has sequence identity with the first of the at least two double-stranded nucleic acid molecules and a part of the third and fourth essentially complementary single-stranded oligonucleotides has sequence identity with the second of the at least two double-stranded nucleic acid molecules.

Herein, the preferred options are the same as depicted here above where a part of the single-stranded oligonucleotide has sequence identity with the first of the at least two double-stranded nucleic acid molecules and a part of the single-stranded oligonucleotide has sequence identity with the second of the at least two double-stranded nucleic acid molecules. Preferably, the first and second single-stranded oligonucleotides have sequence identity with the 3'-end of the positive strand first double-stranded nucleic acid molecule and the third and fourth single-stranded oligonucleotides have sequence identity with the 5'-end of the positive strand of the first double-stranded nucleic acid molecule. Examples of these embodiments are e.g. depicted in FIGS. 2, 4, 5A1, 5A2, 5B1, 5B2, 5C1, 5C2, 5D1, 5D2, 9A, 9B, 9C, 11A, 11B, 11C, 11D, 13, and 15A, 15B, 15C, 15D, 15E. The person skilled in the art comprehends that the region in the second of the at least two double-stranded nucleic acid molecules where part of the first single-strand oligonucleotide has sequence identity to, will be at a desired site of assembly. This region may be close to or several nucleotides away from the break (when present) in the second of the at least two double-stranded nucleic acid molecules. The region may be at least 1, 2, 3, 4, 5, 6, 7, 8, 9, 10 or more nucleotides away from the 3'-end of the break for the first and second single-stranded oligonucleotides and may be at least 1, 2, 3, 4, 5, 6, 7, 8, 9, 10 or more nucleotides away from the 5'-end of the break for the third and fourth single-stranded oligonucleotide. See e.g. FIGS. 4A-C. The present invention is not limited to the assembly in a cell of two double-stranded nucleic acid molecules into a single double-stranded nucleic acid construct of pre-determined sequence. The invention can conveniently be used in a multiplex system of assembly of multiple double-stranded nucleic acid molecules into a single or into multiple double-stranded nucleic acid construct of pre-determined sequence. Accordingly, there is provided for the use according to the invention in a multiplex system of assembly within a cell of double-stranded nucleic acid molecules into single or into multiple double-stranded nucleic acid constructs. In this context, within the scope of the invention is the use of a plurality of single-stranded oligonucleotides in the assembly of a plurality of (n) distinct first double-stranded nucleic acid molecules and a plurality of (m) distinct second double-stranded nucleic acid molecules into a single or into multiple double-stranded nucleic acid constructs, wherein n and m are independent integers of at least 1, such as 1 and 2, 1-3, 1-4, 1-5, 1-6, up to e.g. 1-100. In addition, a library of single-stranded oligonucleotides can be used for the assembly of one or more first and/or second double-stranded nucleic acid molecules into a double-stranded nucleic acid construct. E.g. the various deletions depicted in FIG. 4 may be obtained by single reaction using a set of single-stranded oligonucleotides for each deletion of 0 kb, 1 kb, 3 kb and 10 kb, but may also be obtained using a mix of all single-stranded oligonucleotides to provide some variation in the results, if desired. In addition, one could e.g. produce a protein engineering library within cells using multiple first double-stranded nucleic acids with a gap of one or a few nucleotides/amino acids and assemble using a single-stranded oligonucleotide library to generate the protein engineering library.

In an embodiment, there is provided for the use of a plurality of single-stranded oligonucleotides in the assembly of a plurality of (n) distinct first double-stranded nucleic acid molecules and a plurality of (m) distinct second double-stranded nucleic acid molecules into a single or into multiple double-stranded nucleic acid constructs, wherein the plurality (n) of first double-stranded nucleic acid molecules integrate into a single or into a plurality of (m) distinct second double-stranded nucleic acid molecules to result into a single or into multiple double-stranded nucleic acid constructs, wherein n and m are independent integers of at least 1, such as 1 and 2, 1-3, 1-4, 1-5, 1-6, up to e.g. 1-100. A specific example of such multiplex approach is depicted in Example 4 (see FIG. 13 for simplified schematic) where two genes (yellow fluorescent protein, YFP and red fluorescent protein, RFP) are integrated in a genomic locus of a cell. A further specific example is depicted in Example 5 (see FIG. 15 for simplified schematic) where a promoter, gene (YFP) and a terminator are assembled to result in an expression cassette which is integrated into a genomic locus of a cell.

Preferably, in the use according to the invention, the integration occurs within the proximity of an induced single-stranded or double-stranded break in the second of the at least two double-stranded nucleic acid molecules, and wherein the break is induced by a functional genome editing system, preferably TALENs, CRISPR/Cas, CRISPR/Cpf1, I-SceI and NgAgo.

Suitable functional genome editing systems for use in all embodiments of the invention are known to the person skilled in the art and include: Transcription Activator-Like Effector Nucleases (TALENs, Gaj et al., 2013), zinc finger nucleases (ZFNs, Gaj et al., 2013), meganucleases such as I-SceI (Pâques et al., 2007, Stoddard 2011), RNA-guided endonucleases like CRISPR/Cas (Mali et al., 2013; Cong et al., 2013) or CRISPR/Cpf1 (Zetsche et al., 2015) or a DNA-guided nuclease based-system like Argonaute of Natronobacterium gregoryi (NgAgo, Gao et al., 2016).

Within the proximity is defined previous herein. Functional genome editing systems are known to the person skilled in the art and the person skilled in the art knows how to select and use an appropriate system. A preferred functional genome editing system is an RNA- or DNA-guided nuclease system, preferably an RNA- or DNA-guided DNA nuclease system, more preferably an RNA- or DNA-guided DNA nuclease system that is Protospacer Adjacent Motif (PAM) independent, for example NgAgo (Gao et al., 2016).

Preferably, in the use according to the invention, the functional genome editing system is present within the cell, more preferably the cell expresses a functional heterologous genome editing enzyme, such as a Cas enzyme, preferably Cas9 or Cas9 nickase; Cpf1; I-SceI; NgAgo, or in the cell a heterologous genome editing enzyme, preferably a Cas enzyme, preferably Cas9 or Cas9 nickase; Cpf1; I-SceI; NgAgo, is present. It is within the scope of the invention that the functional heterologous genome editing enzyme is either expressed within the cell (from e.g. a plasmid or from an integrated copy in the genome), or that the functional heterologous genome editing enzyme is brought into the cell as a protein, preferably the enzyme in its active form.

Preferably, in the use according to the invention there is a guide-polynucleotide present in the cell. Such guide-polynucleotide may be a DNA or an RNA. A guide-polynucleotide according to the present invention comprises at least a guide-sequence that is able to hybridize with a target-polynucleotide and is able to direct sequence-specific binding of the heterologous genome editing system to the target-polynucleotide. The guide-polynucleotide is a polynucleotide according to the general definition of a polynucleotide set out here above; a preferred guide-polynucleotide comprises ribonucleotides, a more preferred guide-polynucleotide is a RNA (guide-RNA). The guide-sequence is herein also referred as the target sequence and is essentially the complement of a target-polynucleotide such that the guide-polynucleotide is able to hybridize with the target-polynucleotide, preferably under physiological conditions in a host cell. The degree of complementarity, when optimally aligned using a suitable alignment algorithm, is preferably higher than 50%, 60%, 75%, 80%, 85%, 90%, 95%, 97.5%, 99% sequence identity. Such guide-polynucleotide is known to the person skilled in the art (e.g. Mali et al., 2013; Cong et al., 2013; Zetsche et al., 2015; Gao et al., 2016) and may be expressed from a vector, preferably a plasmid, or may be brought into the cell in its active from or in an inactive pre-form. As such, the invention can conveniently be used in the techniques depicted in WO2016110453, WO2016110511, WO2016110512, WO2016100272, WO2016100568 and WO2016100571, which are herein incorporated by reference. For the sake of completeness, "a" guide-polynucleotide is to be construed "at least one" guide-polynucleotide; meaning that more than one guide-polynucleotides may be present, allowing a multiplex system as described elsewhere herein wherein e.g. multiple guide-polynucleotides can be assembled and used in combination with multiple first and/or second double-stranded nucleic acid molecules according to the invention.

The present invention can conveniently be combined with the techniques from WO2015095804 wherein a linear plasmid is assembled within a cell; WO2015095804 is herein incorporated by reference. Preferably, in the use according to the invention, the vector or plasmid from which the guide-polynucleotide is expressed, is assembled within the cell by integration of a single-stranded or double-stranded oligonucleotide comprising the target sequence of the guide-polynucleotide into the plasmid. This is an efficient way of providing the guide-polynucleotide since the plasmid comprising all basis features required for expression of a guide-polynucleotide, preferably a guide-RNA, can be universally used while the single-stranded or double-stranded oligonucleotide comprising the target sequence can varied, depending on the target sequence. In addition to a more versatile and straightforward system, it is especially convenient for multiplexing where multiple guide-polynucleotides are desired. The double-stranded oligonucleotide may be comprised of two essentially complementary single-stranded oligonucleotides that are annealed before or after transfer into the cell. When assembly of the vector or plasmid from which the guide-polynucleotide is expressed, is within the cell by integration of a single-stranded or double-stranded oligonucleotide comprising the target sequence of the guide-polynucleotide into the plasmid, the vector or plasmid is preferably linear or has preferably been linearized at the site where the target sequence is to integrate. The single-stranded oligonucleotide or double-stranded oligonucleotide preferably has sequence identity with both the 5'-side and with the 3'-side adjacent to the integration site, while the sequence in between contains the target sequence. An example of such configuration is e.g. 30-20-30, wherein two stretches of 30 nucleotides have sequence identity with the plasmid or vector and a stretch of 20 nucleotides has no sequence identity with the vector of plasmid but comprises or consists of the target sequence. Examples of other configurations are 40-20-40, 50-20-50 and 60-20-60. It will be understood that the 20-nucleotide target site may be larger or smaller than 20 nucleotides.

Preferably, in the use according to the invention, the assemblies of the at least two double-stranded nucleic acid molecules into a single double-stranded nucleic acid construct of pre-determined sequence and the plasmid expressing the guide-polynucleotide occur essentially simultaneously within the cell. Essentially simultaneously preferably means that the assemblies occur during a single cell-cycle. Most preferably, the components necessary for all assemblies are brought into the cell in a single event.

In the embodiments of the invention, when at least a first and a second essentially complementary single-stranded oligonucleotides are used, these are annealed before introduction into the cell, preferably the essentially complementary single-stranded oligonucleotides are annealed within a single container. However, preferably in the embodiments of the invention, the first and a second essentially complementary single-stranded oligonucleotides and, if present, further essentially complementary single-stranded oligonucleotides, are not annealed before introduction into the cell.

The present invention can conveniently be used for the assembly of a polynucleotide construct within a cell. Accordingly, in a second aspect the present invention provides for a method for the assembly within a cell of at least two double-stranded nucleic acid molecules into a single double-stranded nucleic acid construct of pre-determined sequence, wherein the assembly is mediated by at least a first and a second single-stranded oligonucleotide, wherein the first and second single-stranded oligonucleotide are essentially complementary to each other, said method comprising contacting the cell with the single-stranded oligonucleotides and at least one of the double-stranded nucleic acid molecules such that the single-stranded oligonucleotides and at least one of the double-stranded nucleic acid molecules are introduced into the cell. Said method is herein referred to as a method according to the invention. All features in this aspect of the invention are preferably the corresponding features defined in the first aspect of the invention.

Preferably, in the method according to the invention, the cell may be any cell as defined elsewhere herein. Preferably, the cell is a eukaryotic cell, preferably a fungus, an algae, a microalgae or a marine eukaryote, more preferably a yeast cell or a filamentous fungal cell, a Labyrinthulomycetes host cell as defined elsewhere herein. Preferably, the cell is deficient in an NHEJ (non-homologous end joining) component. Preferably, the cell is deficient in an NHEJ (non-homologous end joining) component. Said component associated with NHEJ is preferably a yeast Ku70, Ku80, MRE11, RAD50, RAD51, RAD52, XRS2, SIR4, LIF1, NEJ1 and/or LIG4 or homologue thereof.

In the method according to the invention, preferably a first of the at least two double-stranded nucleic acid molecules integrates into a second of the at least two double-stranded nucleic acid molecules to result into a single double-stranded nucleic acid construct. Preferably, the integration occurs within the proximity of a break in the second of the at least two double-stranded nucleic acid molecules, wherein the break is one selected from the group consisting of a single-stranded break (nick), an induced single-stranded break, a double-stranded break and an induced double-stranded break. Preferably, the break is an induced single-stranded break or an induced double-stranded break. Within the proximity is previously defined herein. In an embodiment, the integration occurs at the site of the break, i.e. the first of the at least two double-stranded nucleic acid molecules integrates into a second of the at least two double-stranded nucleic acid wherein the break is repaired by recombination. e.g. by homologous recombination of a single-stranded oligonucleotide and the at least two double-stranded nucleic acid molecules to result into a single double-stranded nucleic acid construct of pre-determined sequence within a cell. In this process, homologous end joining will introduce (or actually reproduce) the corresponding nucleotides of the single-stranded oligonucleotide and of the first double-stranded nucleic acid molecule around the break in the second double-stranded polynucleotide. Examples of these embodiments are e.g. depicted in FIGS. 2, 4, 5A1-5D2, 9, 11, 13, and 15A-E.

In the method according to the invention, the second of the at least two double-stranded nucleic acid molecule may be any double-stranded nucleic acid molecule. Preferably, the second double-stranded nucleic acid molecule is a vector or a genome; preferably a genome locus, all as defined in the first aspect of the invention.

Preferably, in the method according to invention, a part of the first single-stranded oligonucleotide has sequence identity with the first of the at least two double-stranded nucleic acid molecules and a part of the first single-stranded oligonucleotide has sequence identity with the second of the at least two double-stranded nucleic acid molecules, wherein the sequence identity is sufficient for assembly of the double-stranded nucleic acid construct. Preferably, the sequence identity, when optimally aligned using a suitable alignment algorithm, is at least 50%, 60%, 75%, 80%, 85%, 90%, 95%, 97.5%, 99% sequence identity and results in hybridization of complementary strands at physiological conditions in a cell according to the invention. The term "hybridization" herein refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence-specific manner. The complex may comprise two strands forming a duplex structure, three or more strands forming a multi stranded complex, a single self-hybridizing strand, or any combination of these. A hybridization reaction may constitute a step in a more extensive process, such as the cleavage of a polynucleotide by an enzyme. Preferred hybridization conditions are physiological conditions as within a cell according to the invention.

The part of the first single-strand oligonucleotide that has sequence identity with the first of the at least two double-stranded nucleic acid molecules is preferably about half of the length of the first single-strand oligonucleotide and the part that has sequence identity with the second of the at least two double-stranded nucleic acid molecules is preferably about the other half of the length of the first single-strand oligonucleotide. More preferably, part of the first single-strand oligonucleotide that has sequence identity with the first of the at least two double-stranded nucleic acid molecules is preferably half of the length of the first single-strand oligonucleotide and the part that has sequence identity with the second of the at least two double-stranded nucleic acid molecules is preferably the other half of the length of the first single-strand oligonucleotide. As an example, a single-strand oligonucleotide according to the invention of 80 nucleotides in length may have 40 nucleotides sequence identity with the first of the at least two double-stranded nucleic acid molecules and may have 40 nucleotides sequence identity with the second of the at least two double-stranded nucleic acid molecules (depicted as a 40-40 configuration). Other examples would be a 20-20 configuration, 20-30, 30-20, 30-40, 20-40, 40-40, 50-50, 60-60, 80-80, 50-60, 60-50, 60-80, 80-60 etc. The person skilled in the art knows that hybridization conditions may vary dependent on the sequence and may adapt the parts appropriately. Since the first and second single-stranded oligonucleotides are essentially complementary, the second single-stranded oligonucleotide will also have parts that have sequence identity with the first and second of the at least two double-stranded nucleic acid molecules. Examples of these embodiments are e.g. depicted in FIGS. 2, 4, 5A1, 5A2, 5B1, 5B2, 5C1, 5C2, 5D1, 5D2, 9A, 9B, 9C, 11A, 11B, 11 C, 11D, 13, and 15A, 15B, 15C, 15D and 15E. The person skilled in the art comprehends that the region in the second of the at least two double-stranded nucleic acid molecules where part of the first single-strand oligonucleotide has sequence identity to, will be at a desired site of assembly.

This region may be close to or several nucleotides away from the break (when present) in the in the second of the at least two double-stranded nucleic acid molecules. The region may be at least 1, 2, 3, 4, 5, 6, 7, 8, 9, 10, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000 or at least 100000 nucleotides away from the break; see e.g. FIGS. 4A, 4B and 4C. All features are preferably as defined in the first aspect of the invention. Preferably, in the method according to the invention, at least a first, second, third and fourth single-stranded oligonucleotide are used, wherein the first and second single-stranded oligonucleotide are essentially complementary to each other and wherein the third and fourth single-stranded oligonucleotide are essentially complementary to each other, all as defined in the first aspect of the invention.

Preferably, in the method according to the invention:
a part of the first and second essentially complementary single-stranded oligonucleotides has sequence identity with the first of the at least two double-stranded nucleic acid molecules and a part of the first and second essentially complementary single-stranded oligonucleotides has sequence identity with the second of the at least two double-stranded nucleic acid molecules; and
a part of the third and fourth essentially complementary single-stranded oligonucleotides has sequence identity with the first of the at least two double-stranded nucleic acid molecules and a part of the third and fourth essentially complementary single-stranded oligonucleotides has sequence identity with the second of the at least two double-stranded nucleic acid molecules; all as defined in the first aspect of the invention.

Preferably, in the method according to the invention, the method is a multiplex method of assembly within a cell of multiple double-stranded nucleic acid molecules assembled into single or multiple double-stranded nucleic acid constructs mediated by a plurality of single-stranded oligonucleotides.

In this context, within the scope of the invention is a method for assembly of a plurality of (n) distinct first double-stranded nucleic acid molecules and a plurality of (m) distinct second double-stranded nucleic acid molecules into a single or into multiple double-stranded nucleic acid constructs, mediated by a plurality of single-stranded oligonucleotides, wherein n and m are independent integers of at least 1, such as 1 and 2, 1-3, 1-4, 1-5, 1-6, up to e.g. 1-100. All features are preferably as defined in the first aspect of the invention.

In an embodiment, there is provided for a method of assembly of a plurality of (n) distinct first double-stranded nucleic acid molecules and a plurality of (m) distinct second double-stranded nucleic acid molecules into a single or into multiple double-stranded nucleic acid constructs, mediated by a plurality of single-stranded oligonucleotides, wherein the plurality (n) of first double-stranded nucleic acid molecules integrate into a single or into a plurality of (m) distinct second double-stranded nucleic acid molecules to result into a single or into multiple double-stranded nucleic acid constructs, wherein n and m are independent integers of at least 1, such as 1 and 2, 1-3, 1-4, 1-5, 1-6, up to e.g. 1-100. All features are preferably as defined in the first aspect of the invention. A specific example of such multiplex approach is depicted in Example 4 (see FIG. 13 for simplified schematic) where two genes (yellow fluorescent protein, YFP and red fluorescent protein, RFP) are integrated in a genomic locus of a cell. A further specific example is depicted in Example 5 (see FIG. 15 for simplified schematic) where a promoter, gene (YFP) and a terminator are assembled to result in an expression cassette which is integrated into a genomic locus of a cell. Preferably, in the method according to the invention, the integration occurs within the proximity of an induced single-stranded or double-stranded break in the second of the at least two double-stranded nucleic acid molecules, and wherein the break is induced by a functional genome editing system, preferably TALENs, CRISPR/Cas, CRISPR/Cpf1, I-Scel and NgAgo; all as defined in the first aspect of the invention.

Preferably, in the method according to the invention, the cell expresses a functional heterologous genome editing enzyme, preferably a Cas enzyme, preferably Cas9 or Cas9 nickase; Cpf1; I-Scel; NgAgo, or in the cell a heterologous genome editing enzyme, preferably a Cas enzyme, preferably Cas9 or Cas9 nickase; Cpf1; I-Scel; NgAgo, is present; all as defined in the first aspect of the invention.

Preferably, in the method according to the invention, in the cell a guide-polynucleotide is present, preferably as defined in the first aspect of the invention.

Preferably, in the method according to the invention, the guide-polynucleotide in the cell is expressed from a vector, preferably a plasmid, preferably the vector is introduced into the cell together with the single-stranded oligonucleotide and at least one of the double-stranded nucleic acid molecules; all as defined in the first aspect of the invention.

Preferably, in the method according to the invention, the plasmid from which the guide-polynucleotide is expressed, is assembled within the cell by integration of a single-stranded or double-stranded oligonucleotide comprising the target sequence of the guide-polynucleotide into the plasmid, wherein in the single-stranded or double-stranded oligonucleotide comprising the target sequence of the guide-polynucleotide and the plasmid are introduced into the cell either simultaneously or consecutively with the single-stranded oligonucleotide and at least one of the double-stranded nucleic acid molecules; all as defined in the first aspect of the invention. Accordingly, the double-stranded oligonucleotide may be comprised of two essentially complementary single-stranded oligonucleotides that are annealed before or after transfer into the cell. When assembly of the vector or plasmid from which the guide-polynucleotide is expressed, is within the cell by integration of a single-stranded or double-stranded oligonucleotide comprising the target sequence of the guide-polynucleotide into the plasmid, the vector or plasmid is preferably linear or has preferably been linearized at the site where the target sequence is to integrate. The single-stranded oligonucleotide or double-stranded oligonucleotide preferably has sequence identity with both the 5'-side and with the 3'-side adjacent to the integration site, while the sequence in between contains the target sequence. An example of such configuration is e.g. 30-20-30, wherein two stretches of 30 nucleotides have sequence identity with the plasmid or vector and a stretch of 20 nucleotides has no sequence identity with the vector of plasmid but comprises the target sequence. Examples of other configurations are 40-20-40, 50-20-50 and 60-20-60. It will be understood that the 20-nucleotide target site may be larger or smaller than 20 nucleotides. Preferably, in the method according to the invention, the assembly of the single-stranded or double-stranded oligonucleotide comprising the target sequence of the guide-polynucleotide into the plasmid and the assembly of at least two double-stranded nucleic acid molecules into a single double-stranded nucleic acid construct occur essentially simultaneously within the cell; all as defined in the first aspect of the invention.

Preferably, in the method according to the invention, at least the first and second essentially complementary single-stranded oligonucleotides are annealed before introduction into the cell, preferably the essentially complementary single-stranded oligonucleotides are annealed within a single container; all as defined in the first aspect of the invention.

In a third aspect, the present invention provides for a composition comprising the at least first and second essentially complementary single-stranded oligonucleotides, the cell and at least one of at least two double-stranded nucleic acid molecules as defined in the first aspect according to the invention. Preferably, the composition further comprises a further single-stranded oligonucleotide and/or a further double-stranded nucleic acid molecule as defined in the first and second aspect of the invention, and, optionally, further comprises the vector, preferably a plasmid, as defined in the first and second aspect of the invention, or, optionally further comprises the single-stranded or double-stranded oligonucleotide comprising the target sequence of the guide-polynucleotide and the plasmid as defined in the first and second aspect of the invention. Said composition is herein referred to as a composition according to the invention.

In a fourth aspect, the present invention provides for a cell comprising an assembled double-stranded nucleic acid construct, obtainable by the method according to the second aspect of the invention. Preferably, said cell is produced by or obtained by the method according to the second aspect of the invention. Said cell is herein referred to as a cell according to the invention. Preferably, a cell according to the invention, further comprises a polynucleotide encoding a compound of interest. More preferably, said cell expresses the compound of interest. The compound of interest may be native to the cell, or may be foreign to the cell.

In a fifth aspect, the present invention provides for a method for the production of a compound of interest, comprising culturing the cell according to the invention under conditions conducive to the production of the compound of interest, and, optionally, purifying or isolating the compound of interest.

A compound of interest in the context of all embodiments of the invention may be any biological compound. The biological compound may be biomass or a biopolymer or a metabolite. The biological compound may be encoded by a single polynucleotide or a series of polynucleotides composing a biosynthetic or metabolic pathway or may be the direct result of the product of a single polynucleotide or products of a series of polynucleotides, the polynucleotide may be a gene, the series of polynucleotide may be a gene cluster. In all embodiments of the present invention, the single polynucleotide or series of polynucleotides encoding the biological compound of interest or the biosynthetic or metabolic pathway associated with the biological compound of interest, are preferred targets for the compositions and methods according to the present invention. The biological compound may be native to the host cell or heterologous to the host cell.

The term "heterologous biological compound" is defined herein as a biological compound which is not native to the cell; or a native biological compound in which structural modifications have been made to alter the native biological compound.

The term "biopolymer" is defined herein as a chain (or polymer) of identical, similar, or dissimilar subunits (monomers). The biopolymer may be any biopolymer. The biopolymer may for example be, but is not limited to, a nucleic acid, polyamine, polyol, polypeptide (or polyamide), or polysaccharide.

The biopolymer may be a polypeptide. The polypeptide may be any polypeptide having a biological activity of interest. The term "polypeptide" is not meant herein to refer to a specific length of the encoded product and, therefore, encompasses peptides, oligopeptides, and proteins. The term polypeptide refers to polymers of amino acids of any length. The polymer may he linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. Polypeptides further include naturally occurring allelic and engineered variations of the above-mentioned polypeptides and hybrid polypeptides. The polypeptide may be native or may be heterologous to the host cell. The polypeptide may be a collagen or gelatine, or a variant or hybrid thereof. The polypeptide may be an antibody or parts thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, ceramidases, epoxide hydrolase, aminopeptidase, acylases, aldolase, hydroxylase, aminopeptidase, lipase. The polypeptide may also be an enzyme secreted extracellularly. Such enzymes may belong to the groups of oxidoreductase, transferase, hydrolase, lyase, isomerase, ligase, catalase, cellulase, chitinase, cutinase, deoxyribonuclease, dextranase, esterase. The enzyme may be a carbohydrase, e.g. cellulases such as endoglucanases, β-glucanases, cellobiohydrolases or β-glucosidases, hemicellulases or pectinolytic enzymes such as xylanases, xylosidases, mannanases, galactanases, galactosidases, pectin methyl esterases, pectin lyases, pectate lyases, endo polygalacturonases, exopolygalacturonases rhamnogalacturonases, arabanases, arabinofuranosidases, arabinoxylan hydrolases, galacturonases, lyases, or amylolytic enzymes; hydrolase, isomerase, or ligase, phosphatases such as phytases, esterases such as lipases, proteolytic enzymes, oxidoreductases such as oxidases, transferases, or isomerases. The enzyme may be a phytase. The enzyme may be an aminopeptidase, asparaginase, amylase, a maltogenic amylase, carbohydrase, carboxypeptidase, endo-protease, metallo-protease, serine-protease catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, protein deaminase, invertase, laccase, lipase, mannosidase, mutanase, oxidase, pectinolytic enzyme, peroxidase, phospholipase, galactolipase, chlorophyllase, polyphenoloxidase, ribonuclease, transglutaminase, or glucose oxidase, hexose oxidase, monooxygenase.

According to the invention, a compound of interest can be a polypeptide or enzyme with improved secretion features as described in WO2010/102982. According to the present invention, a compound of interest can be a fused or hybrid polypeptide to which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide.

Techniques for producing fusion polypeptides are known in the art, and include, ligating the coding sequences encoding the polypeptides so that they are in frame and expression of the fused polypeptide is under control of the same promoter(s) and terminator. The hybrid polypeptides may comprise a combination of partial or complete polypeptide sequences obtained from at least two different polypeptides wherein one or more may be heterologous to the host cell. Example of fusion polypeptides and signal sequence fusions are for example as described in WO2010/121933. The biopolymer may be a polysaccharide. The polysaccharide may be any polysaccharide, including, but not limited to, a mucopolysaccharide (e.g., heparin and hyaluronic acid) and nitrogen-containing polysaccharide (e.g., chitin). In a preferred option, the polysaccharide is hyaluronic acid. A polynucleotide coding for the compound of interest or coding for a compound involved in the production of the compound of interest according to the invention may encode an enzyme involved in the synthesis of a primary or secondary metabolite, such as organic acids, carotenoids, (beta-lactam) antibiotics, and vitamins. Such metabolite may be considered as a biological compound according to the present invention.

The term "metabolite" encompasses both primary and secondary metabolites; the metabolite may be any metabolite. Preferred metabolites are citric acid, gluconic acid, adipic acid, fumaric acid, itaconic acid and succinic acid.

A metabolite may be encoded by one or more genes, such as in a biosynthetic or metabolic pathway. Primary metabolites are products of primary or general metabolism of a cell, which are concerned with energy metabolism, growth, and structure. Secondary metabolites are products of secondary metabolism (see, for example, R. B. Herbert, The Biosynthesis of Secondary Metabolites, Chapman and Hall, New York, 1981).

A primary metabolite may be, but is not limited to, an amino acid, fatty acid, nucleoside, nucleotide, sugar, triglyceride, or vitamin.

A secondary metabolite may be, but is not limited to, an alkaloid, coumarin, flavonoid, polyketide, quinine, steroid, peptide, or terpene. The secondary metabolite may be an antibiotic, antifeedant, attractant, bacteriocide, fungicide, hormone, insecticide, or rodenticide. Preferred antibiotics are cephalosporins and beta-lactams. Other preferred metabolites are exo-metabolites. Examples of exo-metabolites are Aurasperone B, Funalenone, Kotanin, Nigragillin, Orlandin, Other naphtho-y-pyrones, Pyranonigrin A, Tensidol B, Fumonisin B2 and Ochratoxin A.

The biological compound may also be the product of a selectable marker. A selectable marker is a product of a polynucleotide of interest which product provides for biocide or viral resistance, resistance to heavy metals, prototrophy to auxotrophs, and the like. Selectable markers include, but are not limited to, amdS (acetamidase), argB (ornithinecarbamoyltransferase), bar (phosphinothricinacetyltransferase), hygB (hygromycin phosphotransferase), niaD (nitrate reductase), pyrG (orotidine-5'-phosphate decarboxylase), sC (sulfate adenyltransferase), trpC (anthranilate synthase), ble (phleomycin resistance protein), hyg (hygromycin), NAT or NTC (Nourseothricin) as well as equivalents thereof.

According to the invention, a compound of interest is preferably a polypeptide as described in the list of compounds of interest.

According to another embodiment of the invention, a compound of interest is preferably a metabolite.

A cell according to the invention may already be capable of producing a compound of interest. A cell according to the invention may also be provided with a homologous or heterologous nucleic acid construct that encodes a polypeptide wherein the polypeptide may be the compound of interest or a polypeptide involved in the production of the compound of interest. The person skilled in the art knows how to modify a microbial host cell such that it is capable of producing a compound of interest.

EMBODIMENTS AND FURTHER EMBODIMENTS

The following embodiments and further embodiments of the invention are provided; the features in these embodiments are preferably those as defined previously herein.

EMBODIMENTS

1. Use of at least a first and a second single-stranded oligonucleotide in the assembly within a cell of at least two double-stranded nucleic acid molecules into a single double-stranded nucleic acid construct of pre-determined sequence, wherein the first and second single-stranded oligonucleotide are essentially complementary to each other.

2. Use according to embodiment 1, wherein the at least two-double-stranded nucleic acid molecules are not capable of recombining with each other such as via homology-mediated recombination.

3. Use according to embodiment 1 or 2, wherein the cell is a eukaryotic cell, preferably a fungus (yeast or filamentous fungus) and/or wherein the cell is deficient in an NHEJ (non-homologous end joining) component.

4. Use according to any of the preceding embodiments, wherein a first of the at least two double-stranded nucleic acid molecules integrates into a second of the at least two double-stranded nucleic acid molecules to result into a single double-stranded nucleic acid construct.

5. Use according to embodiment 4, wherein the integration occurs within the proximity of a break in the second of the at least two double-stranded nucleic acid molecules, wherein the break is one selected from the group consisting of a single-stranded break (nick), an induced single-stranded break, a double-stranded break and an induced double-stranded break.

6. Use according any of the preceding embodiments, wherein the second of the at least two double-stranded nucleic acid molecule is a plasmid (integrative or autonomously replicating) or a genome locus.

7. Use according to any of the preceding embodiments, wherein at least one of the at least two double-stranded nucleic acid molecules is an exogenous nucleic acid molecule.

8. Use according to any of the preceding embodiments, wherein a part of the first single-stranded oligonucleotide has sequence identity with the first of the at least two double-stranded nucleic acid molecules and wherein a part of the first single-stranded oligonucleotide has sequence identity with the second of the at least two double-stranded nucleic acid molecules, wherein the sequence identity is sufficient for assembly of the double-stranded nucleic acid construct.

9. Use according to any of the preceding embodiments, wherein at least a first, second, third and fourth single-stranded oligonucleotide are used, wherein the first and second single-stranded oligonucleotide are essentially complementary to each other and wherein the third and fourth single-stranded oligonucleotide are essentially complementary to each other.

10. Use according to embodiment 9, wherein:
a part of the first and second essentially complementary single-stranded oligonucleotides has sequence identity with the first of the at least two double-stranded nucleic acid molecules and wherein a part of the first and second essentially complementary single-stranded oligonucleotides has sequence identity with the second of the at least two double-stranded nucleic acid molecules; and
wherein a part of the third and fourth essentially complementary single-stranded oligonucleotides has sequence identity with the first of the at least two double-stranded nucleic acid molecules and wherein a part of the third and fourth essentially complementary single-stranded oligonucleotides has sequence identity with the second of the at least two double-stranded nucleic acid molecules.

11. The use according to any of the preceding embodiments in a multiplex system of assembly within a cell of double-stranded nucleic acid molecules into single or into multiple double-stranded nucleic acid constructs.

12. The use according to any of the preceding embodiments, wherein the integration occurs within the proximity of an induced single-stranded or double-stranded break in the second of the at least two double-stranded nucleic acid molecules, and wherein the break is induced by a functional genome editing system, preferably TALENs, CRISPR/Cas, CRISPR/Cpf1, I-SceI and NgAgo.

13. The use according to any one of the preceding embodiments, wherein the cell expresses a functional heterologous genome editing enzyme, preferably a Cas enzyme, preferably Cas9 or Cas9 nickase; Cpf1; I-SceI; NgAgo, or wherein in the cell a heterologous genome editing enzyme, preferably a Cas enzyme, preferably Cas9 or Cas9 nickase; Cpf1; I-SceI; NgAgo, is present.

14. The use according to embodiment 13, wherein in the cell a guide-polynucleotide is present.

15. The use according to embodiment 14, wherein the guide-polynucleotide in the cell is expressed from a vector, preferably a plasmid.

16. The use according to embodiment 15, wherein the plasmid from which the guide-polynucleotide is expressed, is assembled within the cell by integration of a single-stranded or double-stranded oligonucleotide comprising the target sequence of the guide-polynucleotide into the plasmid.

17. The use according to embodiment 16, wherein the assemblies occur essentially simultaneously within the cell.

18. The use according to any one of the preceding embodiments, wherein at least the first and second essentially complementary single-stranded oligonucleotides are annealed before introduction into the cell, preferably the essentially complementary single-stranded oligonucleotides are annealed within a single container.

19. A method for the assembly within a cell of at least two double-stranded nucleic acid molecules into a single double-stranded nucleic acid construct of pre-determined sequence, wherein the assembly is mediated by at least a first and a second single-stranded oligonucleotide, wherein the first and second single-stranded oligonucleotide are essentially complementary to each other, said method comprising contacting the cell with the single-stranded oligonucleotides and at least one of the double-stranded nucleic acid molecules such that the single-stranded oligonucleotides and at least one of the double-stranded nucleic acid molecules are introduced into the cell.

20. the method according to embodiment 19, wherein the at least two-double-stranded nucleic acid molecules are preferably not capable of recombining with each other such as via homology-mediated recombination.

21. The method according to embodiment 19 or 20, wherein the cell is a eukaryotic cell, preferably a fungus (yeast or filamentous fungus) and/or wherein the cell is deficient in an NHEJ (non-homologous end joining) component.

22. The method according to any one of embodiments 19-21, wherein a first of the at least two double-stranded nucleic acid molecules integrates into a second of the at least two double-stranded nucleic acid molecules to result into a single double-stranded nucleic acid construct.

23. The method according to any one of embodiments 19-22, wherein the integration occurs within the proximity of a break in the second of the at least two double-stranded nucleic acid molecules, wherein the break is one selected from the group consisting of a single-stranded break (nick), an induced single-stranded break, a double-stranded break and an induced double-stranded break.

24. The method according to any one of embodiments 19-23, wherein the second of the at least two double-stranded nucleic acid molecule is a plasmid (integrative or autonomously replicating) or a genome locus.

25. The method according to any one of embodiments 19-24, wherein a part of the first single-stranded oligonucleotide has sequence identity with the first of the at least two double-stranded nucleic acid molecules and wherein a part of the first single-stranded oligonucleotide has sequence identity with the second of the at least two double-stranded nucleic acid molecules, wherein the sequence identity is sufficient for assembly of the double-stranded nucleic acid construct.

26. The method according to any one of embodiments 19-25, wherein at least a first, second, third and fourth single-stranded oligonucleotide are used, wherein the first and second single-stranded oligonucleotide are essentially complementary to each other and wherein the third and fourth single-stranded oligonucleotide are essentially complementary to each other.

27. The method according to embodiment 26, wherein:
a part of the first and second essentially complementary single-stranded oligonucleotides has sequence identity with the first of the at least two double-stranded nucleic acid molecules and wherein a part of the first and second essentially complementary single-stranded oligonucleotides has sequence identity with the second of the at least two double-stranded nucleic acid molecules; and
wherein a part of the third and fourth essentially complementary single-stranded oligonucleotides has sequence identity with the first of the at least two double-stranded nucleic acid molecules and wherein a part of the third and fourth essentially complementary single-stranded oligonucleotides has sequence identity with the second of the at least two double-stranded nucleic acid molecules.

28. The method according to any one of embodiments 19-27, wherein the method is a multiplex method of assembly within a cell of multiple double-stranded nucleic acid molecules assembled into single or multiple double-stranded nucleic acid constructs.

29. The method according to any one of embodiments 19-28, wherein the integration occurs within the proximity of an induced single-stranded or double-stranded break in the second of the at least two double-stranded nucleic acid molecules, and wherein the break is induced by a functional genome editing system, preferably TALENs, CRISPR/Cas, CRISPR/Cpf1, I-SceI and NgAgo.

30. The method according to any one of embodiments 19-29, wherein the cell expresses a functional heterologous genome editing enzyme, preferably a Cas enzyme, preferably Cas9 or Cas9 nickase; Cpf1; I-SceI; NgAgo, or wherein in the cell a heterologous genome editing enzyme, preferably a Cas enzyme, preferably Cas9 or Cas9 nickase; Cpf1; I-SceI; NgAgo, is present.

31. The method according to any one of embodiments 19-30, wherein in the cell a guide-polynucleotide is present.

32. The method according to any one of embodiments 19-31, wherein the guide-polynucleotide in the cell is expressed from a vector, preferably a plasmid, preferably the vector is introduced into the cell together with the single-stranded oligonucleotide and at least one of the double-stranded nucleic acid molecules.

33. The method according to embodiment 32, wherein the plasmid from which the guide-polynucleotide is expressed, is assembled within the cell by integration of a single-stranded or double-stranded oligonucleotide comprising the target sequence of the guide-polynucleotide into the plasmid, wherein in the single-stranded or double-stranded oligonucleotide comprising the target sequence of the guide-polynucleotide and the plasmid are introduced into the cell either simultaneously or consecutively with the single-stranded oligonucleotide and at least one of the double-stranded nucleic acid molecules.

34. The method according to embodiment 33, wherein the assembly of the single-stranded or double-stranded oligonucleotide comprising the target sequence of the guide-polynucleotide into the plasmid and the assembly of at least two double-stranded nucleic acid molecules into a single double-stranded nucleic acid construct occur essentially simultaneously within the cell.

35. The method according to any one of embodiments 19-34, wherein at least the first and second essentially complementary single-stranded oligonucleotides are annealed before introduction into the cell, preferably the essentially complementary single-stranded oligonucleotides are annealed within a single container.

36. A composition comprising the at least first and second essentially complementary single-stranded oligonucleotides, the cell and at least one of at least two double-stranded nucleic acid molecules as defined in any one of embodiments 1-35.

37. The composition according to embodiment 36, further comprising a further single-stranded oligonucleotide and/or a further double-stranded nucleic acid molecule as defined in any one of embodiments 1-35, and, optionally, further comprising the vector, preferably a plasmid, as defined in embodiment 15 or embodiment 32, or, optionally further comprising the single-stranded or double-stranded oligonucleotide comprising the target sequence of the guide-polynucleotide and the plasmid as defined in embodiment 16 or embodiment 33.

38. A cell comprising an assembled double-stranded nucleic acid construct, obtainable by the method according to any one of embodiments 19-35.

39. A cell obtainable by or produced by a method according to any one of embodiments 19-35, or the cell according to embodiment 38, further comprising a polynucleotide encoding a compound of interest.

40. The cell according to embodiment 39, expressing the compound of interest.

41. The cell according to embodiment 39 or 40, wherein the compound of interest is foreign to the cell.

42. A method for the production of a compound of interest, comprising culturing the cell according to any one of embodiments 97-40 under conditions conducive to the production of the compound of interest, and, optionally, purifying or isolating the compound of interest.

Further Embodiments

1. Use of a single-stranded oligonucleotide in the assembly within a cell of at least two double-stranded nucleic acid molecules into a single double-stranded nucleic acid construct of pre-determined sequence, wherein:

a first of the at least two double-stranded nucleic acid molecules integrates into a second of the at least two double-stranded nucleic acid molecules to result into a single double-stranded nucleic acid construct, the integration occurs within the proximity of a break in the second of the at least two double-stranded nucleic acid molecules, and a part of the single-stranded oligonucleotide has sequence identity with the first of the at least two double-stranded nucleic acid molecules and a part of the single-stranded oligonucleotide has sequence identity with the second of the at least two double-stranded nucleic acid molecules in a region at least five nucleotides away from the break, wherein the sequence identity is sufficient for assembly of the double-stranded nucleic acid construct. The region is preferably at least 5, 6, 7, 8, 9, 10, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000 or at least 100000 nucleotides away from the break.

2. Use according to further embodiment 1, wherein the cell is a eukaryotic cell, preferably a fungus (yeast or filamentous fungus) and/or wherein the cell is deficient in an NHEJ (non-homologous end joining) component.

3. Use according to further embodiment 2, wherein the break is one selected from the group consisting of a single-stranded break (nick), an induced single-stranded break, a double-stranded break and an induced double-stranded break.

4. Use according any of the preceding further embodiments, wherein the second of the at least two double-stranded nucleic acid molecule is a plasmid (integrative or autonomously replicating) or a genome locus.

5. Use according to any of the preceding further embodiments, wherein at least one of the at least two double-stranded nucleic acid molecules is an exogenous nucleic acid molecule.

6. Use according to any of the preceding further embodiments, wherein at least a first and second single-stranded oligonucleotide are used, and wherein the first and second single-stranded oligonucleotide are essentially complementary to each other.

7. Use according to any of the preceding further embodiments, wherein at least a first, second, third and fourth single-stranded oligonucleotide are used, wherein the first and second single-stranded oligonucleotide are essentially complementary to each other and wherein the third and fourth single-stranded oligonucleotide are essentially complementary to each other.

8. Use according to further embodiment 7, wherein:

a part of the first and second essentially complementary single-stranded oligonucleotides has sequence identity with the first of the at least two double-stranded nucleic acid molecules and wherein a part of the first and second essentially complementary single-stranded oligonucleotides has sequence identity with the second of the at least two double-stranded nucleic acid molecules in a region at least five nucleotides away from the break; and wherein a part of the third and fourth essentially complementary single-stranded oligonucleotides has sequence identity with the first of the at least two double-stranded nucleic acid molecules and wherein a part of the third and fourth essentially complementary single-stranded oligonucleotides has sequence identity with the second of the at least two double-stranded nucleic acid molecules, in a region at least five nucleotides away from the break;

and wherein the sequence identity is sufficient for assembly of the double-stranded nucleic acid construct. The region is preferably at least 5, 6, 7, 8, 9, 10, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000 or at least 100000 nucleotides away from the break.

9. The use according to any of the preceding further embodiments in a multiplex system of assembly within a cell of double-stranded nucleic acid molecules into single or into multiple double-stranded nucleic acid constructs.

10. The use according to any of the preceding further embodiments, wherein the integration occurs within the proximity of an induced single-stranded or double-stranded break in the second of the at least two double-stranded nucleic acid molecules, and wherein the break is induced by a functional genome editing system, preferably TALENs, CRISPR/Cas, CRISPR/Cpf1, I-Scel and NgAgo.

11. The use according to any one of the preceding further embodiments, wherein the cell expresses a functional heterologous genome editing enzyme, preferably a Cas enzyme, preferably Cas9 or Cas9 nickase; Cpf1; I-Scel; NgAgo, or wherein in the cell a heterologous genome editing enzyme, preferably a Cas enzyme, preferably Cas9 or Cas9 nickase; Cpf1; I-Scel; NgAgo, is present.

12. The use according to further embodiment 11, wherein in the cell a guide-polynucleotide is present.

13. The use according to further embodiment 12, wherein the guide-polynucleotide in the cell is expressed from a vector, preferably a plasmid.

14. The use according to further embodiment 13, wherein the plasmid from which the guide-polynucleotide is expressed, is assembled within the cell by integration of a single-stranded or double-stranded oligonucleotide comprising the target sequence of the guide-polynucleotide into the plasmid.

15. The use according to further embodiment 14, wherein the assemblies occur essentially simultaneously within the cell.

16. The use according to any one of further embodiments 6-15, wherein at least the first and second essentially complementary single-stranded oligonucleotides are annealed before introduction into the cell, preferably the essentially complementary single-stranded oligonucleotides are annealed within a single container.

17. A method for the assembly within a cell of at least two double-stranded nucleic acid molecules into a single double-stranded nucleic acid construct of pre-determined sequence, wherein the assembly is mediated by a single-stranded oligonucleotide, said method comprising contacting the cell with the single-stranded oligonucleotide and at least one of the double-stranded nucleic acid molecules such that the single-stranded oligonucleotide and at least one of the double-stranded nucleic acid molecules are introduced into the cell, wherein:

a first of the at least two double-stranded nucleic acid molecules integrates into a second of the at least two double-stranded nucleic acid molecules to result into a single double-stranded nucleic acid construct, the integration occurs within the proximity of a break in the second of the at least two double-stranded nucleic acid molecules, and a part of the single-stranded oligonucleotide has sequence identity with the first of the at least two double-stranded nucleic acid molecules and a part of the single-stranded oligonucleotide has sequence identity with the second of the at least two double-stranded nucleic acid molecules in a region at least five nucleotides away from the break, wherein the sequence identity is sufficient for assembly of the double-stranded nucleic acid construct. The region is preferably at least 5, 6, 7, 8, 9, 10, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000 or at least 100000 nucleotides away from the break.

18. The method according to further embodiment 17, wherein the cell is a eukaryotic cell, preferably a fungus (yeast or filamentous fungus) and/or wherein the cell is deficient in an NHEJ (non-homologous end joining) component.

19. The method according to further embodiment 18, wherein the break is one selected from the group consisting of a single-stranded break (nick), an induced single-stranded break, a double-stranded break and an induced double-stranded break.

20. The method according to any one of further embodiments 17-19, wherein the second of the at least two double-stranded nucleic acid molecule is a plasmid (integrative or autonomously replicating) or a genome locus.

21. The method according to any one of further embodiments 17-20, wherein at least a first and second single-stranded oligonucleotide are used, and wherein the first and second single-stranded oligonucleotide are essentially complementary to each other.

22. The method according to any one of further embodiments 17-21, wherein at least a first, second, third and fourth single-stranded oligonucleotide are used, wherein the first and second single-stranded oligonucleotide are essentially complementary to each other and wherein the third and fourth single-stranded oligonucleotide are essentially complementary to each other.

23. The method according to further embodiment 22, wherein:
  a part of the first and second essentially complementary single-stranded oligonucleotides has sequence identity with the first of the at least two double-stranded nucleic acid molecules and wherein a part of the first and second essentially complementary single-stranded oligonucleotides has sequence identity with the second of the at least two double-stranded nucleic acid molecules in a region at least five nucleotides away from the break; and
  wherein a part of the third and fourth essentially complementary single-stranded oligonucleotides has sequence identity with the first of the at least two double-stranded nucleic acid molecules and wherein a part of the third and fourth essentially complementary single-stranded oligonucleotides has sequence identity with the second of the at least two double-stranded nucleic acid molecules, in a region at least five nucleotides away from the break;
  and wherein the sequence identity is sufficient for assembly of the double-stranded nucleic acid construct. The region is preferably at least 5, 6, 7, 8, 9, 10, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000 or at least 100000 nucleotides away from the break.

24. The method according to any one of further embodiments 17-23, wherein the method is a multiplex method of assembly within a cell of multiple double-stranded nucleic acid molecules assembled into single or multiple double-stranded nucleic acid constructs.

25. The method according to any one of further embodiments 17-24, wherein the integration occurs within the proximity of an induced single-stranded or double-stranded break in the second of the at least two double-stranded nucleic acid molecules, and wherein the break is induced by a functional genome editing system, preferably TALENS, CRISPR/Cas, CRISPR/Cpf1, I-ScelI and NgAgo.

26. The method according to any one of further embodiments 17-25, wherein the cell expresses a functional heterologous genome editing enzyme, preferably a Cas enzyme, preferably Cas9 or Cas9 nickase; Cpf1; I-ScelI; NgAgo, or wherein in the cell a heterologous genome editing enzyme, preferably a Cas enzyme, preferably Cas9 or Cas9 nickase; Cpf1; I-ScelI; NgAgo, is present.

27. The method according to any one of further embodiments 17-26, wherein in the cell a guide-polynucleotide is present.

28. The method according to any one of further embodiments 17-27, wherein the guide-polynucleotide in the cell is expressed from a vector, preferably a plasmid, preferably the vector is introduced into the cell together with the single-stranded oligonucleotide and at least one of the double-stranded nucleic acid molecules.

29. The method according to further embodiment 28, wherein the plasmid from which the guide-polynucleotide is expressed, is assembled within the cell by integration of a single-stranded or double-stranded oligonucleotide comprising the target sequence of the guide-polynucleotide into the plasmid, wherein in the single-stranded or double-stranded oligonucleotide comprising the target sequence of the guide-polynucleotide and the plasmid are introduced into the cell either simultaneously or consecutively with the single-stranded oligonucleotide and at least one of the double-stranded nucleic acid molecules.

30. The method according to further embodiment 29, wherein the assembly of the single-stranded or double-stranded oligonucleotide comprising the target sequence of the guide-polynucleotide into the plasmid and the assembly of at least two double-stranded nucleic acid molecules into a single double-stranded nucleic acid construct occur essentially simultaneously within the cell.

31. The method according to any one of further embodiments 21-30, wherein at least the first and second essentially complementary single-stranded oligonucleotides are annealed before introduction into the cell, preferably the essentially complementary single-stranded oligonucleotides are annealed within a single container.

32. A composition comprising the single-stranded oligonucleotide, the cell and at least one of at least two double-stranded nucleic acid molecules as defined in any one of further embodiments 1-31.

33. The composition according to further embodiment 32, further comprising a further single-stranded oligonucleotide and/or a further double-stranded nucleic acid molecule as defined in any one of further embodiments 1-31, and, optionally, further comprising the vector, preferably a plasmid, as defined in further embodiment 13 or further embodiment 28, or, optionally further comprising the single-stranded or double-stranded oligonucleotide comprising the target sequence of the guide-polynucleotide and the plasmid as defined in further embodiment 14 or further embodiment 29.

34. A cell comprising an assembled double-stranded nucleic acid construct obtainable by the method according to any one of further embodiments 17-33.

35. A cell obtainable by or produced by the method according to any one of further embodiments 17-33, or the cell according to further embodiment 34, further comprising a polynucleotide encoding a compound of interest.

36. The cell according to further embodiment 35, expressing the compound of interest.

37. The cell according to further embodiment 35 or 36, wherein the compound of interest is foreign to the cell.

38. A method for the production of a compound of interest, comprising culturing the cell according to any one of further embodiments 35-37 under conditions conducive to the production of the compound of interest, and, optionally, purifying or isolating the compound of interest.

General Definitions

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The terms "a" and "an" are used herein to refer to one or to more than one (i.e. to one or at least one) of the grammatical object of the article. By way of example, "an element" may mean one element or more than one element.

The word "about" or "approximately" when used in association with a numerical value (e.g. about 10) preferably means that the value may be the given value (of 10) more or less 1% of the value.

Cas9, the single protein component in the class 2 type II-a CRISPR/Cas system (Mohanraju et al., 2016), is capable of complexing with two small RNAs named CRISPR RNA (crRNA) and trans-activating crRNA (tracrRNA) to form a sequence-specific RNA-guided endonuclease (RGEN) whose target specificity is readily reprogrammed by either modifying the crRNA or using a single-chain guide RNA (sgRNA) composed of essential portions of crRNA and tracrRNA (Jinek et al., 2012). Cas9 RGENs cleave chromosomal DNA to produce site-specific DNA double-strand blunt-end breaks (DSBs) that are repaired by homologous recombination (HR) or non-homologous end-joining (NHEJ) to yield genetic modifications (Sander and Joung, 2014).

Cpf1 is a novel class 2 type V-a CRISPR RNA guided nuclease (Zetsche et al., 2015; Mohanraju et al., 2016). Cpf1 is different compared to Cas9 in various ways. Cpf1 is a single-RNA-guided nuclease and does not require a trans-activating CRISPR RNA (tracrRNA), thus gRNAs are shorter in length than those for Cas9 by about 50%. Cpf1 cleavage produces cohesive (not blunt) double-stranded DNA breaks leaving 4-5-nt overhanging "sticky" ends, which might facilitate NHEJ-mediated transgene knock-in at target sites. Cpf1 recognizes thymidine-rich DNA PAM sequences, for example, 5'-TTTN-3' or 5'-TTN-3', which are located at the 5' end of target sequences (Zetsche et al., 2015) while Cas9 recognizes guanine-rich (NGG) PAMs located at the 3'-end of the target sequence (Jinek et al., 2012).

Cpf1 is found in various bacteria including *Francisella*, *Acidaminococcus* and *Lachnospiraceae* (Zetsche et al., 2015). Heterologous Cpf1 RGEN activity was demonstrated in mammalian cells (Zetsche et al., 2015; Kim D. et al., 2015), mice (Kim, Y. et al., 2016, Hur et al., 2016), *Drosophila* (Port and Bullock, 2016) and rice plant (Xu et al., 2016).

A preferred nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. It is further preferred that the linkage between a residue in a backbone does not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage. A further preferred nucleotide analogue or equivalent comprises a substitution of at least one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, aryl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; aminoxy, methoxyethoxy; -dimethylaminooxyethoxy; and-dimethylaminoethoxyethoxy. The sugar moiety can be a pyranose or derivative thereof, or a deoxypyranose or derivative thereof, preferably a ribose or a derivative thereof, or deoxyribose or derivative thereof. Such preferred derivatized sugar moieties comprise Locked Nucleic Acid (LNA), in which the 2'-carbon atom is linked to the 3' or 4' carbon atom of the sugar ring thereby forming a bicyclic sugar moiety. A preferred LNA comprises 2'-0,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target.

"Sequence identity" or "identity" in the context of the present invention of an amino acid- or nucleic acid-sequence is herein defined as a relationship between two or more amino acid (peptide, polypeptide, or protein) sequences or two or more nucleic acid (nucleotide, oligonucleotide, polynucleotide) sequences, as determined by comparing the sequences. In the art, "identity" also means the degree of sequence relatedness between amino acid or nucleotide sequences, as the case may be, as determined by the match between strings of such sequences. Within the present invention, sequence identity with a particular sequence preferably means sequence identity over the entire length of said particular polypeptide or polynucleotide sequence.

"Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole sequence (SEQ ID NO:) as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps). Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons. Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A polynucleotide according to the present invention is represented by a nucleotide sequence. A polypeptide according to the present invention is represented by an amino acid sequence. A nucleic acid construct according to the present invention is defined as a polynucleotide which is isolated from a naturally occurring gene or which has been modified to contain segments of polynucleotides which are combined or juxtaposed in a manner which would not otherwise exist in nature. Optionally, a polynucleotide present in a nucleic acid construct according to the present invention is operably linked to one or more control sequences, which direct the production or expression of the encoded product in a host cell or in a cell-free system.

The sequence information as provided herein should not be so narrowly construed as to require inclusion of erroneously identified bases. The skilled person is capable of identifying such erroneously identified bases and knows how to correct for such errors.

All embodiments of the present invention, preferably refer to a cell, not to a cell-free in vitro system; in other words, the systems according to the invention are preferably cell systems, not cell-free in vitro systems.

In all embodiments of the present invention, e.g., the cell according to the present invention may be a haploid, diploid or polyploid cell.

A cell according to the invention is interchangeably herein referred as "a cell", "a cell according to the invention", "a host cell", and as "a host cell according to the invention"; said cell may be any cell, preferably a fungus, i.e. a yeast cell or a filamentous fungus cell, or it may be an algae, a microalgae or a marine eukaryote, e.g. a Labyrinthulomycetes host cell. Preferably, the cell is deficient in an NHEJ (non-homologous end joining) component. Said component associated with NHEJ is preferably a yeast Ku70, Ku80, MRE11, RAD50, RAD51, RAD52, XRS2, SIR4, LIF1, NEJ1 and/or LIG4 or homologue thereof.

When the cell according to the invention is a yeast cell, a preferred yeast cell is from a genus selected from the group consisting of *Candida, Hansenula, Issatchenkia, Kluyveromyces, Pichia, Saccharomyces, Schizosaccharomyces, Yarrowia* or *Zygosaccharomyces*; more preferably a yeast host cell is selected from the group consisting of *Kluyveromyces lactis, Kluyveromyces lactis* NRRL Y-1140, *Kluyveromyces marxianus, Kluyveromyces. thermotolerans, Candida krusei, Candida sonorensis, Candida glabrata, Saccharomyces cerevisiae, Saccharomyces cerevisiae* CEN.PKI13-7D, *Schizosaccharomyces pombe, Hansenula polymorpha, Issatchenkia orientalis, Yarrowia lipolytica, Yarrowia lipolytica* CLIB122, *Pichia stipidis* and *Pichia pastoris*. The host cell according to the present invention is a filamentous fungal host cell. Filamentous fungi as defined herein include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK).

The filamentous fungal host cell may be a cell of any filamentous form of the taxon Trichocomaceae (as defined by Houbraken and Samson in Studies in Mycology 70: 1-51. 2011). In another preferred embodiment, the filamentous fungal host cell may be a cell of any filamentous form of any of the three families Aspergillaceae, Thermoascaceae and Trichocomaceae, which are accommodated in the taxon Trichocomaceae.

The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mortierella, Mucor, Myceliophthora, Neocallimastix, Neurospora, Paecilomyces, Penicillium, Piromyces, Panerochaete, Pleurotus, Schizophyllum, Talaromyces, Rasamsonia, Thermoascus, Thielavia, Tolypocladium*, and *Trichoderma*. A preferred filamentous fungal host cell according to the present invention is from a genus selected from the group consisting of *Acremonium, Aspergillus, Chrysosporium, Myceliophthora, Penicillium, Talaromyces, Rasamsonia, Thielavia, Fusarium* and *Trichoderma*; more preferably from a species selected from the group consisting of *Aspergillus niger, Acremonium alabamense, Aspergillus awamori, Aspergillus foetidus, Aspergillus sojae, Aspergillus fumigatus, Talaromyces emersonii, Rasamsonia emersonii, Rasamsonia emersonii* CBS393.64, *Aspergillus oryzae, Chrysosporium lucknowense, Fusarium oxysporum, Mortierella alpina, Mortierella alpina* ATCC 32222, *Myceliophthora thermophila, Trichoderma reesei, Thielavia terrestris, Penicillium chrysogenum* and *P. chrysogenum* Wisconsin 54-1255(ATCC28089); even more preferably the filamentous fungal host cell according to the present invention is an *Aspergillus niger*. When the host cell according to the present invention is an *Aspergillus niger* host cell, the host cell preferably is CBS 513.88, CBS124.903 or a derivative thereof.

Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), Agricultural Research Service Patent Culture Collection, Northern Regional Research Center (NRRL), and All-Russian Collection of Microorganisms of Russian Academy of Sciences, (abbreviation in Russian—VKM, abbreviation in English—RCM), Moscow, Russia. Preferred strains as host cells according to the present invention are *Aspergillus niger* CBS 513.88, CBS124.903, *Aspergillus oryzae* ATCC 20423, IFO 4177, ATCC 1011, CBS205.89, ATCC 9576, ATCC14488-14491, ATCC 11601, ATCC12892, *P. chrysogenum* CBS 455.95, *P. chrysogenum* Wisconsin54-1255 (ATCC28089), *Penicillium citrinum* ATCC 38065, *Penicillium chrysogenum* P2, *Thielavia terrestris* NRRL8126, *Rasamsonia emersonii* CBS393.64, *Talaromyces emersonii* CBS 124.902, *Acremonium chrysogenum* ATCC 36225 or ATCC 48272, *Trichoderma reesei* ATCC 26921 or ATCC 56765 or ATCC 26921, *Aspergillus sojae* ATCC11906, *Myceliophthora thermophila* C1, Garg 27K, VKM-F 3500 D, *Chrysosporium lucknowense* C1, Garg 27K, VKM-F 3500 D, ATCC44006 and derivatives thereof. Preferably, and more preferably when the microbial host cell according to the invention is a filamentous fungal host cell, a host cell according to the present invention further comprises one or more modifications in its genome such that the host cell is deficient in the production of at least one product selected from glucoamylase (glaA), acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE if compared to a parent host cell and measured under the same conditions. Oxalic acid hydrolase (oahA) is a component of the synthesis pathway of oxalic acid in many host cells. A host cell deficient in oahA will be deficient in oxalic acid. Oxalic acid is an unwanted by-product in many applications such as food applications. Furthermore, oxalic acid lowers the pH of the medium cultivations of host cell producing this component, resulting in lowered yields; i.e. yield is increased in oxalic acid deficient host cells. It is therefore advantageous if a host cell according to the present invention is deficient in oahA. OahA deficient host cells and preferred methods of producing said host cells are extensively described in WO 2000/50576 and WO2004/070022. A preferred method to produce an oahA deficient host cell is the recombinant method of disruption described in WO 2000/50576. Preferably, a host cell according to the present invention is deficient in oahA. Preferably, the oahA is a fungal oahA. More preferably, the oahA is the oahA from *Aspergillus*. Even more preferably the oahA is the oahA from *Aspergillus niger*. Even more preferably the oahA is the oahA from *Aspergillus niger* CBS 513.88. Most preferably, the oahA comprises the sequence of An10g00820.

PrtT is a transcriptional activator of proteases in eukaryotic cells. Several fungal transcriptional activators of proteases have been recently described in WO 00/20596, WO 01/68864, WO 2006/040312 and WO 2007/062936. These transcriptional activators were isolated from *Aspergillus niger* (*A. niger*), *Aspergillus fumigatus* (*A. fumigatus*), *Penicillium chrysogenum* (*P. chrysogenum*) and *Aspergillus oryzae* (*A. oryzae*). These transcriptional activators of protease genes can be used to improve a method for producing a polypeptide in a host cell, wherein the polypeptide is sensitive for protease degradation. When a host cell according to the present invention is deficient in prtT, the host cell will produce less proteases that are under transcriptional control of prtT. It is therefore advantageous when a host cell according to the invention is deficient in prtT. PrtT deficient hosts and preferred methods to produce these hosts are extensively described in WO 01/68864, WO 2006/040312. WO 01/68864 and WO 2006/040312 describe recombinant and classic methods to disrupt the prtT coding sequence. WO 2007/062936 describes disruption of the prtT binding site in a protease promoter. Disruption of the binding site impedes binding of prtT to the binding site. Consequently, the transcription of the protease is not activated by prtT and less protease is produced.

Preferably, a host cell according to the present invention comprises a polynucleotide encoding prtT, said polynucleotide comprising a modification such that the host cell is deficient in the production of prtT compared to a parent cell it originates from when cultivated under comparable conditions. Preferably, the prtT is a fungal prtT. More preferably, the prtT is the prtT from *Aspergillus*. Even more preferably the prtT is the prtT from *Aspergillus niger*. Even more preferably the prtT is the prtT from *Aspergillus niger* CBS 513.88. Most preferably, the prtT comprises the sequence of An04g06940.

The term "glucoamylase" (glaA) is identical to the term "amyloglucosidase" and is defined herein as an enzyme having dextrin 6-alpha-D-glucanohydrolase activity which catalyzes the endo hydrolysis of 1,6-alpha-D-glucoside linkages at points of branching in chains of 1,4-linked alpha-D-glucose residues and terminal 1,4-linked alpha-D-glucose residues. Glucoamylase activity can be measured as AGIU/ml by determining the liberation of paranitrofenol from the substrate p-nitrophenyl-a-D-glucopyranoside (Sigma). This results in a yellow colour, whose absorbance can be measured at 405 nm using a spectrophotometer. 1 AGIU is the quantity of enzyme, which produces 1 µmole of glucose per minute at pH 4.3 and 60° C. from a soluble starch substrate. In WO98/46772 additional details of the assay can be found.

Preferably, a host cell according to the present invention comprises a polynucleotide encoding glaA, said polynucleotide comprising a modification such that the host cell is deficient in the production of glaA compared to a parent cell it originates from when cultivated under comparable conditions. Preferably, the glaA is a fungal glaA. More preferably, the glaA is the glaA from *Aspergillus*. Even more preferably the glaA is the glaA from *Aspergillus niger*. Even more preferably the glaA is the glaA from *Aspergillus niger* CBS 513.88. Most preferably, the glaA comprises the sequence of An03g06550.

The term "alpha-amylase" is defined herein as 1,4-alpha-D-glucan glucanohydrolase activity which catalyzes the endohydrolysis of polysaccharides with three or more alpha-1,4-linked glucose units in the presence of water to malto-oligosaccharides. To determine the (neutral) alpha-amylase activity, the Megazyme cereal alpha-amylase kit is used (Megazyme, CERALPHA alpha amylase assay kit, catalogus. ref. K-CERA, year 2000-2001), according a protocol of the supplier. The measured activity is based on hydrolysis of non-reducing-endblocked p-nitrophenyl maltoheptaoside in the presence of excess glucoamylase and α-glucosidase at a pH of 7.0. The amount of formed p-nitrophenol is a measure for alpha-amylase activity present in a sample. The term "acid stable alpha-amylase" (amyA) is defined herein as an enzyme having alpha-amylase activity with optimal activity in the acid pH range. To determine the acid stable alpha-amylase activity, also the Megazyme cereal alpha-amylase kit is used (Megazyme, CERALPHA alpha amylase assay kit, catalogus. ref. K-CERA, year 2000-2001), according a protocol of the supplier but at an acid pH. The measured activity is based on hydrolysis of non-reducing-endblocked p-nitrophenyl maltoheptaoside in the presence of excess glucoamylase and α-glucosidase at a pH of 4.5. The amount of formed p-nitrophenol is a measure for acid stable alpha-amylase activity present in a sample.

Preferably, a host cell according to the present invention comprises a polynucleotide encoding AmyA, said polynucleotide comprising a modification, wherein the host cell is deficient in amyA compared to the parent cell it originates from when cultivated under comparable conditions. Preferably, the amyA is a fungal amyA. More preferably, the amyA is the amyA from *Aspergillus*. Even more preferably the amyA is the amyA from *Aspergillus niger*. Even more preferably the amyA is the amyA from *Aspergillus niger*CBS 513.88. Most preferably, the amyA comprises the sequence of An11g03340.

The term "neutral alpha-amylase activity" (amy) is defined herein as an enzyme having alpha-amylase activity with optimal activity in the neutral pH range.

Preferably, a host cell according to the present invention comprises a polynucleotide encoding AmyB, said polynucleotide comprising a modification, wherein the host cell is deficient in amyBI and/or amyBII compared to the parent cell it originates from when cultivated under comparable conditions. More preferably, a host cell according to the present invention is deficient in amyBI and amy BII. Preferably, the amyB a is a fungal amyB. More preferably, the amyB is the amyB from *Aspergillus*. Even more preferably the amyB is the amyBI from *Aspergillus niger*. Even more preferably the amyB is the amyBI from *Aspergillus niger* CBS 513.88. Most preferably, the amyBI comprises the sequence of An12g06930. Even more preferably the amyB is the amyBII from *Aspergillus niger*. Even more preferably the amyB is the amyBII from *Aspergillus niger*CBS 513.88. Most preferably, the amyBII comprises the sequence of An05g02100.

The term toxin associated polynucleotide is defined herein as a gene cluster, a multitude of genes, a gene or part thereof encoding a compound, or biochemical pathway responsible for the biosynthesis or secretion of at least one toxin or toxin intermediate compound. Said compound may e.g. be a polypeptide, which may be an enzyme.

A number of host cells, especially filamentous fungal host cells, which are used as for the production of polypeptides of interest, comprise genes encoding enzymes involved in the biosynthesis of various toxins. For example, cyclopiazonic acid, kojic acid, 3-nitropropionic acid and aflatoxins are known toxins, which are formed in, e.g., *Aspergillus flavus*. Similarly, trichothecenes are formed in a number of filamentous fungi, e.g., in *Fusarium* sp. such as *Fusarium venenatum* as well as in *Trichoderma*; ochratoxin may be produced by *Aspergillus*. Recently, sequencing of the genome of an industrial *Aspergillus niger* host strain revealed an inactive fumonisin gene cluster (Pel et al., "Genome sequencing and analysis of the versatile cell factory *Aspergillus niger* CBS 513.88". Nat Biotechnol. 2007 February; 25 (2):221-231). The formation of such toxins during the fermentation of compounds of interest is highly undesirable as these toxins may present a health hazard to operators, customers and the environment. Consequently, a toxin deficient host cell enables toxin-free production of a compound of interest. The toxin-free compound is easier to produce since no toxin has to be removed from the product. Furthermore, the regulatory approval procedure for the compound is easier.

Preferably, a host cell according to the present invention comprises a toxin associated polynucleotide encoding a compound (which may e.g. be a polypeptide which may be an enzyme) or biochemical pathway, said toxin associated polynucleotide comprising a modification, wherein the host cell is deficient in the production of said toxin or a toxin intermediate compound compared to the parent cell it originates from when cultivated under comparable conditions. Preferably, the toxin or toxin intermediate compound is a fungal toxin or toxin intermediate compound. More preferably, the toxin or toxin intermediate compound is a toxin or toxin intermediate compound from *Aspergillus*. Even more preferably the toxin or the toxin intermediate compound is a toxin or toxin intermediate compound from *Aspergillus niger*. Even more preferably the toxin or toxin intermediate compound is a toxin or toxin intermediate compound from *Aspergillus niger* CBS 513.88. Even more preferably, the toxin or the toxin intermediate compound is fumonisin or a fumonisin intermediate compound. Even more preferably, the toxin or the toxin intermediate compound is ochratoxin or an ochratoxin intermediate compound. Most preferably, the toxin or the toxin intermediate compound is ochratoxin or fumonisin or an ochratoxin or a fumonisin intermediate compound.

Preferably, the toxin associated polynucleotide encodes a compound (which may e.g. be a polypeptide which may be an enzyme) or a biochemical pathway which is involved in the production of a fungal toxin or toxin intermediate compound. More preferably, said toxin or toxin intermediate compound is from *Aspergillus*. Even more preferably, said toxin or toxin intermediate compound is from *Aspergillus niger*. Even more preferably, said toxin or toxin intermediate compound is from *Aspergillus niger* CBS 513.88. Even more preferably, said toxin or toxin intermediate compound is a fumonisin or a fumonisin intermediate compound; even more preferably, a fumonisin-B or a fumonisin-B intermediate compound; even more preferably, a fumonisin-B2 or a fumonisin-B2 intermediate compound. Preferably, the toxin associated polynucleotide comprises the sequence of the fumonisin cluster from An01g06820 until An01g06930; more preferably, the toxin associated polynucleotide comprises the sequence of An01g06930. Alternatively or in combination when the toxin or toxin intermediate compound is a fumonisin or a fumonisin intermediate compound, the toxin associated polynucleotide encodes a compound (which may e.g. be a polypeptide which may be an enzyme) or a biochemical pathway, which is involved in ochratoxin or an ochratoxin intermediate compound; preferably, an ochratoxin A or an ochratoxin A intermediate compound; more preferably, the toxin associated polynucleotide comprises the sequence of the cluster from An15g07880 until An15g07930; most preferably, the toxin associated polynucleotide comprises the sequence of An15g07910 and/or the sequence of An15g07920.

Preferably, a host cell according to the present invention comprises at least one toxin associated polynucleotide encoding a compound (which may e.g. be a polypeptide which may be an enzyme) or biochemical pathway, said toxin associated polynucleotide comprising at least one modification, wherein the host cell is deficient in the production of a toxin or, toxin intermediate compound compared to the parent cell it originates from when cultivated under comparable conditions. More preferably, a host cell according to the present invention comprises two toxin associated polynucleotides, said two toxin associated polynucleotides each comprising at least one modification, wherein the host cell is preferably deficient in the production of fumonisin and ochratoxin compared to the parent cell it originates from when cultivated under comparable conditions. Even more preferably, a mutant microbial host cell according to the invention comprises three or more toxin associated polynucleotides, said three or more toxin associated polynucleotides each comprising at least one modification, wherein the host cell is preferably deficient in the production of fumonisin, ochratoxin and at least one additional toxin or toxin intermediate compound compared to the parent cell it originates from when cultivated under comparable conditions. Preferably, a host cell according to the present invention comprises one or more modifications in its genome to result in a deficiency in the production of the major extracellular aspartic protease PepA. Preferably, the host cell according to the present invention comprises a disruption of the pepA gene encoding the major extracellular aspartic protease PepA; more preferably, the pepA is the pepA from *Aspergillus*; even more preferably the pepA is the pepA from *Aspergillus niger*, even more preferably the pepA is the pepA from *Aspergillus niger* CBS 513.88; most preferably, the pepA comprises the sequence of An14g04710.

When a host cell according to the present invention is a filamentous fungal host cell, said host cell preferably additionally comprises one or more modifications in its genome to result in a deficiency in the production of the product encoded by the hdfA gene (as depicted in SEQ ID NO: 3 of WO 2005/095624) and/or hdfB gene (as depicted in SEQ ID NO: 6 of WO 2005/095624). A host cell according to the present invention preferably further comprises a disruption of the hdfA and/or hdfB gene. Filamentous fungal host cells which are deficient in a product encoded by the hdfA and/or hdfB gene have been described in WO 2005/095624.

When a host cell according to the present invention is a filamentous fungal host cell, said host cell preferably further comprises a modification in its genome which results in the deficiency in the production of the non-ribosomal peptide synthase npsE, preferably the npsE depicted in SEQ ID NO: 38 of WO2012/001169. Such host cells deficient in the production of non-ribosomal peptide synthase npsE have been described in WO2012/001169 (npsE has a genomic sequence as depicted in SEQ ID NO: 35, a coding sequence as depicted in SEQ ID NO: 36, an mRNA as depicted in SEQ ID NO: 37 and the nrps protein as depicted in SEQ ID NO: 38 of WO2012/001169).

A host cell according to the present invention preferably further comprises a modification in its genome which results in the deficiency in the production of the α-amylase amyC, preferably the mature AmyC protein shown in SEQ ID NO: 4 and 8 of WO2014/013073. Such host cells deficient in the production of the α-amylase amyC have been described in WO2014/013073. AmyC has a genomic sequence as depicted in SEQ ID NO: 1 or 5 and a coding sequence depicted in SEQ ID NO: 2 or 6 and the AmyC protein as depicted in SEQ ID NO: 3 or 7 with the mature AmyC protein shown in SEQ ID NO: 4 and 8 of WO2014/013073).

A host cell according to the present invention preferably further comprises a modification in its genome which results in the deficiency in the production of the AgsE protein, preferably the mature AgsE protein shown in SEQ ID NO: 3 or comprised in SEQ ID NO: 3 of WO2014/013074. Such host cells deficient in the production of the AgsE protein have been described in WO2014/013074. AgsE has a genomic sequence as depicted in SEQ ID NO: 1 and a coding sequence depicted in SEQ ID NO: 2 and the AgsE protein as depicted in SEQ ID NO: 3 with the mature AgsE protein comprised in SEQ ID NO: 3 of WO2014/013074).

The deficiency in the production of at least one product selected from glucoamylase (glaA), acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE, amylase amyC if compared to a parent host cell and measured under the same conditions may already be present in a parent host cell from which a host cell according to the present invention that is deficient in a further product selected from the group consisting of glucoamylase (glaA), acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE, amylase amyC is derived.

The deficiency in the production of at least one product selected from glucoamylase (glaA), acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE, amylase amyC, protein AgsE if compared to a parent host cell and measured under the same conditions may already be present in a parent host cell from which a host cell according to the present invention that is deficient in a further product selected from the group consisting of glucoamylase (glaA), acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE, amylase amyC, protein AgsE is derived.

A preferred host cell according to the present invention comprises a deficiency in the production of glaA and optionally at least another product selected from the group consisting of acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE, amylase amyC if compared to a parent host cell and measured under the same conditions.

A further preferred host cell according to the present invention comprises a deficiency in the production of glaA, PepA and optionally at least another product selected from the group consisting of acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, a product encoded by the gene hdfA and/or hdfB, a non-ribosomal peptide synthase npsE, amylase amyC if compared to a parent host cell and measured under the same conditions. A further preferred host cell according to the present invention comprises a deficiency in the production of glaA, PepA, acid stable alpha-amylase (amyA) and optionally at least another product selected from the group consisting of neutral alpha-amylase (amyBI and amyBII), oxalic acid hydrolase (oahA), a toxin, preferably ochratoxin and/or fumonisin, a protease transcriptional regulator prtT, a product encoded by the gene hdfA and/or hdfB, a non-ribosomal peptide synthase npsE, amylase amyC if compared to a parent host cell and measured under the same conditions. A further preferred host cell according to the present invention comprises a deficiency in the production of glaA, PepA, acid stable alpha-amylase (amyA), neutral alpha-amylase amyBI and optionally at least another product selected from the group consisting of neutral alpha-amylase amyBII, oxalic acid hydrolase (oahA), a toxin, preferably ochratoxin and/or fumonisin, a protease transcriptional regulator prtT, a product encoded by the gene hdfA and/or hdfB, a non-ribosomal peptide synthase npsE, amylase amyC if compared to a parent host cell and measured under the same conditions.

A further preferred host cell according to the present invention comprises a deficiency in the production of glaA, PepA, acid stable alpha-amylase (amyA), neutral alpha-amylase amyBI and amyBII, and optionally at least another product selected from the group consisting of oxalic acid hydrolase (oahA), a toxin, preferably ochratoxin and/or fumonisin, a protease transcriptional regulator prtT, a product encoded by the gene hdfA and/or hdfB, a non-ribosomal peptide synthase npsE, amylase amyC if compared to a parent host cell and measured under the same conditions. A further preferred host cell according to the present invention comprises a deficiency in the production of glaA, PepA, acid stable alpha-amylase (amyA), neutral alpha-amylase amyBI and amyBII, a product encoded by the gene hdfA and optionally at least another product selected from the group consisting of oxalic acid hydrolase (oahA), a toxin, preferably ochratoxin and/or fumonisin, a protease transcriptional regulator prtT, a product encoded by the gene hdfB, a non-ribosomal peptide synthase npsE, amylase amyC if compared to a parent host cell and measured under the same conditions.

A further preferred host cell according to the present invention comprises a deficiency in the production of glaA, PepA, acid stable alpha-amylase (amyA), neutral alpha-amylase amyBI and amyBII, a product encoded by the gene hdfA, oxalic acid hydrolase (oahA) and optionally at least another product selected from the group consisting of, a toxin, preferably ochratoxin and/or fumonisin, a protease transcriptional regulator prtT, a product encoded by the gene hdfB, a non-ribosomal peptide synthase npsE, amylase amyC if compared to a parent host cell and measured under the same conditions.

A further preferred host cell according to the present invention comprises a deficiency in the production of glaA, PepA, acid stable alpha-amylase (amyA), neutral alpha-amylase amyBI and amyBII, a product encoded by the gene hdfA, oxalic acid hydrolase (oahA), ochratoxin, fumonisin, and optionally at least another product selected from the group consisting of a protease transcriptional regulator prtT, a product encoded by the gene hdfB, a non-ribosomal peptide synthase npsE, amylase amyC if compared to a parent host cell and measured under the same conditions.

A further preferred host cell according to the present invention comprises a deficiency in the production of glaA, PepA, acid stable alpha-amylase (amyA), neutral alpha-amylase amyBI and amyBII, a product encoded by the gene hdfA, oxalic acid hydrolase (oahA), ochratoxin, fumonisin, a protease transcriptional regulator prtT and optionally at least another product selected from the group consisting of a product encoded by the gene hdfB, a non-ribosomal peptide synthase npsE, amylase amyC if compared to a parent host cell and measured under the same conditions.

A further preferred host cell according to the present invention comprises a deficiency in the production of glaA, PepA, acid stable alpha-amylase (amyA), neutral alpha-amylase amyBI and amyBII, a product encoded by the gene hdfA, oxalic acid hydrolase (oahA), ochratoxin, fumonisin, a protease transcriptional regulator prtT, a non-ribosomal peptide synthase npsE and optionally at least another product selected from the group consisting of a product encoded by the gene hdfB, amylase amyC if compared to a parent host cell and measured under the same conditions.

A further preferred host cell according to the present invention comprises a deficiency in the production of glaA, PepA, acid stable alpha-amylase (amyA), neutral alpha-amylase amyBI and amyBII, a product encoded by the gene hdfA, oxalic acid hydrolase (oahA), ochratoxin, fumonisin, a protease transcriptional regulator prtT, amylase amyC and optionally at least another product selected from the group consisting of a product encoded by the gene hdfB, a non-ribosomal peptide synthase npsE, if compared to a parent host cell and measured under the same conditions.

A further preferred host cell according to the present invention comprises a reduced amylase background and comprises a deficiency in the production of glaA, acid stable alpha-amylase (amyA), neutral alpha-amylase amyBI and amyBII, if compared to a parent host cell and measured under the same conditions. Such host cell preferably also comprises a deficiency in the production of a filamentous fungal homolog of KU70 or KU80. Such host cell preferably also comprises a deficiency in the production of a toxin. Such a host cell preferably also comprises a deficiency in the production of a filamentous fungal homolog of KU70 or KU80 and a deficiency in the production of a toxin.

A further preferred host cell according to the present invention comprises a reduced amylase background and further comprises a deficiency in the production of glaA, acid stable alpha-amylase (amyA), neutral alpha-amylase amyBI, amyBII and amyC if compared to a parent host cell and measured under the same conditions. Such a host cell may preferably also comprises a filamentous fungal homolog of KU70 or KU80. Such host cell preferably also comprises a deficiency in the production of a toxin. Such host cell preferably also comprises a deficiency in the production of a filamentous fungal homolog of KU70 or KU80 and a deficiency in the production of a toxin.

A preferred host cell according to the present invention is a filamentous fungal host cell which comprises a deficiency in the production of glaA and optionally at least another product selected from the group consisting of acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE, amylase amyC, a protein AgsE if compared to a parent host cell and measured under the same conditions.

In one embodiment the host cell according to the present invention comprises a deficiency in the production of glaA, PepA, and optionally at least another product selected from the group consisting of acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, a product encoded by the gene hdfA and/or hdfB, a non-ribosomal peptide synthase npsE, amylase amyC, a protein AgsE if compared to a parent host cell and measured under the same conditions.

In one embodiment the host cell according to the present invention comprises a deficiency in the production of glaA, PepA, acid stable alpha-amylase (amyA) and optionally at least another product selected from the group consisting of neutral alpha-amylase (amyBI and amyBII), oxalic acid hydrolase (oahA), a toxin, preferably ochratoxin and/or fumonisin, a protease transcriptional regulator prtT, a product encoded by the gene hdfA and/or hdfB, a non-ribosomal peptide synthase npsE, amylase amyC, a protein AgsE if compared to a parent host cell and measured under the same conditions.

In one embodiment the host cell according to the present invention comprises a deficiency in the production of glaA, PepA, acid stable alpha-amylase (amyA), neutral alpha-amylase amyBI and optionally at least another product selected from the group consisting of neutral alpha-amylase amyBII, oxalic acid hydrolase (oahA), a toxin, preferably ochratoxin and/or fumonisin, a protease transcriptional regulator prtT, a product encoded by the gene hdfA and/or hdfB, a non-ribosomal peptide synthase npsE, amylase amyC, a protein AgsE if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII and optionally at least another product selected from the group consisting of oxalic acid hydrolase (oahA), a toxin, preferably ochratoxin and/or fumonisin, a protease transcriptional regulator prtT, a product encoded by the gene hdfA and/or hdfB, a non-ribosomal peptide synthase npsE, amylase amyC, a protein AgsE if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA and optionally at least another product selected from the group consisting of oxalic acid hydrolase (oahA), a toxin, preferably ochratoxin and/or fumonisin, a protease transcriptional regulator prtT, a product encoded by the gene hdfB, a non-ribosomal peptide synthase npsE, amylase amyC, a protein AgsE if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, oxalic acid hydrolase (oahA), and optionally at least another product selected from the group consisting of a toxin, preferably ochratoxin and/or fumonisin, a protease transcriptional regulator prtT, a product encoded by the gene hdfB, a non-ribosomal peptide synthase npsE, amylase amyC, a protein AgsE if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, oxalic acid hydrolase (oahA), a protein AgsE and optionally at least another product selected from the group consisting of a toxin, preferably ochratoxin and/or fumonisin, a protease transcriptional regulator prtT, a product encoded by the gene hdfB, a non-ribosomal peptide synthase npsE, amylase amyC, if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, oxalic acid hydrolase (oahA), a protein AgsE, a toxin, preferably ochratoxin and/or fumonisin, and optionally at least another product selected from the group consisting of a protease transcriptional regulator prtT, a product encoded by the gene hdfB, a non-ribosomal peptide synthase npsE, amylase amyC, if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, oxalic acid hydrolase (oahA), a protein AgsE, a toxin, preferably ochratoxin and/or fumonisin, amylase amyC, and optionally at least another product selected from the group consisting of a protease transcriptional regulator prtT, a product encoded by the gene hdfB, a non-ribosomal peptide synthase npsE, if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, a toxin, preferably ochratoxin and/or fumonisin, and optionally at least another product selected from the group consisting of oxalic acid hydrolase (oahA), a protease transcriptional regulator prtT, a product encoded by the gene hdfB, a non-ribosomal peptide synthase npsE, amylase amyC, a protein AgsE if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, a toxin, preferably ochratoxin and/or fumonisin, amylase amyC, and optionally at least another product selected from the group consisting of oxalic acid hydrolase (oahA), a protease transcriptional regulator prtT, a product encoded by the gene hdfB, a non-ribosomal peptide synthase npsE, a protein AgsE if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, a toxin, preferably ochratoxin and/or fumonisin, a non-ribosomal peptide synthase npsE, and optionally at least another product selected from the group consisting of oxalic acid hydrolase (oahA), a protease transcriptional regulator prtT, a product encoded by the gene hdfB, amylase amyC, a protein AgsE if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, a toxin, preferably ochratoxin and/or fumonisin, a protein AgsE, and optionally at least another product selected from the group consisting of oxalic acid hydrolase (oahA), a protease transcriptional regulator prtT, a product encoded by the gene hdfB, a non-ribosomal peptide synthase npsE, amylase amyC, if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, a toxin, preferably ochratoxin and/or fumonisin, a protein AgsE, amylase amyC, and optionally at least another product selected from the group consisting of oxalic acid hydrolase (oahA), a protease transcriptional regulator prtT, a product encoded by the gene hdfB, a non-ribosomal peptide synthase npsE, if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, a toxin, preferably ochratoxin and/or fumonisin, a protein AgsE, a non-ribosomal peptide synthase npsE, and optionally at least another product selected from the group consisting of oxalic acid hydrolase (oahA), a protease transcriptional regulator prtT, a product encoded by the gene hdfB, amylase amyC, if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, a toxin, preferably ochratoxin and/or fumonisin, amylase amyC, a non-ribosomal peptide synthase npsE, and optionally at least another product selected from the group consisting of oxalic acid hydrolase (oahA), a protease transcriptional regulator prtT, a protein AgsE, a product encoded by the gene hdfB, if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, a toxin, preferably ochratoxin and/or fumonisin, a protein AgsE, amylase amyC, a non-ribosomal peptide synthase npsE, and optionally at least another product selected from the group consisting of oxalic acid hydrolase (oahA), a protease transcriptional regulator prtT, a product encoded by the gene hdfB, if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, a toxin, preferably ochratoxin and/or fumonisin, oxalic acid hydrolase (oahA), and optionally at least another product selected from the group consisting of a protease transcriptional regulator prtT, a product encoded by the gene hdfB, a non-ribosomal peptide synthase npsE, amylase amyC, a protein AgsE if compared to a parent host cell and measured under the same conditions.

In one embodiment the host cell according to the present invention comprises a deficiency in the production of glaA, PepA, acid stable alpha-amylase (amyA), neutral alpha-amylase amyBI and amyBII, a product encoded by the gene hdfA, a toxin, preferably ochratoxin and/or fumonisin, oxalic acid hydrolase (oahA), a non-ribosomal peptide synthase npsE, and optionally at least another product selected from the group consisting of a protease transcriptional regulator prtT, a product encoded by the gene hdfB, amylase amyC, a protein AgsE if compared to a parent host cell and measured under the same conditions.

A further preferred host cell according to the present invention comprises a reduced alpha-amylase background and comprises a deficiency in the production of acid stable alpha-amylase (amyA), neutral alpha-amylase amyBI and amyBII and, optionally, amyC if compared to a parent host cell and measured under the same conditions. Such host cell preferably also comprises a filamentous fungal homolog of KU70 or KU80. Such host cell preferably also comprise a deficiency in the production of a toxin. Such host cell preferably also comprises a deficiency in the production of a filamentous fungal homolog of KU70 or KU80 and a deficiency in the production of a toxin.

When a host cell according to the present invention is a filamentous fungal host cell, the host cell preferably further comprises at least two substantially homologous DNA domains suitable for integration of one or more copies of a polynucleotide according to the present invention or of a polynucleotide encoding a compound of interest, wherein at least one of the at least two substantially homologous DNA domains is adapted to have enhanced integration preference for the polynucleotide encoding a compound of interest compared to the substantially homologous DNA domain it originates from, and wherein the substantially homologous DNA domain where the adapted substantially homologous DNA domain originates from has a gene conversion frequency that is at least 10% higher than one of the other of the at least two substantially homologous DNA domains. Such host cells have extensively been described in WO2011/009700. Strains containing two or more copies of these substantially homologous DNA domains are also referred herein as strain containing two or more amplicons. Examples of host cells comprising such amplicons are inter alia described in van Dijck et al, 2003, Regulatory Toxicology and Pharmacology 28; 27-35: On the safety of a new generation of DSM *Aspergillus niger* enzyme production strains. In van Dijck et al, an *Aspergillus niger* strain is described that comprises 7 amplified glucoamylase gene loci, i.e. 7 amplicons. Preferred host cells according to the present invention are filamentous fungus host cells, preferably *A. niger* host cells, comprising two or more amplicons, preferably two or more ΔglaA amplicons, more preferably comprising 2, 3, 4, 5, 6, 7 ΔglaA amplicons, wherein the amplicon which has the highest frequency of gene conversion has been adapted to have enhanced integration preference for the polynucleotide according to the present invention or the polynucleotide encoding a compound of interest, compared to the amplicon it originates from. Adaptation of the amplicon can be performed according to any one of the methods described in WO2011/009700 (which is here fully incorporated by reference). Host cells comprising two or more amplicons wherein one amplicon has been adapted to have enhanced integration preference for a polynucleotide encoding a compound of interest compared to the amplicon it originates from are herein referred as host cells comprising an adapted amplicon. Preferred host cells with adapted amplicons, described in WO2011/009700, are host cells comprising three ΔglaA amplicons being a BamHI truncated amplicon, a SalI truncated amplicon and a BglII truncated amplicon and wherein the BamHI amplicon has been adapted to have enhanced integration preference for a polynucleotide according to the present invention or polynucleotide encoding a compound of interest, compared to the BamHI amplicon it originates from.

When a host cell according to the present invention is a filamentous fungal host cell, the host cell according to the present invention preferably further comprises a modification of Sec61. A preferred SEC61 modification is a modification which results in a one-way mutant of SEC61; i.e. a mutant wherein the de novo synthesized protein can enter the ER via SEC61, but the protein cannot leave the ER via SEC61. Such modifications are extensively described in WO2005/123763. In a preferred embodiment the mutant microbial host cell comprises a modification in a Sec61 as depicted in SEQ ID NO: 3 of WO2005/123763. Most preferably, the SEC 61 modification is the S376W mutation in which Serine 376 is replaced by Tryptophan in SEQ ID NO: 3 of WO2005/123763.

In the embodiments of the invention, the host cell may be an algae, a microalgae or a marine eukaryote. The host cell may be a Labyrinthulomycetes host cell, preferably of the order Thraustochytriales, more preferably of the family Thraustochytriaceae, more preferably a member of a genus selected from the group consisting of *Aurantiochytrium, Oblongichytrium, Schizochytrium, Thraustochytrium*, and *Ulkenia*, even more preferably *Schizochytrium* sp. ATCC #20888.

A modification, preferably in the genome, is construed herein as one or more modifications. A modification, preferably in the genome of a host cell according to the present invention, can either be effected by
  a) subjecting a parent host cell to recombinant genetic manipulation techniques; and/or
  b) subjecting a parent host cell to (classical) mutagenesis; and/or
  c) subjecting a parent host cell to an inhibiting compound or composition. Modification of a genome of a host cell is herein defined as any event resulting in a change in a polynucleotide sequence in the genome of the host cell.

Preferably, a host cell according to the present invention has a modification, preferably in its genome which results in a reduced or no production of an undesired compound as defined herein if compared to the parent host cell that has not been modified, when analysed under the same conditions.

A modification can be introduced by any means known to the person skilled in the art, such as but not limited to classical strain improvement, random mutagenesis followed by selection. Modification can also be introduced by site-directed mutagenesis.

Modification may be accomplished by the introduction (insertion), substitution (replacement) or removal (deletion) of one or more nucleotides in a polynucleotide sequence. A full or partial deletion of a polynucleotide coding for an undesired compound such as a polypeptide may be achieved. An undesired compound may be any undesired compound listed elsewhere herein; it may also be a protein and/or enzyme in a biological pathway of the synthesis of an undesired compound such as a metabolite. Alternatively, a polynucleotide coding for said undesired compound may be partially or fully replaced with a polynucleotide sequence which does not code for said undesired compound or that codes for a partially or fully inactive form of said undesired compound. In another alternative, one or more nucleotides can be inserted into the polynucleotide encoding said undesired compound resulting in the disruption of said polynucleotide and consequent partial or full inactivation of said undesired compound encoded by the disrupted polynucleotide.

In one embodiment the mutant microbial host cell according to the invention comprises a modification in its genome selected from
  a) a full or partial deletion of a polynucleotide encoding an undesired compound,
  b) a full or partial replacement of a polynucleotide encoding an undesired compound with a polynucleotide sequence which does not code for said undesired compound or that codes for a partially or fully inactive form of said undesired compound.
  c) a disruption of a polynucleotide encoding an undesired compound by the insertion of one or more nucleotides in the polynucleotide sequence and consequent partial or full inactivation of said undesired compound by the disrupted polynucleotide.

This modification may for example be in a coding sequence or a regulatory element required for the transcription or translation of said undesired compound. For example, nucleotides may be inserted or removed so as to result in the introduction of a stop codon, the removal of a start codon or a change or a frame-shift of the open reading frame of a coding sequence. The modification of a coding sequence or a regulatory element thereof may be accomplished by site-directed or random mutagenesis, DNA shuffling methods, DNA reassembly methods, gene synthesis (see for example Young and Dong, (2004), Nucleic Acids Research 32, (7) electronic access http://nar.oupjournals.org/cgi/reprint/32/7/e59 or Gupta et al. (1968), *Proc. Natl. Acad. Sci USA,* 60: 1338-1344; Scarpulla et al. (1982), *Anal. Biochem.* 121: 356-365; Stemmer et al. (1995), *Gene* 164: 49-53), or PCR generated mutagenesis in accordance with methods known in the art. Examples of random mutagenesis procedures are well known in the art, such as for example chemical (NTG for example) mutagenesis or physical (UV for example) mutagenesis. Examples of site-directed mutagenesis procedures are the QuickChange™ site-directed mutagenesis kit (Stratagene Cloning Systems, La Jolla, Calif.), the 'The Altered Sites® II in vitro Mutagenesis Systems' (Promega Corporation) or by overlap extension using PCR as described in Gene. 1989 Apr. 15; 77(1):51-9. (Ho S N, Hunt H D, Horton R M, Pullen J K, Pease L R "Site-directed mutagenesis by overlap extension using the polymerase chain reaction") or using PCR as described in *Molecular Biology: Current Innovations and Future Trends.* (Eds. A. M. Griffin and H. G. Griffin. ISBN 1-898486-01-8; 1995 Horizon Scientific Press, PO Box 1, Wymondham, Norfolk, U.K.).

Preferred methods of modification are based on recombinant genetic manipulation techniques such as partial or complete gene replacement or partial or complete gene deletion.

For example, in case of replacement of a polynucleotide, nucleic acid construct or expression cassette, an appropriate DNA sequence may be introduced at the target locus to be replaced. The appropriate DNA sequence is preferably present on a cloning vector. Preferred integrative cloning vectors comprise a DNA fragment, which is homologous to the polynucleotide and/or has homology to the polynucleotides flanking the locus to be replaced for targeting the integration of the cloning vector to this pre-determined locus. In order to promote targeted integration, the cloning vector is preferably linearized prior to transformation of the cell. Preferably, linearization is performed such that at least one but preferably either end of the cloning vector is flanked by sequences homologous to the DNA sequence (or flanking sequences) to be replaced. This process is called homologous recombination and this technique may also be used in order to achieve (partial) gene deletion.

For example a polynucleotide corresponding to the endogenous polynucleotide may be replaced by a defective polynucleotide; that is a polynucleotide that fails to produce a (fully functional) polypeptide. By homologous recombination, the defective polynucleotide replaces the endogenous polynucleotide. It may be desirable that the defective polynucleotide also encodes a marker, which may be used for selection of transformants in which the nucleic acid sequence has been modified. Alternatively or in combination with other mentioned techniques, a technique based on recombination of cosmids in an *E. coli* cell can be used, as described in: A rapid method for efficient gene replacement in the filamentous fungus *Aspergillus nidulans* (2000) Chaveroche, M-K., Ghico, J-M. and d'Enfert C; Nucleic acids Research, vol 28, no 22.

Alternatively, modification, wherein said host cell produces less of or no protein such as the polypeptide having amylase activity, preferably α-amylase activity as described herein and encoded by a polynucleotide as described herein, may be performed by established anti-sense techniques using a nucleotide sequence complementary to the nucleic acid sequence of the polynucleotide. More specifically, expression of the polynucleotide by a host cell may be reduced or eliminated by introducing a nucleotide sequence complementary to the nucleic acid sequence of the polynucleotide, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. An example of expressing an antisense-RNA is shown in Appl. Environ. Microbiol. 2000 February; 66(2):775-82. (Characterization of a foldase, protein disulfide isomerase A, in the protein secretory pathway of *Aspergillus niger*. Ngiam C, Jeenes D J, Punt P J, Van Den Hondel C A, Archer D B) or (Zrenner R, Willmitzer L, Sonnewald U. Analysis of the expression of potato uridinediphosphate-glucose pyrophosphorylase and its inhibition by antisense RNA. Planta. (1993); 190(2):247-52.).

A modification resulting in reduced or no production of undesired compound is preferably due to a reduced production of the mRNA encoding said undesired compound if compared with a parent microbial host cell which has not been modified and when measured under the same conditions. A modification which results in a reduced amount of the mRNA transcribed from the polynucleotide encoding the undesired compound may be obtained via the RNA interference (RNAi) technique (Mouyna et al., 2004). In this method identical sense and antisense parts of the nucleotide sequence, which expression is to be affected, are cloned behind each other with a nucleotide spacer in between, and inserted into an expression vector. After such a molecule is transcribed, formation of small nucleotide fragments will lead to a targeted degradation of the mRNA, which is to be affected. The elimination of the specific mRNA can be to various extents. The RNA interference techniques described in WO2008/053019, WO2005/05672A1, WO2005/026356A1, Oliveira et al.; Crook et al., 2014; and/or Barnes et al., may be used at this purpose.

A modification which results in decreased or no production of an undesired compound can be obtained by different methods, for example by an antibody directed against such undesired compound or a chemical inhibitor or a protein inhibitor or a physical inhibitor (Tour O. et al, (2003) Nat. Biotech: Genetically targeted chromophore-assisted light inactivation. Vol. 21. no. 12:1505-1508) or peptide inhibitor or an anti-sense molecule or RNAi molecule (R. S. Kamath_et al, (2003) Nature: Systematic functional analysis of the *Caenorhabditis elegans* genome using RNAi. Vol. 421, 231-237).

In addition of the above-mentioned techniques or as an alternative, it is also possible to inhibiting the activity of an undesired compound, or to re-localize the undesired compound such as a protein by means of alternative signal sequences (Ramon de Lucas, J., Martinez O, Perez P., Isabel Lopez, M., Valenciano, S. and Laborda, F. The *Aspergillus nidulans* carnitine carrier encoded by the acuH gene is exclusively located in the mitochondria. FEMS Microbiol Lett. 2001 Jul. 24; 201(2):193-8.) or retention signals (Derkx, P. M. and Madrid, S. M. The foldase CYPB is a component of the secretory pathway of *Aspergillus niger* and contains the endoplasmic reticulum retention signal HEEL. Mol. Genet. Genomics. 2001 December; 266(4): 537-545), or by targeting an undesired compound such as a polypeptide to a peroxisome which is capable of fusing with a membrane-structure of the cell involved in the secretory pathway of the cell, leading to secretion outside the cell of the polypeptide (e.g. as described in WO2006/040340).

Alternatively or in combination with above-mentioned techniques, decreased or no production of an undesired compound can also be obtained, e.g. by UV or chemical mutagenesis (Mattern, I. E., van Noort J. M., van den Berg, P., Archer, D. B., Roberts, I. N. and van den Hondel, C. A., Isolation and characterization of mutants of *Aspergillus niger* deficient in extracellular proteases. Mol Gen Genet. 1992 August; 234(2):332-6.) or by the use of inhibitors inhibiting enzymatic activity of an undesired polypeptide as described herein (e.g. nojirimycin, which function as inhibitor for β-glucosidases (Carrel F. L. Y. and Canevascini G. *Canadian Journal of Microbiology* (1991) 37(6): 459-464; Reese E. T., Parrish F. W. and Ettlinger M. *Carbohydrate Research* (1971) 381-388)).

In an embodiment of the present invention, the modification in the genome of the host cell according to the invention is a modification in at least one position of a polynucleotide encoding an undesired compound.

A deficiency of a cell in the production of a compound, for example of an undesired compound such as an undesired polypeptide and/or enzyme is herein defined as a mutant microbial host cell which has been modified, preferably in its genome, to result in a phenotypic feature wherein the cell: a) produces less of the undesired compound or produces substantially none of the undesired compound and/or b) produces the undesired compound having a decreased activity or decreased specific activity or the undesired compound having no activity or no specific activity and combinations of one or more of these possibilities as compared to the parent host cell that has not been modified, when analysed under the same conditions.

Preferably, a modified host cell according to the present invention produces 1% less of the un-desired compound if compared with the parent host cell which has not been modified and measured under the same conditions, at least 5% less of the un-desired compound, at least 10% less of the un-desired compound, at least 20% less of the un-desired compound, at least 30% less of the un-desired compound, at least 40% less of the un-desired compound, at least 50% less of the un-desired compound, at least 60% less of the un-desired compound, at least 70% less of the un-desired compound, at least 80% less of the un-desired compound, at least 90% less of the un-desired compound, at least 91% less of the un-desired compound, at least 92% less of the un-desired compound, at least 93% less of the un-desired compound, at least 94% less of the un-desired compound, at least 95% less of the un-desired compound, at least 96% less of the un-desired compound, at least 97% less of the un-desired compound, at least 98% less of the un-desired compound, at least 99% less of the un-desired compound, at least 99.9% less of the un-desired compound, or most preferably 100% less of the un-desired compound.

A reference herein to a patent document or other matter which is given as prior art is not to be taken as an admission that that document or matter was known or that the information it contains was part of the common general knowledge as at the priority date of any of the claims.

The sequence information as provided herein should not be so narrowly construed as to require inclusion of erroneously identified bases. The skilled person is capable of identifying such erroneously identified bases and knows how to correct for such errors.

The disclosure of each reference set forth herein is incorporated herein by reference in its entirety.

The present invention is further illustrated by the following examples:

EXAMPLES

In the following Examples, various embodiments of the invention are illustrated. From the above description and these Examples, one skilled in the art can make various changes and modifications of the disclosure to adapt it to various usages and conditions.

In the context of the present invention OMCI is herewith defined as a method that applies single-stranded (ss) oligonucleotide sequences (ODNs) for ssODN-Mediated Construct Integration (OMCI) in a eukaryotic cell. Extensions of the method include amongst others, but are not limited to:

ssODN-mediated construct assembly and integration at a genomic locus in an eukaryotic cell;

ssODN-mediated vector assembly in an eukaryotic cell; ssODN-mediated modification of a eukaryotic cell; ssODN-mediated guide-RNA vector assembly in an eukaryotic cell;

ssODN-mediated assembly and/or integration of DNA construct, pathway, RNAi or mutagenesis libraries in an eukaryotic cell.

As set forward in the description, OMCI is preferably used together with one or more induced single (DNA-nick) or double-stranded DNA breaks, e.g. induced (or introduced) by transcription activator-like effector nucleases (TALENs, Gaj et al., 2013), zinc finger nucleases (ZFNs, Gaj et al., 2013) meganucleases such as I-SceI (Paques et al., 2007, Stoddard 2011), RNA-guided endonucleases like CRISPR/Cas (Mali et al., 2013; Cong et al., 2013) or Cpf1 (Zetsche et al., 2015) or a DNA-guided nuclease based-system like Argonaute of *Natronobacterium gregoryi* (NgAgo, Gao et al., 2016).

Example 1: ssODN-Mediated Construct Integration (OMCI) in a Cell of a Yellow Fluorescent Protein (YFP) Expression Cassette at a Genomic Locus Using CRISPR/Cas9

This experiment describes the replacement of stretches of genomic DNA in a range from about 0-10 kbp by an YFP expression cassette (Nagai et al., 2002) using a CRISPR/Cas9 system with donor DNA sequences that integrate via homologous recombination. The YFP cassette has 50 basepair (bp) connector sequences at both the 5' and 3' ends (SEQ ID NO: 10). These 50 bp connector sequences share homology with 50 bp of 100 bp flank DNA sequences which flank DNA sequences are added as separate DNA oligonucleotides to the transformation mix. In addition, these 100 bp flanks have 50 bp homology with the genomic locus for the intended stretch of DNA knock-out. This set-up allows for a flexible choice of knock-out design by using short oligonucleotides (here 100 bp) to specify the knock-out, which is visually shown in FIG. 4.

Furthermore, a comparison was made between the use of flanks in the form of double-stranded DNA (dsDNA) (FIG. 4 B) and flanks in the form of single-stranded oligodeoxynucleotides (ssODNs) (FIG. 4 C) for recombination in a cell and integration of the YFP expression cassette. The experimental design with 32 transformations is outlined in Table 1 and Table 2. A1, A2, B1, B2, C1, C2, D1 and D2 are 8 subsets of experiments. In each subset 4 transformations are performed to replace, 0, 1, 3, 10 kbp, respectively, around the CRISPR/Cas9 induced double-stranded break at the genomic DNA, respectively.

For the expression of gRNA sequences in *S. cerevisiae*, a gRNA expression cassette with control elements as previously described by DiCarlo et al., 2013 was used. The gRNA expression cassette comprises the SNR52 promoter, the gRNA sequence consisting of the guide-sequence or genomic target sequence, and the guide RNA structural component, followed by the SUP4 terminator.

Figure 1:
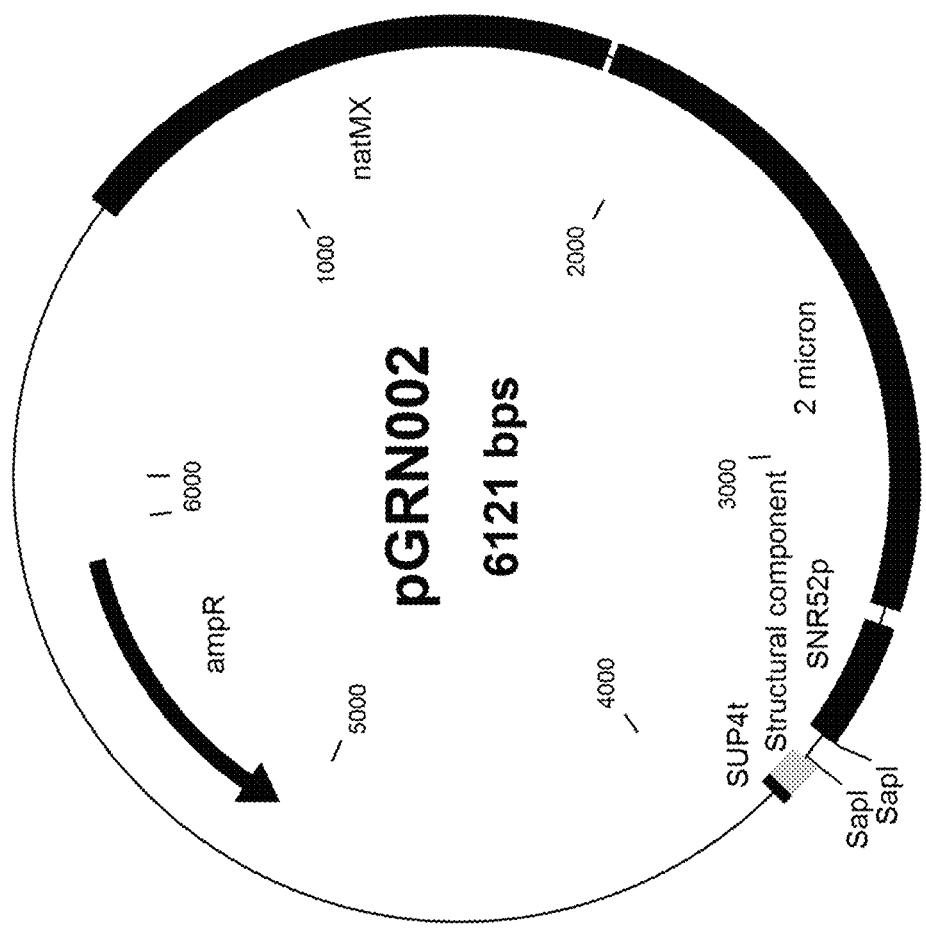
FIG. 1 depicts a vector map of multi copy (2 micron) vector pGRN002, containing a guide RNA expression cassette in which the genomic target can be cloned/assembled by making use of the SapI sites. A NatMX (nourseothricin) resistance marker is present on the vector.
Figure 2:
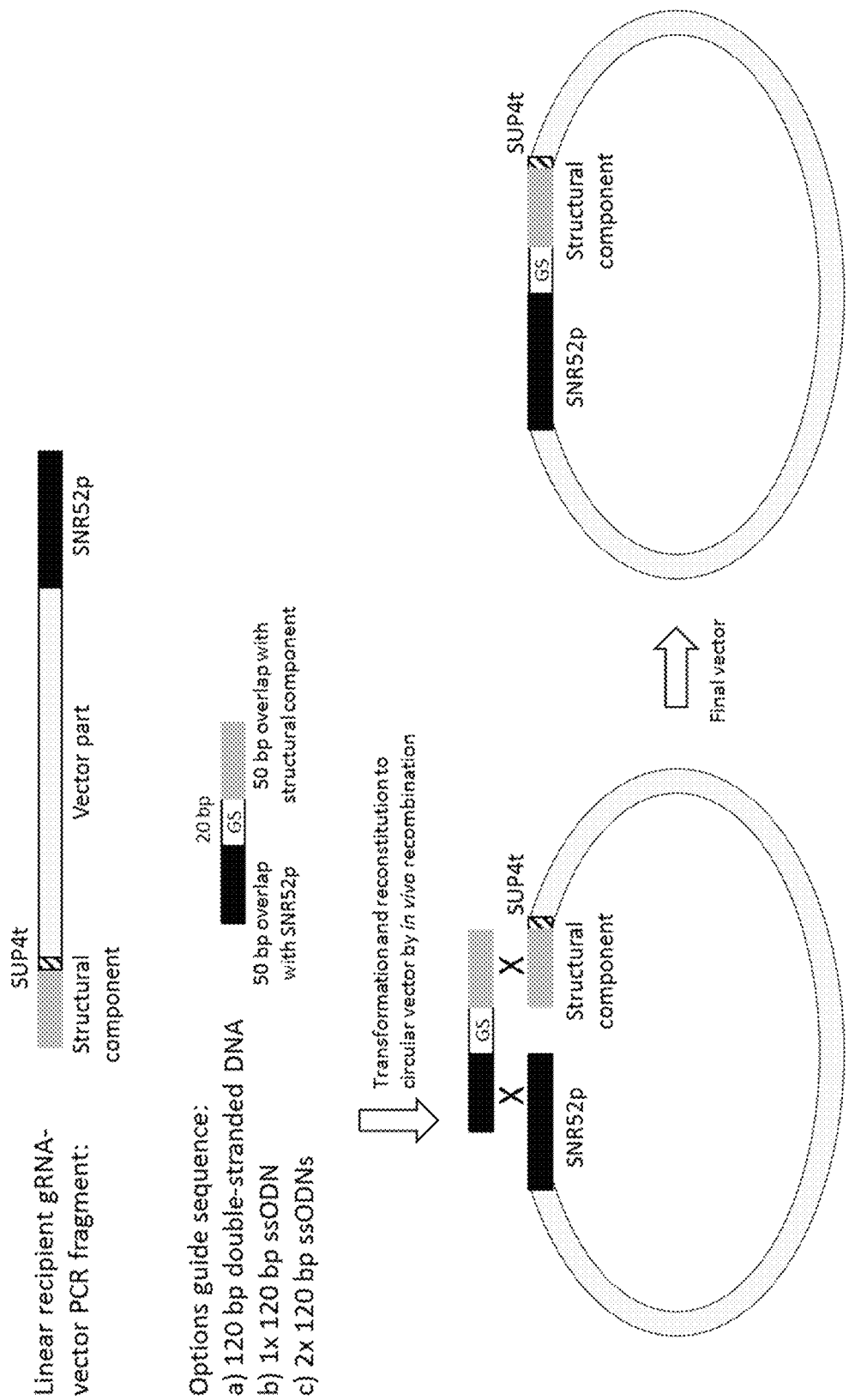
FIG. 2 describes three approaches to obtain a functional guide RNA expression vector in S. cerevisiae. A so-called linear recipient gRNA-vector PCR fragment (SEQ ID NO: 8) was obtained by PCR using multicopy yeast vector pRN1120, in which a SapI site was removed (SEQ ID NO: 5), as template in the PCR reaction. The linear recipient gRNA-vector PCR fragment consists of the following DNA elements: guide RNA structural component, SUP4 terminator, pRN1120 vector part (including 2 micron element and NatMX marker), SNR52 promoter. To obtain a circular expression vector in yeast by in vivo recombination, allowing selection on a nourseothricin (NatMX) selection marker, the linear recipient gRNA-vector PCR fragment was transformed with fragments as described in a), b) or c) to yield the final vector: a) a 120 bp double-stranded DNA fragment, obtained by annealing two single-stranded complementary oligodeoxynucleotides (ssODNs) prior to transformation. The double-stranded DNA fragment has 50 base pairs (bp) overlap with the SNR52p, a 20 nucleotide (nt) guide polynucleotide sequence (GS), 50 bp complementarity (sequence identity) with the gRNA structural component; b) one ssODN which has 50 bp complementarity (sequence identity) with the SNR52p, a 20 nt guide polynucleotide sequence (GS), 50 bp complementarity (sequence identity) with the gRNA structural component; c) two ssODNs which have 50 bp complementarity (sequence identity) with the SNR52p, a 20 nt guide polynucleotide sequence (GS), 50 bp complementarity (sequence identity) with the gRNA structural component and are complementary to each other. Using approaches a, b, or c a functional guide RNA will be produced in the cell.

In these transformations, also the vector expressing the guide RNA for the CRISPR/Cas9 system was created by assembly in a cell, either by a 120 bp double-stranded DNA containing the 20 bp guide sequence and 2×50 bp sequences to allow for vector assembly in a cell, or by one (lower strand) or two (upper and lower strand) 120 bp ssODNs containing the 20 bp guide sequence and 2×50 bp sequences to allow vector assembly in a cell, that after correct assembly into a linear recipient gRNA-vector PCR fragment, which is described below, form a functional gRNA expression cassette that is part of the resulting circular vector, as schematically depicted in FIG. 2.

Linear Recipient gRNA-Vector PCR Fragment Used for Assembly in a Cell of a Guide Sequence Resulting in a Circular Vector The linear recipient gRNA-vector PCR fragment was obtained as follows: Vector pRN1120 (SEQ ID NO: 1) is a yeast multi-copy vector (2 micron) that contains a functional NatMX marker cassette conferring resistance against nourseothricin. The backbone of this vector is based on pRS305 (Sikorski and Hieter, 1989), including a functional 2 micron ORI sequence and a functional NatMX (nourseothricin resistance) marker cassette (see http://www.euroscarf.de). The SapI restriction site was removed from the pRN1120 backbone by PCR using the primers set out in SEQ ID NO: 2 and SEQ ID NO: 3, changing the SapI restriction site from GCTCTTC to cCTCTTC. Recircularization of the intermediate PCR fragment without a SapI site was performed using the KLD enzyme mix of the Q5 site directed mutagenesis kit (New England Biolabs, supplied by Bioké, Leiden, the Netherlands. Cat no. E0554S) according to the supplier's manual. The resulting vector was digested by EcoRI and XhoI. By Gibson assembly, a gBlock containing amongst others a SNR52 promoter, a guide RNA structural component and a SUP4 terminator sequence (Integrated DNA Technologies, Leuven, Belgium), for which the sequence is provided in SEQ ID NO: 4, was added to the pRN1120-SapI backbone. Gibson assembly was performed using Gibson Assembly HiFi 1 Step Kit (SGI-DNA, La Jolla, Calif., USA. Cat no. GA1100-50) according to supplier's manual. The resulting vector was designated pGRN002 (SEQ ID NO: 5, FIG. 1), containing a SNR52 promoter, a guide RNA structural component and a SUP4 terminator sequence in which the guide sequence can be cloned or assembled, for example by making use of the SapI sites and/or recombination in a cell.

Vector pGRN002 was used as template in a PCR reaction using forward primer (SEQ ID NO: 6) and reverse primer (SEQ ID NO: 7), resulting in the linear recipient gRNA-vector PCR fragment (SEQ ID NO: 8, FIG. 2). KAPA DNA polymerase in combination with the HiFi Hotstart Ready Mix (Kapa Biosystems, supplied by VWR, Amsterdam, the Netherlands, Cat.no. KK2602) was used in the PCR reactions. The PCR reaction was performed according to manufacturer's instructions. The PCR fragment was purified using the NucleoSpin Gel and PCR Clean-up kit (Machery-Nagel, distributed by Bioké, Leiden, the Netherlands) according to manufacturer's instructions.

Assembly of the Guide Sequence in the Cell

Upon transformation to yeast, the linear recipient gRNA-vector PCR fragment containing a partial gRNA expression cassette was used for assembly in the cell of the guide sequence insert that is part of a linear DNA insert sequence comprising the 20 bp guide sequence to form a functional guide RNA expression cassette (as depicted in FIG. 2). Three different approaches to supply the linear guide sequence insert were used in this example:

a) A 120 bp double-stranded DNA sequence consisting of
  a. 50 bp homology region with the 5'-terminus of the linear recipient gRNA-vector PCR fragment being the SNR52p, followed by
  b. a 20 bp guide sequence, followed by
  c. a 50 bp homology region with 3'-terminus of the linear recipient gRNA-vector PCR fragment being the structural component of the sgRNA.
b) A ssODN sequence of 120 bp consisting of the same elements a., b. and c. as indicated in a)
c) Two complementary ssODN sequences of 120 bp consisting of the same elements a., b. and c. as indicated in a)

The guide sequence used in this example will guide the CAS9 protein to the INT1 locus in genomic DNA of *S. cerevisiae*. The INT1 integration site is located at the non-coding region between NTR1 (YOR071c) and GYP1 (YOR070c) located on chromosome XV.

Upon transformation and assembly in the cell, the NatMX marker present on the circular vector can be used for selection transformants on nourseothricin. The resulting circular vector contained a functional guide RNA expression cassette, producing a sgRNA that was used to target the CAS9 protein to an intended genomic target site present in genomic DNA of the host.

Construction of a CAS9-Expressing *Saccharomyces cerevisiae* Strain

Figure 3:
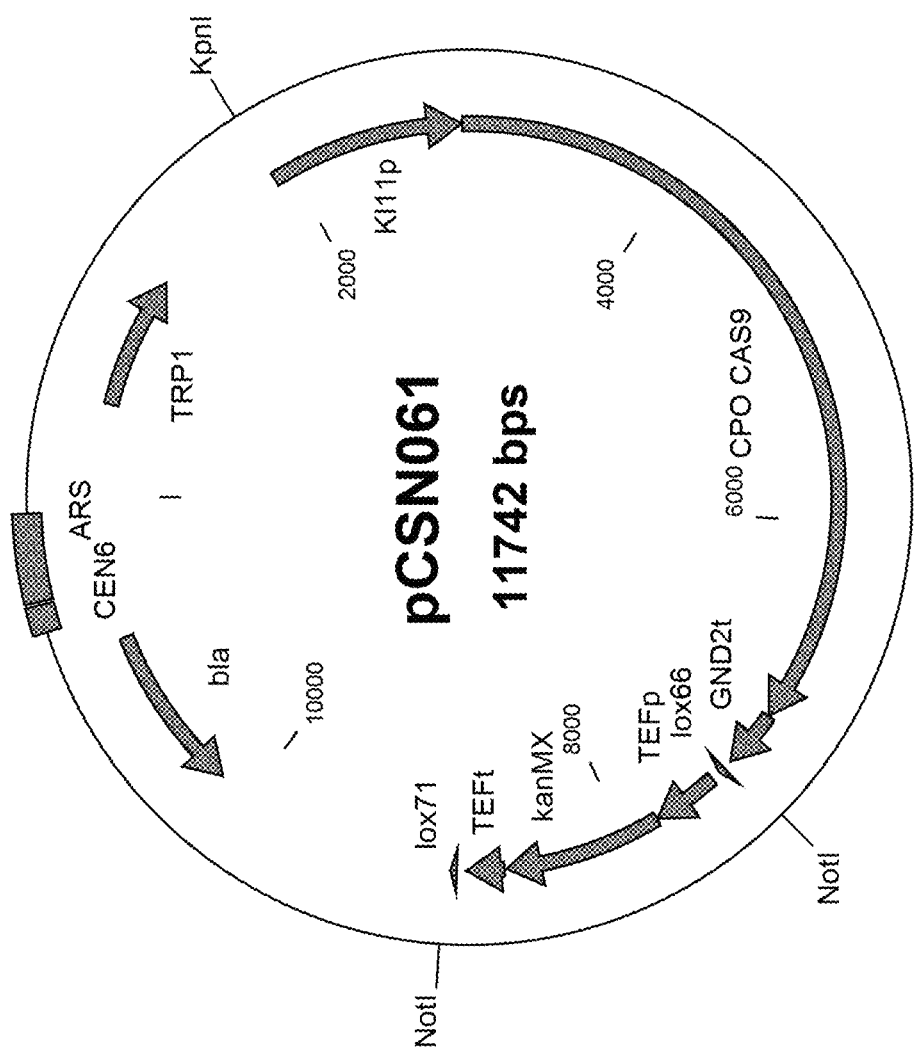
FIG. 3 depicts a vector map of single copy (CEN/ARS) vector pCSN061 expressing CAS9 codon pair optimized for expression in S. cerevisiae. The CAS9 sequence included a nuclear localization signal. A KanMX marker is present on the vector.

Yeast vector pCSN061 is a single copy vector (CEN/ARS) that contains a CAS9 expression cassette consisting of a CAS9 codon optimized variant expressed from the KI11 promoter (*Kluyveromyces lactis* promoter of KLLA0F20031g) and the *S. cerevisiae* GND2 terminator, and a functional KanMX marker cassette conferring resistance against G418. The CAS9 expression cassette was KpnI/NotI ligated into pRS414 (Sikorski and Hieter, 1989), resulting in intermediate vector pCSN004. Subsequently, a functional expression cassette conferring G418 resistance (see http://www.euroscarf.de) was NotI restricted from vector pUG7-KanMX and NotI ligated into pCSN004, resulting in vector pCSN061 that is depicted in FIG. 3 and the sequence is set out in SEQ ID NO: 9.

The vector pCSN061 containing the CAS9 expression cassette was first transformed to *S. cerevisiae* strain CEN.PKI13-7D (MATa URA3 HIS3 LEU2 TRP1 MAL2-8 SUC2) using the LiAc/salmon sperm (SS) carrier DNA/PEG method (Gietz and Woods, 2002). Strain CEN.PKI13-7D is available from the EUROSCARF collection (http://www.euroscarf.de, Frankfurt, Germany) or from the Centraal Bureau voor Schimmelcultures (Utrecht, the Netherlands, entry number CBS 8340). The origin of the CEN.PK family of strains is described by van Dijken et al., 2000. In the transformation mixture one microgram of vector pCNS061 was used. The transformation mixture was plated on YPD-agar (10 grams per liter of yeast extract, 20 grams per liter of peptone, 20 grams per liter of dextrose, 20 grams per liter of agar) containing 200 microgram (µg) G418 (Sigma Aldrich, Zwijndrecht, the Netherlands) per ml. After two to four days of growth at 30° C. transformants appeared on the transformation plate. A transformant conferring resistance to G418 on the plate, now referred as strain CSN001, was inoculated on YPD-G418 medium (10 grams per liter of yeast extract, 20 grams per liter of peptone, 20 grams per liter of dextrose, 200 μg G418 (Sigma Aldrich, Zwijndrecht, the Netherlands) per ml, was used in subsequent transformation experiments.

Double-Stranded DNA (Ds-DNA) Donor YFP Expression Cassette with 50 bp Connector Flanks A double-stranded donor DNA cassette coding for the Yellow Fluorescent Protein (YFP) variant Venus (Nagai et al., 2002), was prepared via a Golden-Gate assembly reaction of individual promoter (P), orf (O) and terminator (T) sequences in an appropriate E. coli vector. The assembled POT cassette was amplified via a PCR reaction with primers indicated in SEQ ID NO: 11 and SEQ ID NO: 12. In a second PCR, 50 bp connector sequences are added using primer sets indicated in SEQ ID NO: 13 and SEQ ID NO: 14. This resulted in an YFP expression cassette that included 50 bp connector sequences at the 5' and 3' ends of the expression cassette (SEQ ID NO: 10, FIG. 4A). The Q5 DNA polymerase (part of the Q5® High-Fidelity 2× Master Mix, New England Biolabs, supplied by Bioké, Leiden, the Netherlands. Cat no. M0492S) was used in the PCR reaction, which was performed according to manufacturer's instructions. The PCR fragment was purified using the NucleoSpin Gel and PCR Clean-up kit (Machery-Nagel, distributed by Bioké, Leiden, the Netherlands) according to manufacturer's instructions.

100 bp Knock-Out Flanks DNA Sequences

Figure 4:
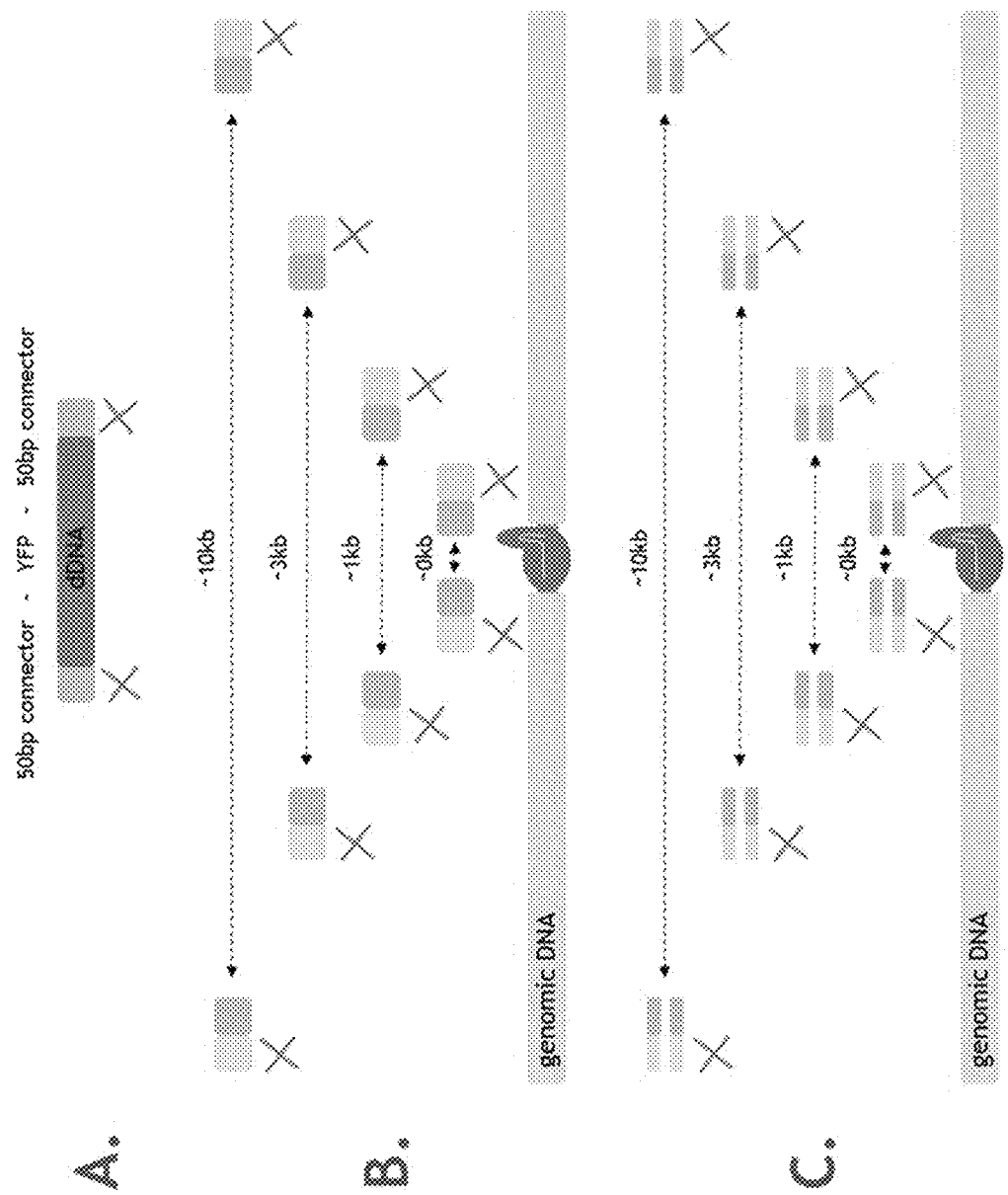
FIG. 4 depicts the knock-out/YFP knock-in approach of Example 1. (A). depicts the double-stranded (DS) expression cassette with the Yellow Fluorescent Protein (Venus) donor DNA: connector 5'-THD3p-YFP (Venus)-ENO1t-connector 3' (SEQ ID NO: 10); (B) schematically visualizes the ~0, ~1, ~3, ~10 kbp knockout using flexible knock-out/knock-in ds-DNA flanks; (C) schematically visualizes the ~0, ~1, ~3, ~10 kbp knockout using flexible knock-out/knock-in ssODN flanks, here as complementary ssODN pairs.

Together with the ds-DNA YFP expression cassette containing 50 bp connector flanks, so-called knock-out (k.o.) flanks of 100 bp were supplied in the transformation experiments to specify the k.o. target. These left k.o. flank (LF) and right k.o. flank (RF) sequences have 50 bp homology with the 5'-terminus and 3'-terminus of the ds-DNA YFP expression cassette, and 50 bp homology with the left and right sequence of k.o. genomic deletion stretch, respectively (FIG. 4). In this experiment, the left flank (LF) and right flank (RF) sequences were used in the transformations to replace stretches of 0, 1, 3 and 10 kb genomic DNA, respectively, at the INT1 locus by the YFP ds-DNA expression cassette.

Yeast Transformation Experiments

Strain CSN001 which is pre-expressing CAS9, was transformed using the LiAc/salmon sperm (SS) carrier DNA/PEG method (Gietz and Woods, 2002). An overview of all transformation experiments of Example 1 is shown in Table 1 and Table 2. The experimental set ups are depicted in FIG. 5 A1-A 2, 5 B1-B2, 5 C1-C2, 5 D1-D2. In each transformation experiment, 100 ng of the linear recipient gRNA-vector PCR fragment, 100 ng of the ds-DNA YFP expression cassette containing 50 bp connector flank sequences at the 5' and 3' end of the sequence and the specific amount of 120 bp gRNA insert oligonucleotides (ds-DNA or ssODN(s)), 100 bp ssODNs flank sequences or 100 bp ds-DNA flank sequences as indicated in Table 1 was included.

The transformation mixtures were plated on YPD-agar (10 grams per liter of yeast extract, 20 grams per liter of peptone, 20 grams per liter of dextrose, 20 grams per liter of agar) containing 200 μg nourseothricin (NatMX, Jena Bioscience, Germany) and 200 μg G418 (Sigma Aldrich, Zwijndrecht, the Netherlands) per ml.

TABLE 1

Overview of the amounts of DNA used in the different transformation experiments, here indicated as subsets.

| Subset | ds-DNA[1] gRNA insert (50-20-50) | ssODN[2] gRNA insert (50-20-50) | ds-DNA[1] flanks (50-50) | ssODN[2] flanks (50-50) |
|---|---|---|---|---|
| A1 | 1000 ng | | 2 × 100 ng | |
| A2 | 1000 ng | | 2 × 4 ng | |
| B1 | | 1 × 1000 ng | 2 × 100 ng | |
| B2 | | 2 × 500 ng | 2 × 100 ng | |
| C1 | 1000 ng | | | 2 × 100 ng |
| C2 | 1000 ng | | | 4 × 50 ng |
| D1 | 1000 ng * | | 2 × 100 ng * | |
| D2 | | 2 × 500 ng | | 4 × 50 ng |

[1]The ssODNs were pre-annealed to form a double-stranded DNA (ds-DNA) and added to the transformation.
[2]The ssODNs were directly added in the transformation (no pre-annealing).
* Six ssODNs (two gRNA insert ODNs, four ssODN flanks) were pre-annealed in one reaction and added to the transformation. For the ds-DNA or ssODN gRNA insert (50-20-50) means 50 bp complementarity (sequence identity) with the linear recipient gRNA-vector PCR fragment (SEQ ID NO: 8, FIG. 2)-20 bp guide sequence-50 bp complementarity (sequence identity) with the recipient linear gRNA-vector PCR fragment. ds-DNA/ssODN flanks (50-50) means 50 bp complementarity (sequence identity) with the left flank integration site in genomic DNA and the 50 bp connector sequence at the 5'terminus of the donor DNA, or 50 bp complementarity (sequence identity) with the connector sequence at the 3'-terminus of the donor DNA and 50 bp complementarity (sequence identity) with the right flank integration site in genomic DNA.

TABLE 2

Overview of different subsets of transformation experiments.

| Subset | Deletion in kbp | ds-DNA[1] gRNA insert (50-20-50) | ssODN[2] gRNA insert (50-20-50) | ds-DNA[1] flanks (50-50) | ssODN[2] flanks (50-50) |
|---|---|---|---|---|---|
| A1 | 0 | SEQ ID NO: 15<br>SEQ ID NO: 16 | | SEQ ID NO: 23<br>SEQ ID NO: 24<br>SEQ ID NO: 25<br>SEQ ID NO: 26 | |
| A1 | 1 | SEQ ID NO: 15<br>SEQ ID NO: 16 | | SEQ ID NO: 21<br>SEQ ID NO: 22<br>SEQ ID NO: 27<br>SEQ ID NO: 28 | |
| A1 | 3 | SEQ ID NO: 15<br>SEQ ID NO: 16 | | SEQ ID NO: 19<br>SEQ ID NO: 20<br>SEQ ID NO: 29<br>SEQ ID NO: 30 | |
| A1 | 10 | SEQ ID NO: 15<br>SEQ ID NO: 16 | | SEQ ID NO: 17<br>SEQ ID NO: 18<br>SEQ ID NO: 31<br>SEQ ID NO: 32 | |
| A2 | 0 | SEQ ID NO: 15<br>SEQ ID NO: 16 | | SEQ ID NO: 23<br>SEQ ID NO: 24<br>SEQ ID NO: 25<br>SEQ ID NO: 26 | |

TABLE 2-continued

Overview of different subsets of transformation experiments.

| Subset | Deletion in kbp | ds-DNA[1] gRNA insert (50-20-50) | ssODN[2] gRNA insert (50-20-50) | ds-DNA[1] flanks (50-50) | ssODN[2] flanks (50-50) |
|---|---|---|---|---|---|
| A2 | 1 | *SEQ ID NO: 15*<br>*SEQ ID NO: 16* | | SEQ ID NO: 21<br>SEQ ID NO: 22<br>SEQ ID NO: 27<br>SEQ ID NO: 28 | |
| A2 | 3 | *SEQ ID NO: 15*<br>*SEQ ID NO: 16* | | SEQ ID NO: 19<br>SEQ ID NO: 20<br>SEQ ID NO: 29<br>SEQ ID NO: 30 | |
| A2 | 10 | *SEQ ID NO: 15*<br>*SEQ ID NO: 16* | | SEQ ID NO: 17<br>SEQ ID NO: 18<br>SEQ ID NO: 31<br>SEQ ID NO: 32 | |
| B1 | 0 | | SEQ ID NO: 16 | SEQ ID NO: 23<br>SEQ ID NO: 24<br>SEQ ID NO: 25<br>SEQ ID NO: 26 | |
| B1 | 1 | | SEQ ID NO: 16 | SEQ ID NO: 21<br>SEQ ID NO: 22<br>SEQ ID NO: 27<br>SEQ ID NO: 28 | |
| B1 | 3 | | SEQ ID NO: 16 | SEQ ID NO: 19<br>SEQ ID NO: 20<br>SEQ ID NO: 29<br>SEQ ID NO: 30 | |
| B1 | 10 | | SEQ ID NO: 16 | SEQ ID NO: 17<br>SEQ ID NO: 18<br>SEQ ID NO: 31<br>SEQ ID NO: 32 | |
| B2 | 0 | | SEQ ID NO: 15<br>SEQ ID NO: 16 | SEQ ID NO: 23<br>SEQ ID NO: 24<br>SEQ ID NO: 25<br>SEQ ID NO: 26 | |
| B2 | 1 | | SEQ ID NO: 15<br>SEQ ID NO: 16 | SEQ ID NO: 21<br>SEQ ID NO: 22<br>SEQ ID NO: 27<br>SEQ ID NO: 28 | |
| B2 | 3 | | SEQ ID NO: 15<br>SEQ ID NO: 16 | SEQ ID NO: 19<br>SEQ ID NO: 20<br>SEQ ID NO: 29<br>SEQ ID NO: 30 | |
| B2 | 10 | | SEQ ID NO: 15<br>SEQ ID NO: 16 | SEQ ID NO: 17<br>SEQ ID NO: 18<br>SEQ ID NO: 31<br>SEQ ID NO: 32 | |
| C1 | 0 | *SEQ ID NO: 15*<br>*SEQ ID NO: 16* | | | SEQ ID NO: 24<br>SEQ ID NO: 26 |
| C1 | 1 | *SEQ ID NO: 15*<br>*SEQ ID NO: 16* | | | SEQ ID NO: 22<br>SEQ ID NO: 28 |
| C1 | 3 | *SEQ ID NO: 15*<br>*SEQ ID NO: 16* | | | SEQ ID NO: 19<br>SEQ ID NO: 29 |
| C1 | 10 | *SEQ ID NO: 15*<br>*SEQ ID NO: 16* | | | SEQ ID NO: 17<br>SEQ ID NO: 32 |
| C2 | 0 | *SEQ ID NO: 15*<br>*SEQ ID NO: 16* | | | SEQ ID NO: 23<br>SEQ ID NO: 24<br>SEQ ID NO: 25<br>SEQ ID NO: 26 |
| C2 | 1 | *SEQ ID NO: 15*<br>*SEQ ID NO: 16* | | | SEQ ID NO: 21<br>SEQ ID NO: 22<br>SEQ ID NO: 27<br>SEQ ID NO: 28 |
| C2 | 3 | *SEQ ID NO: 15*<br>*SEQ ID NO: 16* | | | SEQ ID NO: 19<br>SEQ ID NO: 20<br>SEQ ID NO: 29<br>SEQ ID NO: 30 |
| C2 | 10 | *SEQ ID NO: 15*<br>*SEQ ID NO: 16* | | | SEQ ID NO: 17<br>SEQ ID NO: 18<br>SEQ ID NO: 31<br>SEQ ID NO: 32 |
| D1 | 0 | *SEQ ID NO: 15**<br>*SEQ ID NO: 16** | | SEQ ID NO: 23*<br>SEQ ID NO: 24*<br>SEQ ID NO: 25*<br>SEQ ID NO: 26* | |

TABLE 2-continued

Overview of different subsets of transformation experiments.

| Subset | Deletion in kbp | ds-DNA[1] gRNA insert (50-20-50) | ssODN[2] gRNA insert (50-20-50) | ds-DNA[1] flanks (50-50) | ssODN[2] flanks (50-50) |
|---|---|---|---|---|---|
| D1 | 1 | *SEQ ID NO: 15\** *SEQ ID NO: 16\** | | <u>SEQ ID NO: 21\*</u> <u>SEQ ID NO: 22\*</u> SEQ ID NO: 27\* SEQ ID NO: 28\* | |
| D1 | 3 | *SEQ ID NO: 15\** *SEQ ID NO: 16\** | | <u>SEQ ID NO: 19\*</u> <u>SEQ ID NO: 20\*</u> SEQ ID NO: 29\* SEQ ID NO: 30\* | |
| D1 | 10 | *SEQ ID NO: 15\** *SEQ ID NO: 16\** | | <u>SEQ ID NO: 17\*</u> <u>SEQ ID NO: 18\*</u> SEQ ID NO: 31\* SEQ ID NO: 32\* | |
| D2 | 0 | | SEQ ID NO: 15 SEQ ID NO: 16 | | SEQ ID NO: 23 SEQ ID NO: 24 SEQ ID NO: 25 SEQ ID NO: 26 |
| D2 | 1 | | SEQ ID NO: 15 SEQ ID NO: 16 | | SEQ ID NO: 21 SEQ ID NO: 22 SEQ ID NO: 27 SEQ ID NO: 28 |
| D2 | 3 | | SEQ ID NO: 15 SEQ ID NO: 16 | | SEQ ID NO: 19 SEQ ID NO: 20 SEQ ID NO: 29 SEQ ID NO: 30 |
| D2 | 10 | | SEQ ID NO: 15 SEQ ID NO: 16 | | SEQ ID NO: 17 SEQ ID NO: 18 SEQ ID NO: 31 SEQ ID NO: 32 |

[1]The ssODNs were pre-annealed to form a double-stranded DNA (ds-DNA) and added to the transformation. The ssODNs indicated in italics, underlined ssODNs or ssODN depicted in bold were pre-annealed with each other, respectively, (i.e. e.g. in sub-set A1 SEQ ID NO: 23 was pre-anealed with SEQ ID NO: 24, while SEQ ID NO: 25 was pre-anealed with SEQ ID NO: 26) and added to the transformation.
[2]The ssODNs were directly added in the transformation (no pre-annealing).
*Six ssODNs (two gRNA insert ssODNs, four ssODN flanks) were pre-annealed in one reaction and added to the transformation. For the ds-DNA or ssODN gRNA insert (50-20-50) means 50 bp complementarity (sequence identity) with the linear recipient gRNA-vector PCR fragment (SEQ ID NO: 8, FIG. 2)-20 bp guide sequence-50 bp complementarity (sequence identity) with the linear recipient gRNA-vector PCR fragment. ds-DNA/ssODN flanks (50-50) means 50 bp complementarity (sequence identity) with the left flank integration site in genomic DNA and the 50 bp connector sequence at the 5'-terminus of the donor DNA, or 50 bp complementarity (sequence identity) with the connector sequence at the 3'-terminus of the donor DNA and 50 bp complementarity (sequence identity) with the right flank integration site in genomic DNA.

Pre-Annealing of the ssODNs.

For some of the transformation experiments (Table 2), two ssODNs were annealed to form a double-stranded DNA (ds-DNA) gRNA insert or ds-DNA connector-flank sequence. Oligo nucleotides were ordered at IDT (Integrated DNA Technologies, Leuven, Belgium) as standard desalted primers. The oligonucleotides were dissolved to a concentration of 100 µM (100 µmol/µl). Subsequently, the annealing reactions were performed between complementary oligonucleotides as follows: 20 µl of 100 µM of the forward and 20 µl of 100 µM of the reverse oligonucleotide were mixed with 10 µl of 5×T4 ligase buffer (ThermoFisher, Life Technologies, Bleiswijk, the Netherlands, supplied with T4 ligase Cat no. 15224041). The mixture was kept at 100 degrees Celsius for 5 minutes to denature the oligonucleotides. Subsequently, the temperature was decreased to 25 degrees by a gradual decrease of 1 degree Celsius for 30 seconds in 75 cycles (which is an approximate decrease of 0.0333 degrees per second), allowing the ss oligonucleotides to anneal with each other. The mixture was kept at 10 degrees Celsius if required. In case of subset D1, 2×6.7 µl of 100 µM oligonucleotides and 4×6.7 µl of 100 µM oligonucleotides were directly mixed with 10 µl of 5×T4 ligase buffer (ThermoFisher, Life Technologies, Bleiswijk, the Netherlands, supplied with T4 ligase Cat no. 15224041). After annealing, the oligonucleotides were directly used in the transformation (no purification step).

Before and after annealing, the concentrations of single ssODNs or two annealed ssODNs (double strand DNA (ds-DNA) gRNA insert or ds-DNA connector-flank sequence) were determined using a NanoDrop device (ThermoFisher, Life Technologies, Bleiswijk, the Netherlands), providing the concentrations in nanogram per microliter. Based on these measurements, the amounts as shown in Table 1 of single ssODNs or two annealed ssODNs (ds-DNA) were used in the transformation experiments.

Results

The experiment outlined above was performed and after transformation, the cells were plated out in a 1:10 dilution in milliQ water. After about 3 days of growth, by UV light (Qpix 450 Transformant Picker—Molecular devices LLC) a discrimination was made between fluorescent transformants (indicating YFP integration) and white transformants (indicating no YFP integration) that appeared on the plates. The total number white and fluorescent transformants on a transformation plate were counted. In case of fluorescent transformants, the donor DNA was successfully integrated into the genomic DNA of the yeast cells. The results are provided in FIG. 6. A summary of the results is reported in Table 3. Below, the experimental results for the subsets A1 to D2 are shortly discussed, for which the experimental set-ups are schematically depicted in FIG. 5 A1-A2, 5 B1-B2, 5 C1-C2, 5 D1-D2.

A1-A2: As it can be seen in FIG. 6 and Table 3, when using ds-DNA for the gRNA and ds-DNA flanks for the YFP insertion (FIG. 5 A1-A2), only a low frequency of recombination with the linear recipient gRNA-vector PCR fragment to form a functional circular vector and/or YFP insertion via genome editing. Overall, subset A2 might be slightly lower than A1 in number of obtained transformants, which might be expected by the 25×reduced amount of flank ds-DNA.

B1-B2: As it can be seen in FIG. 6 and Table 3, when using one or two ssODNs for the gRNA vector repair and ds-DNA for the YFP insertion (as depicted in FIG. 5 B1-B2), both the use of one ssODN or two ssODNs clearly show that the 20 bp guide insertion/repair using ssODNs for recombination with the linear recipient gRNA-vector PCR fragment (FIG. 2) leads to successful genome editing and clearly improves compared to the use of same amount of ds-DNA as in A1.

C1-C2: As it can be seen in FIG. 6 and Table 3, when using one or two ssODNs for both flanks for the recombination with the YFP construct and genomic insertion and ds-DNA for recombination with the linear recipient gRNA-vector PCR fragment to form a functional circular vector (as depicted in FIG. 5 C1-C2), insertion of the YFP expression cassette using two ssODNs for each flank facilitates the assembly in a cell and integration of donor DNA, using a CRISPR/Cas9 induced double-stranded break at the genomic DNA.

D1: When using two ssODNs for the guide RNA repair vector and four ssODNs that were pre-anealed prior to addition to the transformation mixture, the total number of transformats increases if compared to experiments A1 and A2. However the number of transformants where YFP integration took place is still low.

D2: When using two ssODNs for recombination with the linear recipient gRNA-vector PCR fragment to form a functional circular vector and four ssODNs for the recombination with the YFP construct and genomic insertion, a high number of transformants, including transformats with correct YFP integration were obtained.

an YFP expression cassette. The use of two complementary ssODNs for each flank clearly improves the efficiency in comparison with use of one ssODN, e.g. (C1, D1) versus (C2, D2).

Also surprisingly, applying the ssODN method only for in vivo assembly of the 20 bp guide sequence with the linear recipient gRNA-vector PCR fragment to form a functional circular vector, instead of ds-DNA (both at a same concentration), resulted in an increased number of both florescent and non-fluorescent transformants, e.g. (A1) versus (B1, B2).

When combining the ssODNs assembly in a cell and insertion (of a ds-construct) with ssODN-based recombination in a cell of the 20 bp guide sequence with the linear recipient gRNA-vector PCR fragment to form a functional circular vector for a CRISPR/Cas9 system, the amount of edited cells increased about 2-fold (D2 versus C2), and clearly increased over the control experiment A1.

Overall, this example clearly demonstrated the successful use of at least a first and a second single ssODN which are essentially complementary to each other in the in vivo assembly of at least two double-stranded nucleic acid molecules, e.g. wherein a first double-stranded nucleic acid molecule integrates into a second double-stranded nucleic acid molecule (e.g. YFP integrated in the genomic locus, or a gRNA fragment integrated into a gRNA vector) together with the CRISPR/Cas9 system.

Additionally, the system also circumvents a step of pre-hybridizing ssODNs to form double-stranded DNA. As was applied in A1, A2, B1, B2 for the guide sequence fragment required for recombination in the cell with the linear recipient gRNA-vector PCR fragment to form a functional circular vector, and in A1-A2, C1-C2 for the recombination in the cell and integration flanks for the ds-construct insertion.

Confirmation of Correct Integration into Genomic DNA

To confirm correct integration of the YFP expression cassette (SEQ ID NO: 10), and to demonstrate deletion of 1 kbp of genomic DNA at the INT1 locus, five transformants of subset B2 (1 kbp deletion, FIG. 5a) and five transformants

TABLE 3

Figure 6:
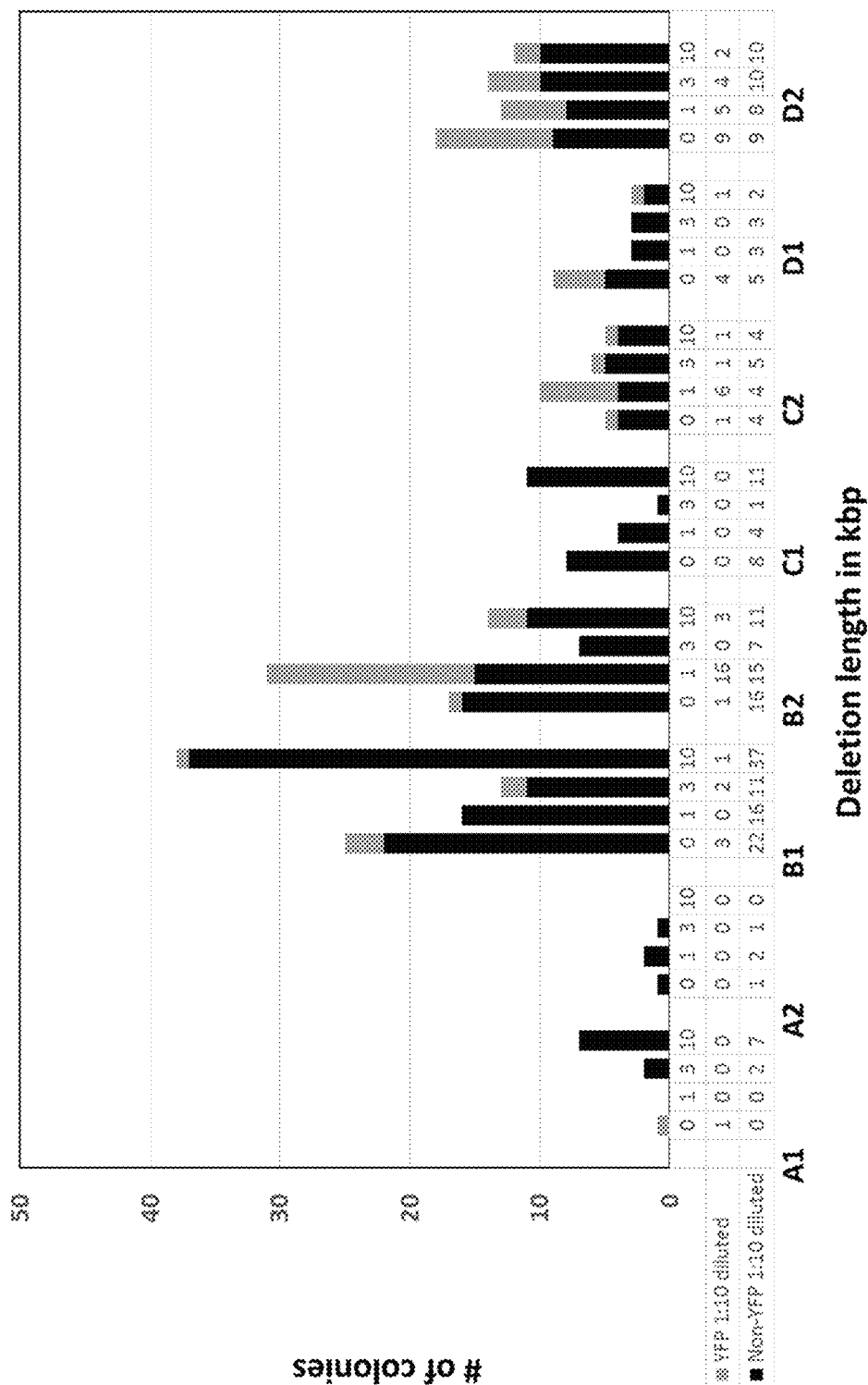
FIG. 6 depicts a stacked bar chart visualizing the number of non-fluorescent (black) and fluorescent (grey) colonies that appeared at a 48-well Qtray from a 1:10 diluted transformation mixture for the 32 transformations outlined in Table 1 and Table 2. The subsets A1 to D2 are detailed in Table 1. The numbers at the X-axis represent: designed knock-out stretch in kbp (top row), #of fluorescent Yellow Fluorescent Protein (YFP) (middle row) and number of non-fluorescent colonies (bottom row).

Overview of results for transformation experiments depicted in FIG. 6.

| Experiment | dsDNA[1] gRNA insert | ssODN[2] gRNA insert | dsDNA[1] flanks | ssODN[2] flanks | no.f/no.w obtained in each deletion length[3] | | | |
|---|---|---|---|---|---|---|---|---|
| | | | | | 0 kbp | 1 kbp | 3 kbp | 10 kbp |
| A1 | + | | + | | 1f/0w | 0f/0w | 0f/2w | 0f/7w |
| A2 | + | | + | | 0f/1w | 0f/2w | 0f/1w | 0f/0w |
| B1 | | + | + | | 3f/22w | 0f/16w | 2f/11w | 1f/37w |
| B2 | | + | + | | 1f/16w | 16f/15w | 0f/7w | 3f/11w |
| C1 | + | | | + | 0f/8w | 0f/4w | 0f/1w | 0f/11w |
| C2 | + | | | + | 1f/4w | 6f/4w | 1f/5w | 1f/4w |
| D1* | + | | + | | 4f/5w | 0f/3w | 0f/3w | 1f/2w |
| D2 | | + | | + | 9f/9w | 5f/5w | 4f/10w | 2f/10w |

[1] The ssODNs were pre-annealed to form a double-stranded DNA (ds-DNA) and added to the transformation.
[2] The ssODNs were directly added in the transformation (no pre-annealing).
*Six ssODNs (two gRNA insert ssODNs, four ssODN flanks) were pre-annealed in one reaction and added to the transformation.
[3] For each transformation experiments the number of fluorescent transformants (indicating YFP integration) and white transformants (indicating no YFP integration) that appeared on the plates is given as no.f/no.w.

Figure 7:
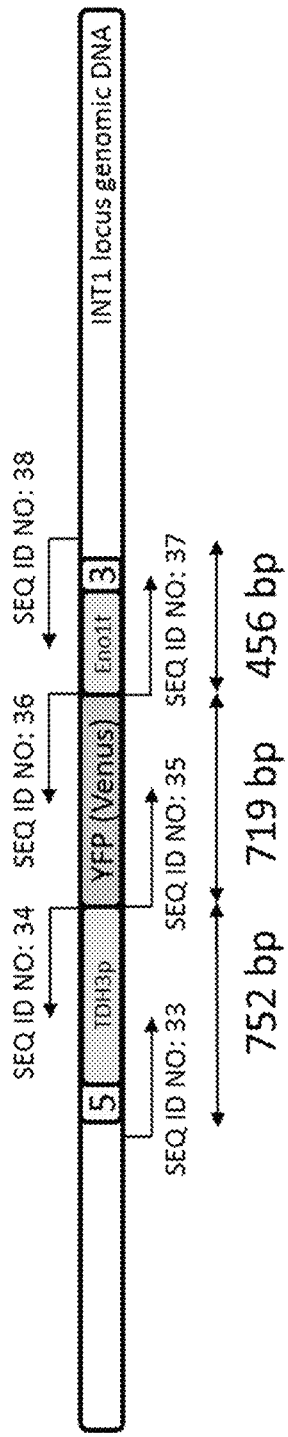
FIG. 7 depicts the PCR approach to confirm correct integration of the YFP expression cassette and deletion of ~1 kB of genomic DNA at the INT1 locus. 5 and 3 represent connector sequences, which are non-coding DNA sequences added to the expression cassette.
Figure 8:
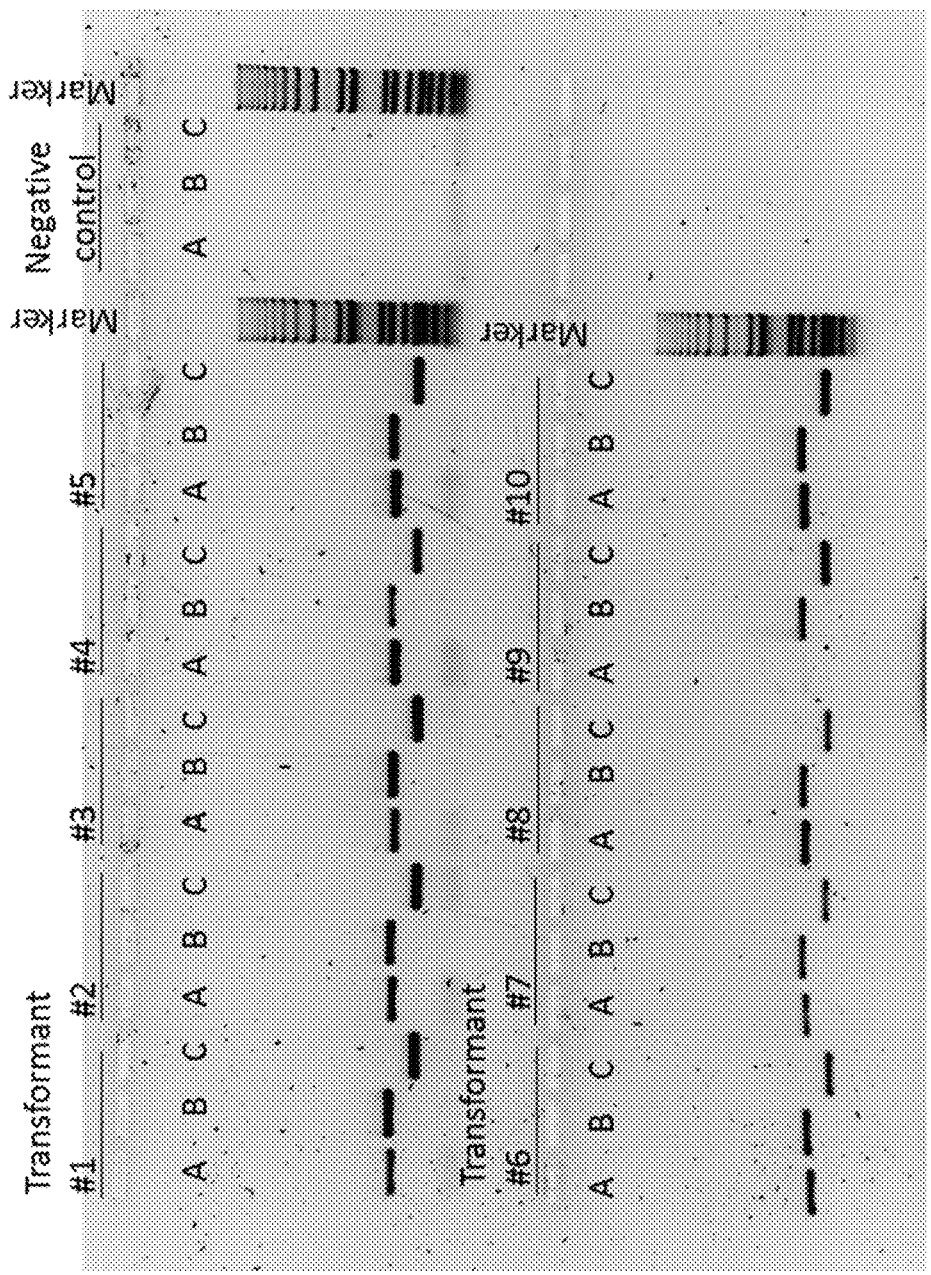
FIG. 8 depicts an agarose gel, used for analysis of PCR products to confirm correct integration of the YFP expression cassette in genomic DNA and to confirm deletion of ~1 kB genomic DNA at the INT1 locus. A. Confirmation of integration of the YFP expression cassette (719 bp band). B. Confirmation correct deletion of 1 kB genomic DNA at 5' end (752 bp band). C. Confirmation correct deletion of 1 kB genomic DNA at 3' end (456 bp band). Transformants #1 to #5: Fluorescent transformants subset B2. Transformants #6 to #10: Fluorescent transformants subset D2. Negative control: strain CEN-PKI13-7D. Marker: 1 kB+ marker (ThermoFisher, Bleiswijk, the Netherlands, Cat no. 10787018).

Surprisingly, the use of single-stranded oligonucleotides instead of double-stranded oligonucleotides for recombination in a cell and integration of a ds-DNA construct (in this case an YFP expression cassette) at a genomic locus increases the frequency of such an event. The example showed 0, 1, 3 and 10 kbp replacement of genomic DNA by of subset D2 (1 kbp deletion, FIG. 5b), were further analyzed. Genomic DNA of fluorescent transformants was isolated as described by Lōoke et al., 2011 and was used as template in the PCR reaction. The primers used in the PCR to confirm the integration of the YFP expression cassette into the genome and 1 kbp deletion of genomic DNA surrounding the INT1 locus are schematically depicted in FIG. 6. The PCR reaction was performed using Phusion DNA polymerase (New England Biolabs, USA) according to manufacturer's instructions and a PCR program known to the person skilled in the art. When using the primers set out in SEQ ID NO: 33 and SEQ ID NO: 34 in the PCR reaction, correct integration at the 5' end of the INT1 site was demonstrated, because the PCR reaction resulted in a band of 752 bp upon analysis on a 0.8% agarose gel (FIG. 7). When using the primers set out in SEQ ID NO: 35 and SEQ ID NO: 36 in the PCR reaction, genomic integration of the YFP expression cassette was demonstrated, because the PCR reaction resulted in a band of 719 bp upon analysis on a 0.8% agarose gel (FIG. 7). When using the primers set out in SEQ ID NO: 37 and SEQ ID NO: 38 in the PCR reaction, correct integration at the 3' end of the INT1 site was demonstrated, because the PCR reaction resulted in a band of 456 bp upon analysis on a 0.8% agarose gel (FIG. 7). The results of the PCR reactions are shown in FIG. 8.

The PCR results are summarized in Table 4. The PCR results confirmed that ~1 kB of genomic DNA was deleted by integration of the YFP expression cassette (SEQ ID NO: 10) using the methods as described for subsets B2, and D2 in all of the fluorescent transformants that were tested.

cassette with ssODN flanking regions. It was thus demonstrated that the technique according to the invention does not introduce indel mutations.

Example 2: ssODN-Mediated Construct Integration (OMCI) of a Marker (NatMX) Expression Cassette at a Genomic Locus in a Cell This experiment describes the replacement of stretches of genomic DNA in a range from about 0-10 kbp by a marker (NatMX) expression cassette at a genomic locus. The experimental set-up contains three subsets A, B and C (as depicted in FIG. 9).

Subset A. uses a NatMX expression cassette with 50-bp homology flanks with the genome, and replaces about 0, 1, 3 and 10 kbp of genomic DNA in the various transformations.

Subset B. uses a NatMX expression cassette with 50-bp linker connectors. In addition double-stranded ds-DNA of 100 bp are applied with 50-bp homology with the 3' and 5' connectors of the NatMX expression cassette and 50-bp homology with the genome.

Subset C. uses a NatMX expression cassette with 50-bp linker connectors. In addition two sets of complementary

TABLE 4

Summary of PCR results confirming correct integration of the YFP expression cassette at the INT1 locus and deletion of 1 kbp deletion of genomic DNA.

| Subset | Number of fluorescent transformants tested | Correct PCR band using primers of SEQ ID NO: 33 and SEQ ID NO: 34 | Correct PCR band using primers of SEQ ID NO: 35 and SEQ ID NO: 36 | Correct PCR band using primers of SEQ ID NO: 37 and SEQ ID NO: 38 |
|---|---|---|---|---|
| B2 | 5 | 5 | 5 | 5 |
| D2 | 5 | 5 | 5 | 5 |

The correct integration of the YFP expression cassette was corroborated by sequencing to to establish whether indel mutations had occurred. In brief, the transition of the genomic DNA sequence and the connector sequence of the ssODN was sequenced for five transformants in subset B2 and D2 on both the 5' and 3' ends. The fragments for transition of the 5' end were obtained by PCR using oligoset SEQ ID NO: 33 and SEQ ID NO: 34 and for the 3' end the fragments were obtained by PCR using oligoset SEQ ID NO: 37 and SEQ ID NO: 38. The PCR reactions were performed using Phusion DNA polymerase (New England Biolabs, USA) according to manufacturer's instructions and a PCR program known to the person skilled in the art. Sequencing of the resulting PCR fragments (FIG. 8) was performed using the oligo's as set forward in SEQ ID NO: 34 for the 5' end and in SEQ ID NO: 37 for the 3' end, respectively. Sequencing PCR was performed using Big-Dye® Terminator v3.1 Cycle Sequencing Kit (ThermoFisher Catno. 4337456) according to supplier's manual. Sequencing reactions were subsequently column purified using NucleoSEQ® columns (Machery Nagel, Catno. 740523.50). Purified sequencing reactions were analysed by the 3500XL Genetic Analyzer® (Applied Biosystems). The resulting sequences were aligned to the genome reference sequence using CloneManager software. The sequence assemblies demonstrated correct integration of the YFP cassette into the genome, where the obtained sequences from the sequencing reactions fully aligned with the predicted sequences. The correct integration was checked up to 40 bp upstream and 40 bp downstream of the inserted YFP ssODNs of 100 bp are applied with 50-bp homology with the 3' and 5' connectors of the NatMX expression cassette and 50-bp homology with the genome.

Ds-DNA NatMX Marker Cassettes with Connectors and Flank Sequences

A double-stranded donor cassette coding for the nourseothricin resistance marker including a 50 bp connector sequence (Con5) at the 5' end and a 50 bp connector sequence (Con3) at the 3' end of the NatMX marker expression cassette (SEQ ID NO: 39, FIG. 9A) was obtained by PCR using vector pGRN002 (SEQ ID NO: 5) as template using the FW primer of SEQ ID NO: 40 and the reverse primer of SEQ ID NO: 41. For subset A, flank sequences were added to the ds-DNA NatMX marker by PCR. Using the primers of SEQ ID NO: 42 and SEQ ID NO: 43, the ds-DNA NatMX marker cassette with 50 bp connector sequences and 50 bp flank sequences for direct integration at the INT1 locus (0 bp deletion) was obtained by PCR. Using the primers of SEQ ID NO: 44 and SEQ ID NO: 45, the ds-DNA NatMX marker cassette with 50 bp connector sequences and 50 bp flank sequences for deletion of 1 kbp of genomic DNA was obtained by PCR. Using the primers of SEQ ID NO: 46 and SEQ ID NO: 47, the ds-DNA NatMX marker cassette with 50 bp connector sequences and 50 bp flank sequences for deletion of 3 kbp of genomic DNA was obtained by PCR. Using the primers of SEQ ID NO: 48 and SEQ ID NO: 49, the ds-DNA NatMX marker cassette with 50 bp connector sequences and 50 bp flank sequences for deletion of 1 kbp of genomic DNA was obtained by PCR.

The Q5 DNA polymerase (part of the Q5® High-Fidelity 2× Master Mix, New England Biolabs, supplied by Bioké, Leiden, the Netherlands. Cat no. M0492S) was used in the PCR reactions, which were performed according to manufacturer's instructions. The PCR fragments were purified using the NucleoSpin Gel and PCR Clean-up kit (Machery-Nagel, distributed by Bioké, Leiden, the Netherlands) according to manufacturer's instructions.

100 bp Knock-Out Flanks DNA Sequences

Together with the ds-DNA NatMX marker cassette containing a 50 bp Con5 sequence at the 5' end and a 50 bp Con3 sequence at the 3' end (SEQ ID NO: 39), so-called knock-out (k.o.) flanks of 100 bp were supplied to specify the k.o. target. These left k.o. flank (LF) and right k.o. flank (RF) sequences have 50 bp homology with the 5' and 3' ds-DNA NatMX marker cassette, and 50 bp homology with the left and right sequence of k.o. genomic deletion stretch, respectively (see FIG. 4; in Example 2 YFP was replaced by NatMX). In Example 2, the left flank (LF) and right flank (RF) sequences were used in the transformations to replace stretches of 0, 1, 3 and 10 kb genomic DNA at the INT1 locus by the ds-DNA NatMX marker cassette.

DNA concentrations

All DNA concentrations, including the single ssODNs or two annealed ssODNs, or the NatMX marker cassette PCR fragment were determined using a NanoDrop device (ThermoFisher, Life Technologies, Bleiswijk, the Netherlands), providing the concentrations in nanogram per microliter. Based on these measurements, specific DNA amounts as for example shown in Table 4, were used in the transformation experiments.

Yeast Transformation

S. cerevisiae strain CSN001 which is pre-expressing Cas9, described in Example 1, was transformed using the LiAc/salmon sperm (SS) carrier DNA/PEG method (Gietz and Woods, 2002).

An overview of all transformation experiments of this Example is shown in Table 5 and Table 6. In each transformation experiment, 100 ng of the ds-DNA NatMX marker cassette containing 50 bp connector flank sequences at the 5' and 3' end of the sequence and the specific amount of 100 bp ssODN flank sequences or 100 bp ds-DNA flank sequences as indicated in Table 5 was included. Pre-annealing of the ssODNs (subset B) was performed as described in Example 1.

The transformation mixtures were plated on YPD-agar (10 grams per liter of yeast extract, 20 grams per liter of peptone, 20 grams per liter of dextrose, 20 grams per liter of agar) containing 200 μg nourseothricin (NatMX, Jena Bioscience, Germany) and 200 μg G418 (Sigma Aldrich, Zwijndrecht, the Netherlands) per ml.

TABLE 5

Overview of the amounts of flank DNA used in the different transformation experiments, here indicated as subsets.

| Subset | ds-DNA[1] flanks (50-50) | ssODN[2] flanks (50-50) |
|---|---|---|
| A | n.a. | n.a. |
| B | 2 × 100 ng | |
| C | | 4 × 50 ng |

[1]The ssODNs were pre-annealed to form a double-stranded DNA (ds-DNA) and added to the transformation.

[2]The ssODNs were directly added in the transformation (no pre-annealing). ds-DNA/ssODN flanks (50-50) means 50 bp complementarity (sequence identity) with the left flank integration site in genomic DNA and the 50 bp connector 5 sequence of the donor DNA, or 50 bp complementarity (sequence identity) with the connector 3 sequence of the donor DNA and 50 bp complementarity (sequence identity) with the right flank integration site in genomic DNA.

n.a.: Not applicable; in subset A, one PCR fragment was transformed.

TABLE 6

Overview of different subsets of transformation experiments.

| Subset | Deletion in kbp | ds-DNA NatMX cassette | ds-DNA[1] flanks (50-50) | ssODN[2] flanks (50-50) |
|---|---|---|---|---|
| A | 0 | PCR product using SEQ ID NO: 39 as template using primers of SEQ ID NO: 42 and SEQ ID NO: 43. | | |
| A | 1 | PCR product using SEQ ID NO: 39 as template using primers of SEQ ID NO: 44 and SEQ ID NO: 45. | | |
| A | 3 | PCR product using SEQ ID NO: 39 as template using primers of SEQ ID NO: 46 and SEQ ID NO: 47. | | |
| A | 10 | PCR product using SEQ ID NO: 39 as template using primers of SEQ ID NO: 48 and SEQ ID NO: 49. | | |
| B | 0 | SEQ ID NO: 39 | SEQ ID NO: 23<br>SEQ ID NO: 24<br>SEQ ID NO: 25<br>SEQ ID NO: 26 | |
| B | 1 | SEQ ID NO: 39 | SEQ ID NO: 21<br>SEQ ID NO: 22<br>SEQ ID NO: 27<br>SEQ ID NO: 28 | |
| B | 3 | SEQ ID NO: 39 | SEQ ID NO: 19<br>SEQ ID NO: 20<br>SEQ ID NO: 29<br>SEQ ID NO: 30 | |

TABLE 6-continued

Overview of different subsets of transformation experiments.

| Subset | Deletion in kbp | ds-DNA NatMX cassette | ds-DNA[1] flanks (50-50) | ssODN[2] flanks (50-50) |
|---|---|---|---|---|
| B | 10 | SEQ ID NO: 39. | SEQ ID NO: 17<br>SEQ ID NO: 18<br>SEQ ID NO: 31<br>SEQ ID NO: 32 | |
| C | 0 | SEQ ID NO: 39 | | SEQ ID NO: 23<br>SEQ ID NO: 24<br>SEQ ID NO: 25<br>SEQ ID NO: 26 |
| C | 1 | SEQ ID NO: 39 | | SEQ ID NO: 21<br>SEQ ID NO: 22<br>SEQ ID NO: 27<br>SEQ ID NO: 28 |
| C | 3 | SEQ ID NO: 39 | | SEQ ID NO: 19<br>SEQ ID NO: 20<br>SEQ ID NO: 29<br>SEQ ID NO: 30 |
| C | 10 | SEQ ID NO: 39. | | SEQ ID NO: 17<br>SEQ ID NO: 18<br>SEQ ID NO: 31<br>SEQ ID NO: 32 |

[1]The ssODNs were pre-annealed to form a double-stranded DNA (ds-DNA) and added to the transformation. Underlined ssODNs or ssODN depicted in bold were pre-annealed and added to the transformation.
[2]The ssODNs were directly added in the transformation (no pre-annealing). ds-DNA/ssODN flanks (50-50) means 50 bp complementarity (sequence identity) with the left flank integration site in genomic DNA and the 50 bp Con5 sequence of the donor DNA, or 50 bp complementarity (sequence identity) with the Con3 sequence of the donor DNA and 50 bp complementarity (sequence identity) with the right flank integration site in genomic DNA.

Results

The transformation experiment outlined above in Example 2 was performed and after transformation, the cells were plated out in a 1:10, 1:5 and 1:3 dilution in milliQ water. After about 3 days of growth, transformants appeared on the transformation plates, indicating that the NatMX expression cassette, encoding the NatMX resistance marker, was integrated into the genomic DNA of the transformants. The total number was counted.

Results of the experiment are shown in FIG. 10 for the 1:10, 1:5 and 1:3 dilution of the transformants. The subset B and C show similar range of transformants for the different knock-out fragment lengths. While subset A is on average at least 5-fold lower in number of transformants.

These results show that the "separate homology flank" approach B and C gives significant higher number of NatMX resistant transformants as compared to approach A, suggesting a higher percentage of cells with correct integration of the NatMX expression cassette and deletion of the intended regions of genomic DNA at the INT1 locus. However, approach C is easier to implement as the oligonucleotides annealing step is avoided. Approaches B and C provided a flexible way to insert a double-stranded nucleic acid molecule at a genomic target directly, by using ssODNs.

This experiment shows the successful use of at least a first and a second single-stranded oligonucleotide which are essentially complementary to each other (and are preferably not annealed before introduction into the cell) in the in vivo (within a scell) assembly of at least two double-stranded nucleic acid molecules wherein a first double-stranded nucleic acid molecule integrates into a second double-stranded nucleic acid molecule (here the NatMX expression cassette replaces a portion of the genomic locus). In this experiment no single-stranded or double-stranded break is present in the second double-stranded nucleotide and no functional genome editing system such as e.g. CRISPR-CAS, is used.

Example 3: ssODN-Mediated Construct Integration (OMCI) of a Yellow Fluorescent Protein (YFP) Expression Cassette at a Genomic Locus in a Cell Using CRISPR/Cas9 with Comparison Complementary Pairs of ssODNs Versus Single ssODNs In this experiment the effect of transformation of a yellow fluorescent protein expression cassette in combination with ssODN-mediated construct integration (OMCI) was evaluated. In addition, it was determined whether parts of genomic DNA could be deleted using this approach. The OMCI method was evaluated in combination with the CRISPR-CAS9 system.

Experimental Details

The components required in this Example are as follows:
Yeast strain CSN001 which is pre-expressing CAS9. Construction of strain CSN001 is described in Example 1.
A linear recipient gRNA-vector PCR fragment (SEQ ID NO: 8, FIG. 2) used for assembly in a cell of a guide RNA expression cassette resulting in a circular vector. Generation of the linear recipient gRNA-vector PCR fragment is described in Example 1.
A guide RNA expression cassette, containing homologous sequences with the linear recipient gRNA-vector PCR fragment, was obtained by PCR to allow recombination in the cell as follows: A synthetic DNA cassette (gBlock) was ordered at Integrated DNA Technologies, Leuven, Belgium (SEQ ID NO: 50). This gBlock consisted of the SNR52p RNA polymerase III promoter, a guide sequence, the gRNA structural component and the SUP4 3' flanking region as described in DiCarlo et al., 2013, and it contains homology at its 5' and 3' ends with vector pGRN002 (SEQ ID NO: 5) or pRN1120 (SEQ ID NO: 1).

The transformed guide RNA expression cassette, of which the sequence is set out in SEQ ID NO: 53, was obtained by PCR the gBlock of SEQ ID NO: 50 as template, using primers of SEQ ID NO: 51 and SEQ ID NO: 52. Phusion DNA polymerase was used (New England Biolabs, USA) in the PCR reaction according to manufacturer's instructions. The guide RNA expression cassette PCR fragment was purified using the NucleoSpin Gel and PCR Clean-up kit (Machery-Nagel, distributed by Bioké, Leiden, the Netherlands) according to manufacturer's instructions.

The transformed guide RNA PCR fragments contained at its 5' end 304 bp homology with the linear recipient gRNA-vector PCR fragment and at its 3' end 135 bp homology with the linear recipient gRNA-vector PCR fragment. The presence of homologous DNA sequences at the 5' and 3' end of the guide RNA cassette will promote reconstitution of a circular vector by homologous recombination in a cell (gap repair) (Orr-Weaver et al., 1983), which allows selection of transformants using nourseothricin in the transformation plates.

The guide RNA was used to direct the CAS9 protein to the INT1 locus. The INT1 integration site is located on chromosome XV at the non-coding region between NTR1 (YOR071c) and GYP1 (YOR070c).

A PCR fragment of the ds-DNA connector 5-YFP expression cassette-connector 3 sequence (SEQ ID NO: 10). Generation of this fragment is described in Example 1.

100 bp ssODN flank sequences or 100 bp ds-DNA flank sequences as indicated in Table 6 and Table 7. A description of the 100 bp knock-out flanks sequences is provided in Example 1. Pre-annealing conditions of two ssODNs is described in Example 1.

DNA Concentrations

All DNA concentrations, including the single ssODNs or two annealed ssODNs, the guide RNA expression cassette PCR fragment or the ds-DNA YPF expression cassette PCR fragment were determined using a NanoDrop device (ThermoFisher, Life Technologies, Bleiswijk, the Netherlands), providing the concentrations in nanogram per microliter. Based on these measurements, specific DNA amounts as for example shown in Table 6 were used in the transformation experiments.

Yeast Transformation

*S. cerevisiae* strain CSN001 was transformed using the LiAc/salmon sperm (SS) carrier DNA/PEG method (Gietz and Woods, 2002).

An overview of all transformation experiments of this Example is shown in Table 7 and Table 8. In each transformation experiment (subset), 100 ng of the ds-DNA YPF expression cassette containing 50 bp connector flank sequences at the 5' and 3' end of the sequence (SEQ ID NO: 10), and the specific amounts of 100 bp ssODN flank sequences or 100 bp ds-DNA flank sequences as indicated in Table 6 were included. In addition, 100 ng linear recipient gRNA-vector PCR fragment (SEQ ID NO: 8) and 1000 ng of the guide RNA expression cassette PCR fragment containing homology with the linear recipient gRNA-vector PCR fragment (SEQ ID NO: 53) were included in each transformation.

TABLE 7

Overview of the amounts of flank DNA used in the different transformation experiments, here indicated as subsets.

| Subset | ds-DNA[1] flanks (50-50) | ssODN[2] flanks (50-50) |
|---|---|---|
| A | 2 × 100 ng | |
| B | | 2 × 100 ng |
| C | | 2 × 100 ng |
| D | | 4 × 50 ng |

[1]The ssODNs were pre-annealed to form a double-stranded DNA (ds-DNA) and added to the transformation.
[2]The ssODNs were directly added in the transformation (no pre-annealing). ds-DNA/ssODN flanks (50-50) means 50 bp complementarity (sequence identity) with the left flank integration site in genomic DNA and the 50 bp connector 5 sequence of the donor DNA, or 50 bp complementarity (sequence identity) with the connector 3 sequence of the donor DNA and 50 bp complementarity (sequence identity) with the right flank integration site in genomic DNA.

TABLE 8

Overview of different subsets of transformation experiments.

| Subset | Deletion in kbp | ds-DNA[1] flanks (50-50) | ssODN[2] flanks (50-50) |
|---|---|---|---|
| A | 0 | SEQ ID NO: 23<br>SEQ ID NO: 24<br>SEQ ID NO: 25<br>SEQ ID NO: 26 | |
| A | 1 | SEQ ID NO: 21<br>SEQ ID NO: 22<br>SEQ ID NO: 27<br>SEQ ID NO: 28 | |
| A | 3 | SEQ ID NO: 19<br>SEQ ID NO: 20<br>SEQ ID NO: 29<br>SEQ ID NO: 30 | |
| A | 10 | SEQ ID NO: 17<br>SEQ ID NO: 18<br>SEQ ID NO: 31<br>SEQ ID NO: 32 | |
| B | 0 | | SEQ ID NO: 23<br>SEQ ID NO: 25 |
| B | 1 | | SEQ ID NO: 21<br>SEQ ID NO: 27 |
| B | 3 | | SEQ ID NO: 19<br>SEQ ID NO: 29 |
| B | 10 | | SEQ ID NO: 17<br>SEQ ID NO: 31 |
| C | 0 | | SEQ ID NO: 24<br>SEQ ID NO: 26 |
| C | 1 | | SEQ ID NO: 22<br>SEQ ID NO: 28 |
| C | 3 | | SEQ ID NO: 20<br>SEQ ID NO: 30 |
| C | 10 | | SEQ ID NO: 18<br>SEQ ID NO: 32 |
| D | 0 | | SEQ ID NO: 23<br>SEQ ID NO: 24<br>SEQ ID NO: 25<br>SEQ ID NO: 26 |
| D | 1 | | SEQ ID NO: 21<br>SEQ ID NO: 22<br>SEQ ID NO: 27<br>SEQ ID NO: 28 |
| D | 3 | | SEQ ID NO: 19<br>SEQ ID NO: 20<br>SEQ ID NO: 29<br>SEQ ID NO: 30 |

TABLE 8-continued

Overview of different subsets of transformation experiments.

| Subset | Deletion in kbp | ds-DNA[1] flanks (50-50) | ssODN[2] flanks (50-50) |
|---|---|---|---|
| D | 10 | | SEQ ID NO: 17 |
| | | | SEQ ID NO: 18 |
| | | | SEQ ID NO: 31 |
| | | | SEQ ID NO: 32 |

[1]The ssODNs were pre-annealed to form a double-stranded DNA (ds-DNA) and added to the transformation. Underlined ssODNs or ssODN depicted in bold were pre-annealed and added to the transformation.
[2]The ssODNs were directly added in the transformation (no pre-annealing). ds-DNA/ssODN flanks (50-50) means 50 bp complementarity (sequence identity) with the left flank integration site in genomic DNA and the 50 bp connector 5 sequence of the donor DNA, or 50 bp complementarity (sequence identity) with the connector 3 sequence of the donor DNA and 50 bp complementarity (sequence identity) with the right flank integration site in genomic DNA.

The transformation mixtures were plated on YPD-agar (10 grams per liter of yeast extract, 20 grams per liter of peptone, 20 grams per liter of dextrose, 20 grams per liter of agar) containing 200 μg nourseothricin (NatMX, Jena Bioscience, Germany) and 200 μg G418 (Sigma Aldrich, Zwijndrecht, the Netherlands) per ml.

Results

Figure 11:
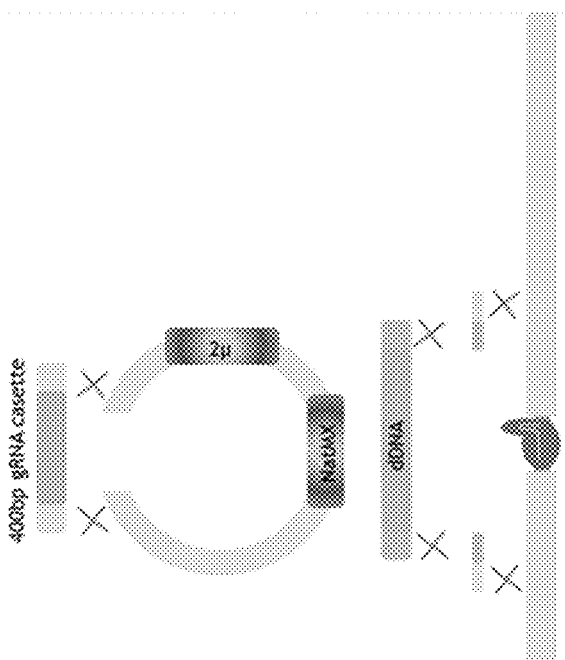
Figure 11:
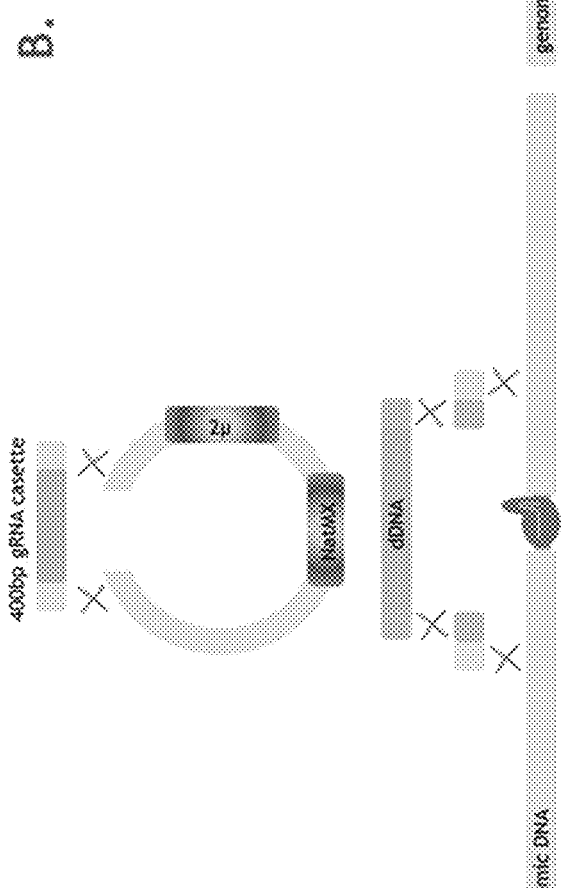
Figure 11:
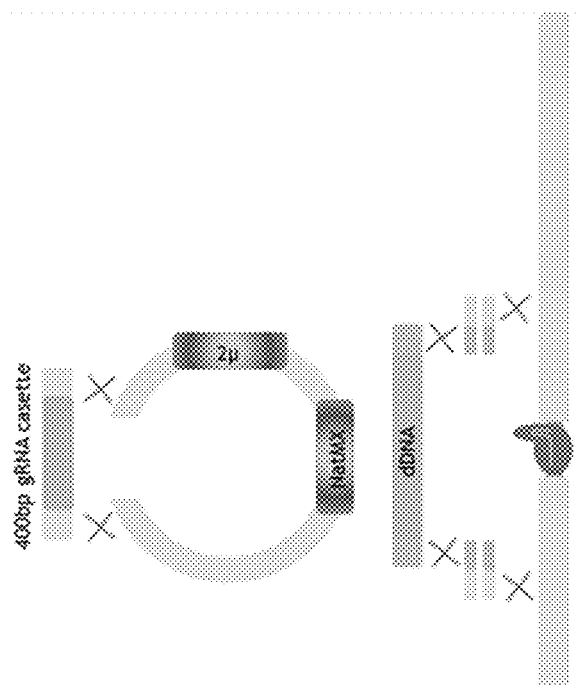
Figure 11:
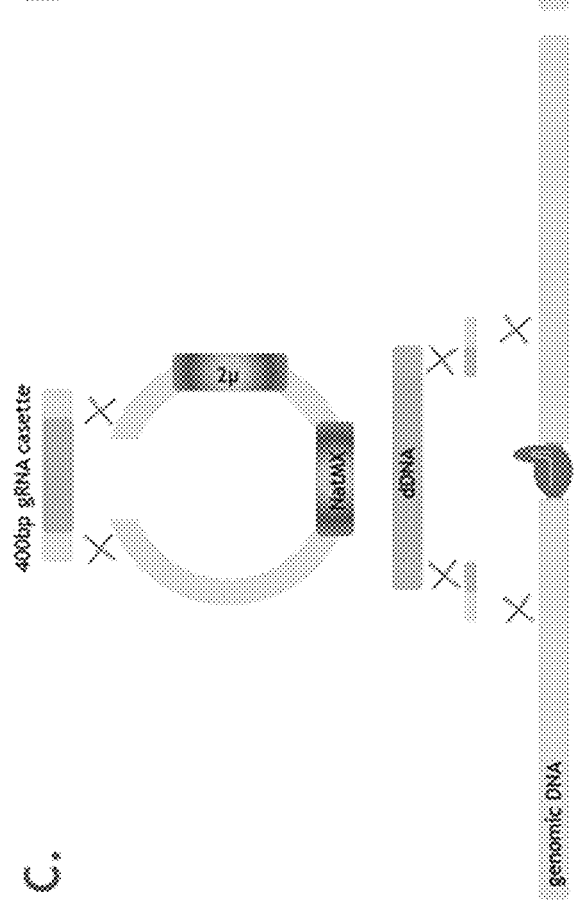

The experiment outlined above was performed and after transformation, the cells were plated out in a 1:5 dilution in milliQ water. After about 3 days of growth, by UV light (Qpix 450 Transformant Picker—Molecular devices LLC) a discrimination was made between fluorescent transformants (indicating YFP integration) and white transformants (indicating no YFP integration) that appeared on the plates. The total number white and fluorescent transformants on a transformation plate were counted. In case of fluorescent transformants, the donor DNA was successfully integrated into the genomic DNA of the yeast cells. The results are provided in FIG. 12 and in Table 9. The experimental set-ups are schematically depicted in FIG. 11. Below, the experimental results for the subsets A to D are summarized.

give surprisingly similar good results (see FIG. 12). Approach D has a big advantage as compared to approach A, because no pre-annealing step of ssODNs is required.

Example 4: ssODN-Mediated Construct Integration (OMCI) of a Yellow Fluorescent Protein (YFP) Expression Cassette and a Second Fluorescent Protein (RFP) Expression Cassette at a Genomic Locus in a Cell Using CRISPR/Cas9

In this experiment, it was determined whether the OMCI method could be used to transform an YPF and RFP expression cassette in tandem (first the YPF expression cassettes, subsequent the RFP expression cassette) at one genomic locus. The YFP and GFP expression cassettes do not contain homology with each other or with genomic DNA. The homology is provided by the ssODNs included in the transformation, as schematically depicted in FIG. 13. In addition, it was determined whether parts of genomic DNA could be deleted using this approach. The OMCI method was evaluated in combination with the CRISPR-CAS9 system.

Experimental Details

The components required in Example 4 are as follows:
Yeast strain CSN001 which is pre-expressing CAS9. Construction of strain CSN001 is described in Example 1.
A linear recipient gRNA-vector PCR fragment (SEQ ID NO: 8, FIG. 2) used for assembly in a cell of a guide sequence resulting in a circular vector. Generation of the linear recipient gRNA-vector PCR fragment is described in Example 1.
A guide sequence that is part of a linear DNA insert sequence comprising the 20 bp guide sequence to form a functional guide RNA expression cassette (as depicted in FIG. 2, approach c)). This approach comprises two complementary ssODN sequences of 120 bp consisting of 50 bp homology with 5' part of the linear recipient gRNA-vector PCR fragment being the SNR52p, a 20 bp guide sequence targeting the IN1 locus, and 50 bp homology with 3' part of the linear recipient gRNA-vector PCR fragment being the structural component of the sgRNA. The two ssODN guide sequences used are set out in SEQ ID NO: 15 and SEQ ID NO: 16.

The guide sequence used in this example will guide the CAS9 protein to the INT1 locus in genomic DNA of S. cerevisiae. The INT1 integration site is located at the non-

TABLE 9

Overview of results for transformation experiments depicted in FIG. 12.

| Experiment | dsDNA[1] flanks | ssODN[2] flanks | No. ssODN | no.f/no.w obtained in each deletion length[3] | | | |
|---|---|---|---|---|---|---|---|
| | | | | 0 kbp | 1 kbp | 3 kbp | 10 kbp |
| A | + | | 0 | 32f/27w | 36f/21w | 22f/22w | 3f/12w |
| B | | + | 2* | 2f/21w | 0f/8w | 0f/13w | 0f/19w |
| C | | + | 2* | 0f/8w | 1f/17w | 0f/11w | 0f/11w |
| D | | + | 4 | 47f/18w | 27f/15w | 16f/27w | 13f/17w |

[1]The ssODNs were pre-annealed to form a double-stranded DNA (ds-DNA) and added to the transformation.
[2]The ssODNs were directly added in the transformation (no pre-annealing).
*The 2 ssODNs added to this experiment are not complementary with each other.
[3]For each transformation experiments the number of fluorescent transformants (indicating YFP integration) and white transformants (indicating no YFP integration) that appeared on the plates is given as no.f/no.w.

This experiment shows the successful use of at least a first and a second single ssODN which are essentially complementary to each other in the in vivo assembly of at least two double-stranded nucleic acid molecules, e.g. wherein a first double-stranded nucleic acid molecule integrates into a second double-stranded nucleic acid molecule, in a CRISPR-CAS9 mediated transformation. These results show that when two single non complementary ssODNs are used in the transformation experiment (FIG. 12) only a low number of correct YFP transformants is obtained. Approach A and B, where four pre-annealed ssODNs as flanks were used for integration of the YFP expression cassette, and approach D, where four non pre-annealed ssODNs are used coding region between NTR1 (YOR071c) and GYP1 (YOR070c) located on chromosome XV.

Upon transformation and assembly in the cell, the NatMX marker present on the circular vector can be used for selection transformants on nourseothricin. The resulting circular vector contained a functional guide RNA expression cassette, producing a sgRNA that was used to target the CAS9 protein to an intended genomic target site present in genomic DNA of the host.

- A synthetic DNA sequence (gBlock) of the ds-DNA connector 5-YFP expression cassette-connector A sequence (SEQ ID NO: 54). The gBlock was ordered at Integrated DNA Technologies (Leuven, Belgium).
- A synthetic DNA sequence (gBlock) of the ds-DNA connector B-Red Fluorescence Protein (RFP) expression cassette-connector 3 sequence (SEQ ID NO: 55). The gBlock was ordered at Integrated DNA Technologies (Leuven, Belgium).
- 100 bp ssODN flank sequences or 100 bp ds-DNA flank sequences as indicated in Table 8. A description of the 100 bp knock-out flanks sequences is provided in Example 1. The ssODNs were not pre-annealed in this experiment.

DNA Concentrations

All DNA concentrations, including all single ssODNs, and the ds-DNA YPF and RFP expression cassette gBlocks were determined using a NanoDrop device (ThermoFisher, Life Technologies, Bleiswijk, the Netherlands), providing the concentrations in nanogram per microliter. Based on these measurements, specific DNA amounts were used in the transformation experiments.

Yeast Transformation

*S. cerevisiae* strain CSN001 was transformed using the LiAc/salmon sperm (SS) carrier DNA/PEG method (Gietz and Woods, 2002).

An overview of all transformation experiments of this Example is shown in Table 10. In each transformation experiment (subset), 100 ng of the ds-DNA con 5-YPF expression cassette-con A gBlock (SEQ ID NO: 54), 100 ng of the ds-DNA con B-RFP expression cassette-con 3 gBlock (SEQ ID NO: 55) and the 50 ng of each of the six 100 bp ssODN flank sequences (Table 10) were included. In addition, 100 ng linear recipient gRNA-vector PCR fragment (SEQ ID NO: 8) and 500 ng of each ssODN guide sequence containing homology with the linear recipient gRNA-vector PCR fragment (SEQ ID NO: 15 and SEQ ID NO: 16) were included in each transformation.

TABLE 10

Overview of different subsets of transformation experiments. The amounts of ds-DNA or ssODN used in each subset is indicated. The ssODNs were directly added in the transformation (no pre-annealing). ds-DNA/ssODN flanks (50-50) means 50 bp complementarity (sequence identity) with the left flank integration site in genomic DNA and the 50 bp connector 5 sequence of the donor DNA, or 50 bp complementarity (sequence identity) with the connector 3 sequence of the donor DNA and 50 bp complementarity (sequence identity) with the right flank integration site in genomic DNA.

| Subset | Deletion in kbp | ssODN flanks (50-50) (integration to genomic DNA) | ssODNs (conA - conB complementarity (sequence identity)) |
|---|---|---|---|
| A | 0 | SEQ ID NO: 23<br>SEQ ID NO: 24<br>SEQ ID NO: 25<br>SEQ ID NO: 26 | SEQ ID NO: 56<br>SEQ ID NO: 57 |

TABLE 10-continued

Overview of different subsets of transformation experiments. The amounts of ds-DNA or ssODN used in each subset is indicated. The ssODNs were directly added in the transformation (no pre-annealing). ds-DNA/ssODN flanks (50-50) means 50 bp complementarity (sequence identity) with the left flank integration site in genomic DNA and the 50 bp connector 5 sequence of the donor DNA, or 50 bp complementarity (sequence identity) with the connector 3 sequence of the donor DNA and 50 bp complementarity (sequence identity) with the right flank integration site in genomic DNA.

| Subset | Deletion in kbp | ssODN flanks (50-50) (integration to genomic DNA) | ssODNs (conA - conB complementarity (sequence identity)) |
|---|---|---|---|
| A | 1 | SEQ ID NO: 21<br>SEQ ID NO: 22<br>SEQ ID NO: 27<br>SEQ ID NO: 28 | SEQ ID NO: 56<br>SEQ ID NO: 57 |
| A | 3 | SEQ ID NO: 19<br>SEQ ID NO: 20<br>SEQ ID NO: 29<br>SEQ ID NO: 30 | SEQ ID NO: 56<br>SEQ ID NO: 57 |
| A | 10 | SEQ ID NO: 17<br>SEQ ID NO: 18<br>SEQ ID NO: 31<br>SEQ ID NO: 32 | SEQ ID NO: 56<br>SEQ ID NO: 57 |

The transformation mixtures were plated on YPD-agar (10 grams per liter of yeast extract, 20 grams per liter of peptone, 20 grams per liter of dextrose, 20 grams per liter of agar) containing 200 µg nourseothricin (NatMX, Jena Bioscience, Germany) and 200 µg G418 (Sigma Aldrich, Zwijndrecht, the Netherlands) per ml.

Results

The experiment outlined above was performed and after transformation, the cells were plated out in a 1:10, 1:5 and 1:3 dilution in milliQ water. After about 3 days of growth, transformants appeared on the transformation plates. The total number of transformants as well as the number of fluorescent (FP) transformants were counted by UV light (Qpix 450 Transformant Picker-Molecular devices LLC).

Results of the experiment are shown in FIG. 14 for the 1:5 dilution of the transformants. The experiment gives an efficiency for in tandem introduction of 2 gene constructs using double complementary ODNs. Editing efficiencies are 0, 11, 19, 18% for the ~0, ~1, ~3, ~10 kbp knockout and insertion YFP and/or RFP, respectively. Similar frequency ranges are observed for the 1:3 and 1:10 dilutions. The fluorescence measurement in FIG. 14, YFP and RFP were not measured separately.

To confirm correct tandem integration of YFP and RFP expression cassettes (SEQ ID NO: 54 and SEQ ID NO: 55), and to demonstrate deletion of 1 kbp of genomic DNA at the INT1 locus, three transformants for which both YFP as well as RFP fluorescence was confirmed by the BioLector® (M2P labs—Germany) were further analyzed. Genomic DNA of the fluorescent transformants was isolated as described by Lōoke et al., 2011 and was used as template in the PCR reaction. The primers used in the PCR to confirm the integration of the YFP and RFP expression cassettes into the genome and 1 kbp deletion of genomic DNA surrounding the INT1 locus are schematically depicted in FIG. 17. The PCR reaction was performed using Phusion DNA polymerase (New England Biolabs, USA) according to manufacturer's instructions and a PCR program known to the person skilled in the art. When using the primers set out in SEQ ID NO: 68 and SEQ ID NO: 69 in the PCR reaction, genomic integration of the RFP expression cassette was demonstrated by the resulting PCR fragment of 711 bp upon analysis on a 0.8% agarose gel (FIG. 18). When using the primers set out in SEQ ID NO: 70 and SEQ ID NO: 69 in the PCR reaction, tandem integration of the YFP and RFP expression cassettes was demonstrated by the resulting PCR fragment of 2277 bp upon analysis on a 0.8% agarose gel (FIG. 18). When using the primers set out in SEQ ID NO: 33 and SEQ ID NO: 34 in the PCR reaction, correct deletion of 1 kb genomic DNA at 5' end was demonstrated by the resulting PCR fragment of 752 bp upon analysis on a 0.8% agarose gel (FIG. 18). When using the primers set out in SEQ ID NO: 71 and SEQ ID NO: 38 in the PCR reaction, correct deletion of 1 kb genomic DNA at the 3' end was demonstrated by the resulting PCR fragment of 1872 bp upon analysis on a 0.8% agarose gel (FIG. 18). When using the primers set out in SEQ ID NO: 72 and SEQ ID NO: 38 in the PCR reaction, correct deletion of 1 kb genomic DNA at the 3' end was demonstrated by the resulting PCR fragment of 1822 bp upon analysis on a 0.8% agarose gel (FIG. 18). When using the primers set out in SEQ ID NO: 35 and SEQ ID NO: 36 in the PCR reaction, genomic integration of the YFP expression cassette was demonstrated by the resulting PCR fragment of 719 bp upon analysis on a 0.8% agarose gel (FIG. 18).

The PCR results are summarized in Table 11. The PCR results confirmed that ~1 kB of genomic DNA was deleted by tandem integration of the YFP and RFP expression cassettes (SEQ ID NO: 54 and SEQ ID NO: 55) using the methods as described for three fluorescent transformants that were analyzed.

using a CRISPR/Cas9 system with donor DNA sequences that integrate via homologous recombination.

In this experiment, separate double-stranded DNA cassettes comprising a promoter (P), a yellow fluorescent protein (O or YFP), and a terminator T are assembled together using ssODNs to form a functional expression cassette at a genomic locus INT1 using CRISPR/Cas9 as schematically depicted in FIG. 15. YFP fluorescence can be used as a readout to demonstrate that the expression cassette was correctly assembled in the genomic DNA using this approach.

The resulting YFP cassette is similar to the one applied in Example 1, and has 50 basepair (bp) connector sequences at both the 5' and 3' ends (SEQ ID NO: 10). These 50 bp connector sequences interact with 100 bp flank DNA sequences, having 50 bp homology with the YFP expression cassette, and are added as separate DNA oligonucleotides to the transformation mix. In addition, these 100 bp flanks have 50 bp homology with the genomic locus for the intended stretch of knock-out of genomic DNA.

This set-up allows for a flexible choice of knock-out design by using short oligonucleotides (here 100 bp) to specify the knock-out, and in addition flexible build-up of expression cassette where each ds-DNA module, in this case a promoter (pro; P), an open reading frame (orf; O) and a terminator (ter; T) fragment can easily be varied in an experimental set-up, allowing for modular construct integration in a cell using OMCI, which is visually shown in FIG. 15.

TABLE 11

Summary of PCR results confirming correct integration of the YFP expression cassette at the INT1 locus and deletion of 1 kbp deletion of genomic DNA. Correct PCR band means that the PCR product obtained was a specific product of the correct size as determined by agarose gel electrophoresis (see FIG. 18).

| Number of fluorescent transformants tested | Number of correct transformants using PCR primers: SEQ ID NO: 68 and SEQ ID NO: 69 | Using PCR primers: SEQ ID NO: 70 and SEQ ID NO: 69 | Using PCR primers: SEQ ID NO: 33 and SEQ ID NO: 34 | Using PCR primers: SEQ ID NO: 71 and SEQ ID NO: 38 | Using PCR primers: SEQ ID NO: 72 and SEQ ID NO: 38 | Using PCR primers: SEQ ID NO: 35 and SEQ ID NO: 36 |
|---|---|---|---|---|---|---|
| 3 | 3 | 3 | 3 | 3 | 3 | 3 |

This experiment demonstrates the successful use of at least a first and a second single-stranded oligonucleotide in the assembly within a cell of three double-stranded nucleic acid molecules into a single double-stranded nucleic acid construct of pre-determined sequence, wherein pairs of single-stranded oligonucleotide are essentially complementary to each other. In this experiment a first and second double-stranded nucleic acid molecule were integrated as a tandem into a third double-stranded nucleic acid molecule.

Example 5: ssODN-Mediated Construct Integration (OMCI) of a Promoter (P), a Yellow Fluorescent Protein (O or YFP), a Terminator T to Form a Functional Expression Cassette at a Genomic Locus Using CRISPR/Cas9

This experiment describes the replacement of stretches of genomic DNA in a range from about 0-10 kbp by an YFP expression cassette (YFP protein, see Nagai et al., 2002)

Furthermore, a comparison was made between the use of double complementary ssODNs (subset A), single ssODNs (subset D), and direct homology-based assembly in the cell (subset C). As negative control experiment, we used an YFP expression construct with same gRNA and marker vector, but left out the 100 bp integration flanks (subset B), and also included a control experiment where we only supplied the gRNA and marker vector (subset E). In all subsets, the 20-bp gRNA to be inserted in the marker vector is supplied as 2 complementary ssODNs.

In case of the direct homology-based assembly in a cell (subset C) (FIG. 15b "C"), the first ds-DNA contains "50 bp flank-50 bp con5-complete pro-5' 50 bp of YFP", the second ds-DNA contains "3' 50 bp pro-complete YFP-5' 50 bp ter", the third ds-DNA contains "3' 50 bp YFP-complete ter-50 bp con3-50 bp flank". These fragments can assemble in the cell (100-bp homology between first and second ds-DNA fragments, and also 100 bp homology between second and third ds-DNA fragment) to form a functional YFP expression cassette and integrate at the genome, using 50 bp flanks with homology to the genome (in this case~1 kbp knockout around INT1 locus).

Experimental Details

The components required in Example 4 are as follows:

Yeast strain CSN001 which is pre-expressing CAS9. Construction of strain CSN001 is described in Example 1.

A linear recipient gRNA-vector PCR fragment (SEQ ID NO: 8, FIG. 2) used for assembly in a cell of a guide sequence resulting in a circular vector. Generation of the linear recipient gRNA-vector PCR fragment is described in Example 1.

A guide sequence that is part of a linear DNA insert sequence comprising the 20 bp guide sequence to form a functional guide RNA expression cassette (as depicted in FIG. 2, approach c)). This approach comprises two complementary ssODN sequences of 120 bp consisting of 50 bp homology with 5' part of the linear recipient gRNA-vector PCR fragment being the SNR52p, a 20 bp guide sequence targeting the INT1 locus, and 50 bp homology with 3' part of the linear recipient gRNA-vector PCR fragment being the structural component of the sgRNA. The two ssODN guide sequences used are set out in SEQ ID NO: 15 and SEQ ID NO: 16.

The guide sequence used in this example will guide the CAS9 protein to the INT1 locus in genomic DNA of *S. cerevisiae*. The INT1 integration site is located at the non-coding region between NTR1 (YOR071c) and GYP1 (YOR070c) located on chromosome XV.

Upon transformation and assembly in the cell, the NatMX marker present on the circular vector can be used for selection transformants on nourseothricin. The resulting circular vector contained a functional guide RNA expression cassette, producing a sgRNA that was used to target the CAS9 protein to an intended genomic target site present in genomic DNA of the host.

A synthetic DNA sequence (gBlock) of the ds-DNA connector 5-TDH3 promoter sequence (SEQ ID NO: 58). The gBlock was ordered at Integrated DNA Technologies (Leuven, Belgium).

A synthetic DNA sequence (gBlock) of the ds-DNA YFP sequence (SEQ ID NO: 59). The gBlock was ordered at Integrated DNA Technologies (Leuven, Belgium).

A synthetic DNA sequence (gBlock) of the ds-DNA ENO1 t-connector 3 (SEQ ID NO: 60). The gBlock was ordered at Integrated DNA Technologies (Leuven, Belgium).

A synthetic DNA sequence (gBlock) of the ds-DNA 1 kb deletion flank genomic DNA (50 bp complementarity (sequence identity))-con5-TDH3p-YFP (100 bp complementarity (sequence identity) in total) (SEQ ID NO: 65). The gBlock was ordered at Integrated DNA Technologies (Leuven, Belgium).

A synthetic DNA sequence (gBlock) of the ds-DNA TDH3p (100 bp complementarity (sequence identity) in total)-YFP-ENO1t (100 bp complementarity (sequence identity) in total) (SEQ ID NO: 66). The gBlock was ordered at Integrated DNA Technologies (Leuven, Belgium).

A synthetic DNA sequence (gBlock) of the ds-DNA YFP-ENO1t (100 bp complementarity (sequence identity) in total)-Con3-1 kb deletion flank genomic DNA (50 bp complementarity (sequence identity)) (SEQ ID NO: 67). The gBlock was ordered at Integrated DNA Technologies (Leuven, Belgium).

A PCR fragment of the Yellow Fluorescent Protein (Venus) donor DNA expression cassette: connector 5-THD3p-YFP (Venus)-ENO1t-connector 3 (SEQ ID NO: 10), which is further described in Example 1.

100 bp ssODN flank sequences as indicated in Table 13. A description of the 100 bp knock-out flanks sequences is provided in Example 1. The ssODNs were not pre-annealed in this experiment. ssODNs were ordered at Integrated DNA Technologies (Leuven, Belgium).

DNA Concentrations

All DNA concentrations were determined using a Nano-Drop device (ThermoFisher, Life Technologies, Bleiswijk, the Netherlands), providing the concentrations in nanogram per microliter. Based on these measurements, specific DNA amounts were used in the transformation experiments.

Yeast Transformation

*S. cerevisiae* strain CSN001 was transformed using the LiAc/salmon sperm (SS) carrier DNA/PEG method (Gietz and Woods, 2002).

An overview of all transformation experiments (subsets) of Example 5 is shown in Table 12 and Table 13. The amount of DNA used in each subset is indicated in Table 12 and SEQ ID NO's in Table 13. In each transformation experiment, 100 ng linear recipient gRNA-vector PCR fragment (SEQ ID NO: 8) was included.

TABLE 12

Overview of the amounts of DNA used in the different transformation experiments and donor DNA sequences (P, O, T or POT), here indicated as subsets.

| Subset | P | O | T | POT (con5-YFP-con3; SEQ ID NO: 10) |
|---|---|---|---|---|
| A | 25 ng (SEQ ID NO: 58) | 50 ng (SEQ ID NO: 59) | 25 ng (SEQ ID NO: 60) | |
| B | | | | 100 ng |
| C | 100 ng (SEQ ID NO: 65) | 100 ng (SEQ ID NO: 66) | 100 ng (SEQ ID NO: 67) | |
| D | 25 ng (SEQ ID NO: 58) | 50 ng (SEQ ID NO: 59) | 25 ng (SEQ ID NO: 60) | |
| E | | | | |

TABLE 12-continued

Overview of the amounts of DNA used in the different transformation experiments and donor DNA sequences (P, O, T or POT), here indicated as subsets.

| Subset | ssODN[1] guide sequence (50-20-50) | ssODN[1] flanks (50-50) | ssODN[1] PO/OT complementarity (sequence identity) (50-50) |
|---|---|---|---|
| A | 2 × 500 ng | 4 × 50 ng | 4 × 50 ng |
| B | 2 × 500 ng | | |
| C | 2 × 500 ng | | |
| D | 2 × 500 ng | 2 × 100 ng | 2 × 100 ng |
| E | 2 × 500 ng | | |

[1]The ssODNs were directly added in the transformation (without pre-annealing). ssODN gRNA insert (50-20-50) means 50 bp complementarity (sequence identity) with the linear recipient gRNA-vector PCR fragment (SEQ ID NO: 8, FIG. 2)-20 bp guide sequence-50 bp complementarity (sequence identity) with the recipient linear gRNA-vector PCR fragment. ssODN flanks (50-50) means 50 bp complementarity (sequence identity) with the left flank integration site in genomic DNA and the 50 bp connector 5 sequence of the donor DNA, or 50 bp complementarity (sequence identity) with the connector 3 sequence of the donor DNA and 50 bp complementarity (sequence identity) with the right flank integration site in genomic DNA. ssODN PO/OT means the oligonucleotide has complementarity (sequence identity) (50-50) means 50 bp complementarity (sequence identity) with the promoter and 50 bp complementarity (sequence identity) with the ORF, or 50 bp complementarity (sequence identity) with the ORF and 50 bp complementarity (sequence identity) with the terminator.

TABLE 13

Overview of different subsets of transformation experiments. The ssODNs were directly added in the transformation (no pre-annealing). gBlock donor DNA was directly added to the transformation. For short description see legend of Table 12.

| Subset | Deletion in kbp | ssODN guide sequence (50-20-50) | ssODN flanks (50-50) (integration to genomic DNA) | ssODN PO/OT complementarity (sequence identity) (50-50) | Donor DNA (ds-DNA) |
|---|---|---|---|---|---|
| A | 0 | SEQ ID NO: 15 | SEQ ID NO: 23 | SEQ ID NO: 61 | SEQ ID NO: 58 |
|   |   | SEQ ID NO: 16 | SEQ ID NO: 24 | SEQ ID NO: 62 | SEQ ID NO: 59 |
|   |   |               | SEQ ID NO: 25 | SEQ ID NO: 63 | SEQ ID NO: 60 |
|   |   |               | SEQ ID NO: 26 | SEQ ID NO: 64 |               |
| A | 1 | SEQ ID NO: 15 | SEQ ID NO: 21 | SEQ ID NO: 61 | SEQ ID NO: 58 |
|   |   | SEQ ID NO: 16 | SEQ ID NO: 22 | SEQ ID NO: 62 | SEQ ID NO: 59 |
|   |   |               | SEQ ID NO: 27 | SEQ ID NO: 63 | SEQ ID NO: 60 |
|   |   |               | SEQ ID NO: 28 | SEQ ID NO: 64 |               |
| A | 3 | SEQ ID NO: 15 | SEQ ID NO: 19 | SEQ ID NO: 61 | SEQ ID NO: 58 |
|   |   | SEQ ID NO: 16 | SEQ ID NO: 20 | SEQ ID NO: 62 | SEQ ID NO: 59 |
|   |   |               | SEQ ID NO: 29 | SEQ ID NO: 63 | SEQ ID NO: 60 |
|   |   |               | SEQ ID NO: 30 | SEQ ID NO: 64 |               |
| A | 10 | SEQ ID NO: 15 | SEQ ID NO: 17 | SEQ ID NO: 61 | SEQ ID NO: 58 |
|   |   | SEQ ID NO: 16 | SEQ ID NO: 18 | SEQ ID NO: 62 | SEQ ID NO: 59 |
|   |   |               | SEQ ID NO: 31 | SEQ ID NO: 63 | SEQ ID NO: 60 |
|   |   |               | SEQ ID NO: 32 | SEQ ID NO: 64 |               |
| B | No deletion | SEQ ID NO: 15 SEQ ID NO: 16 | | | SEQ ID NO: 10 |
| C | 1 | SEQ ID NO: 15 | SEQ ID NO: 21 | | SEQ ID NO: 65 |
|   |   | SEQ ID NO: 16 | SEQ ID NO: 22 | | SEQ ID NO: 66 |
|   |   |               | SEQ ID NO: 27 | | SEQ ID NO: 67 |
|   |   |               | SEQ ID NO: 28 | |               |
| D | 1 | SEQ ID NO: 15 | SEQ ID NO: 21 | SEQ ID NO: 61 | SEQ ID NO: 58 |
|   |   | SEQ ID NO: 16 | SEQ ID NO: 27 | SEQ ID NO: 63 | SEQ ID NO: 59 |
|   |   |               |               |               | SEQ ID NO: 60 |
| E | No deletion | SEQ ID NO: 15 SEQ ID NO: 16 | | | |

The transformation mixtures were plated on YPD-agar (10 grams per liter of yeast extract, 20 grams per liter of peptone, 20 grams per liter of dextrose, 20 grams per liter of agar) containing 200 µg nourseothricin (NatMX, Jena Bioscience, Germany) and 200 µg G418 (Sigma Aldrich, Zwijndrecht, the Netherlands) per ml.

Results

The experiment outlined above was performed and after transformation, the cells were plated out in a 1:10, 1:5 and 1:3 dilution in milliQ water. After about 3 days of growth, transformants appeared on the transformation plates. The total numbers as well as the number of fluorescent (YFP) transformants were counted. Results of the experiment are shown in FIG. 16 for the 1:5 dilution of the transformants.

Subset A shows that in all cases, i.e., 0, 1, 3, 10 kbp knock-out of genomic DNA and replacement by a functional YFP cassette, fluorescent transformants are obtained in a frequency range from 2-15%.

Subset B, where no flanks are added, serves as a control for random integration. A similar amount of transformants as subset A was observed, however no fluorescent transformants.

Subset C, where 3 ds-DNA fragments, containing promoter (P), orf (0) and terminator (T), respectively, with 100 bp homology with each other and 50-bp homology for "P" ds-DNA fragment and "T" ds-DNA fragment with the genome, were added (FIG. 15b "C"). This serves as a reference for direct homology-based integration at the genome using CRISPR/Cas9. Here about half the amount of transformants as subset A was observed, with 3/34 fluorescent transformants a frequency of 8%.

Subset D, where only single ssODNs were added, shows a similar amount of transformants as subset A was observed, however no fluorescent transformants were obtained. This indicated that the ssODN approach with double complementary ssODNs worked well, while the single ssODNs approach gave no positive result.

Subset E, the negative control, where no donor DNA material was added, showed less transformants than subset A. The transformants are the result of an assembled gRNA-marker cassette, which allows selection on nourseothricin present in the transformation plate.

Concluding, this experiment demonstrates the use of at least a first and a second single-stranded oligonucleotide in the assembly within a cell of at least two double-stranded nucleic acid molecules into a single double-stranded nucleic acid construct of pre-determined sequence, wherein pairs of single-stranded oligonucleotide are essentially complementary to each other. In this experiment, pairs of single-stranded oligonucleotides were used for the modular assembly of promoter, orf, terminator dsDNA fragments and integration into a genomic locus is shown to work here in combination with an induced double-stranded break in the genomic DNA and in combination with single-stranded oligonucleotide-mediated assembly in the cell of the gRNA-marker vector. The method according to the invention can be further applied to introduce other elements like signal sequences or protein tags. It can also be applied to build expression constructs in a modular way for example by having a protein ds-DNA in 2 or more fragments and by that have a method for combinatorial multi-fragment protein assembly, as long as there is homology and overlap (both 80% or more) with the applied ssODNs to connect ds-DNA fragments.

Example 6: ssODN-Mediated DNA Construct Integration (OMCI) at a Genomic Locus in a Cell Using CRISPR/Cpf1

This experiment describes the replacement of stretches of genomic DNA in a range from about 0 or 1 kbp by a yellow fluorescent protein (YFP) expression cassette (for YFP see Nagai et al., 2002) or expression cassettes encoding a carotenoid production pathway (Verwaal et al., 2007) using a CRISPR/Cpf1 system with donor DNA sequences that integrate via homologous recombination.

When performing precision genome editing experiments, an easy readout of successful expression or expression levels of genes that were modified or introduced, for example based on a colour change of the organisms in which such experiments are performed, is beneficial. When three genes, crtE, crtYB and crtI from *Xanthophyllomyces dendrorhous* are introduced and overexpressed in *Saccharomyces cerevisiae*, the transformants will produce carotenoids which are colored compounds and consequently result in yellow, orange or red colored transformants (Verwaal et al., 2007). Coloring of the cells is a result of carotenoid production and can be achieved either by expressing crtE, crtYB and crtI from a vector, or by integration of the genes into genomic DNA, using promoters and terminators functional in *S. cerevisiae* to express these genes (Verwaal et al., 2007). Introduction of YFP results in fluorescent (colored) transformants, which is visible using for example a fluorescence microscope or by UV light using a Qpix 450 Transformant Picker (Molecular devices LLC), as known by a person skilled in the art.

The carotenoid gene expression cassettes that serve as donor DNA, resulting in expression of crtE, crtYB and crtI, all have 50 bp connector sequences at their 5' and 3' ends, which allow in vivo recombination into one linear DNA fragment in the yeast cell (FIG. 19). To allow targeted integration of the carotenoid gene donor DNA cassettes into genomic DNA, 100 bp single-stranded oligodeoxynucleotides (ssODNs) that contain 50 bp homology with a connector sequence and 50 bp homology with the genomic locus for the intended stretch of DNA knock-out, were added to the transformation mix. The YFP expression cassette that serves as donor DNA contains 50 basepair (bp) connector sequences at both the 5' and 3' ends. To allow targeted integration of the YFP donor DNA into genomic DNA, 100 bp single-stranded oligodeoxynucleotides (ssODNs) that contain 50 bp homology with a connector sequence and 50 bp homology with the genomic locus for the intended stretch of DNA knock-out, were added to the transformation mix.

These set-ups allow for a flexible choice of knock-out design by using short oligonucleotides (here 100 bp) to specify the knock-out, which is visually shown in FIG. 4 and FIG. 19, to replace 0 and 1 kbp with donor DNA around the CRISPR/Cpf1 induced double-stranded break at the genomic DNA, respectively.

Cpf1 was expressed from a single copy yeast vector, as described below in this Example. For the expression of the crRNA sequences, required to target Cpf1 to the desired locus in genomic DNA in *S. cerevisiae*, a crRNA expression cassette with control elements as previously described by DiCarlo et al., 2013 was used. The crRNA expression cassette comprises a SNR52 promoter, a 20 nt direct repeat sequence and a 20 nt spacer sequence comprising the guide-sequence or genomic target sequence, followed by the SUP4 terminator. The crRNA expression cassette was expressed from a multicopy yeast vector as described below in the Example.

Construction of Cpf1 Expression Vectors

Single copy yeast vectors to express a Cpf1 variant were constructed as follows: Yeast vector pCSN061 is a single copy vector (CEN/ARS) that contains a CAS9 expression cassette consisting of a CAS9 codon optimized variant expressed from the Kl11 promoter (*Kluyveromyces lactis* promoter of KLLA0F20031g) and the *S. cerevisiae* GND2 terminator, and a functional KanMX marker cassette conferring resistance against G418. The CAS9 expression cassette was KpnI/NotI ligated into pRS414 (Sikorski and Hieter, 1989), resulting in intermediate vector pCSN004. Subsequently, a functional expression cassette conferring G418 resistance (http://www.euroscarf.de) was NotI restricted from vector pUG7-KanMX and NotI ligated into pCSN004, resulting in vector pCSN061 that is depicted in FIG. 3 and the sequence is set out in SEQ ID NO: 9.

A linear PCR fragment of the pCSN061 vector omitting the CAS9 expression cassette, thus including the KL11p, the pCSN061 single copy vector backbone and a KanMX marker cassette, was obtained by PCR using vector pCSN061 as template by including a forward (SEQ ID NO: 73) and reverse primer (SEQ ID NO: 74) and Phusion as DNA polymerase (New England Biolabs, USA) in the reaction. The PCR reaction was performed according to manufacturer's instructions. The three Cpf1 orthologues tested in this Example, being AsCpf1 from *Acidaminococcus* spp. BV3L6, LbCpf1 from *Lachnospiraceae* bacterium ND2006 and FnCpf1 from *Francisella novicida* U112 (Zetsche et al, 2015) were obtained as follows: A linker protein sequence (SRAD) and a SV40 nuclear localization signal (PKKKRKV) were added to the carboxy terminus of the Cpf1 orthologues, resulting in the AsCpf1 protein sequence (SEQ ID NO: 75), the LbCpf1 protein sequence (SEQ ID NO: 76) and the FnCpf1 protein sequences (SEQ ID NO: 77). These protein sequences were codon pair optimized for expression in *S. cerevisiae* as described in WO2008/000632, resulting in the nucleotide sequences as set out in SEQ ID NO: 78 for AsCpf1, SEQ ID NO: 79 for LbCpf1 and SEQ ID NO: 80 for FnCpf1. These nucleotide sequences were ordered as synthetic DNA at Thermo Fisher Scientific (GeneArt Gene Synthesis and Services).

The synthetic AsCpf1 (SEQ ID NO: 78), LbCpf1 (SEQ ID NO: 79) and FnCpf1 (SEQ ID NO: 80) sequences were used as template in a PCR reaction with FW and REV primers (SEQ ID NO: 81 and SEQ ID NO: 82 for AsCpf1; SEQ ID NO: 83 and SEQ ID NO: 84 for LbCpf1; SEQ ID NO: 85 and SEQ ID NO: 86 for FnCpf1) using Phusion as DNA polymerase (New England Biolabs, USA) in the reaction. The PCR reaction was performed according to manufacturer's instructions. The three Cpf1 PCR fragments have homology at their 5' end (part of KI11p sequence) and 3' end (part of GND2t sequence) with the linear PCR fragment of the pCSN061 vector.

All PCR fragments were purified using the NucleoSpin Gel and PCR Clean-up kit (Machery-Nagel, distributed by Bioké, Leiden, the Netherlands) according to manufacturer's instructions. Subsequently the three purified Cpf1 PCR fragments were individually assembled into the purified linear PCR fragment of the pCSN061 vector using Gibson assembly (Gibson et al., 2009). The resulting single copy yeast expression vector were named pCSN066 (AsCpf1, FIG. 20, SEQ ID NO: 87), pCSN067 (LbCpf1, FIG. 21, SEQ ID NO: 88) and pCSN068 (FnCpf1, FIG. 22, SEQ ID NO: 89).

pRN1120 Vector Construction (Multi-Copy Recipient crRNA Expression Vector, NatMX Marker)

Yeast vector pRN1120 is a multi-copy vector (2 micron) that contains a functional NatMX marker cassette conferring resistance against nourseothricin. The backbone of this vector is based on pRS305 (Sikorski and Hieter, 1989), including a functional 2 micron ORI sequence and a functional NatMX marker cassette (http://www.euroscarf.de). Vector pRN1120 is depicted in FIG. 23 and the sequence is set out in SEQ ID NO: 1. Vector pRN1120 can be equipped with a crRNA expression cassette as explained in this example (FIG. 24). Prior to transformation, vector pRN1120 was restricted with the restriction enzymes EcoRI and XhoI. Next, the linearized vector was purified using the NucleoSpin Gel and PCR Clean-up kit (Machery-Nagel, distributed by Bioké, Leiden, the Netherlands) according to manufacturer's instructions.

Donor DNA

Donor DNA sequences consist of DNA expression cassettes or donor DNA flanks. Donor DNA expression cassettes are double-stranded DNA (dsDNA) sequences of carotenoid gene expression cassettes (crtE, crtYB and crtI) or the yellow fluorescent protein (YFP) expression cassette flanked by a functional promoter and terminator sequence. Donor DNA flank sequences are used to allow integration of the carotenoid gene expression cassettes or the YFP expression cassette into the desired locus within the genomic DNA. Donor DNA flank sequences are composed of double-stranded DNA (dsDNA) flanks sequences or pairs of single-stranded oligodeoxynucleotides (ssODNs) complementary to each other but which are not annealed prior to the transformation experiment. PCR fragments were used as dsDNA donor DNA or flank DNA sequences in the transformation experiment using synthetic DNA (ordered at DNA2.0, Menlo Park, Calif., USA) or chromosomal DNA as template (Table 14). Oligo nucleotides ordered as standard desalted primers at IDT (Integrated DNA Technologies, Leuven, Belgium), were used as ssODNs in the transformation experiment. An overview of the different donor DNA sequences used in this experiment is provided in Table 14.

TABLE 14

Overview of different donor DNA sequences used in this experiment. Under description, the following elements are indicated: Connector (Con) sequences are 50 bp DNA sequences that are required for in vivo recombination as described in WO2013144257A1. Promoter sequences originated from *S. cerevisiae* (Sc) or *K. lactis* (Kl), all terminators originate from *S. cerevisiae*. This table includes the SEQ ID NO's of the primers used to obtain the donor DNA sequences by amplification by PCR.

| Donor DNA SEQ ID NO: | Description donor DNA | Template for PCR | Forward primer | Reverse primer |
|---|---|---|---|---|
| SEQ ID NO: 90 | con5 - KlTDH2p - crtE - ScTDH3t - conA | Synthetic DNA | SEQ ID NO: 95 | SEQ ID NO: 96 |
| SEQ ID NO: 91 | conA - KlYDR1p - crtYB - ScPDC1t - conB | Synthetic DNA | SEQ ID NO: 97 | SEQ ID NO: 98 |
| SEQ ID NO: 92 | conB - ScPRE3p - crtI - ScTAL1t - con3 | Synthetic DNA | SEQ ID NO: 99 | SEQ ID NO: 100 |
| SEQ ID NO: 10 | THD3p - YFP (Venus) - ENO1t | Synthetic DNA | SEQ ID NO: 13 | SEQ ID NO: 14 |
| SEQ ID NO: 93 | 1 kb deletion flank: 5' INT1 - con5 | CEN.PK113-7D genomic DNA | SEQ ID NO: 101 | SEQ ID NO: 102 |
| SEQ ID NO: 94 | 1 kb deletion flank: con3 - 3' INT1 | CEN.PK113-7D genomic DNA | SEQ ID NO: 103 | SEQ ID NO: 104 |
| SEQ ID NO: 23 | ssODN 5' flank 0 kb deletion upper strand sequence. | n.a | n.a | n.a |
| SEQ ID NO: 24 | ssODN 5' flank 0 kb deletion lower strand sequence. | n.a. | n.a. | n.a. |

TABLE 14-continued

Overview of different donor DNA sequences used in this experiment. Under description, the following elements are indicated: Connector (Con) sequences are 50 bp DNA sequences that are required for in vivo recombination as described in WO2013144257A1. Promoter sequences originated from S. cerevisiae (Sc) or K. lactis (Kl), all terminators originate from S. cerevisiae. This table includes the SEQ ID NO's of the primers used to obtain the donor DNA sequences by amplification by PCR.

| Donor DNA SEQ ID NO: | Description donor DNA | Template for PCR | Forward primer | Reverse primer |
|---|---|---|---|---|
| SEQ ID NO: 25 | ssODN 3' flank 0 kb deletion upper strand sequence. | n.a | n.a | n.a |
| SEQ ID NO: 26 | ssODN 3' flank 0 kb deletion lower strand sequence. | n.a. | n.a. | n.a. |
| SEQ ID NO: 21 | ssODN 5' flank 1 kb deletion upper strand sequence. | n.a | n.a | n.a |
| SEQ ID NO: 22 | ssODN 5' flank 1 kb deletion lower strand sequence. | n.a. | n.a. | n.a. |
| SEQ ID NO: 27 | ssODN 3' flank 1 kb deletion upper strand sequence. | n.a | n.a | n.a |
| SEQ ID NO: 28 | ssODN 3' flank 1 kb deletion lower strand sequence. | n.a. | n.a. | n.a. | n.a.: not applicable.

The carotenoid gene expression cassettes which were part of the donor DNA sequences were ordered at DNA 2.0 (Menlo Park, Calif., USA) and were used as template for PCR reactions of which the products were used as donor DNA expression cassettes that were integrated into genomic DNA using the approach described in this example (Vide infra). In this example, a carotenoid gene expression cassette was composed of the following elements:

(i) at the 5' and 3' positions of the DNA sequence 50 basepair connector sequences are present. The presence of connector sequences allowed in vivo homologous recombination between highly homologous connector sequences that are part of other donor DNA expression cassettes or donor DNA flank sequences as is described in WO2013144257A1. As a result, multiple donor DNA fragments were assembled into the genomic DNA at a desired location and in a desired order, as is schematically depicted in FIG. 19.

(ii) A promoter sequence, which can be homologous (i.e. from S. cerevisiae) or heterologous (e.g. from Kluyveromyces lactis) and a terminator sequence derived from S. cerevisiae, were used to control the expression of the carotenogenic genes crtE, crtYB or crtI.

(iii) The crtE, crtYB and crtI nucleotide sequences were codon pair optimized for expression in S. cerevisiae as described in WO2008/000632.

PCR fragments for the donor DNA expression cassette sequences were generated using Phusion DNA polymerase (New England Biolabs, USA) according to manufacturer's instructions. In case of the expression cassettes of the carotenogenic genes, the synthetic DNA provided by DNA2.0 was used as a template in the PCR reactions, using the specific forward and reverse primer combinations depicted in Table 12. For example, in order to obtain the PCR fragment set out in SEQ ID NO: 90 (con5-crtE-conA expression cassette), the synthetic DNA construct provided by DNA2.0 was used as a template, using primer sequences set out in SEQ ID NO: 95 and SEQ ID NO: 96. In total, three different donor DNA sequences containing the carotenoid gene expression cassettes were generated by PCR, as set out in SEQ ID NO: 91, 92 and 93.

The YFP donor DNA expression cassette was obtained as follows: A double-stranded donor DNA cassette coding for the Yellow Fluorescent Protein (YFP) variant Venus (Nagai et al., 2002), was prepared via a Golden-Gate assembly reaction of individual promoter (P), orf (0) and terminator (T) sequences in an appropriate E. coli vector. The assembled POT cassette was amplified via a PCR reaction with primers indicated in SEQ ID NO: 11 and SEQ ID NO: 12. In a second PCR, 50 bp connector sequences are added using primer sets indicated in SEQ ID NO: 13 and SEQ ID NO: 14. This resulted in an YFP expression cassette that included 50 bp connector sequences at the 5' and 3' ends of the expression cassette (SEQ ID NO: 10, FIG. 4A). The Q5 DNA polymerase (part of the Q5® High-Fidelity 2× Master Mix, New England Biolabs, supplied by Bioké, Leiden, the Netherlands. Cat no. M0492S) was used in the PCR reaction, which was performed according to manufacturer's instructions. The PCR fragment was purified using the NucleoSpin Gel and PCR Clean-up kit (Machery-Nagel, distributed by Bioké, Leiden, the Netherlands) according to manufacturer's instructions.

Genomic DNA (gDNA) was isolated from the yeast strain CEN.PKI13-7D (MATa URA3 HIS3 LEU2 TRP1 MAL2-8 SUC2) using the lithium acetate SDS method (Lōoke et al., 2011). Strain CEN.PKI13-7D is available from the EUROSCARF collection (http://www.euroscarf.de, Frankfurt, Germany) or from the Centraal Bureau voor Schimmelcultures (Utrecht, the Netherlands, entry number CBS 8340). The origin of the CEN.PK family of strains is described by van Dijken et al., 2000. This genomic DNA was used as a template to obtain the PCR fragments that were used as donor for DNA flanking sequences (comprising the overlap (complementarity, sequence identity) with the genomic DNA for genomic integration), using the specific forward and reverse primer combinations depicted in Table 12. In order to obtain the PCR fragment set out in SEQ ID NO: 93, genomic DNA isolated from strain CEN.PKI13-7D was used as a template, using primer sequences set out in SEQ ID NO: 101 and SEQ ID NO: 102. In order to obtain the PCR fragment set out in SEQ ID NO: 94, genomic DNA isolated from strain CEN.PKI13-7D was used as a template, using primer sequences set out in SEQ ID NO: 103 and SEQ ID NO: 104.

The donor DNA flank sequences contained 50 basepair connector sequences at the 5' or 3' position. The presence of connector sequences allowed in vivo homologous recombination between highly homologous connector sequences that are part of the donor DNA expression cassettes as is described in WO2013144257A1.

All donor DNA PCR fragments were purified using the NuceloSpin Gel and PCR Clean-up kit (Machery-Nagel, distributed by Bioké, Leiden, the Netherlands) according to manufacturer's instructions. The concentrations of ssODNs were determined using a NanoDrop device (ThermoFisher, Life Technologies, Bleiswijk, the Netherlands), providing the concentrations in nanogram per microliter.

crRNA Expression Cassettes and Genomic Target Sequences crRNA expression cassettes were ordered as synthetic DNA cassettes (gBlocks) at Integrated DNA Technologies, Leuven, Belgium (for an overview see Table 13). Each Cpf1 orthologue tested in this experiment uses its own specific crRNA sequence (Zetsche et al., 2015). For the expression of the crRNA sequences, required to target Cpf1 to the desired locus in genomic DNA in *S. cerevisiae*, a crRNA expression cassette with control elements as previously described by DiCarlo et al., 2013 was used. The crRNA expression cassette comprises the *S. cerevisiae* SNR52 promoter (SEQ ID NO: 105), a 20 nt direct repeat sequence and a 20 nt spacer sequence comprising the guide-sequence or genomic target sequence, followed by the *S. cerevisiae* SUP4 terminator (SEQ ID NO: 112). An overview of the direct repeat and spacer/genomic target sequences is provided in Table 15. The genomic target sequence is present in the INT1 locus, which is located at the non-coding region between NTR1 (YOR071c) and GYP1 (YOR070c) located on chromosome XV.

Using the gBlock as template, Phusion DNA polymerase (New England Biolabs, USA), and the primers as set out in SEQ ID NO: 117 and 118, guide RNA expression cassette PCR fragments (sgRNA expression cassette for Cas9, crRNA expression cassettes for Cpf1 orthologues) were generated according to manufacturer's instructions. All guide RNA expression cassette PCR fragments were purified using the NucleoSpin Gel and PCR Clean-up kit (Machery-Nagel, distributed by Bioké, Leiden, the Netherlands) according to manufacturer's instructions.

Transformations

The components required for the transformation experiments are depicted in FIG. 24. Prior to transformation, DNA concentrations of the donor DNA's (dsDNAs and ssODNs), guide RNA expression cassette PCR fragments and vectors were measured using the NanoDrop (ND-1000 Spectrophotometer, ThermoFisher, Life Technologies, Bleiswijk, the Netherlands).

Vectors pCSN066 expressing AsCpf1, pCSN067 expressing LbCpf1, pCSN068 expressing FnCpf1or pCSN061 expressing CAS9 were first transformed separately to *S. cerevisiae* strain CEN.PKI13-7D (MATa URA3 HIS3 LEU2 TRP1 MAL2-8 SUC2) using the LiAc/salmon sperm (SS) carrier DNA/PEG method (Gietz and Woods, 2002). In the transformation mixture 1 microgram of vector pCSN061 (FIG. 3) was used. The transformation mixture was plated on YPD-agar (10 grams per litre of yeast extract, 20 grams per litre of peptone, 20 grams per litre of dextrose, 20 grams per litre of agar) containing 200 microgram (µg) G418 (Sigma Aldrich, Zwijndrecht, the Netherlands) per ml. After two to four days of growth at 30° C. colonies appeared on the transformation plate.

A yeast colony conferring resistance to G418 on the plate was inoculated on YPD-G418 medium (10 grams per litre of yeast extract, 20 grams per litre of peptone, 20 grams per litre of dextrose, 200 µg G418 (Sigma Aldrich, Zwijndrecht, the Netherlands) per ml). These transformants express AsCpf1, LbCpf1, FnCpf1 or Cas9. Subsequently, the Cpf1 or Cas9 pre-expressing strain was transformed with the

TABLE 15

Overview of guide RNA expression cassette sequences and their components. Each Cpf1 crRNA is expressed using the SNR52 promoter (SEQ ID NO: 105) and the SUP4 terminator sequence (SEQ ID NO: 112) and are part of the crRNA expression cassette sequences as listed in this table. The SpCas9 guide RNA is composed of a guide-polynucleotide and structural component sequence and is expressed using the SNR52p and SUP4t.

| Endonuclease | Direct repeat sequence/ structural component sequence | Spacer sequence | crRNA/guide RNA expression cassette |
|---|---|---|---|
| AsCpf1 | SEQ ID NO: 106 | SEQ ID NO: 109 | SEQ ID NO: 113 |
| LbCpf1 | SEQ ID NO: 107 | SEQ ID NO: 110 | SEQ ID NO: 114 |
| FnCpf1 | SEQ ID NO: 108 | SEQ ID NO: 109 | SEQ ID NO: 115 |
| SpCas9 | SEQ ID NO: 136 | SEQ ID NO: 111 | SEQ ID NO: 116 |

The guide RNA gBlocks contained at their 5'-terminus 78 basepairs sequence identity and at their 3'-terminus 87 bp sequence identity with vector pRN1 120 (after restriction of the vector with EcoRI and XhoI). The presence of homologous DNA sequences at the 5'- and 3'-termini of the guide RNA cassette will promote reconstitution of a circular vector in vivo by homologous recombination (gap repair) (Orr-Weaver et al., 1983) as described below and visualized in FIG. 24.

following DNA fragments using the LiAc/SS carrier DNA/PEG method (Gietz and Woods, 2002):
a) 100 ng of purified linearized vector pRN1120;
b) 750 ng of a PCR fragment of a crRNA (for Cpf1 orthologues) or a guide RNA (for Cas9) expression cassette containing homology at the 5' and 3' end with vector pRN1120;
c) Two donor DNA flank PCR fragments (100 ng each) with homology to the integration sites or four ssODNs (50 ng each);

d) Donor DNA expression cassette PCR fragments (20 ng each), being the three donor DNA expression cassette PCR fragments (encoding crtE, crtYB, crtI) or a YFP expression cassette PCR fragment.

As explained earlier in this example and in WO2013144257A1, because of the presence of highly homologous 50 bp connector DNA sequences, the donor DNA expression cassettes and donor DNA flank sequences will assemble to one stretch of DNA at the desired location and in the desired order into the genomic DNA as visualized in FIG. 19. The crRNA or guide RNA expression cassette, which contains 78 bp homology at the 5'-terminus and 87 bp homology at the 3'-terminus with vector pRN1120, will assemble into the linearized vector pRN1120 to form a functional circular vector (FIG. 24) by in vivo homologous recombination (gap repair, Orr-Weaver et al., 1983), which allows selection of transformants on nourseothricin.

As shown in Table 16, different transformation experiments were performed for targeted integration of donor DNA expression cassettes (carotenoid genes or YFP), guided by donor DNA flank sequences (dsDNA or ssODNs) using CRISPR/Cpf1 with its cognate crRNA, or CRISPR/Cas9 with guide RNA as control. Different Cpf1 orthologues or CAS9 were targeted by the crRNA or guide RNA to the INT1 locus and the double-stranded break that was introduced by Cpf1 or CAS9 was repaired by the transformed donor DNA PCR fragments as visualized in FIG. 4 and FIG. 19.

TABLE 16

Overview of transformation experiments performed in this example. In the first transformation vector pCSN066, pCSN067, pCSN068 or pCSN061 was transformed to CEN.PK113-7D. In a second transformation, linearized vector pRN1120 was transformed together with with donor DNA expression fragments (donor DNA expression cassettes and donor DNA flanks, dsDNA or ssODNs) in the transformation mixture. In transformations 1-23 carotenoid gene expression cassettes were used as donor DNA, in transformations 24-46 the YFP expression cassette was used as donor DNA. Trafo No. means Transofrmation number.

| Transformation no. | Description experiment | Endo-nuclease | Vector with endo-nuclease | crRNA/ guide RNA cassette SEQ ID NO: | Donor DNA expression cassettes SEQ ID NO: | Donor DNA flanks (dsDNA) SEQ ID NO: | Donor DNA flanks (ssODN) SEQ ID NO: |
|---|---|---|---|---|---|---|---|
| 1 | Control 1 kb deletion dsDNA flanks | AsCpf1 | pCSN066 | 113 | 90 91 92 | 93 94 | |
| 2 | Control random integration (Cas9 guide RNA) | AsCpf1 | pCSN066 | 116 | 90 91 92 | 93 94 | |
| 3 | Control no guide | AsCpf1 | pCSN066 | | 90 91 92 | 93 94 | |
| 4 | OMCI 0 kb deletion | AsCpf1 | pCSN066 | 113 | 90 91 92 | | 23 24 25 26 |
| 5 | OMCI 1 kb deletion | AsCpf1 | pCSN066 | 113 | 90 91 92 | | 21 22 27 28 |
| 6 | Control 1 kb deletion dsDNA flanks | LbCpf1 | pCSN067 | 114 | 90 91 92 | 93 94 | |
| 7 | Control random integration (Cas9 guide RNA) | LbCpf1 | pCSN067 | 116 | 90 91 92 | 93 94 | |
| 8 | Control no guide | LbCpf1 | pCSN067 | | 90 91 92 | 93 94 | |
| 9 | OMCI 0 kb deletion | LbCpf1 | pCSN067 | 114 | 90 91 92 | | 23 24 25 26 |
| 10 | OMCI 1 kb deletion | LbCpf1 | pCSN067 | 114 | 90 91 92 | | 21 22 27 28 |
| 11 | Control 1 kb deletion dsDNA flanks | FnCpf1 | pCSN068 | 115 | 90 91 92 | 93 94 | |
| 12 | Control random integration (Cas9 guide RNA) | FnCpf1 | pCSN068 | 116 | 90 91 92 | 93 94 | |
| 13 | Control no guide | FnCpf1 | pCSN068 | | 90 91 92 | 93 94 | |
| 14 | OMCI 0 kb deletion | FnCpf1 | pCSN068 | 115 | 90 91 92 | | 23 24 25 26 |
| 15 | OMCI 1 kb deletion | FnCpf1 | pCSN068 | 115 | 90 91 92 | | 21 22 27 28 |

TABLE 16-continued

Overview of transformation experiments performed in this example. In the first transformation vector pCSN066, pCSN067, pCSN068 or pCSN061 was transformed to CEN.PK113-7D. In a second transformation, linearized vector pRN1120 was transformed together with with donor DNA expression fragments (donor DNA expression cassettes and donor DNA flanks, dsDNA or ssODNs) in the transformation mixture. In transformations 1-23 carotenoid gene expression cassettes were used as donor DNA, in transformations 24-46 the YFP expression cassette was used as donor DNA. Trafo No. means Transofrmation number.

| Transformation no. | Description experiment | Endo-nuclease | Vector with endo-nuclease | crRNA/ guide RNA cassette SEQ ID NO: | Donor DNA expression cassettes SEQ ID NO: | Donor DNA flanks (dsDNA) SEQ ID NO: | Donor DNA flanks (ssODN) SEQ ID NO: |
|---|---|---|---|---|---|---|---|
| 16 | Control 1 kb deletion dsDNA flanks | Cas9 | pCSN061 | 116 | 90 91 92 | 93 94 | |
| 17 | Control 1 kb deletion dsDNA flanks | Cas9 | pCSN061 | 116 | 90 91 92 | 93 94 | |
| 18 | Control random integration (FnCpf1 crRNA) | Cas9 | pCSN061 | 115 | 90 91 92 | 93 94 | |
| 19 | Control no guide | Cas9 | pCSN061 | | 90 91 92 | 93 94 | |
| 20 | OMCI 0 kb deletion | Cas9 | pCSN061 | 116 | 90 91 92 | | 23 24 25 26 |
| 21 | OMCI 0 kb deletion | Cas9 | pCSN061 | 116 | 90 91 92 | | 23 24 25 26 |
| 22 | OMCI 1 kb deletion | Cas9 | pCSN061 | 116 | 90 91 92 | | 21 22 27 28 |
| 23 | OMCI 1 kb deletion | Cas9 | pCSN061 | 116 | 90 91 92 | | 21 22 27 28 |
| 24 | Control 1 kb deletion dsDNA flanks | AsCpf1 | pCSN066 | 113 | 10 | 93 94 | |
| 25 | Control random integration (Cas9 guide RNA) | AsCpf1 | pCSN066 | 116 | 10 | 93 94 | |
| 26 | Control no guide | AsCpf1 | pCSN066 | | 10 | 93 94 | |
| 27 | OMCI 0 kb deletion | AsCpf1 | pCSN066 | 113 | 10 | | 23 24 25 26 |
| 28 | OMCI 1 kb deletion | AsCpf1 | pCSN066 | 113 | 10 | | 21 22 27 28 |
| 29 | Control 1 kb deletion dsDNA flanks | LbCpf1 | pCSN067 | 114 | 10 | 93 94 | |
| 30 | Control random integration (Cas9 guide RNA) | LbCpf1 | pCSN067 | 116 | 10 | 93 94 | |
| 31 | Control no guide | LbCpf1 | pCSN067 | | 10 | 93 94 | |
| 32 | OMCI 0 kb deletion | LbCpf1 | pCSN067 | 114 | 10 | | 23 24 25 26 |
| 33 | OMCI 1 kb deletion | LbCpf1 | pCSN067 | 114 | 10 | | 21 22 27 28 |
| 34 | Control 1 kb deletion dsDNA flanks | FnCpf1 | pCSN068 | 115 | 10 | 93 94 | |
| 35 | Control random integration (Cas9 guide RNA) | FnCpf1 | pCSN068 | 116 | 10 | 93 94 | |
| 36 | Control no guide | FnCpf1 | pCSN068 | | 10 | 93 94 | |
| 37 | OMCI 0 kb deletion | FnCpf1 | pCSN068 | 115 | 10 | | 23 24 25 26 |

TABLE 16-continued

Overview of transformation experiments performed in this example. In the first transformation vector pCSN066, pCSN067, pCSN068 or pCSN061 was transformed to CEN.PK113-7D. In a second transformation, linearized vector pRN1120 was transformed together with with donor DNA expression fragments (donor DNA expression cassettes and donor DNA flanks, dsDNA or ssODNs) in the transformation mixture. In transformations 1-23 carotenoid gene expression cassettes were used as donor DNA, in transformations 24-46 the YFP expression cassette was used as donor DNA. Trafo No. means Transofrmation number.

| Transformation no. | Description experiment | Endo-nuclease | Vector with endo-nuclease | crRNA/ guide RNA cassette SEQ ID NO: | Donor DNA expression cassettes SEQ ID NO: | Donor DNA flanks (dsDNA) SEQ ID NO: | Donor DNA flanks (ssODN) SEQ ID NO: |
|---|---|---|---|---|---|---|---|
| 38 | OMCI 1 kb deletion | FnCpf1 | pCSN068 | 115 | 10 | | 21<br>22<br>27<br>28 |
| 39 | Control 1 kb deletion dsDNA flanks | Cas9 | pCSN061 | 116 | 10 | 93<br>94 | |
| 40 | Control 1 kb deletion dsDNA flanks | Cas9 | pCSN061 | 116 | 10 | 93<br>94 | |
| 41 | Control random integration (FnCpf1 crRNA) | Cas9 | pCSN061 | 115 | 10 | 93<br>94 | |
| 42 | Control no guide | Cas9 | pCSN061 | | 10 | 93<br>94 | |
| 43 | OMCI 0 kb deletion | Cas9 | pCSN061 | 116 | 10 | | 23<br>24<br>25<br>26 |
| 44 | OMCI 0 kb deletion | Cas9 | pCSN061 | 116 | 10 | | 23<br>24<br>25<br>26 |
| 45 | OMCI 1 kb deletion | Cas9 | pCSN061 | 116 | 10 | | 21<br>22<br>27<br>28 |
| 46 | OMCI 1 kb deletion | Cas9 | pCSN061 | 116 | 10 | | 21<br>22<br>27<br>28 |

The transformation mixtures were plated on YPD-agar (10 grams per litre of yeast extract, 20 grams per litre of peptone, 20 grams per litre of dextrose, 20 grams per litre of agar) containing 200 µg nourseothricin (NatMX, Jena Bioscience, Germany) and 2004 G418 (Sigma Aldrich, Zwijndrecht, the Netherlands) per ml. Alternatively, transformation mixtures were plated on YPD-agar (10 grams per litre of yeast extract, 20 grams per litre of peptone, 20 grams per litre of dextrose, 20 grams per litre of agar) containing only 200 µg nourseothricin (NatMX, Jena Bioscience, Germany) per ml. After two to four days of growth at 30° C., colonies appeared on the transformation plates.

Results Transformation Experiments: Genome Editing Efficiencies

Transformation of crtE, crtYB and crtI expression cassettes resulted in colored transformants, by the integration of the three donor DNA expression cassettes and donor DNA flank sequences that were used to enable targeting to the desired locus into genomic DNA to repair the double strand break introduced by Cpf1. After transformation, the total number of colonies on a transformation plate were counted. Colored and non-colored transformants were visible on the transformation plates. In case of colored transformants, the crtE, crtYB and crtI expression cassettes were successfully integrated into the genomic DNA of the yeast cells. In case of non-colored transformants, crtE, crtYB and crtI expression cassettes were not successfully integrated into the genomic DNA of the yeast cells. The percentage of successfully engineered cells, i.e. transformants that have integrated the crtE, crtYB and crtI expression cassettes into genomic DNA, was calculated by dividing the number of colored transformants by the number of total transformants. The results of the carotenoid genes transformation experiments (Table 16 transformations 1-23) are depicted in FIG. 25.

Transformation of the YPF expression cassette resulted in fluorescent transformants, by the integration of the donor expression cassette and donor DNA flank sequences that were used to enable targeting to the desired locus into genomic DNA. After transformation, the total number of colonies on a transformation plate were counted. Fluorescent and/or non-fluorescent transformants were visible on the transformation plates by UV light using a Qpix 450 Transformant Picker (Molecular devices LLC). In case of colored transformants, YFP expression cassette was successfully integrated into the genomic DNA of the yeast cells. In case of non-colored transformants, the YFP expression cassettes was not successfully integrated into the genomic DNA of the yeast cells. The percentage of successfully engineered cells, i.e. transformants that have integrated the YFP expression cassettes into genomic DNA, was calculated by dividing the number of colored transformants by the number of total transformants. The results of the YFP transformation experiments (Table 16 transformations 24-46) are depicted in FIG. 26.

A combination of the results of the carotenoid expression cassettes transformation experiments (Table 16 transformations 1-23) and the YFP expression cassette transformation experiments (Table 16 transformations 24-46) are depicted in FIG. 27.

In the description of the results below, colored or fluorescent transformants represent transformants that have introduced the carotenoid gene expression cassettes or the YFP expression cassette and flanks as donor DNA into genomic DNA as a measure for genome editing efficiency.

Using carotenoid gene expression cassettes and 1 kb dsDNA flanks as donor DNA, colored transformants were obtained with an efficiency between 19% to 87% for the Cpf1 orthologues and with an efficiency of 98% for CAS9 (FIG. 25, transformations 1, 6, 11, 16 and 17).

Using carotenoid gene expression cassettes and ssODNs as donor DNA, colored transformants were obtained with an efficiency between 38% and 77% for the Cpf1 orthologues and with an efficiency of up to 90% for CAS9 to delete a stretch of ~0 kb of genomic DNA at the INT1 locus (FIG. 25, transformations 4, 9, 14, 20 and 21). For deletion of a stretch of ~1 kb of genomic DNA at the INT1 locus, the editing efficiency was between 7% and 92% for the Cpf1 orthologues and with an efficiency of up to 91% for CAS9 (FIG. 25, transformations 5, 10, 15, 22 and 23).

As a control for random integration of donor DNA, Cpf1 orthologues were combined with a Cas9 specific guide RNA and Cas9 was combined with an FnCpf1 crRNA: Cpf1 or Cas9 were not targeted to the INT1 locus and cannot make a double-stranded break. Results are shown in FIG. 25, transformations 2, 7, 12, 18. Only when LbCpf1 was expressed in combination with Cas9 guide RNA (SEQ ID NO: 116), a small number of colored transformants were observed (~1% of the transformants). These results indicate that the carotenoid gene expression cassettes as donor DNA could integrate with a very low efficiency in the absence of functional CRISPR/Cpf1. When no crRNA or guide RNA was transformed, no functional pRN1120 plasmid can be formed by in vivo recombination (FIG. 24). In all these control transformations (FIG. 25, transformations 3, 8, 13, 19) the number of transformants on the plates was 20 at highest, indicative of non-linearized pRN1120 present in the transformation mixture and none of these transformants were colored.

Using the YFP expression cassette and 1 kb dsDNA flanks as donor DNA, fluorescent transformants were obtained with an efficiency between 58% to 88% for the Cpf1 orthologues and with an efficiency of up to 79% for CAS9 (FIG. 26, transformations 1, 6, 11, 16 and 17).

Using the YFP expression cassette and ssODNs as donor DNA, fluorescent transformants were obtained with an efficiency between 23% and 86% for the Cpf1 orthologues and with an efficiency of up to 76% for CAS9 to delete a stretch of ~0 kb of genomic DNA at the INT1 locus (FIG. 26, transformations 4, 9, 14, 20 and 21). For deletion of a stretch of ~1 kb of genomic DNA at the INT1 locus, the editing efficiency was between 9% and 78% for the Cpf1 orthologues and with an efficiency of up to 77% for CAS9 (FIG. 26, transformations 5, 10, 15, 22 and 23).

As a control for random integration of donor DNA, Cpf1 orthologues were combined with a Cas9 specific guide RNA and Cas9 was combined with an FnCpf1 crRNA: Cpf1 or Cas9 were not targeted to the INT1 locus and cannot make a double-stranded break. Results are shown in FIG. 26, transformations 2, 7, 12, 18. When AsCpf1 or LbCpf1 were expressed in combination with Cas9 guide RNA (SEQ ID NO: 116), or when Cas9 was expressed in combination with FnCpf1 crRNA (SEQ ID NO: 115) a small number of colored transformants were observed (~1% of the transformants). These results indicate that the carotenoid gene expression cassettes as donor DNA could integrate with a very low efficiency in the absence of functional CRISPR/ Cpf1 or CRISPR/Cas9. When no crRNA or guide RNA was transformed, no functional pRN1120 plasmid can be formed by in vivo recombination (FIG. 24). In all these control transformations (FIG. 26, transformations 3, 8, 13, 19) the number of transformants on the plates was 12 at highest, indicative of non-linearized pRN1120 present in the transformation mixture and none of these transformants were fluorescent.

The results demonstrate that CRISR/Cpf1 functional in *S. cerevisiae*. LbCpf1 and FnCpf1 are more efficient as compared to AsCpf1 in term of genome editing efficiency. LbCpf1 and FnCpf1 have similar genome editing efficiencies as SpCas9 for introduction of donor DNA expression cassettes into genomic DNA using dsDNA or ssODNs (OMCI method) as flanks (FIG. 27). The CRISRP/Cpf1 system provides a valuable tool in addition to the CRISPR/ Cas9 system for genome precision engineering in *Saccharomyces cerevisiae*.

Example 7: OMCI in *Aspergillus niger* Using a GFP Expression Cassette PCR Fragment as Donor DNA This example describes the disruption of the fnwA locus in genomic DNA of *A. niger* using CAS9 in combination with the Alt-R™ system of Integrated DNA technologies (IDT, Leuven, Belgium). A PCR fragment of a GFP expression cassette was used as donor DNA. The donor DNA will disrupt the fwnA6 gene which is involved in spore color formation. Strains with the GFP expression cassette integrated in the fwnA6 gene will have a color change in the spores from black to fawn (Jorgensen et al., 2011). In combination with the GFP expression cassette as donor DNA, separate single-stranded oligonucleotide sequences (ssODNs) or double-stranded DNA (ds-DNA, being ssODNs annealed before addition to the transformation mixture) flanks were added in the transformation mixture, used to target the donor DNA to the fwnA6 locus. The GFP expression cassette PCR fragment contained unique 50 basepair (bp) sequences, named connector sequences, at the 5' and 3' end of the fragment. These 50 bp connector sequences interact with ssODN or ds-DNA oligonucleotide flank sequences that are 100 bp in size. The 100 bp ssODN or ds-DNA oligonucleotide flank sequences have 50 bp homology with the GFP expression cassette, and 50 bp homology with the fwnA6 locus for the intended disruption.

Construction of the GFP Expression Cassette

The Anid.TEF (SEQ ID NO: 119) promoter, the GFP ORF (SEQ ID NO: 120) and Re.FT016 (SEQ ID NO: 121) terminator fragments were synthesized at DNA2.0 (Menlo Park, Calif., USA). The synthetic DNA fragments were delivered in three separate standard cloning vectors. The three separate DNA vectors were constructed using a Golden Gate reaction (according to Example 1 in patent application WO2013/144257) into the receiving backbone vector CD (SEQ ID NO: 122). This resulted in the vector named GFP vector (SEQ ID NO: 123), containing a functional GFP expression cassette. A vector map of the GFP vector is depicted in FIG. 28.

Donor DNA

PCR amplification of the donor DNA GFP expression cassette using the GFP vector as template was performed using Phusion DNA polymerase (New England Biolabs) with the forward primer as set out in SEQ ID NO: 124 and the reverse primer as set out in SEQ ID NO: 125, using a standard PCR protocol. The PCR fragment was purified with the PCR purification kit from Macherey Nagel (distributed by Bioké, Leiden, the Netherlands) according to manufacturer's instructions. The DNA concentration was measured using the NanoDrop (ND-1000 Spectrophotometer, Thermo Fisher Scientific).

As integration flanks, 100 bp ssODNs containing 50 bp homology to the genome at the fnwA6 target site and 50 bp homology to the GFP expression cassette were ordered at IDT (Leuven, Belgium) as standard desalted primers. Two ssODNs could be annealed to form a double-stranded DNA (ds-DNA) flank. The ssODNs were dissolved to a concentration of 100 μM (100 μmol/μl). Subsequently, the annealing reactions were performed between complementary oligonucleotides as follows: 20 μl of 100 μM of the upper strand ssODN and 20 μl of 100 μM of the lower strand ssODN were mixed with 10 μl of 5×T4 ligase buffer (Thermo Fisher, Life Technologies, Bleiswijk, the Netherlands, supplied with T4 ligase Cat no. 15224041). The mixture was kept at 100 degrees Celsius for 5 minutes to denature the oligonucleotides. Subsequently, the temperature was decreased to 25 degrees Celcius by a gradual decrease of 1 degree Celsius for 30 seconds in 75 cycles, allowing the ssONDs to anneal with each other. The mixture was kept at 10 degrees Celsius if required. After annealing, the mixture was directly used in the transformation to *A. niger* (no purification step). SEQ ID NO's of the primers used as ssODN or ds-DNA flanks in the transformation mixture can be found in Table 17.

Before and after annealing, the concentrations of single ssODNs or two annealed ssODNs (ds-DNA) sequences were determined using a NanoDrop device (Thermo Fisher, Life Technologies, Bleiswijk, the Netherlands), providing the concentrations in nanogram per microliter. Based on these measurements, the amounts as shown in Table 18 of single ssODNs or two annealed ssODNs (ds-DNA) were used in the transformation experiments.

FIG. 29 provides a graphical representation of the approaches to integrate the GFP expression cassette (GFP-cassette) using four ssODNs or two ds-DNAs into the genome of *A. niger* at the fnwA6 locus.

TABLE 17

Overview of SEQ ID NO: of ssODN and ds-DNA used as flanks for the integration of the GFP expression cassette in the fwnA6 gene.

| Name | ssODN upper strand | ssODN lower strand | ds-DNA |
|---|---|---|---|
| 5' flank | SEQ ID NO: 126 | SEQ ID NO: 127 | SEQ ID NO: 126 + SEQ ID NO: 127 annealed |

TABLE 17-continued

Overview of SEQ ID NO: of ssODN and ds-DNA used as flanks for the integration of the GFP expression cassette in the fwnA6 gene.

| Name | ssODN upper strand | ssODN lower strand | ds-DNA |
|---|---|---|---|
| 3' flank | SEQ ID NO: 128 | SEQ ID NO: 129 | SEQ ID NO: 128 + SEQ ID NO: 129 annealed |

IDT Alt-R™ System

As guide RNA, the Alt-R™ system from IDT (Integrated DNA Technologies, Leuven, Belgium) was used. For this purpose, the crRNA with the genomic target sequence or guide-polynucleotide as set out in SEQ ID NO: 130 and tracrRNA were ordered at IDT (Leuven, Belgium). Annealing of the crRNA and tracrRNA parts were performed by incubating the following components for 5 minutes at 95 degrees Celcius: 9/20 part tracrRNA (0.2 nmol/μl) with 9/20 part of crRNA (0.2 nmol/μl) and 2/20 part of 10×Duplex buffer (1 M Potassium acetate, 300 mM HEPES pH7.5 in milliQ water). The mixture was cooled down to room temperature.

Strain

In this example described, *Aspergillus niger* strain GBA 302 (ΔglaA, ΔpepA, ΔhdfA) is used. The construction of GBA 302 is described in patent application WO2011/009700.

Transformation

Protoplast transformation was performed as described in patent applications WO1999/32617 and WO1998/46772, except for the use of ATA (Aurintricarboxylic acid, a nuclease inhibitor) in the transformation mixture. In these transformations Cas9 protein with NLS (PNA Bio, Newbury Park, Calif., USA) was used. 50 μg of the CAS9 protein was dissolved in 50 μl nuclease free water (Ambion, Thermo Fisher, Bleiswijk, the Netherlands) to a final concentration of 1 μg/μl. As selection marker AMA-vector BG-AMA8 (SEQ ID NO: 131; FIG. 30) was added in the transformation. The construction of BG-AMA8 is described in WO2016110453A1. Table 18 shows the specific amounts of DNA (GFP donor DNA and ssODNs or ds-DNAs), guide RNA (Alt-R™ components as described above) and CAS9 protein transformed to strain GBA 302 in each separate transformation.

TABLE 18

Overview of performed transformations. For overview of flank sequences, see Table 17.

| Transformation | Strain | AMA-plasmid | GFP Donor DNA | Flanks ssODNs | Flanks ds-DNAs | Cas9 protein | AltR™ gRNA |
|---|---|---|---|---|---|---|---|
| 1 | GBA 302 | 1.5 μg BG-AMA8 | 0 μg | 0 μg | 0 μg | 0 μg | 0 μl |
| 2 | GBA 302 | 1.5 μg BGAMA8 | 0 μg | 0 μg | 0 μg | 1.5 μg | 2 μl |
| 3 | GBA 302 | 1.5 μg BG-AMA8 | 2 μg GFP cassette | 0 μg | 0 μg | 1.5 μg | 2 μl |
| 4 | GBA 302 | 1.5 μg BG-AMA8 | 0 μg | 4× 0.25 μg | 0 μg | 1.5 μg | 2 μl |
| 5 | GBA 302 | 1.5 μg BG-AMA8 | 0 μg | 0 μg | 2× 0.5 μg | 1.5 μg | 2 μl |
| 6 | GBA 302 | 1.5 μg BG-AMA8 | 2 μg GFP cassette | 4× 0.1 μg | 0 μg | 1.5 μg | 2 μl |
| 7 | GBA 302 | 1.5 μg BG-AMA8 | 2 μg GFP cassette | 4× 0.25 μg | 0 μg | 1.5 μg | 2 μl |
| 8 | GBA 302 | 1.5 μg BG-AMA8 | 2 μg GFP cassette | 0 μg | 2× 0.2 μg | 1.5 μg | 2 μl |

TABLE 18-continued

Overview of performed transformations. For overview of flank sequences, see Table 17.

| Transformation | Strain | AMA-plasmid | GFP Donor DNA | Flanks ssODNs | Flanks ds-DNAs | Cas9 protein | AltR™ gRNA |
|---|---|---|---|---|---|---|---|
| 9 | GBA 302 | 1.5 µg BG-AMA8 | 2 µg GFP cassette | 0 µg | 2× 0.5 µg | 1.5 µg | 2 µl |

After transformation the protoplasts were plated on regeneration media plates containing 60 µg/ml hygromycin (Invitrogen, Thermo Fisher Scientific, Bleiswijk, the Netherlands) and incubated at 30° C. for 4-6 days. The results of the transformation experiment can be found in Table 19.

TABLE 19

Results of the transformation experiments indicated as the number of transformants with a fwnA phenotype, the total number of transformants obtained and the percentage of transformants with a fwnA phenotype.

| Transformation | Donor DNA (GFP cassette) added | Flanks ssODNs added | Flanks ds-DNAs added | Cas9 protein + AltR™ gRNA added | No. of transformants with fwnA phenotype | Total no. of transformants | % of transformants with fwnA phenotype |
|---|---|---|---|---|---|---|---|
| 1 | No | No | No | No | 0 | 0 | 0 |
| 2 | No | No | No | Yes | 0 | 21 | 0 |
| 3 | Yes | No | No | Yes | 0 | 313 | 0 |
| 4 | No | Yes 4× | No | Yes | 0 | 283 | 0 |
| 5 | No | No | Yes 2× | Yes | 0 | 457 | 0 |
| 6 | Yes | Yes 4× | No | Yes | 9 | 127 | 7 |
| 7 | Yes | Yes 4× | No | Yes | 57 | 269 | 21 |
| 8 | Yes | No | Yes 2× | Yes | 22 | 299 | 7 |
| 9 | Yes | No | Yes 2× | Yes | 35 | 189 | 19 |

The transformants from all transformation plates were counted and scored for the fawn spore phenotype characteristic of the fwnA6 mutation. Plates were also checked with UV-light to check for integration of the GFP expression cassette in transformants. Transformants with black spores did not show fluorescence, and 90-95% transformants with a fawn phenotype did show fluorescence, which is indicative for expression of GFP.

No fawn phenotype transformants were obtained when BG-AMA8 (transformation 1), BG-AMA8+Cas9 protein and Alt-R™ gRNA (transformation 2), BG-AMA8+Cas9 protein and Alt-R™ gRNA+GFP donor DNA (transformation 3), or only BG-AMA8+Cas9 protein and Alt-R™ gRNA+ssODN or ds-DNA flanks (transformations 4 and 5) were transformed.

When comparing transformations 5-9, where strain GBA 302 was transformed with BG-AMA8, Cas9 protein and Alt-R™ gRNA together with the GFP expression cassette as donor DNA and different amounts of ssODNs or ds-DNAs as flanks, fawn phenotype transformants were obtained and, in most cases (90-95%), expressing GFP.

By adding a higher amount of ssODNs or ds-DNAs as flanks (transformations 7 and 9), more fawn phenotype transformants (19-21%) were obtained as compared to adding a lower amount of ssODNs or ds-DNAs as flanks (transformations 6 and 8, 7% fawn colonies).

Colony PCR SDS/LiAC to Produce a DNA Fragment for Sequencing

Spores of transformations 6 to 9 were plated twice on a PDA plate (Difco) and grown for 2-3 days at 30° C. in an incubator. For each tested colony a sample of the colony was taken with an inoculation loop and put in 25 µl Glucanex™ solution (50 mg/ml Glucanex™ dissolved in KC buffer (60 g/l KCl, 2 g/l Citric acid, adjusted with KOH/HCl to pH 6.2)) in an Eppendorf tube. After 1 hour of incubation at 37 degrees Celcius, 75 µl DNA dilution buffer (10 mM Tris.Cl, 10 mM NaCl, 1 mM EDTA, pH 7.5) was added to each tube followed by boiling for 5 minutes in a PCR apparatus with heated lid. After boiling, 100 µl milliQ water was added and mixed very mildly by pipetting up and down three times. Subsequently, 5 µl solution containing chromosomal DNA template was pipetted carefully from the top of the solution and added in the PCR-mix for each reaction (without including cell debris present at the bottom of the tube). The PCR reactions were performed according to standard PCR protocols using Phusion DNA polymerase (New England Biolabs, supplied by Bioké, Leiden, the Netherlands) amplifying the genomic fwnA6 location by using the forward primer as set out in SEQ ID NO: 132 and reverse primer as set out in SEQ ID NO: 134 for the 5' part of the integration site and by using the forward primer as set out in SEQ ID NO: 135 and reverse primer as set out in SEQ ID NO: 133 for the 3' part of the integration site. The PCR fragments were purified with the PCR purification kit from Macherey Nagel (distributed by Bioké, Leiden, the Netherlands) according to the manual.

Confirming Correct Integration of GFP Cassette by Sequencing

PCR for sequencing was done with a BigDye Terminator v3.1 Cycle Sequencing kit of Applied Biosystems (Thermo Fisher, Life Technologies, Bleiswijk, the Netherlands) according to the manual by using the forward primer as set out in SEQ ID NO: 132 for the 5' part of the integration site and the reverse primer as set out in SEQ ID NO: 133 for the 3'part of the integration site, including the fwnA6 sequence fragment as template. The sequencing PCR product was cleaned by ethanol/EDTA precipitation according to the supplier's manual. The fwnA6 sequence PCR fragment pellet was dissolved in 10 µl HiDi Formamide of Applied Biosystems and the suspension was used for sequence analysis with the 3500 Genetic Analyzer of Applied Biosystems (Sanger sequencing). For each transformation, a maximum of 10 transformants showing a fwnA phenotype and GFP expression were sequenced. Most sequenced transformants of transformations 6, 7, 8 and 9 showed correct integration (respective 67%, 100%, 78% and 70%) on both 5' and 3' flank of the fwnA integration site on the genome and the GFP cassette part.

Taken together, the results demonstrate that the OMCI approach is functional in *A. niger* and allows for a flexible way to integrate a donor DNA construct at a genomic target site directly, by using ssODNs, without the need to pre-assemble flanks into the donor DNA construct.

REFERENCES de Kok S, L H Stanton, T Slaby, M Durot, V F Holmes, K G Patel, D Platt, E B Shapland, Z Serber, J Dean, J D Newman, S S Chandran (2014). Rapid and Reliable DNA Assembly via Ligase Cycling Reaction. ACS Synth. Biol., 2014, 3 (2), pp 97-106

Cong L, Ran F A, Cox D, Lin S, Barretto R, Habib N, Hsu P D, Wu X, Jiang W, Marraffini L A, Zhang F. Science. 2013 Feb. 15; 339(6121):819-23. doi: 10.1126/science.1231143. Epub 2013 Jan. 3. Multiplex genome engineering using CRISPR/Cas systems.

DiCarlo J E, Norville J E, Mali P, Rios X, Aach J, Church G M. Nucleic Acids Res. 2013 April; 41(7):4336-43. Genome engineering in *Saccharomyces cerevisiae* using CRISPR-Cas systems.

Gaj T, Gersbach C A, Barbas C F 3$^{rd}$. Trends Biotechnol. 2013 July; 31(7):397-405. doi: 10.1016/j.tibtech.2013.04.004. Epub 2013 May 9. ZFN, TALEN, and CRISPR/Cas-based methods for genome engineering.

Gao F, Shen X Z, Jiang F, Wu Y, Han C. Nat Biotechnol. 2016 May 2. doi: 10.1038/nbt.3547. [Epub ahead of print]. DNA-guided genome editing using the Natronobacterium gregoryi Argonaute.

Glaser A., McColl B. and Vadolas J. (2016). GFP to BFP Conversion: A Versatile Assay for the Quantification of CRISPR/Cas9-mediated Genome Editing. Molecular Therapy Nucleic Acids (2016) 5, e334

Gibson D G (2009) Synthesis of DNA fragments in yeast by one-step assembly of overlapping oligonucleotides. Nucleic Acids Research 37(20), 6984-6990

Gibson D G; Young L; Chuang R-Y; Venter J C; Hutchison C A III; Smith H O (2009). Enzymatic assembly of DNA molecules up to several hundred kilobases. Nature Methods 6(5), p 343, 5 p Gietz R D, Woods R A. Methods Enzymol. 2002; 350:87-96. Transformation of yeast by lithium acetate/single-stranded carrier DNA/polyethylene glycol method.

Hur J K, Kim K, Been K W, Baek G, Ye S, Hur J W, Ryu S M, Lee Y S, Kim J S. Nat Biotechnol. 2016 August; 34(8):807-8. doi: 10.1038/nbt.3596. Epub 2016 Jun. 6. Targeted mutagenesis in mice by electroporation of Cpf1 ribonucleoproteins.

Inui M, Miyado M, Igarashi M, Tamano M, Kubo A, Yamashita S, Asahara, H, Fukami, M., Takada S (2014). Rapid generation of mouse models with defined point mutations by the CRISPR/Cas9 system. Scientific Reports 4, Article number: 5396

Jinek M, Chylinski K, Fonfara I, Hauer M, Doudna J A, Charpentier E. Science. 2012 Aug. 7; 337(6096):816-21. doi: 10.1126/science.1225829. Epub 2012 Jun. 28. A programmable dual-RNA-guided DNA endonuclease in adaptive bacterial immunity.

Jorgensen T R, Park J, Arentshorst M, van Welzen A M, Lamers G, Vankuyk P A, Damveld R A, van den Hondel C A, Nielsen K F, Frisvad J C, Ram A F. Fungal Genet Biol. 2011 May; 48(5):544-53. The molecular and genetic basis of conidial pigmentation in *Aspergillus niger*.

Kim D, Kim J, Hur J K, Been K W, Yoon S H, Kim J S. Nat Biotechnol. 2016 August; 34(8):863-8. doi: 10.1038/nbt.3609. Genome-wide analysis reveals specificities of Cpf1 endonucleases in human cells.

Kim Y, Cheong S A, Lee J G, Lee S W, Lee M, Baek I J, Sung Y H. Nat Biotechnol. 2016 August; 34(8):808-10. doi: 10.1038/nbt.3614. Epub 2016 Jun. 6. Generation of knockout mice by Cpf1-mediated gene targeting.

Lōoke M, Kristjuhan K, Kristjuhan A. Biotechniques. 2011 May; 50(5):325-8. Extraction of genomic DNA from yeasts for PCR-based applications Mali P, Yang L, Esvelt K M, Aach J, Guell M, DiCarlo J E, Norville J E, Church G M. Mali P, Yang L, Esvelt K M, Aach J, Guell M, DiCarlo J E, Norville J E, Church G M. Science. 2013 Feb. 15; 339(6121):823-6. doi: 10.1126/science.1232033. Epub 2013 Jan. 3. RNA-guided human genome engineering via Cas9.

Mohanraju P, Makarova K S, Zetsche B, Zhang F, Koonin E V, van der Oost J. Science. 2016 Aug. 5; 353(6299): aad5147. doi: 10.1126/science.aad5147. Diverse evolutionary roots and mechanistic variations of the CRISPR-Cas systems.

Nagai T, Ibata K, Park E S, Kubota M, Mikoshiba K, Miyawaki A. Nat Biotechnol. 2002 January; 20(1):87-90. A variant of yellow fluorescent protein with fast and efficient maturation for cell-biological applications.

Orr-Weaver T L, Szostak J W, Rothstein R J. Methods Enzymol. 1983; 101:228-45. Genetic applications of yeast transformation with linear and gapped plasmids.

Paques F, Duchateau P. Curr. Gene Ther. 2007; 7:49-66. Meganucleases and DNA double-strand break-induced recombination: perspectives for gene therapy.

Port F, Bullock S L. Nat Methods. 2016 October; 13(10): 852-4. doi: 10.1038/nmeth.3972. Epub 2016 Sep. 5. Augmenting CRISPR applications in *Drosophila* with tRNA-flanked sgRNAs.

Sander J D, Joung J K. Nat Biotechnol. 2014 April; 32(4): 347-55. doi: 10.1038/nbt.2842. Epub 2014 Mar. 2. CRISPR-Cas systems for editing, regulating and targeting genomes.

Sikorski R S, Hieter P. Genetics. 1989 May; 122(1):19-27. A system of shuttle vectors and yeast host strains designed for efficient manipulation of DNA in *Saccharomyces cerevisiae*.

Singh P., Schimenti J C, Bolcun-Filas E (2015). A Mouse Geneticist's Practical Guide to CRISPR Applications, Genetics, Vol. 199, 1-15

Stoddard B L. Homing endonucleases: from microbial genetic invaders to reagents for targeted DNA modification. Structure. 2011; 19:7-15.

van Dijken J P, Bauer J, Brambilla L, Duboc P, Francois J M, Gancedo C, Giuseppin M L, Heijnen J J, Hoare M, Lange H C, Madden E A, Niederberger P, Nielsen J, Parrou J L, Petit T, Porro D, Reuss M, van Riel N, Rizzi M, Steensma H Y, Verrips C T, Vindel0v J, Pronk J T. An interlaboratory comparison of physiological and genetic properties of four *Saccharomyces cerevisiae* strains.

Enzyme Microb Technol. 2000 Jun. 1; 26(9-10):706-714. Verwaal R, Wang J, Meijnen J P, Visser H, Sandmann G, van den Berg J A, van Ooyen A J. Appl Environ Microbiol. 2007 July; 73(13):4342-50. Epub 2007 May 11. High-level production of beta-carotene in *Saccharomyces cerevisiae* by successive transformation with carotenogenic genes from Xanthophyllomyces dendrorhous.

Xu R, Qin R, Li H, Li D, Li L, Wei P, Yang J. Plant Biotechnol J. 2016 Nov. 22. doi: 10.1111/pbi.12669. [Epub ahead of print]Generation of targeted mutant rice using a CRISPR-Cpf1 system.

Yoshimi K, Yayoi Kunihiro Y,Kaneko T,Nagahora H, Voigt B, Tomoji Mashimo T (2016). ssODN-mediated knock-in with CRISPR-Cas for large genomic regions in zygotes. Nature Communications 7:10431, 10p Zetsche B, Gootenberg J S, Abudayyeh O O, Slaymaker I M, Makarova K S, Essletzbichler P, Volz S E, Joung J, van der Oost J, Regev A, Koonin E V, Zhang F. Cell. 2015 Oct. 22; 163(3):759-71. Cpf1 is a single RNA-guided endonuclease of a class 2 CRISPR-Cas system.

Zhumbayeva B, Chang C, McKinley J, Diatchenko L, Siebert P. BioTechniques. 2001; 30:520-523. Oligonucleotide-Mediated, PCR-Independent Cloning by Homologous Recombination

SEQUENCE LISTING

```
<160> NUMBER OF SEQ ID NOS: 136

<210> SEQ ID NO 1
<211> LENGTH: 5712
<212> TYPE: DNA
<213> ORGANISM: Artificial Sequence
<220> FEATURE:
<223> OTHER INFORMATION: Vector pRN1120

<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatcga ctacgtcgta aggccgtttc tgacagagta aaattcttga gggaactttc     240
accattatgg gaaatggttc aagaaggtat tgacttaaac tccatcaaat ggtcaggtca     300
ttgagtgttt tttatttgtt gtatttttt tttttagag aaaatcctcc aatatcaaat     360
taggaatcgt agtttcatga ttttctgtta cacctaactt tttgtgtggt gccctcctcc     420
ttgtcaatat taatgttaaa gtgcaattct ttttccttat cacgttgagc cattagtatc     480
aatttgctta cctgtattcc tttactatcc tccttttcct ccttcttgat aaatgtatgt     540
agattgcgta tatagtttcg tctaccctat gaacatattc cattttgtaa tttcgtgtcg     600
tttctattat gaatttcatt tataaagttt atgtacacct aggatccgtc gacactggat     660
ggcggcgtta gtatcgaatc gacagcagta tagcgaccag cattcacata cgattgacgc     720
atgatattac tttctgcgca cttaacttcg catctgggca gatgatgtcg aggcgaaaaa     780
aaatataaat cacgctaaca tttgattaaa atagaacaac tacaatataa aaaaactata     840
caaatgacaa gttcttgaaa acaagaatct ttttattgtc agtactaggg gcagggcatg     900
ctcatgtaga gcgcctgctc gccgtccgag gcggtgccgt cgtacagggc ggtgtccagg     960
ccgcagaggg tgaaccccat ccgccggtac gcgtggatcg ccggtgcgtt gacgttggtg    1020
acctccagcc agaggtgccc ggcgccccgc tcgcgggcga actccgtcgc gagcccatc     1080 aacgcgcgcc cgaccccgtg cccccggtgc tccgggcga cctcgatgtc ctcgacggtc     1140
agccggcggt tccagccgga gtacgagacg accacgaagc ccgccaggtc gccgtcgtcc    1200
ccgtacgcga cgaacgtccg ggagtccggg tcgccgtcct ccccggcgtc cgattcgtcg    1260
tccgattcgt cgtcggggaa caccttggtc aggggcgggt ccaccggcac ctcccgcagg    1320
gtgaagccgt ccccggtggc ggtgacgcgg aagacggtgt cggtggtgaa ggacccatcc    1380
agtgcctcga tggcctcggc gtccccgggg acactggtgc ggtaccggta agccgtgtcg    1440
tcaagagtgg tcattttaca tggttgttta tgttcggatg tgatgtgaga actgtatcct    1500
```

```
agcaagattt taaaaggaag tatatgaaag aagaacctca gtggcaaatc ctaaccfttt     1560 atatttctct acaggggcgc ggcgtgggga caattcaacg cgtctgtgag gggagcgttt     1620
ccctgctcgc aggtctgcag cgaggagccg taattttgc ttcgcgccgt gcggccatca      1680
aaatgtatgg atgcaaatga ttatacatgg ggatgtatgg gctaaatgta cgggcgacag     1740
tcacatcatg cccctgagct gcgcacgtca agactgtcaa ggagggtatt ctgggcctcc    1800
atgtcgctgg ccgggtgacc cggcggggac gaggccttaa gttcgaacgt acgagctccg    1860
gcattgcgaa taccgctttc cacaaacatt gctcaaaagt atctctttgc tatatatctc     1920
tgtgctatat ccctatataa cctacccatc cacctttcgc tccttgaact tgcatctaaa    1980
ctcgacctct acatttttta tgtttatctc tagtattact ctttagacaa aaaaattgta    2040
gtaagaacta ttcatagagt gaatcgaaaa caatacgaaa atgtaaacat ttcctatacg    2100
tagtatatag agacaaaata gaagaaaccg ttcataattt tctgaccaat gaagaatcat    2160
caacgctatc actttctgtt cacaaagtat gcgcaatcca catcggtata gaatataatc    2220
ggggatgcct ttatcttgaa aaaatgcacc cgcagcttcg ctagtaatca gtaaacgcgg    2280
gaagtggagt caggcttttt ttatggaaga gaaatagac accaaagtag ccttcttcta    2340
accttaacgg acctacagtg caaaaagtta tcaagagact gcattataga gcgcacaaag    2400
gagaaaaaaa gtaatctaag atgctttgtt agaaaaatag cgctctcggg atgcattttt    2460
gtagaacaaa aaagaagtat agattctttg ttggtaaaat agcgctctcg cgttgcattt    2520
ctgttctgta aaatgcagc tcagattctt tgtttgaaaa attagcgctc tcgcgttgca     2580
tttttgtttt acaaaatga agcacagatt cttcgttggt aaaatagcgc tttcgcgttg     2640
catttctgtt ctgtaaaaat gcagctcaga ttctttgttt gaaaaattag cgctctcgcg    2700
ttgcattttt gttctacaaa atgaagcaca gatgcttcgt taacaaagat atgctattga    2760
agtgcaagat ggaaacgcag aaaatgaacc ggggatgcga cgtgcaagat tacctatgca    2820
atagatgcaa tagtttctcc aggaaccgaa atacatacat tgtcttccgt aaagcgctag    2880
actatatatt attatacagg ttcaaatata ctatctgttt cagggaaaac tcccaggttc    2940
ggatgttcaa aattcaatga tgggtaacaa gtacgatcgt aaatctgtaa acagtttgt    3000 cggatattag gctgtatctc ctcaaagcgt attcgaatat cattgagaag ctgcagcgtc    3060
acatcggata taatgatgg cagccattgt agaagtgcct tttgcatttc tagtctcttt     3120
ctcggtctag ctagttttac tacatcgcga agatagaatc ttagatcaca ctgcctttgc    3180
tgagctggat caatagagta acaaagagt ggtaaggcct cgttaaagga caaggacctg     3240
agcggaagtg tatcgtacag tagacggagt atactaggta tagtctatag tccgtggaat    3300
taattctcat gtttgacagc ttatcatcga taatccggag ctagcatgcg gccgctctag    3360
aactagtgga tcccccgggc tgcaggaatt cgatatcaag cttatcgata ccgtcgacct    3420
cgaggggggg cccggtaccc agcttttgtt ccctttagtg agggttaatt ccgagcttgg    3480
cgtaatcatg gtcatagctg tttcctgtgt gaaattgtta tccgctcaca attccacaca    3540
acataggagc cggaagcata aagtgtaaag cctggggtgc ctaatgagtg aggtaactca    3600
cattaattgc gttgcgctca ctgcccgctt tccagtcggg aaacctgtcg tgccagctgc    3660
attaatgaat cggccaacgc gcggggagag gcggtttgcg tattgggcgc tcttccgctt    3720
cctcgctcac tgactcgctg cgctcggtcg ttcggctgcg gcgagcggta tcagctcact    3780
caaaggcggt aatacggtta tccacagaat caggggataa cgcaggaaag aacatgtgag    3840
caaaaggcca gcaaaaggcc aggaaccgta aaaaggccgc gttgctggcg ttttccata     3900
```

-continued

```
ggctcggccc ccctgacgag catcacaaaa atcgacgctc aagtcagagg tggcgaaacc    3960
cgacaggact ataaagatac caggcgttcc ccctggaag ctccctcgtg cgctctcctg     4020
ttccgaccct gccgcttacc ggatacctgt ccgcctttct cccttcggga agcgtggcgc    4080
tttctcaatg ctcacgctgt aggtatctca gttcggtgta ggtcgttcgc tccaagctgg    4140
gctgtgtgca cgaaccccc gttcagcccg accgctgcgc cttatccggt aactatcgtc     4200
ttgagtccaa cccggtaaga cacgacttat cgccactggc agcagccact ggtaacagga    4260
ttagcagagc gaggtatgta ggcggtgcta cagagttctt gaagtggtgg cctaactacg    4320
gctacactag aaggacagta tttggtatct gcgctctgct gaagccagtt accttcggaa    4380
aaagagttgg tagctcttga tccggcaaac aaaccaccgc tggtagcggt ggtttttttg    4440
tttgcaagca gcagattacg cgcagaaaaa aaggatctca agaagatcct ttgatctttt    4500
ctacggggtc tgacgctcag tggaacgaaa actcacgtta agggattttg gtcatgagat    4560
tatcaaaaag gatcttcacc tagatccttt taaattaaaa atgaagtttt aaatcaatct    4620
aaagtatata tgagtaaact tggtctgaca gttaccaatg cttaatcagt gaggcaccta    4680
tctcagcgat ctgtctattt cgttcatcca tagttgcctg actgcccgtc gtgtagataa    4740
ctacgatacg ggagggctta ccatctggcc ccagtgctgc aatgataccg cgagacccac    4800
gctcaccggc tccagattta tcagcaataa accagccagc cggaagggcc gagcgcagaa    4860
gtggtcctgc aactttatcc gcctccatcc agtctattaa ttgttgccgg gaagctagag    4920
taagtagttc gccagttaat agtttgcgca acgttgttgc cattgctaca ggcatcgtgg    4980
tgtcacgctc gtcgtttggt atggcttcat tcagctccgg ttcccaacga tcaaggcgag    5040
ttacatgatc ccccatgttg tgaaaaaaag cggttagctc cttcggtcct ccgatcgttg    5100
tcagaagtaa gttggccgca gtgttatcac tcatggttat ggcagcactg cataattctc    5160
ttactgtcat gccatccgta agatgctttt ctgtgactgg tgagtactca accaagtcat    5220
tctgagaata gtgtatgcgg cgaccgagtt gctcttgccc ggcgtcaata cgggataata    5280
ccgcgccaca tagcagaact ttaaaagtgc tcatcattgg aaaacgttct cggggcgaa     5340 aactctcaag gatcttaccg ctgttgagat ccagttcgat gtaacccact cgtgcaccca    5400
actgatcttc agcatctttt actttcacca gcgtttctgg gtgagcaaaa acaggaaggc    5460
aaaatgccgc aaaaaggga ataagggcga cacggaaatg ttgaatactc atactcttcc     5520 ttttcaata ttattgaagc atttatcagg gttattgtct catgagcgga tacatatttg     5580
aatgtattta gaaaaataaa caataggggg ttccgcgcac atttccccga aaagtgccac    5640
ctgacgtcta agaaaccatt attatcatga cattaaccta taaaaatagg cgtatcacga    5700
ggccctttcg tc                                                        5712
```

<210> SEQ ID NO 2
<211> LENGTH: 21
<212> TYPE: DNA
<213> ORGANISM: Artificial Sequence
<220> FEATURE:
<223> OTHER INFORMATION: FW primer to remove SapI restriction site in
      pRN1120

<400> SEQUENCE: 2
tattgggccc tcttccgctt c                                                21

<210> SEQ ID NO 3
<211> LENGTH: 18

```
<212> TYPE: DNA
<213> ORGANISM: Artificial Sequence
<220> FEATURE:
<223> OTHER INFORMATION: REV primer to remove SapI restriction site in
      pRN1120

<400> SEQUENCE: 3
cgcaaaccgc ctctcccc                                                   18

<210> SEQ ID NO 4
<211> LENGTH: 547
<212> TYPE: DNA
<213> ORGANISM: Artificial Sequence
<220> FEATURE:
<223> OTHER INFORMATION: gBlock allowing direct SapI cloning of genomic
      target, part of vector pGRN002.

<400> SEQUENCE: 4
ggagctagca tgcggccgct ctagaactag tggatccccc gggctgcagg aattctcttt      60
gaaaagataa tgtatgatta tgctttcact catatttata cagaaacttg atgttttctt    120
tcgagtatat acaaggtgat tacatgtacg tttgaagtac aactctagat tttgtagtgc    180
cctcttgggc tagcggtaaa ggtgcgcatt ttttcacacc ctacaatgtt ctgttcaaaa    240
gattttggtc aaacgctgta gaagtgaaag ttggtgcgca tgtttcggcg ttcgaaactt    300
ctccgcagtg aaagataaat gatcagaaga gcctgaggtc gacggtatcg ataagcttga    360
tatcaattcc ccgggggatc cactgctctt ctgttttaga gctagaaata gcaagttaaa    420
ataaggctag tccgttatca acttgaaaaa gtggcaccga gtcggtggtg cttttttgt     480 tttttatgtc tctcgagggg gggcccggta cccagctttt gttcccttta gtgagggtta    540
attccga                                                              547

<210> SEQ ID NO 5
<211> LENGTH: 6121
<212> TYPE: DNA
<213> ORGANISM: Artificial Sequence
<220> FEATURE:
<223> OTHER INFORMATION: Vector pGRN002

<400> SEQUENCE: 5
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatcga ctacgtcgta aggccgtttc tgacagagta aaattcttga gggaactttc    240
accattatgg gaaatggttc aagaaggtat tgacttaaac tccatcaaat ggtcaggtca    300
ttgagtgttt tttatttgtt gtatttttt tttttagag aaaatcctcc aatatcaaat     360
taggaatcgt agtttcatga ttttctgtta cacctaactt tttgtgtggt gccctcctcc    420
ttgtcaatat taatgttaaa gtgcaattct ttttccttat cacgttgagc cattagtatc    480
aatttgctta cctgtattcc tttactatcc tcctttttct ccttcttgat aaatgtatgt    540
agattgcgta tatagtttcg tctaccctat gaacatattc catttgtaa tttcgtgtcg    600 tttctattat gaatttcatt tataaagttt atgtacacct aggatccgtc gacactggat    660
ggcggcgtta gtatcgaatc gacagcagta tagcgaccag cattcacata cgattgacgc    720
atgatattac tttctgcgca cttaacttcg catctgggca gatgatgtcg aggcgaaaaa    780
aaatataaat cacgctaaca tttgattaaa atagaacaac tacaatataa aaaactata    840
```

```
caaatgacaa gttcttgaaa acaagaatct ttttattgtc agtactaggg gcagggcatg    900
ctcatgtaga gcgcctgctc gccgtccgag gcggtgccgt cgtacagggc ggtgtccagg    960
ccgcagaggg tgaaccccat ccgccggtac gcgtggatcg ccggtgcgtt gacgttggtg   1020
acctccagcc agaggtgccc ggcgccccgc tcgcgggcga actccgtcgc gagcccatc    1080 aacgcgcgcc cgaccccgtg ccccggtgc tccggggcga cctcgatgtc ctcgacggtc    1140
agccggcggt tccagccgga gtacgagacg accacgaagc ccgccaggtc gccgtcgtcc   1200
ccgtacgcga cgaacgtccg ggagtccggg tcgccgtcct ccccggcgtc cgattcgtcg   1260
tccgattcgt cgtcggggaa caccttggtc aggggcgggt ccaccggcac ctcccgcagg   1320
gtgaagccgt ccccggtggc ggtgacgcgg aagacggtgt cggtggtgaa ggacccatcc   1380
agtgcctcga tggcctcggc gtccccgggg acactggtgc ggtaccggta agccgtgtcg   1440
tcaagagtgg tcattttaca tggttgttta tgttcggatg tgatgtgaga actgtatcct   1500
agcaagattt taaaggaag tatatgaaag aagaacctca gtggcaaatc ctaaccttt    1560 atatttctct acagggcgc ggcgtgggga caattcaacg cgtctgtgag gggagcgttt   1620
ccctgctcgc aggtctgcag cgaggagccg taattttgc ttcgcgccgt gcggccatca   1680
aaaatgtatg atgcaaatga ttatacatgg ggatgtatgg gctaaatgta cgggcgacag   1740
tcacatcatg cccctgagct gcgcacgtca agactgtcaa ggagggtatt ctgggcctcc   1800
atgtcgctgg ccgggtgacc cggcggggac gaggccttaa gttcgaacgt acgagctccg   1860
gcattgcgaa taccgctttc cacaaacatt gctcaaaagt atctctttgc tatatatctc   1920
tgtgctatat ccctatataa cctacccatc cacctttcgc tccttgaact tgcatctaaa   1980
ctcgacctct acattttta tgtttatctc tagtattact ctttagacaa aaaaattgta   2040
gtaagaacta ttcatagagt gaatcgaaaa caatacgaaa atgtaaacat ttcctatacg   2100
tagtatatag agacaaaata gaagaaaccg ttcataattt tctgaccaat gaagaatcat   2160
caacgctatc actttctgtt cacaaagtat gcgcaatcca catcggtata gaatataatc   2220
ggggatgcct ttatcttgaa aaaatgcacc cgcagcttcg ctagtaatca gtaaacgcgg   2280
gaagtggagt caggcttttt ttatggaaga gaaaatagac accaaagtag ccttcttcta   2340
accttaacgg acctacagtg caaaaagtta tcaagagact gcattataga gcgcacaaag   2400
gagaaaaaaa gtaatctaag atgctttgtt agaaaaatag cgctctcggg atgcattttt   2460
gtagaacaaa aaagaagtat agattctttg ttggtaaaat agcgctctcg cgttgcattt   2520
ctgttctgta aaaatgcagc tcagattctt tgtttgaaaa attagcgctc tcgcgttgca   2580
tttttgtttt acaaaaatga agcacagatt cttcgttggt aaaatagcgc tttcgcgttg   2640
catttctgtt ctgtaaaaat gcagctcaga ttctttgttt gaaaaattag cgctctcgcg   2700
ttgcattttt gttctacaaa atgaagcaca gatgcttcgt taacaaagat atgctattga   2760
agtgcaagat ggaaacgcag aaaatgaacc ggggatgcga cgtgcaagat tacctatgca   2820
atagatgcaa tagtttctcc aggaaccgaa atacatacat tgtcttccgt aaagcgctag   2880
actatatatt attatacagg ttcaaatata ctatctgttt cagggaaaac tcccaggttc   2940
ggatgttcaa aattcaatga tgggtaacaa gtacgatcgt aaatctgtaa aacagtttgt   3000
cggatattag gctgtatctc ctcaaagcgt attcgaatat cattgagaag ctgcagcgtc   3060
acatcggata ataatgatgg cagccattgt agaagtgcct tttgcatttc tagtctcttt   3120
ctcggtctag ctagttttac tacatcgcga agatagaatc ttagatcaca ctgcctttgc   3180
tgagctggat caatagagta acaaaagagt ggtaaggcct cgttaaagga caaggacctg   3240
```

-continued

```
agcggaagtg tatcgtacag tagacggagt atactaggta tagtctatag tccgtggaat    3300
taattctcat gtttgacagc ttatcatcga taatccggag ctagcatgcg ccgctctag     3360
aactagtgga tcccccgggc tgcaggaatt ctctttgaaa agataatgta tgattatgct    3420
ttcactcata tttatacaga aacttgatgt tttctttcga gtatatacaa ggtgattaca    3480
tgtacgtttg aagtacaact ctagattttg tagtgccctc ttgggctagc ggtaaaggtg    3540
cgcatttttt cacaccctac aatgttctgt tcaaaagatt ttggtcaaac gctgtagaag    3600
tgaaagttgg tgcgcatgtt tcggcgttcg aaacttctcc gcagtgaaag ataaatgatc    3660
agaagagcct gaggtcgacg gtatcgataa gcttgatatc aattcccgg gggatccact     3720
gctcttctgt tttagagcta gaaatagcaa gttaaaataa ggctagtccg ttatcaactt    3780
gaaaaagtgg caccgagtcg gtggtgcttt ttttgttttt tatgtctctc gagggggggc    3840
ccggtaccca gcttttgttc cctttagtga gggttaattc cgagcttggc gtaatcatgg    3900
tcatagctgt ttcctgtgtg aaattgttat ccgctcacaa ttccacacaa cataggagcc    3960
ggaagcataa agtgtaaagc ctggggtgcc taatgagtga ggtaactcac attaattgcg    4020
ttgcgctcac tgcccgcttt ccagtcggga acctgtcgt gccagctgca ttaatgaatc      4080
ggccaacgcg cggggagagg cggtttgcgt attgggccct cttccgcttc ctcgctcact    4140
gactcgctgc gctcggtcgt tcggctgcgg cgagcggtat cagctcactc aaaggcggta    4200
atacggttat ccacagaatc aggggataac gcaggaaaga acatgtgagc aaaaggccag    4260
caaaaggcca ggaaccgtaa aaaggccgcg ttgctggcgt ttttccatag gctcggcccc    4320
cctgacgagc atcacaaaaa tcgacgctca agtcagaggt ggcgaaaccc gacaggacta    4380
taaagatacc aggcgttccc ccctggaagc tccctcgtgc gctctcctgt tccgaccctg    4440
ccgcttaccg gatacctgtc cgcctttctc ccttcgggaa gcgtggcgct ttctcaatgc    4500
tcacgctgta ggtatctcag ttcggtgtag gtcgttcgct ccaagctggg ctgtgtgcac    4560
gaaccccccg ttcagcccga ccgctgcgcc ttatccggta actatcgtct tgagtccaac    4620
ccggtaagac acgacttatc gccactggca gcagccactg gtaacaggat tagcagagcg    4680
aggtatgtag gcggtgctac agagttcttg aagtggtggc ctaactacgg ctacactaga    4740
aggacagtat ttggtatctg cgctctgctg aagccagtta ccttcggaaa aagagttggt    4800
agctcttgat ccggcaaaca aaccaccgct ggtagcggtg gtttttttgt ttgcaagcag    4860
cagattacgc gcagaaaaaa aggatctcaa gaagatcctt tgatcttttc tacgggtct    4920
gacgctcagt ggaacgaaaa ctcacgttaa gggattttgg tcatgagatt atcaaaaagg    4980
atcttcacct agatcctttt aaattaaaaa tgaagtttta aatcaatcta agtatatat    5040
gagtaaactt ggtctgacag ttaccaatgc ttaatcagtg aggcacctat ctcagcgatc    5100
tgtctatttc gttcatccat agttgcctga ctgcccgtcg tgtagataac tacgatacgg    5160
gagggcttac catctggccc cagtgctgca atgataccgc gagacccacg ctcaccggct    5220
ccagatttat cagcaataaa ccagccagcc ggaagggccg agcgcagaag tggtcctgca    5280
actttatccg cctccatcca gtctattaat tgttgccggg aagctagagt aagtagttcg    5340
ccagttaata gtttgcgcaa cgttgttgcc attgctacag gcatcgtggt gtcacgctcg    5400
tcgtttggta tggcttcatt cagctccggt tcccaacgat caaggcgagt tacatgatcc    5460
cccatgttgt gaaaaaaagc ggttagctcc ttcggtcctc cgatcgttgt cagaagtaag    5520
ttggccgcag tgttatcact catggttatg gcagcactgc ataattctct tactgtcatg    5580
```

```
ccatccgtaa gatgcttttc tgtgactggt gagtactcaa ccaagtcatt ctgagaatag    5640
tgtatgcggc gaccgagttg ctcttgcccg gcgtcaatac gggataatac cgcgccacat    5700
agcagaactt taaaagtgct catcattgga aaacgttctt cggggcgaaa actctcaagg    5760
atcttaccgc tgttgagatc cagttcgatg taacccactc gtgcacccaa ctgatcttca    5820
gcatctttta ctttcaccag cgtttctggg tgagcaaaaa caggaaggca aaatgccgca    5880
aaaaagggaa taagggcgac acggaaatgt tgaatactca tactcttcct ttttcaatat    5940
tattgaagca tttatcaggg ttattgtctc atgagcggat acatatttga atgtatttag    6000
aaaaataaac aaataggggt tccgcgcaca tttccccgaa aagtgccacc tgacgtctaa    6060
gaaaccatta ttatcatgac attaacctat aaaaataggc gtatcacgag gccctttcgt    6120
c                                                                    6121

<210> SEQ ID NO 6
<211> LENGTH: 23
<212> TYPE: DNA
<213> ORGANISM: Artificial Sequence
<220> FEATURE:
<223> OTHER INFORMATION: FW primer to obtain the linear recipient PCR
      fragment (SEQ ID NO: 8)

<400> SEQUENCE: 6
gttttagagc tagaaatagc aag                                             23

<210> SEQ ID NO 7
<211> LENGTH: 22
<212> TYPE: DNA
<213> ORGANISM: Artificial Sequence
<220> FEATURE:
<223> OTHER INFORMATION: REV primer to obtain the linear recipient PCR
      fragment (SEQ ID NO: 8)

<400> SEQUENCE: 7
gatcatttat ctttcactgc gg                                              22

<210> SEQ ID NO 8
<211> LENGTH: 6053
<212> TYPE: DNA
<213> ORGANISM: Artificial Sequence
<220> FEATURE:
<223> OTHER INFORMATION: Linear recipient PCR fragment used for in-vivo
      assembly of a guide sequence

<400> SEQUENCE: 8
gttttagagc tagaaatagc aagttaaaat aaggctagtc cgttatcaac ttgaaaaagt    60
ggcaccgagt cggtggtgct ttttttgttt tttatgtctc tcgagggggg gcccggtacc   120
cagcttttgt tccctttagt gagggttaat tccgagcttg gcgtaatcat ggtcatagct   180
gtttcctgtg tgaaattgtt atccgctcac aattccacac aacataggag ccggaagcat   240
aaagtgtaaa gcctggggtg cctaatgagt gaggtaactc acattaattg cgttgcgctc   300
actgcccgct ttccagtcgg gaaacctgtc gtgccagctg cattaatgaa tcggccaacg   360
cgcggggaga ggcggtttgc gtattgggcc ctcttccgct tcctcgctca ctgactcgct   420
gcgctcggtc gttcggctgc ggcgagcggt atcagctcac tcaaaggcgg taatacggtt   480
atccacagaa tcaggggata acgcaggaaa gaacatgtga gcaaaaggcc agcaaaaggc   540
caggaaccgt aaaaaggccg cgttgctggc gtttttccat aggctcggcc ccctgacga    600 gcatcacaaa aatcgacgct caagtcagag gtggcgaaac ccgacaggac tataaagata   660
```

```
ccaggcgttc cccctggaa gctccctcgt gcgctctcct gttccgaccc tgccgcttac    720
cggatacctg tccgcctttc tcccttcggg aagcgtggcg cttttctcaat gctcacgctg  780
taggtatctc agttcggtgt aggtcgttcg ctccaagctg ggctgtgtgc acgaaccccc  840
cgttcagccc gaccgctgcg ccttatccgg taactatcgt cttgagtcca acccggtaag  900
acacgactta tcgccactgg cagcagccac tggtaacagg attagcagag cgaggtatgt  960
aggcggtgct acagagttct tgaagtggtg gcctaactac ggctacacta aaggacagt   1020
atttggtatc tgcgctctgc tgaagccagt taccttcgga aaaagagttg gtagctcttg  1080
atccggcaaa caaaccaccg ctggtagcgg tggtttttt gtttgcaagc agcagattac   1140
gcgcagaaaa aaggatctca agaagatcct tttgatcttt tctacggggt ctgacgctca  1200
gtggaacgaa aactcacgtt aagggatttt ggtcatgaga ttatcaaaaa ggatcttcac  1260
ctagatcctt ttaaattaaa aatgaagttt taaatcaatc taaagtatat atgagtaaac  1320
ttggtctgac agttaccaat gcttaatcag tgaggcacct atctcagcga tctgtctatt  1380
tcgttcatcc atagttgcct gactgcccgt cgtgtagata actacgatac gggagggctt  1440
accatctggc cccagtgctg caatgatacc gcgagaccca cgctcaccgg ctccagattt  1500
atcagcaata accagccagc cggaagggc cgagcgcaga agtggtcctg caactttatc   1560
cgcctccatc cagtctatta attgttgccg ggaagctaga gtaagtagtt cgccagttaa  1620
tagtttgcgc aacgttgttg ccattgctac aggcatcgtg gtgtcacgct cgtcgtttgg  1680
tatggcttca ttcagctccg gttcccaacg atcaaggcga gttacatgat ccccccatgtt 1740
gtgaaaaaaa gcggttagct ccttcggtcc tccgatcgtt gtcagaagta agttggccgc  1800
agtgttatca ctcatggtta tggcagcact gcataattct cttactgtca tgccatccgt  1860
aagatgcttt tctgtgactg gtgagtactc aaccaagtca ttctgagaat agtgtatgcg  1920
gcgaccgagt tgctcttgcc cggcgtcaat acgggataat accgcgccac atagcagaac  1980
tttaaaagtg ctcatcattg gaaaacgttc ttcggggcga aaactctcaa ggatcttacc  2040
gctgttgaga tccagttcga tgtaacccac tcgtgcaccc aactgatctt cagcatcttt  2100
tactttcacc agcgtttctg ggtgagcaaa aacaggaagg caaaatgccg caaaaaaggg  2160
aataagggcg acacggaaat gttgaatact catactcttc ctttttcaat attattgaag  2220
catttatcag ggttattgtc tcatgagcgg atacatattt gaatgtattt agaaaaataa  2280
acaaataggg gttccgcgca catttccccg aaaagtgcca cctgacgtct aagaaaccat  2340
tattatcatg acattaacct ataaaaatag gcgtatcacg aggcccttc gtctcgcgcg   2400
tttcggtgat gacggtgaaa acctctgaca catgcagctc ccggagacgg tcacagcttg  2460
tctgtaagcg gatgccggga gcagacaagc ccgtcagggc gcgtcagcgg gtgttggcgg  2520
gtgtcgggc tggcttaact atgcggcatc agagcagatt gtactgagag tgcaccatat  2580
cgactacgtc gtaaggccgt ttctgacaga gtaaaattct tgagggaact ttcaccatta  2640
tgggaaatgg ttcaagaagg tattgactta aactccatca aatggtcagg tcattgagtg  2700
ttttttattt gttgtatttt tttttttta gagaaaatcc tccaatatca aattaggaat   2760
cgtagtttca tgattttctg ttacacctaa cttttgtgt ggtgccctcc tccttgtcaa    2820
tattaatgtt aaagtgcaat tcttttcct tatcacgttg agccattagt atcaatttgc   2880
ttacctgtat tcctttacta tcctcctttt tctccttctt gataaatgta tgtagattgc  2940
gtatatagtt tcgtctaccc tatgaacata ttccattttg taatttcgtg tcgtttctat  3000
tatgaatttc atttataaag tttatgtaca cctaggatcc gtcgacactg gatggcggcg  3060
```

```
ttagtatcga atcgacagca gtatagcgac cagcattcac atacgattga cgcatgatat    3120
tactttctgc gcacttaact tcgcatctgg gcagatgatg tcgaggcgaa aaaaaatata    3180
aatcacgcta acatttgatt aaaatagaac aactacaata taaaaaaact atacaaatga    3240
caagttcttg aaaacaagaa tctttttatt gtcagtacta ggggcagggc atgctcatgt    3300
agagcgcctg ctcgccgtcc gaggcggtgc cgtcgtacag ggcggtgtcc aggccgcaga    3360
gggtgaaccc catccgccgg tacgcgtgga tcgccggtgc gttgacgttg gtgacctcca    3420
gccagaggtg cccggcgccc cgctcgcggg cgaactccgt cgcgagcccc atcaacgcgc    3480
gcccgacccc gtgcccccgg tgctccgggg cgacctcgat gtcctcgacg gtcagccggc    3540
ggttccagcc ggagtacgag acgaccacga agcccgccag gtcgccgtcg tccccgtacg    3600
cgacgaacgt ccgggagtcc gggtcgccgt cctccccggc gtccgattcg tcgtccgatt    3660
cgtcgtcggg gaacaccttg gtcaggggcg ggtccaccgg cacctcccgc agggtgaagc    3720
cgtccccggt ggcggtgacg cggaagacgg tgtcggtggt gaaggaccca tccagtgcct    3780
cgatggcctc ggcgtccccc gggacactgg tgcggtaccg gtaagccgtg tcgtcaagag    3840
tggtcatttt acatggttgt ttatgttcgg atgtgatgtg agaactgtat cctagcaaga    3900
ttttaaaagg aagtatatga aagaagaacc tcagtggcaa atcctaacct tttatatttc    3960
tctacagggg cgcggcgtgg ggacaattca acgcgtctgt gaggggagcg tttccctgct    4020
cgcaggtctg cagcgaggag ccgtaatttt tgcttcgcgc cgtgcggcca tcaaaatgta    4080
tggatgcaaa tgattataca tggggatgta tgggctaaat gtacgggcga cagtcacatc    4140
atgcccctga gctgcgcacg tcaagactgt caaggagggt attctgggcc tccatgtcgc    4200
tggccgggtg accggcggg gacgaggcct taagttcgaa cgtacgagct ccggcattgc    4260
gaataccgct ttccacaaac attgctcaaa agtatctctt tgctatatat ctctgtgcta    4320
tatccctata taacctaccc atccaccttt cgctccttga acttgcatct aaactcgacc    4380
tctacatttt ttatgtttat ctctagtatt actctttaga caaaaaatt gtagtaagaa    4440 ctattcatag agtgaatcga aaacaatacg aaaatgtaaa catttcctat acgtagtata    4500
tagagacaaa atagaagaaa ccgttcataa ttttctgacc aatgaagaat catcaacgct    4560
atcactttct gttcacaaag tatgcgcaat ccacatcggt atagaatata atcggggatg    4620
cctttatctt gaaaaaatgc acccgcagct tcgctagtaa tcagtaaacg cgggaagtgg    4680
agtcaggctt tttttatgga agagaaaata gacaccaaag tagccttctt ctaaccttaa    4740
cggacctaca gtgcaaaaag ttatcaagag actgcattat agagcgcaca aaggagaaaa    4800
aaagtaatct aagatgcttt gttagaaaaa tagcgctctc gggatgcatt tttgtagaac    4860 aaaaagaag tatagattct ttgttggtaa aatagcgctc tcgcgttgca tttctgttct    4920
gtaaaaatgc agctcagatt ctttgtttga aaattagcg ctctcgcgtt gcattttgt    4980 tttacaaaaa tgaagcacag attcttcgtt ggtaaaatag cgctttcgcg ttgcatttct    5040
gttctgtaaa aatgcagctc agattctttg tttgaaaaat tagcgctctc gcgttgcatt    5100
tttgttctac aaaatgaagc acagatgctt cgttaacaaa gatatgctat tgaagtgcaa    5160
gatggaaacg cagaaaatga accggggatg cgacgtgcaa gattacctat gcaatagatg    5220
caatagtttc tccaggaacc gaaatacata cattgtcttc cgtaaagcgc tagactatat    5280
attattatac aggttcaaat atactatctg tttcagggaa aactcccagg ttcggatgtt    5340
caaaattcaa tgatgggtaa caagtacgat cgtaaatctg taaaacagtt tgtcggatat    5400
```

```
taggctgtat ctcctcaaag cgtattcgaa tatcattgag aagctgcagc gtcacatcgg    5460
ataataatga tggcagccat tgtagaagtg cctttgcat ttctagtctc tttctcggtc    5520
tagctagttt tactacatcg cgaagataga atcttagatc acactgcctt tgctgagctg    5580
gatcaataga gtaacaaaag agtggtaagg cctcgttaaa ggacaaggac ctgagcggaa    5640
gtgtatcgta cagtagacgg agtatactag gtatagtcta tagtccgtgg aattaattct    5700
catgtttgac agcttatcat cgataatccg gagctagcat gcggccgctc tagaactagt    5760 ggatccccg gctgcagga attctctttg aaaagataat gtatgattat gctttcactc    5820
atatttatac agaaacttga tgttttcttt cgagtatata caaggtgatt acatgtacgt    5880
ttgaagtaca actctagatt ttgtagtgcc ctcttgggct agcggtaaag gtgcgcattt    5940
tttcacaccc tacaatgttc tgttcaaaag attttggtca aacgctgtag aagtgaaagt    6000
tggtgcgcat gtttcggcgt tcgaaacttc tccgcagtga agataaatg atc          6053
```

<210> SEQ ID NO 9
<211> LENGTH: 11742
<212> TYPE: DNA
<213> ORGANISM: Artificial Sequence
<220> FEATURE:
<223> OTHER INFORMATION: Vector pCSN061

<400> SEQUENCE: 9

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accataaacg acattactat atatataata taggaagcat ttaatagaca gcatcgtaat     240
atatgtgtac tttgcagtta tgacgccaga tggcagtagt ggaagatatt ctttattgaa     300
aaatagcttg tcaccttacg tacaatcttg atccggagct tttctttttt tgccgattaa     360
gaattaattc ggtcgaaaaa agaaaaggag agggccaaga gggagggcat tggtgactat     420
tgagcacgtg agtatacgtg attaagcaca caaaggcagc ttggagtatg tctgttatta     480
atttcacagg tagttctggt ccattggtga agtttgcgg cttgcagagc acagaggccg     540
cagaatgtgc tctagattcc gatgctgact tgctgggtat tatatgtgtg cccaatagaa     600
agagaacaat tgacccggtt attgcaagga aaatttcaag tcttgtaaaa gcatataaaa     660
atagttcagg cactccgaaa tacttggttg gcgtgtttcg taatcaacct aaggaggatg     720
ttttggctct ggtcaatgat tacggcattg atatcgtcca actgcatgga gatgagtcgt     780
ggcaagaata ccaagagttc ctcggtttgc cagttattaa aagactcgta tttccaaaag     840
actgcaacat actactcagt gcagcttcac agaaacctca ttcgtttatt cccttgtttg     900
attcagaagc aggtgggaca ggtgaacttt tggattggaa ctcgatttct gactgggttg     960
gaaggcaaga gagccccgaa agcttacatt ttatgttagc tggtggactg acgccagaaa    1020
atgttggtga tgcgcttaga ttaaatggcg ttattggtgt tgatgtaagc ggaggtgtgg    1080
agacaaatgg tgtaaaagac tctaacaaaa tagcaaattt cgtcaaaaat gctaagaaat    1140
aggttattac tgagtagtat ttatttaagt attgtttgtg cacttgccta tgcggtgtga    1200
aataccgcac agatgcgtaa ggagaaaata ccgcatcagg aaattgtaaa cgttaatatt    1260
ttgttaaaat tcgcgttaaa ttttgttaa atcagctcat ttttaaccaa taggccgaa    1320 atcggcaaaa tcccttataa atcaaaagaa tagaccgaga tagggttgag tgttgttcca    1380
gtttggaaca agagtccact attaaagaac gtggactcca acgtcaaagg gcgaaaaacc    1440
```

```
gtctatcagg gcgatggccc actacgtgaa ccatcaccct aatcaagttt tttggggtcg    1500
aggtgccgta aagcactaaa tcggaaccct aaagggagcc cccgatttag agcttgacgg    1560
ggaaagccgg cgaacgtggc gagaaaggaa gggaagaaag cgaaaggagc gggcgctagg    1620
gcgctggcaa gtgtagcggt cacgctgcgc gtaaccacca cacccgccgc gcttaatgcg    1680
ccgctacagg gcgcgtcgcg ccattcgcca ttcaggctgc gcaactgttg ggaagggcga    1740
tcggtgcggg cctcttcgct attacgccag ctggcgaaag ggggatgtgc tgcaaggcga    1800
ttaagttggg taacgccagg ttttcccag tcacgacgtt gtaaaacgac ggccagtgag    1860
cgcgcgtaat acgactcact ataggggcgaa ttgggtaccc tttcttttt tgcggtcacc    1920 cccatgtggc ggggaggcag aggagtaggt agagcaacga atcctactat ttatccaaat    1980
tagtctagga actctttttc tagattttt agatttgagg gcaagcgctg ttaacgactc    2040
agaaatgtaa gcactacgga gtagaacgag aaatccgcca taggtggaaa tcctagcaaa    2100
atcttgctta ccctagctag cctcaggtaa gctagcctta gcctgtcaaa tttttttcaa    2160
aatttggtaa gtttctacta gcaaagcaaa cacggttcaa caaaccgaaa actccactca    2220
ttatacgtgg aaaccgaaac aaaaaaacaa aaaccaaaat actcgccaat gagaaagttg    2280
ctgcgtttct actttcgagg aagaggaact gagaggattg actacgaaag gggcaaaaac    2340
gagtcgtatt ctcccattat tgtctgctac cacgcggtct agtagaataa gcaaccagtc    2400
aacgctaaga caggtaatca aaataccagt ctgctggcta cgggctagtt tttacctctt    2460
ttagaaccca ctgtaaaagt ccgttgtaaa gcccgttctc actgttggcg tttttttttt    2520
tttggtttag tttcttattt tcatttttt tctttcatga ccaaaaacaa acaaatctcg    2580
cgatttgtac tgcggccact ggggcgtggc caaaaaaatg acaaatttag aaaccttagt    2640
ttctgatttt tcctgttatg aggagatatg ataaaaaata ttactgcttt attgtttttt    2700
ttttatctac tgaaatagag aaacttaccc aaggaggagg caaaaaaaag agtatatata    2760
cagcagctac cattcagatt ttaatatatt cttttctctt cttctacact attattataa    2820
taattttact atattcattt ttagcttaaa acctcataga atattattct tcagtcactc    2880
gcttaaatac ttatcaaaaa tggacaagaa atactctatt ggtttggata tcgggaccaa    2940
ctccgtcggt tgggctgtca tcaccgacga atacaaggtt ccatccaaga aattcaaggt    3000
cttgggtaac actgacagac actctatcaa gaagaatttg atcggtgctt tgttgttcga    3060
ctccggtgaa accgctgaag ctaccagatt gaagcgtacc gctcgtcgta gatacactag    3120
acgtaaaaac cgtatttgtt acttgcaaga aatcttttct aacgaaatgg ccaaggttga    3180
cgactctttc ttccacagat tggaagaatc tttcttggtt gaagaagaca agaagcacga    3240
aagacatcca atcttcggta acatcgttga cgaagttgct taccacgaaa aatacccta    3300 catctaccat ttgagaaaga agttggtcga ttccaccgac aaggctgatt tgagattgat    3360
ctatttggcc ttggctcaca tgatcaagtt cagaggtcac ttcttgattg aaggtgactt    3420
gaacccagac aactctgacg tcgacaaatt gttcatccaa ttggtccaaa cctacaacca    3480
attattcgag gaaacccaa ttaacgcttc tggtgttgat gctaaggcca tcttatctgc    3540
ccgtttgtcc aagtctagac gtttggaaaa cttgattgct caattgcctg gtgaaaagaa    3600
aaacggtttg ttcggtaact tgatcgcttt gtccttgggt ttgacccaa acttcaagtc    3660 caacttcgac ttggctgaag atgccaagtt gcaattgtcc aaggacacct acgacgacga    3720
cttagacaac ttgttggctc aaatcggtga ccaatacgcc gacttgttct ggctgccaa    3780
```

```
aaacttatct gacgctatct tgttgtctga catcttgaga gttaacactg aaattaccaa    3840
ggctccattg tctgcttcta tgatcaaaag atacgacgaa caccaccaag atctgacttt    3900
gttgaaggct ttggttagac aacaattgcc agaaaagtac aaggaaatct tcttcgacca    3960
atccaaaaat ggttacgccg gttacattga cggtggtgct tctcaggaag aattctacaa    4020
gttcatcaag ccaattttgg aaaagatgga tggtactgaa gaattattgg ttaagttgaa    4080
cagagaagac ttattgagaa agcaacgtac cttcgataac ggttctatcc cacaccaaat    4140
ccacttgggt gaattgcacg ccattttgag aagacaggaa gatttctatc cattcctaaa    4200
ggacaacaga gaaaagatcg aaaagatctt aactttcaga atcccatact acgtcggtcc    4260
attggccaga ggtaattcta gattcgcttg gatgaccaga aagtctgaag aaaccatcac    4320
cccatggaac ttcgaagaag tcgtcgacaa gggtgcttct gcccaatctt tcatcgaaag    4380
aatgaccaac tttgataaga acttgccaaa cgagaaggtc ttgccaaagc actctttgtt    4440
gtacgaatac ttcaccgtct acaacgaatt aaccaaggtt aaatacgtta ctgaaggtat    4500
gagaaagcca gctttcctat ccggtgaaca aaagaaggct attgttgact tgttgtttaa    4560
gaccaacaga aaggtcactg ttaagcaatt aaggaagac tacttcaaga agattgaatg    4620
tttcgattcc gtcgaaatct ccggtgttga agaccgtttc aatgcttctt gggcaccta    4680
ccacgatttg ttaaagatca tcaaggacaa ggactttta gataacgaag aaaacgaaga    4740
catcttggaa gatatcgttt tgaccttgac tcttttcgag gacagagaaa tgattgaaga    4800
gagattgaag acctacgctc acttgttcga cgataaagtt atgaagcaac taagagaag    4860
aagatacact ggttggggta gattgtccag aaagttgatt aacggtatca gagacaagca    4920
atccggtaag actatttag actttttgaa atccgatggt ttcgctaaca gaaactttat    4980
gcaattgatt cacgacgatt ctttgacttt caaggaagac attcaaaaag cccaagtctc    5040
tggtcaaggt gattctttgc acgaacacat cgctaacttg gctggttctc cagctattaa    5100
gaagggtatc ttacaaaccg tcaaggtcgt tgatgaattg gtcaaagtca tgggtagaca    5160
caagccagaa atattgtca tcgaaatggc tagagaaaac caaactactc aaaagggtca    5220
aaagaactct agagaacgta tgaagagaat tgaagaaggt atcaaggagt tgggttctca    5280
aatttttgaaa gaacacccag tcgaaaacac tcaattacaa aacgaaaagc tatacttgta    5340
ctacttgcaa aacggtcgtg acatgtacgt cgaccaagaa ttggatatca acagattgtc    5400
tgactacgat gtcgatcata tcgtcccaca atcgttcttg aaggacgatt ccattgacaa    5460
caaagttttg actagatctg acaagaacag aggtaagtct gataacgttc catctgaaga    5520
agttgttaag aagatgaaga actactggag acaattgttg aatgctaagt tgatcactca    5580
aagaaagttc gacaacttga ccaaggctga agaggtggt ttgtccgaat tggacaaagc    5640
cggtttcatc aagagacaat tagtcgaaac tagacaaatc accaagcatg ttgctcaaat    5700
cttggattcc agaatgaaca ctaagtacga tgaaaacgac aaactaatta gagaagttaa    5760
ggtcatcact ttgaagtcta agttggttc tgacttcaga aaggacttcc aattttacaa    5820
ggtcagagaa atcaacaact accatcacgc tcacgatgcc tacttgaacg ctgttgtcgg    5880
tactgcctta atcaaaaagt acccaaagtt ggaatctgaa ttcgtttacg gtgactacaa    5940
ggtttacgat gttagaaaga tgatcgccaa gtctgaacaa gaaattggta aggccactgc    6000
taagtacttc ttctactcta acatcatgaa cttttttcaag actgaaatca ctttagctaa    6060
cggtgaaatt agaagcgtc cattgattga accaatggt gaaactggtg aaattgtctg    6120
ggacaagggt agagatttcg ctaccgtcag aaaggttttg tctatgccac aagttaacat    6180
```

```
cgtcaagaag actgaagttc aaactggtgg tttctctaag gaatccattt tgccaaagag    6240
aaactctgac aagttgattg ctagaaagaa ggactgggat cctaagaagt acggtggttt    6300
cgactctcca actgttgctt actccgtttt ggtcgttgct aaggttgaaa agggtaagtc    6360
taagaagttg aagtctgtta aggaattgtt gggtatcacc atcatggaaa gatcctcctt    6420
cgaaaagaac ccaatcgact ttttggaagc taagggttac aaggaagtca agaaggattt    6480
gatcattaag ttaccaaaat actccttgtt cgaattggaa aacggtagaa agagaatgtt    6540
ggcctccgct ggtgaactac aaaaaggtaa cgaattggct ttaccatcta agtacgttaa    6600
cttcttgtac ttggcttccc actacgaaaa gttgaaaggt tccccagaag acaacgaaca    6660
aaagcaattg tttgttgaac aacacaagca ctacttggat gaaattattg aacaaatctc    6720
cgaattctcc aagagagtca ttttggctga tgctaactta gataaggttt tatccgctta    6780
caacaagcac agagacaaac caatcagaga acaagctgaa acatcattc atttgttcac    6840 tttaaccaac ttgggtgctc cagctgcttt caaatacttc gacactacca ttgacagaaa    6900
gagatacact tccaccaaag aagttttaga tgctactttg attcaccaat ctattaccgg    6960
tttgtacgaa accagaattg acttgtctca attgggtggt gattccagag ctgatccaaa    7020
gaagaagaga aaggtgtaaa ggagttaaag gcaaagtttt cttttctaga gccgttccca    7080
caaataatta tacgtatatg cttcttttcg tttactatat atctatattt acaagccttt    7140
attcactgat gcaatttgtt tccaaatact ttttggaga tctcataact agatatcatg    7200
atggcgcaac ttggcgctat cttaattact ctggctgcca ggcccgtgta gagggccgca    7260
agaccttctg tacgccatat agtctctaag aacttgaaca agtttctaga cctattgccg    7320
cctttcggat cgctattgtt gcggccgcca gctgaagctt cgtacgctgc aggtcgacga    7380
attctaccgt tcgtataatg tatgctatac gaagttatag atctgtttag cttgcctcgt    7440
ccccgccggg tcacccggcc agcgacatgg aggcccagaa taccctcctt gacagtcttg    7500
acgtgcgcag ctcaggggca tgatgtgact gtcgcccgta catttagccc atacatcccc    7560
atgtataatc atttgcatcc atacattttg atggccgcac ggcgcgaagc aaaaattacg    7620
gctcctcgct gcagacctgc gagcagggaa acgctcccct cacagacgcg ttgaattgtc    7680
cccacgccgc gccctgtag agaaatataa aaggttagga tttgccactg aggttcttct    7740
ttcatatact ccttttaaa atcttgctag gatacagttc tcacatcaca tccgaacata    7800
aacaaccatg ggtaaggaaa agactcacgt ttcgaggccg cgattaaatt ccaacatgga    7860
tgctgattta tatgggtata atgggctccg cgataatgtc gggcaatcag gtgcgacaat    7920
ctatcgattg tatgggaagc ccgatgcgcc agagttgttt ctgaaacatg gcaaaggtag    7980
cgttgccaat gatgttacag atgagatggt cagactaaac tggctgacgg aatttatgcc    8040
tcttccgacc atcaagcatt ttatccgtac tcctgatgat gcatggttac tcaccactgc    8100
gatccccggc aaaacagcat tccaggtatt agaagaatat cctgattcag gtgaaaatat    8160
tgttgatgcg ctggcagtgt tcctgcgccg gttgcattcg attcctgttt gtaattgtcc    8220
ttttaacagc gatcgcgtat ttcgtctcgc tcaggcgcaa tcacgaatga ataacggttt    8280
ggttgatgcg agtgattttg atgacgagcg taatggctgg cctgttgaac aagtctggaa    8340
agaaatgcat aagcttttgc cattctcacc ggattcagtc gtcactcatg gtgatttctc    8400
acttgataac cttattttg acgaggggaa attaataggt tgtattgatg ttggacgagt    8460
cggaatcgca gaccgatacc aggatcttgc catcctatgg aactgcctcg gtgagttttc    8520
```

```
tccttcatta cagaaacggc ttttcaaaa atatggtatt gataatcctg atatgaataa   8580
attgcagttt catttgatgc tcgatgagtt tttctaatca gtactgacaa taaaaagatt   8640
cttgttttca agaacttgtc atttgtatag ttttttttata ttgtagttgt tctatttaa    8700
tcaaatgtta gcgtgattta tattttttt cgcctcgaca tcatctgccc agatgcgaag    8760
ttaagtgcgc agaaagtaat atcatgcgtc aatcgtatgt gaatgctggt cgctatactg   8820
ctgtcgattc gatactaacg ccgccatcca gtgtcgaaaa cgagctcata acttcgtata   8880
atgtatgcta tacgaacggt agaattcgaa tcagatccac tagtggccta tgcggccgcc   8940
accgcggtgg agctccagct tttgttccct ttagtgaggg ttaattgcgc gcttggcgta   9000
atcatggtca tagctgtttc ctgtgtgaaa ttgttatccg ctcacaattc cacacaacat   9060
aggagccgga agcataaagt gtaaagcctg gggtgcctaa tgagtgaggt aactcacatt   9120
aattgcgttg cgctcactgc ccgctttcca gtcgggaaac ctgtcgtgcc agctgcatta   9180
atgaatcggc caacgcgcgg ggagaggcgg tttgcgtatt gggcgctctt ccgcttcctc   9240
gctcactgac tcgctgcgct cggtcgttcg gctgcggcga gcggtatcag ctcactcaaa   9300
ggcggtaata cggttatcca cagaatcagg ggataacgca ggaaagaaca tgtgagcaaa   9360
aggccagcaa aaggccagga accgtaaaaa ggccgcgttg ctggcgtttt tccataggct   9420
ccgcccccct gacgagcatc acaaaaatcg acgctcaagt cagaggtggc gaaacccgac   9480
aggactataa agataccagg cgtttccccc tggaagctcc ctcgtgcgct ctcctgttcc   9540
gaccctgccg cttaccggat acctgtccgc cttctccct tcgggaagcg tggcgctttc   9600
tcatagctca cgctgtaggt atctcagttc ggtgtaggtc gttcgctcca agctgggctg   9660
tgtgcacgaa ccccccgttc agcccgaccg ctgcgcctta tccggtaact atcgtcttga   9720
gtccaacccg gtaagacacg acttatcgcc actggcagca gccactggta acaggattag   9780
cagagcgagg tatgtaggcg gtgctacaga gttcttgaag tggtggccta actacggcta   9840
cactagaagg acagtatttg gtatctgcgc tctgctgaag ccagttacct tcggaaaaag   9900
agttggtagc tcttgatccg gcaaacaaac caccgctggt agcggtggtt tttttgtttg   9960
caagcagcag attacgcgca gaaaaaaagg atctcaagaa gatcctttga tcttttctac  10020
ggggtctgac gctcagtgga acgaaaactc acgttaaggg attttggtca tgagattatc  10080
aaaaaggatc ttcacctaga tccttttaaa ttaaaaatga agttttaaat caatctaaag  10140
tatatatgag taaacttggt ctgacagtta ccaatgctta atcagtgagg cacctatctc  10200
agcgatctgt ctatttcgtt catccatagt tgcctgactc cccgtcgtgt agataactac  10260
gatacgggag ggcttaccat ctggccccag tgctgcaatg ataccgcgag acccacgctc  10320
accggctcca gatttatcag caataaacca gccagccgga agggccgagc gcagaagtgg  10380
tcctgcaact ttatccgcct ccatccagtc tattaattgt tgccgggaag ctagagtaag  10440
tagttcgcca gttaatagtt tgcgcaacgt tgttgccatt gctacaggca tcgtggtgtc  10500
acgctcgtcg tttggtatgg cttcattcag ctccggttcc caacgatcaa ggcgagttac  10560
atgatccccc atgttgtgca aaaaagcggt tagctccttc ggtcctccga tcgttgtcag  10620
aagtaagttg gccgcagtgt tatcactcat ggttatggca gcactgcata attctcttac  10680
tgtcatgcca tccgtaagat gcttttctgt gactggtgag tactcaacca agtcattctg  10740
agaatagtgt atgcggcgac cgagttgctc ttgcccggcg tcaatacggg ataataccgc  10800
gccacatagc agaactttaa aagtgctcat cattggaaaa cgttcttcgg ggcgaaaact  10860
ctcaaggatc ttaccgctgt tgagatccag ttcgatgtaa cccactcgtg cacccaactg  10920
```

```
atcttcagca tcttttactt tcaccagcgt ttctgggtga gcaaaaacag gaaggcaaaa   10980
tgccgcaaaa aagggaataa gggcgacacg gaaatgttga atactcatac tcttcctttt   11040
tcaatattat tgaagcattt atcagggtta ttgtctcatg agcggataca tatttgaatg   11100
tatttagaaa ataaacaaa taggggttcc gcgcacattt ccccgaaaag tgccacctgg   11160
gtccttttca tcacgtgcta taaaaataat tataatttaa atttttaat ataaatatat   11220 aaattaaaaa tagaaagtaa aaaagaaat taaagaaaaa atagttttg ttttccgaag   11280 atgtaaaaga ctctagggg atcgccaaca aatactacct tttatcttgc tcttcctgct   11340
ctcaggtatt aatgccgaat tgtttcatct tgtctgtgta gaagaccaca cacgaaaatc   11400
ctgtgatttt acattttact tatcgttaat cgaatgtata tctatttaat ctgcttttct   11460
tgtctaataa atatatatgt aaagtacgct ttttgttgaa atttttaaa cctttgttta   11520 ttttttttc ttcattccgt aactcttcta ccttctttat ttactttcta aaatccaaat   11580
acaaaacata aaaataaata aacacagagt aaattcccaa attattccat cattaaaaga   11640
tacgaggcgc gtgtaagtta caggcaagcg atccgtccta agaaaccatt attatcatga   11700
cattaaccta taaaaatagg cgtatcacga ggccctttcg tc                      11742
```

<210> SEQ ID NO 10
<211> LENGTH: 1726
<212> TYPE: DNA
<213> ORGANISM: Artificial Sequence
<220> FEATURE:
<223> OTHER INFORMATION: Connector 5 - THD3p - YFP (Venus) - ENO1t - connector 3

<400> SEQUENCE: 10

```
aagcgacttc caatcgcttt gcatatccag taccacaccc acaggcgttt gtgcttagtc     60
aaaaaattag ccttttaatt ctgctgtaac ccgtacatgc ccaaaatagg gggcgggtta    120
cacagaatat ataacatcgt aggtgtctgg gtgaacagtt tattcctggc atccactaaa    180
tataatggag cccgcttttt aagctggcat ccagaaaaaa aaagaatccc agcaccaaaa    240
tattgttttc ttcaccaacc atcagttcat aggtccattc tcttagcgca actacagaga    300 acagggcac aaacaggcaa aaacgggca caacctcaat ggagtgatgc aacctgcctg    360
gagtaaatga tgcacaagg caattgaccc acgcatgtat ctatctcatt ttcttacacc    420
ttctattacc ttctgctctc tctgatttgg aaaaagctga aaaaaaaggt tgaaaccagt    480
tccctgaaat tattccccta cttgactaat aagtatataa agacggtagg tattgattgt    540
aattctgtaa atctatttct taaacttctt aaattctact tttatagtta gtcttttttt    600
tagttttaaa acaccaagaa cttagttccg aataaacaca cataaacaaa caaaatgtct    660
aaaggtgaag aattattcac tggtgttgtc ccaattttgg ttgaattaga tggtgatgtt    720
aatggtcaca aattttctgt ctccggtgaa ggtgaaggtg atgctactta cggtaaattg    780
accttaaaat tgatttgtac tactggtaaa ttgccagttc catggccaac cttagtcact    840
actttaggtt atggtttgca atgttttgct agatacccag atcatatgaa acaacatgac    900 ttttcaagt ctgccatgcc agaaggttat gttcaagaaa gaactatttt tttcaaagat    960
gacggtaact acaagaccag agctgaagtc aagtttgaag gtgataccct agttaataga   1020
atcgaattaa aaggtattga ttttaagaa gatggtaaca ttttaggtca caattggaa    1080 tacaactata actctcacaa tgtttacatc actgctgaca acaaaagaa tggtatcaaa   1140 gctaacttca aaattagaca caacattgaa gatggtggtg ttcaattagc tgaccattat   1200
```

-continued

```
caacaaaata ctccaattgg tgatggtcca gtcttgttac cagacaacca ttacttatcc    1260
tatcaatctg ccttatccaa agatccaaac gaaaagagag atcacatggt cttgttagaa    1320
tttgttactg ctgctggtat tacccatggt atggatgaat tgtacaaata aaagcttttg    1380
attaagcctt ctagtccaaa aaacacgttt ttttgtcatt tatttcattt tcttagaata    1440
gtttagttta ttcattttat agtcacgaat gttttatgat tctatatagg gttgcaaaca    1500 agcattttc attttatgtt aaaacaattt caggtttacc ttttattctg cttgtggtga     1560
cgcgtgtatc cgcccgctct tttggtcacc catgtattta attgcataaa taattcttaa    1620
aagtggagct agtctatttc tatttacata cctctcattt ctcatttcct ccctcagaa     1680 agcctgtatg cgaagccaca atcctttcca acagaccata ctaagt                   1726
```

<210> SEQ ID NO 11
<211> LENGTH: 31
<212> TYPE: DNA
<213> ORGANISM: Artificial Sequence
<220> FEATURE:
<223> OTHER INFORMATION: FW primer to obtain YFP (Venus) promoter-ORF-
      terminator

<400> SEQUENCE: 11
gtgcttagtc aaaaaattag cctttaatt c                                     31

<210> SEQ ID NO 12
<211> LENGTH: 23
<212> TYPE: DNA
<213> ORGANISM: Artificial Sequence
<220> FEATURE:
<223> OTHER INFORMATION: REV primer to obtain YFP (Venus) promoter-ORF-
      terminator

<400> SEQUENCE: 12
gaggggagga aatgagaaat gag                                             23

<210> SEQ ID NO 13
<211> LENGTH: 72
<212> TYPE: DNA
<213> ORGANISM: Artificial Sequence
<220> FEATURE:
<223> OTHER INFORMATION: FW primer to obtain connector 5 - THD3p - YFP
      (Venus) - ENO1t - connector 3 PCR fragment

<400> SEQUENCE: 13
aagcgacttc caatcgcttt gcatatccag taccacaccc acaggcgttt gtgcttagtc    60
aaaaaattag cc                                                         72

<210> SEQ ID NO 14
<211> LENGTH: 73
<212> TYPE: DNA
<213> ORGANISM: Artificial Sequence
<220> FEATURE:
<223> OTHER INFORMATION: REV primer to obtain connector 5 - THD3p - YFP
      (Venus) - ENO1t - connector 3 PCR fragment

<400> SEQUENCE: 14
acttagtatg gtctgttgga aaggattgtg gcttcgcata caggctttct gaggggagga    60
aatgagaaat gag                                                        73

<210> SEQ ID NO 15
<211> LENGTH: 120
<212> TYPE: DNA

```
<213> ORGANISM: Artificial Sequence
<220> FEATURE:
<223> OTHER INFORMATION: ssODN 50 bp homology pGRN002 - guide sequence -
      50 bp homology pGRN002 upper strand of vector pGRN002

<400> SEQUENCE: 15
tgcgcatgtt tcggcgttcg aaacttctcc gcagtgaaag ataaatgatc tattagaacc    60
agggaggtcc gttttagagc tagaaatagc aagttaaaat aaggctagtc cgttatcaac   120

<210> SEQ ID NO 16
<211> LENGTH: 120
<212> TYPE: DNA
<213> ORGANISM: Artificial Sequence
<220> FEATURE:
<223> OTHER INFORMATION: ssODN 50 bp homology pGRN002 - guide sequence -
      50 bp homology pGRN002 lower strand of vector pGRN002

<400> SEQUENCE: 16
gttgataacg gactagcctt attttaactt gctatttcta gctctaaaac ggacctccct    60
ggttctaata gatcatttat ctttcactgc ggagaagttt cgaacgccga acatgcgca    120

<210> SEQ ID NO 17
<211> LENGTH: 100
<212> TYPE: DNA
<213> ORGANISM: Artificial Sequence
<220> FEATURE:
<223> OTHER INFORMATION: ssODN 5' flank 10 kb upper strand sequence

<400> SEQUENCE: 17
acgtagtgaa cgaaaccata tatctcttaa tttgcagcag ggatttata aagcgacttc     60 caatcgcttt gcatatccag taccacaccc acaggcgttt                         100

<210> SEQ ID NO 18
<211> LENGTH: 100
<212> TYPE: DNA
<213> ORGANISM: Artificial Sequence
<220> FEATURE:
<223> OTHER INFORMATION: ssODN 5' flank 10 kb lower strand sequence

<400> SEQUENCE: 18
aaacgcctgt gggtgtggta ctggatatgc aaagcgattg gaagtcgctt tataaatcc     60 ctgctgcaaa ttaagagata tatggtttcg ttcactacgt                         100

<210> SEQ ID NO 19
<211> LENGTH: 100
<212> TYPE: DNA
<213> ORGANISM: Artificial Sequence
<220> FEATURE:
<223> OTHER INFORMATION: ssODN 5' flank 3 kb upper strand sequence

<400> SEQUENCE: 19
ctcatctaag tctttgaaat atcgatcacc cttttgtta ggctctgtac aagcgacttc     60
caatcgcttt gcatatccag taccacaccc acaggcgttt                         100

<210> SEQ ID NO 20
<211> LENGTH: 100
<212> TYPE: DNA
<213> ORGANISM: Artificial Sequence
<220> FEATURE:
<223> OTHER INFORMATION: ssODN 5' flank 3 kb lower strand sequence

<400> SEQUENCE: 20
aaacgcctgt gggtgtggta ctggatatgc aaagcgattg gaagtcgctt gtacagagcc    60
```
taacaaaaag ggtgatcgat atttcaaaga cttagatgag         100

<210> SEQ ID NO 21
<211> LENGTH: 100
<212> TYPE: DNA
<213> ORGANISM: Artificial Sequence
<220> FEATURE:
<223> OTHER INFORMATION: ssODN 5' flank 1 kb upper strand sequence.

<400> SEQUENCE: 21
cttcatgcca gcaatagttg cgtgctgagc tcaacagtgc ccaacccttg aagcgacttc    60
caatcgcttt gcatatccag taccacaccc acaggcgttt                         100

<210> SEQ ID NO 22
<211> LENGTH: 100
<212> TYPE: DNA
<213> ORGANISM: Artificial Sequence
<220> FEATURE:
<223> OTHER INFORMATION: ssODN 5' flank 1kb lower strand sequence

<400> SEQUENCE: 22
aaacgcctgt gggtgtggta ctggatatgc aaagcgattg gaagtcgctt caagggttgg    60
gcactgttga gctcagcacg caactattgc tggcatgaag                         100

<210> SEQ ID NO 23
<211> LENGTH: 100
<212> TYPE: DNA
<213> ORGANISM: Artificial Sequence
<220> FEATURE:
<223> OTHER INFORMATION: ssODN 5' INT flank upper strand sequence

<400> SEQUENCE: 23
acttctctac attctctgac tttttaaaac tgtgtactgg cgaccaatcg aagcgacttc    60
caatcgcttt gcatatccag taccacaccc acaggcgttt                         100

<210> SEQ ID NO 24
<211> LENGTH: 100
<212> TYPE: DNA
<213> ORGANISM: Artificial Sequence
<220> FEATURE:
<223> OTHER INFORMATION: ssODN 5' INT flank lower strand sequence

<400> SEQUENCE: 24
aaacgcctgt gggtgtggta ctggatatgc aaagcgattg gaagtcgctt cgattggtcg    60
ccagtacaca gttttaaaaa gtcagagaat gtagagaagt                         100

<210> SEQ ID NO 25
<211> LENGTH: 100
<212> TYPE: DNA
<213> ORGANISM: Artificial Sequence
<220> FEATURE:
<223> OTHER INFORMATION: ssODN 3' flank INT upper strand sequence

<400> SEQUENCE: 25
agaaagcctg tatgcgaagc cacaatcctt ccaacagac catactaagt cgcgatgaaa    60
taaaggccta ttttttgatc caacgccttt gaaaatttcc                         100

<210> SEQ ID NO 26
<211> LENGTH: 100
<212> TYPE: DNA
<213> ORGANISM: Artificial Sequence
<220> FEATURE:

```
<223> OTHER INFORMATION: ssODN 3' flank INT lower strand sequence

<400> SEQUENCE: 26
ggaaattttc aaaggcgttg gatcaaaaaa taggccttta tttcatcgcg acttagtatg    60
gtctgttgga aaggattgtg gcttcgcata caggctttct                         100

<210> SEQ ID NO 27
<211> LENGTH: 100
<212> TYPE: DNA
<213> ORGANISM: Artificial Sequence
<220> FEATURE:
<223> OTHER INFORMATION: ssODN 3' flank 1kb upper strand sequencessODN
      3' flank 1kb upper strand sequence

<400> SEQUENCE: 27
agaaagcctg tatgcgaagc cacaatcctt tccaacagac catactaagt attctttgtc    60
atcagacaac ttgttgagtg gtactaaagg agtgcttttc                         100

<210> SEQ ID NO 28
<211> LENGTH: 100
<212> TYPE: DNA
<213> ORGANISM: Artificial Sequence
<220> FEATURE:
<223> OTHER INFORMATION: ssODN 3' flank 1kb lower strand sequence

<400> SEQUENCE: 28
gaaaagcact cctttagtac cactcaacaa gttgtctgat gacaaagaat acttagtatg    60
gtctgttgga aaggattgtg gcttcgcata caggctttct                         100

<210> SEQ ID NO 29
<211> LENGTH: 100
<212> TYPE: DNA
<213> ORGANISM: Artificial Sequence
<220> FEATURE:
<223> OTHER INFORMATION: ssODN 3' flank 3 kb upper strand sequence

<400> SEQUENCE: 29
agaaagcctg tatgcgaagc cacaatcctt tccaacagac catactaagt aaccgaatct    60
tgaatagtca ctttggttgg tggaacctgg agaaatggaa                         100

<210> SEQ ID NO 30
<211> LENGTH: 100
<212> TYPE: DNA
<213> ORGANISM: Artificial Sequence
<220> FEATURE:
<223> OTHER INFORMATION: ssODN 3' flank 3 kb lower strand sequence

<400> SEQUENCE: 30
ttccatttct ccaggttcca ccaaccaaag tgactattca agattcggtt acttagtatg    60
gtctgttgga aaggattgtg gcttcgcata caggctttct                         100

<210> SEQ ID NO 31
<211> LENGTH: 100
<212> TYPE: DNA
<213> ORGANISM: Artificial Sequence
<220> FEATURE:
<223> OTHER INFORMATION: ssODN 3' flank 10kb upper strand sequence

<400> SEQUENCE: 31
agaaagcctg tatgcgaagc cacaatcctt tccaacagac catactaagt ctgttgtgac    60
agcatcttgt ctattattta ttggatacgc aaaactcatt                         100
```

<210> SEQ ID NO 32
<211> LENGTH: 100
<212> TYPE: DNA
<213> ORGANISM: Artificial Sequence
<220> FEATURE:
<223> OTHER INFORMATION: ssODN 3' flank 10kb lower strand sequence

<400> SEQUENCE: 32
aatgagtttt gcgtatccaa taaataatag acaagatgct gtcacaacag acttagtatg    60
gtctgttgga aaggattgtg gcttcgcata caggctttct                         100

<210> SEQ ID NO 33
<211> LENGTH: 22
<212> TYPE: DNA
<213> ORGANISM: Artificial Sequence
<220> FEATURE:
<223> OTHER INFORMATION: FW primer to confirm correct deletion of 1 kB
      genomic DNA at 5' end

<400> SEQUENCE: 33
agagacaggt aacttccaca ag                                             22

<210> SEQ ID NO 34
<211> LENGTH: 26
<212> TYPE: DNA
<213> ORGANISM: Artificial Sequence
<220> FEATURE:
<223> OTHER INFORMATION: REV primer to confirm correct deletion of 1 kB
      genomic DNA at 5' end

<400> SEQUENCE: 34
tttgtttgtt tatgtgtgtt tattcg                                         26

<210> SEQ ID NO 35
<211> LENGTH: 26
<212> TYPE: DNA
<213> ORGANISM: Artificial Sequence
<220> FEATURE:
<223> OTHER INFORMATION: FW primer to confirm integration of YFP
      expression cassette

<400> SEQUENCE: 35
atgtctaaag gtgaagaatt attcac                                         26

<210> SEQ ID NO 36
<211> LENGTH: 26
<212> TYPE: DNA
<213> ORGANISM: Artificial Sequence
<220> FEATURE:
<223> OTHER INFORMATION: REV primer to confirm integration of YFP
      expression cassette

<400> SEQUENCE: 36
ttttatttgt acaattcatc catacc                                         26

<210> SEQ ID NO 37
<211> LENGTH: 24
<212> TYPE: DNA
<213> ORGANISM: Artificial Sequence
<220> FEATURE:
<223> OTHER INFORMATION: FW primer to confirm correct deletion of 1 kB
      genomic DNA at 3'
      end

<400> SEQUENCE: 37
agcttttgat taagccttct agtc                                           24

<210> SEQ ID NO 38
<211> LENGTH: 23
<212> TYPE: DNA
<213> ORGANISM: Artificial Sequence
<220> FEATURE:
<223> OTHER INFORMATION: REV primer to confirm correct deletion of 1 kB
      genomic DNA at 3'
      end

<400> SEQUENCE: 38
aactagctca gaaaacacta acg                                              23

<210> SEQ ID NO 39
<211> LENGTH: 1287
<212> TYPE: DNA
<213> ORGANISM: Artificial Sequence
<220> FEATURE:
<223> OTHER INFORMATION: NatMX donor DNA expression cassette: connector
      5 - NatMX expression cassette - connector 3 sequence

<400> SEQUENCE: 39
aagcgacttc caatcgcttt gcatatccag taccacaccc acaggcgttt gcctcgtccc       60
cgccgggtca cccggccagc gacatggagg cccagaatac cctccttgac agtcttgacg      120
tgcgcagctc aggggcatga tgtgactgtc gcccgtacat ttagcccata catccccatg      180
tataatcatt tgcatccata cattttgatg gccgcacggc gcgaagcaaa aattacggct      240
cctcgctgca gacctgcgag cagggaaacg ctcccctcac agacgcgttg aattgtcccc      300
acgccgcgcc cctgtagaga aatataaaag gttaggattt gccactgagg ttcttctttc      360
atatacttcc ttttaaaatc ttgctaggat acagttctca catcacatcc gaacataaac      420
aaccatgtaa aatgaccact cttgacgaca cggcttaccg gtaccgcacc agtgtcccgg      480
gggacgccga ggccatcgag gcactggatg gtccttcac caccgacacc gtcttccgcg      540
tcaccgccac cggggacggc ttcaccctgc ggaggtgcc ggtggacccg ccctgacca        600 aggtgttccc cgacgacgaa tcggacgacg aatcggacgc cggggaggac ggcgacccgg      660
actcccggac gttcgtcgcg tacggggacg acggcgacct ggcgggcttc gtggtcgtct      720
cgtactccgg ctggaaccgc cggctgaccg tcgaggacat cgaggtcgcc ccggagcacc      780
gggggcacgg ggtcgggcgc gcgttgatgg ggctcgcgac ggagttcgcc cgcgagcggg      840
gcgccgggca cctctggctg gaggtcacca acgtcaacgc accggcgatc cacgcgtacc      900
ggcggatggg gttcacccctc tgcggcctgg acaccgccct gtacgacggc accgcctcgg      960
acggcgagca ggcgctctac atgagcatgc cctgccccta gtactgacaa taaaaagatt     1020
cttgttttca agaacttgtc atttgtatag ttttttttata ttgtagttgt tctattttaa     1080
tcaaatgtta gcgtgattta tattttttttt cgcctcgaca tcatctgccc agatgcgaag    1140
ttaagtgcgc agaaagtaat atcatgcgtc aatcgtatgt gaatgctggt cgctatactg     1200
ctgtcgattc gatactaacg ccgccatcca gtgtcgaaga aagcctgtat gcgaagccac     1260
aatcctttcc aacagaccat actaagt                                        1287

<210> SEQ ID NO 40
<211> LENGTH: 69
<212> TYPE: DNA
<213> ORGANISM: Artificial Sequence
<220> FEATURE:
<223> OTHER INFORMATION: FW primer to obtain the connector 5 - NatMX
      expression cassette - connector 3 sequence

```
<400> SEQUENCE: 40
aagcgacttc caatcgcttt gcatatccag taccacaccc acaggcgttt gcctcgtccc    60
cgccgggtc                                                            69

<210> SEQ ID NO 41
<211> LENGTH: 69
<212> TYPE: DNA
<213> ORGANISM: Artificial Sequence
<220> FEATURE:
<223> OTHER INFORMATION: REV primer to obtain the connector 5 - NatMX
      expression cassette - connector 3 sequence

<400> SEQUENCE: 41
acttagtatg gtctgttgga aaggattgtg gcttcgcata caggctttct tcgacactgg    60
atggcggcg                                                            69

<210> SEQ ID NO 42
<211> LENGTH: 72
<212> TYPE: DNA
<213> ORGANISM: Artificial Sequence
<220> FEATURE:
<223> OTHER INFORMATION: FW primer to obtain left flank - connector 5 -
      NatMX expression cassette - connector 3 - right flank PCR
      fragment, 0 bp deletion

<400> SEQUENCE: 42
acttctctac attctctgac tttttaaaac tgtgtactgg cgaccaatcg aagcgacttc    60
caatcgcttt gc                                                        72

<210> SEQ ID NO 43
<211> LENGTH: 74
<212> TYPE: DNA
<213> ORGANISM: Artificial Sequence
<220> FEATURE:
<223> OTHER INFORMATION: REV primer to obtain left flank - connector 5 -
      NatMX expression cassette - connector 3 - right flank PCR
      fragment, 0 bp deletion

<400> SEQUENCE: 43
ggaaattttc aaaggcgttg gatcaaaaaa taggccttta tttcatcgcg acttagtatg    60
gtctgttgga aagg                                                      74

<210> SEQ ID NO 44
<211> LENGTH: 72
<212> TYPE: DNA
<213> ORGANISM: Artificial Sequence
<220> FEATURE:
<223> OTHER INFORMATION: FW primer to obtain left flank - connector 5 -
      NatMX expression cassette - connector 3 - right flank PCR
      fragment, 1 kbp deletion

<400> SEQUENCE: 44
cttcatgcca gcaatagttg cgtgctgagc tcaacagtgc ccaacccttg aagcgacttc    60
caatcgcttt gc                                                        72

<210> SEQ ID NO 45
<211> LENGTH: 74
<212> TYPE: DNA
<213> ORGANISM: Artificial Sequence
<220> FEATURE:
<223> OTHER INFORMATION: REV primer to obtain left flank - connector 5 -
      NatMX expression cassette - connector 3 - right flank PCR
      fragment, 1 kbp deletion
```

```
<400> SEQUENCE: 45
gaaaagcact cctttagtac cactcaacaa gttgtctgat gacaaagaat acttagtatg    60
gtctgttgga aagg                                                     74

<210> SEQ ID NO 46
<211> LENGTH: 72
<212> TYPE: DNA
<213> ORGANISM: Artificial Sequence
<220> FEATURE:
<223> OTHER INFORMATION: FW primer to obtain left flank - connector 5 -
      NatMX expression cassette - connector 3 - right flank PCR
      fragment, 3 kbp deletion

<400> SEQUENCE: 46
ctcatctaag tctttgaaat atcgatcacc cttttttgtta ggctctgtac aagcgacttc    60
caatcgcttt gc                                                       72

<210> SEQ ID NO 47
<211> LENGTH: 74
<212> TYPE: DNA
<213> ORGANISM: Artificial Sequence
<220> FEATURE:
<223> OTHER INFORMATION: REV primer to obtain left flank - connector 5 -
      NatMX expression cassette - connector 3 - right flank PCR
      fragment, 3 kbp deletion

<400> SEQUENCE: 47
ttccatttct ccaggttcca ccaaccaaag tgactattca agattcggtt acttagtatg    60
gtctgttgga aagg                                                     74

<210> SEQ ID NO 48
<211> LENGTH: 72
<212> TYPE: DNA
<213> ORGANISM: Artificial Sequence
<220> FEATURE:
<223> OTHER INFORMATION: FW primer to obtain left flank - connector 5 -
      NatMX expression cassette - connector 3 - right flank PCR
      fragment, 10 kbp deletion

<400> SEQUENCE: 48
acgtagtgaa cgaaaccata tatctcttaa tttgcagcag ggattttata aagcgacttc    60
caatcgcttt gc                                                       72

<210> SEQ ID NO 49
<211> LENGTH: 74
<212> TYPE: DNA
<213> ORGANISM: Artificial Sequence
<220> FEATURE:
<223> OTHER INFORMATION: REV primer to obtain left flank - connector 5 -
      NatMX expression cassette - connector 3 - right flank PCR
      fragment, 10 kbp deletion

<400> SEQUENCE: 49
aatgagtttt gcgtatccaa taaataatag acaagatgct gtcacaacag acttagtatg    60
gtctgttgga aagg                                                     74

<210> SEQ ID NO 50
<211> LENGTH: 499
<212> TYPE: DNA
<213> ORGANISM: Artificial Sequence
<220> FEATURE:
<223> OTHER INFORMATION: gBlock of the guide RNA expression cassette to
      target CAS9 to the INT1 locus
```

```
<400> SEQUENCE: 50
ggagctagca tgcggccgct ctagaactag tggatccccc gggctgcagg aattctcttt        60
gaaaagataa tgtatgatta tgctttcact catatttata cagaaacttg atgttttctt       120
tcgagtatat acaaggtgat tacatgtacg tttgaagtac aactctagat tttgtagtgc       180
cctcttgggc tagcggtaaa ggtgcgcatt ttttcacacc ctacaatgtt ctgttcaaaa       240
gattttggtc aaacgctgta gaagtgaaag ttggtgcgca tgtttcggcg ttcgaaactt       300
ctccgcagtg aaagataaat gatctattag aaccagggag gtccgtttta gagctagaaa       360
tagcaagtta aaataaggct agtccgttat caacttgaaa aagtggcacc gagtcggtgg       420
tgcttttttt gttttttatg tctctcgagg gggggcccgg tacccagctt tgttcccttt      480
tagtgagggt taattccga                                                    499

<210> SEQ ID NO 51
<211> LENGTH: 20
<212> TYPE: DNA
<213> ORGANISM: Artificial Sequence
<220> FEATURE:
<223> OTHER INFORMATION: FW primer to obtain the guide RNA cassette with
      homology to the linear recipient gRNA-vector PCR fragment

<400> SEQUENCE: 51
ctagaactag tggatccccc                                                    20

<210> SEQ ID NO 52
<211> LENGTH: 21
<212> TYPE: DNA
<213> ORGANISM: Artificial Sequence
<220> FEATURE:
<223> OTHER INFORMATION: REV primer to obtain the guide RNA cassette
      with homology to the linear recipient gRNA-vector PCR fragment

<400> SEQUENCE: 52
agggaacaaa agctgggtac c                                                  21

<210> SEQ ID NO 53
<211> LENGTH: 459
<212> TYPE: DNA
<213> ORGANISM: Artificial Sequence
<220> FEATURE:
<223> OTHER INFORMATION: guide RNA expression cassette to target CAS9 to
      the INT1 locus

<400> SEQUENCE: 53
ctagaactag tggatccccc gggctgcagg aattctcttt gaaaagataa tgtatgatta        60
tgctttcact catatttata cagaaacttg atgttttctt tcgagtatat acaaggtgat       120
tacatgtacg tttgaagtac aactctagat tttgtagtgc cctcttgggc tagcggtaaa       180
ggtgcgcatt ttttcacacc ctacaatgtt ctgttcaaaa gattttggtc aaacgctgta       240
gaagtgaaag ttggtgcgca tgtttcggcg ttcgaaactt ctccgcagtg aaagataaat       300
gatctattag aaccagggag gtccgtttta gagctagaaa tagcaagtta aaataaggct       360
agtccgttat caacttgaaa aagtggcacc gagtcggtgg tgcttttttt gttttttatg       420
tctctcgagg gggggcccgg tacccagctt tgttccct                                459

<210> SEQ ID NO 54
<211> LENGTH: 1726
<212> TYPE: DNA
<213> ORGANISM: Artificial Sequence
<220> FEATURE:
```

<223> OTHER INFORMATION: con5 - YFP - conA sequence

<400> SEQUENCE: 54

| | | | | | |
|---|---|---|---|---|---|
| aagcgacttc | caatcgcttt | gcatatccag | taccacaccc | acaggcgttt | gtgcttagtc | 60 |
| aaaaaattag | ccttttaatt | ctgctgtaac | ccgtacatgc | ccaaaatagg | gggcgggtta | 120 |
| cacagaatat | ataacatcgt | aggtgtctgg | gtgaacagtt | tattcctggc | atccactaaa | 180 |
| tataatggag | cccgcttttt | aagctggcat | ccagaaaaaa | aaagaatccc | agcaccaaaa | 240 |
| tattgttttc | ttcaccaacc | atcagttcat | aggtccattc | tcttagcgca | actacagaga | 300 |
| acagggcac | aaacaggcaa | aaacgggca | caacctcaat | ggagtgatgc | aacctgcctg | 360 |
| gagtaaatga | tgacacaagg | caattgaccc | acgcatgtat | ctatctcatt | ttcttacacc | 420 |
| ttctattacc | ttctgctctc | tctgatttgg | aaaaagctga | aaaaaaggt | tgaaaccagt | 480 |
| tccctgaaat | tattccccta | cttgactaat | aagtatataa | agacggtagg | tattgattgt | 540 |
| aattctgtaa | atctatttct | taaacttctt | aaattctact | tttatagtta | gtcttttttt | 600 |
| tagttttaaa | acaccaagaa | cttagtttcg | aataaacaca | cataaacaaa | caaaatgtct | 660 |
| aaaggtgaag | aattattcac | tggtgttgtc | ccaattttgg | ttgaattaga | tggtgatgtt | 720 |
| aatggtcaca | aattttctgt | ctccggtgaa | ggtgaaggtg | atgctactta | cggtaaattg | 780 |
| accttaaaat | tgatttgtac | tactggtaaa | ttgccagttc | catggccaac | cttagtcact | 840 |
| actttaggtt | atggtttgca | atgttttgct | agatacccag | atcatatgaa | acaacatgac | 900 |
| tttttcaagt | ctgccatgcc | agaaggttat | gttcaagaaa | gaactatttt | tttcaaagat | 960 |
| gacggtaact | acaagaccag | agctgaagtc | aagtttgaag | tgatacctt | agttaataga | 1020 |
| atcgaattaa | aaggtattga | ttttaaagaa | gatggtaaca | ttttaggtca | caaattggaa | 1080 |
| tacaactata | actctcacaa | tgtttacatc | actgctgaca | acaaaagaa | tggtatcaaa | 1140 |
| gctaacttca | aaattagaca | caacattgaa | gatggtggtg | ttcaattagc | tgaccattat | 1200 |
| caacaaaata | ctccaattgg | tgatggtcca | gtcttgttac | cagacaacca | ttacttatcc | 1260 |
| tatcaatctg | ccttatccaa | agatccaaac | gaaaagagag | atcacatggt | cttgttagaa | 1320 |
| tttgttactg | ctgctgggat | tacccatggt | atggatgaat | tgtacaaata | aaagcttttg | 1380 |
| attaagccctt | ctagtccaaa | aaacacgttt | ttttgtcatt | tatttcatttt | tcttagaata | 1440 |
| gtttagttta | ttcattttat | agtcacgaat | gttttatgat | tctatatagg | gttgcaaaca | 1500 |
| agcattttc | attttatgtt | aaaacaattt | caggtttacc | ttttattctg | cttgtggtga | 1560 |
| cgcgtgtatc | cgcccgctct | tttggtcacc | catgtattta | attgcataaa | taattcttaa | 1620 |
| aagtggagct | agtctatttc | tatttacata | cctctcatt | ctcatttcct | ccctcttgc | 1680 |
| ccatcgaacg | tacaagtact | cctctgttct | ctccttcctt | tgcttt | | 1726 |

<210> SEQ ID NO 55
<211> LENGTH: 1720
<212> TYPE: DNA
<213> ORGANISM: Artificial Sequence
<220> FEATURE:
<223> OTHER INFORMATION: conB - RFP - con3 sequence

<400> SEQUENCE: 55

| | | | | | |
|---|---|---|---|---|---|
| cggatcgatg | tacacaaccg | actgcaccca | acgaacaca | atcttagca | gtgcaacata | 60 |
| tatacacaat | tacagtaaca | ataacaagag | gacagatact | accaaaatgt | gtggggaagc | 120 |
| gggtaagctg | ccacagcaat | taatgcacaa | catttaacct | acattcttcc | ttatcggatc | 180 |
| ctcaaaaccc | ttaaaaacat | atgcctcacc | ctaacatatt | ttccaattaa | ccctcaatat | 240 |

```
ttctctgtca cccggcctct attttccatt ttcttcttta cccgccacgc gtttttttct    300
ttcaaatttt ttcttctttt cttcttttc ttccacgtcc tcttgcataa ataaataaac    360
cgttttgaaa ccaaactcgc ctctctctct ccttttgaa atattttgg gtttgtttga    420 tcctttcctt cccaatctct cttgtttaat atatattcat ttatatcacg ctctcttttt    480
atcttccttt ttcctctc tcttgtattc ttccttcccc tttctactca aaccaagaag    540
aaaaagaaaa ggtcaatctt tgttaaagaa taggatcttc tactcatca gcttttagat    600 ttttcacgct tactgctttt ttcttcccaa gatcgaaaat ttactgaatt aacaatggta    660
agtaagggtg aagaagacaa tatggcgatc attaaggaat tcatgcgttt caaagtacac    720
atggagggaa gcgtgaacgg acatgaattt gaaatcgaag gggaaggcga aggtagacca    780
tacgaaggaa cccagaccgc aaagcttaaa gttaccaaag gcgggccact acctttgca    840 tgggatatct tgagccctca gtttatgtat ggcagtaagg cctacgttaa acacccagct    900
gatattcccg actatttgaa attgtctttt ccagaaggat tcaaatggga agagtaatg    960 aatttcgagg acggcggagt tgttactgtt actcaagatt caagtttgca agacggtgaa    1020
tttatttaca aggtcaaatt aagagggact aatttcccta gtgatggtcc cgtcatgcaa    1080
aagaagacta tgggttggga agcctcatct gaacgtatgt atccagaaga tggcgcgctt    1140
aagggggaaa ttaaacaaag attgaagtta aaagacggtg gtcactacga cgcggaagtt    1200
aagaccactt ataaagctaa aaagcccgtt cagttacctg gtgcatataa cgtaaacatt    1260
aaattggata tcacttcaca taatgaagat tacactattg tggaacaata tgaaagagct    1320
gaaggtaggc actcaacggg tggaatggac gaattgtaca aataaagtga atttacttta    1380
aatcttgcat ttaaataat tttctttta tagcttatg acttagtttc aatttatata    1440
ctattttaat gacattttcg attcattgat tgaaagcttt gtgttttttc ttgatgcgct    1500
attgcattgt tcttgtcttt ttcgccacat gtaatatctg tagtagatac ctgatacatt    1560
gtggatgctg agtgaaattt tagttaataa tggaggcgct cttaataatt ttggggatat    1620 tggcttttt ttttaaagtt tacaaatgaa tttttccgc caggatcctc agaaagcctg    1680
tatgcgaagc cacaatcctt tccaacagac catactaagt                          1720
```

<210> SEQ ID NO 56
<211> LENGTH: 100
<212> TYPE: DNA
<213> ORGANISM: Artificial Sequence
<220> FEATURE:
<223> OTHER INFORMATION: ssODN conA - conB upper strand sequence strand
      sequence

<400> SEQUENCE: 56

```
ttgcccatcg aacgtacaag tactcctctg ttctctcctt cctttgcttt cggatcgatg     60
tacacaaccg actgcaccca aacgaacaca aatcttagca                          100
```

<210> SEQ ID NO 57
<211> LENGTH: 100
<212> TYPE: DNA
<213> ORGANISM: Artificial Sequence
<220> FEATURE:
<223> OTHER INFORMATION: ssODN conA - conB lower strand sequence strand
      sequence

<400> SEQUENCE: 57

```
tgctaagatt tgtgttcgtt tgggtgcagt cggttgtgta catcgatccg aaagcaaagg     60
```
aaggagagaa cagaggagta cttgtacgtt cgatgggcaa            100

<210> SEQ ID NO 58
<211> LENGTH: 654
<212> TYPE: DNA
<213> ORGANISM: Artificial Sequence
<220> FEATURE:
<223> OTHER INFORMATION: con5 - TDH3 promoter sequence

<400> SEQUENCE: 58
aagcgacttc caatcgcttt gcatatccag taccacaccc acaggcgttt gtgcttagtc            60
aaaaaattag cctttttaatt ctgctgtaac ccgtacatgc ccaaaatagg gggcgggtta           120
cacagaatat ataacatcgt aggtgtctgg gtgaacagtt tattcctggc atccactaaa           180
tataatggag cccgcttttt aagctggcat ccagaaaaaa aaagaatccc agcaccaaaa           240
tattgttttc ttcaccaacc atcagttcat aggtccattc tcttagcgca actacagaga           300
acagggcac aaacaggcaa aaacgggca caacctcaat ggagtgatgc aacctgcctg            360
gagtaaatga tgacacaagg caattgaccc acgcatgtat ctatctcatt ttcttacacc           420
ttctattacc ttctgctctc tctgatttgg aaaaagctga aaaaaaggt tgaaaccagt            480
tccctgaaat tattccccta cttgactaat aagtatataa agacggtagg tattgattgt           540
aattctgtaa atctatttct taaacttctt aaattctact tttatagtta gtctttttt            600
tagttttaaa acaccaagaa cttagtttcg aataaacaca cataaacaaa caaa                 654

<210> SEQ ID NO 59
<211> LENGTH: 718
<212> TYPE: DNA
<213> ORGANISM: Artificial Sequence
<220> FEATURE:
<223> OTHER INFORMATION: YFP ORF sequence

<400> SEQUENCE: 59
atgtctaaag gtgaagaatt attcactggt gttgtcccaa ttttggttga attagatggt            60
gatgttaatg gtcacaaatt ttctgtctcc ggtgaaggtg aaggtgatgc tacttacggt           120
aaattgacct taaaattgat ttgtactact ggtaaattgc cagttccatg gccaacctta           180
gtcactactt taggttatgg tttgcaatgt tttgctagat acccagatca tatgaaacaa           240
catgactttt tcaagtctgc catgccagaa ggttatgttc aagaaagaac tatttttttc           300
aaagatgacg gtaactacaa gaccagagct gaagtcaagt ttgaaggtga taccttagtt           360
aatagaatcg aattaaaagg tattgatttt aagaagatg gtaacatttt aggtcacaaa           420
ttggaataca actataactc tcacaatgtt tacatcactg ctgacaaaca aaagaatggt           480
atcaaagcta acttcaaaat tagacacaac attgaagatg gtggtgttca attagctgac           540
cattatcaac aaaatactcc aattggtgat ggtccagtct tgttaccaga caaccattac           600
ttatcctatc aatctgcctt atccaaagat ccaaacgaaa agagagatca catggtcttg           660
ttagaatttg ttactgctgc tggtattacc catggtatgg atgaattgta caaataaa             718

<210> SEQ ID NO 60
<211> LENGTH: 354
<212> TYPE: DNA
<213> ORGANISM: Artificial Sequence
<220> FEATURE:
<223> OTHER INFORMATION: ENO1 terminator - con3 sequence

<400> SEQUENCE: 60
agcttttgat taagccttct agtccaaaaa acacgttttt ttgtcattta tttcattttc            60

```
ttagaatagt ttagtttatt cattttatag tcacgaatgt tttatgattc tatatagggt    120
tgcaaacaag cattttttcat tttatgttaa aacaatttca ggtttaccct ttattctgct    180
tgtggtgacg cgtgtatccg cccgctcttt tggtcaccca tgtatttaat tgcataaata    240
attcttaaaa gtggagctag tctatttcta tttacatacc tctcatttct catttcctcc    300
cctcagaaag cctgtatgcg aagccacaat cctttccaac agaccatact aagt          354
```

<210> SEQ ID NO 61
<211> LENGTH: 100
<212> TYPE: DNA
<213> ORGANISM: Artificial Sequence
<220> FEATURE:
<223> OTHER INFORMATION: ssODN TDH3 promoter - YFP upper strand sequence

<400> SEQUENCE: 61

```
tttaaaacac caagaactta gtttcgaata aacacacata aacaaacaaa atgtctaaag     60
gtgaagaatt attcactggt gttgtcccaa ttttggttga                          100
```

<210> SEQ ID NO 62
<211> LENGTH: 100
<212> TYPE: DNA
<213> ORGANISM: Artificial Sequence
<220> FEATURE:
<223> OTHER INFORMATION: ssODN TDH3 promoter - YFP lower strand sequence

<400> SEQUENCE: 62

```
tcaaccaaaa ttgggacaac accagtgaat aattcttcac ctttagacat tttgtttgtt     60
tatgtgtgtt tattcgaaac taagttcttg gtgttttaaa                          100
```

<210> SEQ ID NO 63
<211> LENGTH: 100
<212> TYPE: DNA
<213> ORGANISM: Artificial Sequence
<220> FEATURE:
<223> OTHER INFORMATION: ssODN YFP - ENO1 terminator upper strand
      sequence

<400> SEQUENCE: 63

```
gttactgctg ctggtattac ccatggtatg gatgaattgt acaaataaaa gcttttgatt     60
aagccttcta gtccaaaaaa cacgtttttt tgtcatttat                          100
```

<210> SEQ ID NO 64
<211> LENGTH: 100
<212> TYPE: DNA
<213> ORGANISM: Artificial Sequence
<220> FEATURE:
<223> OTHER INFORMATION: ssODN YFP - ENO1 terminator lower strand
      sequence

<400> SEQUENCE: 64

```
ataaatgaca aaaaaacgtg ttttttggac tagaaggctt aatcaaaagc ttttatttgt     60
acaattcatc cataccatgg gtaataccag cagcagtaac                          100
```

<210> SEQ ID NO 65
<211> LENGTH: 754
<212> TYPE: DNA
<213> ORGANISM: Artificial Sequence
<220> FEATURE:
<223> OTHER INFORMATION: 1 kb deletion flank genomic DNA (50 bp
      overlap) - con5- TDH3p-YFP (100 bp overlap in total) sequence

<400> SEQUENCE: 65

```
cttcatgcca gcaatagttg cgtgctgagc tcaacagtgc ccaacccttg aagcgacttc      60
caatcgcttt gcatatccag taccacaccc acaggcgttt gtgcttagtc aaaaaattag     120
ccttttaatt ctgctgtaac ccgtacatgc ccaaaatagg gggcgggtta cacagaatat     180
ataacatcgt aggtgtctgg gtgaacagtt tattcctggc atccactaaa tataatggag     240
cccgcttttt aagctggcat ccagaaaaaa aagaatccc agcaccaaaa tattgttttc       300
ttcaccaacc atcagttcat aggtccattc tcttagcgca actacagaga acaggggcac     360
aaacaggcaa aaacgggca caacctcaat ggagtgatgc aacctgcctg gagtaaatga      420
tgacacaagg caattgaccc acgcatgtat ctatctcatt ttcttacacc ttctattacc     480
ttctgctctc tctgatttgg aaaaagctga aaaaaaggt tgaaaccagt tccctgaaat       540
tattccccta cttgactaat aagtatataa agacggtagg tattgattgt aattctgtaa     600
atctatttct taaacttctt aaattctact tttatagtta gtctttttt tagttttaaa       660 acaccaagaa cttagtttcg aataaacaca cataaacaaa caaaatgtct aaaggtgaag     720
aattattcac tggtgttgtc ccaattttgg ttga                                 754

<210> SEQ ID NO 66
<211> LENGTH: 819
<212> TYPE: DNA
<213> ORGANISM: Artificial Sequence
<220> FEATURE:
<223> OTHER INFORMATION: TDH3p (100 bp overlap in total) - YFP - ENO1t
      (100 bp overlap) sequence

<400> SEQUENCE: 66
tttaaaacac caagaactta gtttcgaata aacacacata aacaaacaaa atgtctaaag      60
gtgaagaatt attcactggt gttgtcccaa ttttggttga attagatggt gatgttaatg    120
gtcacaaatt ttctgtctcc ggtgaaggtg aaggtgatgc tacttacggt aaattgacct    180
taaaattgat ttgtactact ggtaaattgc cagttccatg ccaaccctta gtcactactt    240
taggttatgg tttgcaatgt tttgctagat acccagatca tatgaaacaa catgactttt    300
tcaagtctgc catgccagaa ggttatgttc aagaaagaac tatttttttc aaagatgacg    360
gtaactacaa gaccagagct gaagtcaagt ttgaaggtga taccttagtt aatagaatcg    420
aattaaaagg tattgatttt aaagaagatg gtaacatttt aggtcacaaa ttggaataca    480
actataactc tcacaatgtt tacatcactg ctgacaaaca aaagaatggt atcaaagcta    540
acttcaaaat tagacacaac attgaagatg gtggtgttca attagctgac cattatcaac    600
aaaatactcc aattggtgat ggtccagtct tgttaccaga caaccattac ttatcctatc    660
aatctgcctt atccaaagat ccaaacgaaa agagagatca catggtcttg ttagaatttg    720
ttactgctgc tggtattacc catggtatgg atgaattgta caaataaaag cttttgatta    780
agccttctag tccaaaaaac acgttttttt gtcatttat                            819

<210> SEQ ID NO 67
<211> LENGTH: 454
<212> TYPE: DNA
<213> ORGANISM: Artificial Sequence
<220> FEATURE:
<223> OTHER INFORMATION: YFP - ENO1t (100bp overlap in total) - Con3 - 1
      kb deletion flank genomic DNA (50 bp overlap) sequence

<400> SEQUENCE: 67
tgttactgct gctggtatta cccatggtat ggatgaattg tacaaataaa agcttttgat      60
```

-continued

```
taagccttct agtccaaaaa acacgttttt tgtcattta tttcattttc ttagaatagt    120
ttagtttatt cattttatag tcacgaatgt tttatgattc tatataggt tgcaaacaag    180 cattttcat tttatgttaa aacaatttca ggtttacctt ttattctgct tgtggtgacg     240
cgtgtatccg cccgctcttt tggtcaccca tgtatttaat tgcataaata attcttaaaa   300
gtggagctag tctatttcta tttacatacc tctcattct catttcctcc cctcagaaag    360
cctgtatgcg aagccacaat cctttccaac agaccatact aagtattctt tgtcatcaga   420
caacttgttg agtggtacta aaggagtgct tttc                               454
```

<210> SEQ ID NO 68
<211> LENGTH: 24
<212> TYPE: DNA
<213> ORGANISM: Artificial Sequence
<220> FEATURE:
<223> OTHER INFORMATION: FW primer to confirm integration of RFP
      expression cassette

<400> SEQUENCE: 68

```
atggtaagta agggtgaaga agac                                           24
```

<210> SEQ ID NO 69
<211> LENGTH: 23
<212> TYPE: DNA
<213> ORGANISM: Artificial Sequence
<220> FEATURE:
<223> OTHER INFORMATION: REV primer to confirm integration of RFP
      expression cassette

<400> SEQUENCE: 69

```
ttatttgtac aattcgtcca ttc                                            23
```

<210> SEQ ID NO 70
<211> LENGTH: 21
<212> TYPE: DNA
<213> ORGANISM: Artificial Sequence
<220> FEATURE:
<223> OTHER INFORMATION: FW primer to confirm tandem integration of YFP
      and RFP expression cassettes

<400> SEQUENCE: 70

```
cagttccatg gccaacctta g                                              21
```

<210> SEQ ID NO 71
<211> LENGTH: 20
<212> TYPE: DNA
<213> ORGANISM: Artificial Sequence
<220> FEATURE:
<223> OTHER INFORMATION: FW primer to confirm correct deletion of 1 kB
      genomic DNA at the 3 end

<400> SEQUENCE: 71

```
ttgcccatcg aacgtacaag                                                20
```

<210> SEQ ID NO 72
<211> LENGTH: 20
<212> TYPE: DNA
<213> ORGANISM: Artificial Sequence
<220> FEATURE:
<223> OTHER INFORMATION: REV primer to confirm correct deletion of 1 kB
      genomic DNA at the 3 end

<400> SEQUENCE: 72

```
cggatcgatg tacacaaccg                                                20
```

<210> SEQ ID NO 73
<211> LENGTH: 24
<212> TYPE: DNA
<213> ORGANISM: Artificial Sequence
<220> FEATURE:
<223> OTHER INFORMATION: FW primer to amplify the Kl11p-pCSN061
      backbone-GND2t PCR fragment

<400> SEQUENCE: 73
ttttgataag tatttaagcg agtg                                           24

<210> SEQ ID NO 74
<211> LENGTH: 22
<212> TYPE: DNA
<213> ORGANISM: Artificial Sequence
<220> FEATURE:
<223> OTHER INFORMATION: REV primer to amplify the Kl11p-pCSN061
      backbone-GND2t PCR fragment

<400> SEQUENCE: 74
aggagttaaa ggcaaagttt tc                                             22

<210> SEQ ID NO 75
<211> LENGTH: 1318
<212> TYPE: PRT
<213> ORGANISM: Artificial Sequence
<220> FEATURE:
<223> OTHER INFORMATION: Protein sequence of AsCpf1 (from
      Acidaminococcus spp. BV3L6) including a carboxy (C)-terminal
      nuclear localization signal (NLS)

<400> SEQUENCE: 75

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

```
Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
                275                 280                 285

Asp Glu Thr Ala His Ile Ile Ala Ser Leu Pro His Arg Phe Ile Pro
                290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
                515                 520                 525

Glu Lys Phe Lys Leu Asn Phe Gln Met Pro Thr Leu Ala Ser Gly Trp
                530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
                580                 585                 590

Met Tyr Tyr Asp Tyr Phe Pro Asp Ala Ala Lys Met Ile Pro Lys Cys
                595                 600                 605

Ser Thr Gln Leu Lys Ala Val Thr Ala His Phe Gln Thr His Thr Thr
                610                 615                 620

Pro Ile Leu Leu Ser Asn Asn Phe Ile Glu Pro Leu Glu Ile Thr Lys
625                 630                 635                 640
```

```
Glu Ile Tyr Asp Leu Asn Asn Pro Glu Lys Glu Pro Lys Lys Phe Gln
            645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
            690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
            725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
            770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
            805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
            885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
            930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
            965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
            995                 1000                1005

Lys Ala Val Tyr Gln Gln Phe Glu Lys Met Leu Ile Asp Lys Leu
            1010                1015                1020

Asn Cys Leu Val Leu Lys Asp Tyr Pro Ala Glu Lys Val Gly Gly
            1025                1030                1035

Val Leu Asn Pro Tyr Gln Leu Thr Asp Gln Phe Thr Ser Phe Ala
            1040                1045                1050

Lys Met Gly Thr Gln Ser Gly Phe Leu Phe Tyr Val Pro Ala Pro
```

-continued

```
                 1055                1060                1065
Tyr Thr Ser Lys Ile Asp Pro Leu Thr Gly Phe Val Asp Pro Phe
             1070                1075                1080
Val Trp Lys Thr Ile Lys Asn His Glu Ser Arg Lys His Phe Leu
         1085                1090                1095
Glu Gly Phe Asp Phe Leu His Tyr Asp Val Lys Thr Gly Asp Phe
     1100                1105                1110
Ile Leu His Phe Lys Met Asn Arg Asn Leu Ser Phe Gln Arg Gly
     1115                1120                1125
Leu Pro Gly Phe Met Pro Ala Trp Asp Ile Val Phe Glu Lys Asn
     1130                1135                1140
Glu Thr Gln Phe Asp Ala Lys Gly Thr Pro Phe Ile Ala Gly Lys
     1145                1150                1155
Arg Ile Val Pro Val Ile Glu Asn His Arg Phe Thr Gly Arg Tyr
     1160                1165                1170
Arg Asp Leu Tyr Pro Ala Asn Glu Leu Ile Ala Leu Leu Glu Glu
     1175                1180                1185
Lys Gly Ile Val Phe Arg Asp Gly Ser Asn Ile Leu Pro Lys Leu
     1190                1195                1200
Leu Glu Asn Asp Asp Ser His Ala Ile Asp Thr Met Val Ala Leu
     1205                1210                1215
Ile Arg Ser Val Leu Gln Met Arg Asn Ser Asn Ala Ala Thr Gly
     1220                1225                1230
Glu Asp Tyr Ile Asn Ser Pro Val Arg Asp Leu Asn Gly Val Cys
     1235                1240                1245
Phe Asp Ser Arg Phe Gln Asn Pro Glu Trp Pro Met Asp Ala Asp
     1250                1255                1260
Ala Asn Gly Ala Tyr His Ile Ala Leu Lys Gly Gln Leu Leu Leu
     1265                1270                1275
Asn His Leu Lys Glu Ser Lys Asp Leu Lys Leu Gln Asn Gly Ile
     1280                1285                1290
Ser Asn Gln Asp Trp Leu Ala Tyr Ile Gln Glu Leu Arg Asn Ser
     1295                1300                1305
Arg Ala Asp Pro Lys Lys Lys Arg Lys Val
     1310                1315
```

<210> SEQ ID NO 76
<211> LENGTH: 1239
<212> TYPE: PRT
<213> ORGANISM: Artificial Sequence
<220> FEATURE:
<223> OTHER INFORMATION: Protein sequence of LbCpf1 (from
      Lachnospiraceae bacterium ND2006) including a C-terminal NLS

<400> SEQUENCE: 76

```
Met Ser Lys Leu Glu Lys Phe Thr Asn Cys Tyr Ser Leu Ser Lys Thr
1               5                   10                  15
Leu Arg Phe Lys Ala Ile Pro Val Gly Lys Thr Gln Glu Asn Ile Asp
            20                  25                  30
Asn Lys Arg Leu Leu Val Glu Asp Glu Lys Arg Ala Glu Asp Tyr Lys
        35                  40                  45
Gly Val Lys Lys Leu Leu Asp Arg Tyr Tyr Leu Ser Phe Ile Asn Asp
    50                  55                  60
Val Leu His Ser Ile Lys Leu Lys Asn Leu Asn Asn Tyr Ile Ser Leu
65                  70                  75                  80
```

```
Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
```

```
                500             505             510
Gln Lys Pro Tyr Ser Lys Asp Lys Phe Lys Leu Tyr Phe Gln Asn Pro
            515                 520                 525
Gln Phe Met Gly Gly Trp Asp Lys Asp Lys Glu Thr Asp Tyr Arg Ala
        530                 535                 540
Thr Ile Leu Arg Tyr Gly Ser Lys Tyr Tyr Leu Ala Ile Met Asp Lys
545                 550                 555                 560
Lys Tyr Ala Lys Cys Leu Gln Lys Ile Asp Lys Asp Val Asn Gly
                565                 570                 575
Asn Tyr Glu Lys Ile Asn Tyr Lys Leu Leu Pro Gly Pro Asn Lys Met
            580                 585                 590
Leu Pro Lys Val Phe Phe Ser Lys Lys Trp Met Ala Tyr Tyr Asn Pro
        595                 600                 605
Ser Glu Asp Ile Gln Lys Ile Tyr Lys Asn Gly Thr Phe Lys Lys Gly
        610                 615                 620
Asp Met Phe Asn Leu Asn Asp Cys His Lys Leu Ile Asp Phe Phe Lys
625                 630                 635                 640
Asp Ser Ile Ser Arg Tyr Pro Lys Trp Ser Asn Ala Tyr Asp Phe Asn
                645                 650                 655
Phe Ser Glu Thr Glu Lys Tyr Lys Asp Ile Ala Gly Phe Tyr Arg Glu
            660                 665                 670
Val Glu Glu Gln Gly Tyr Lys Val Ser Phe Glu Ser Ala Ser Lys Lys
        675                 680                 685
Glu Val Asp Lys Leu Val Glu Glu Gly Lys Leu Tyr Met Phe Gln Ile
        690                 695                 700
Tyr Asn Lys Asp Phe Ser Asp Lys Ser His Gly Thr Pro Asn Leu His
705                 710                 715                 720
Thr Met Tyr Phe Lys Leu Leu Phe Asp Glu Asn Asn His Gly Gln Ile
                725                 730                 735
Arg Leu Ser Gly Gly Ala Glu Leu Phe Met Arg Arg Ala Ser Leu Lys
            740                 745                 750
Lys Glu Glu Leu Val Val His Pro Ala Asn Ser Pro Ile Ala Asn Lys
        755                 760                 765
Asn Pro Asp Asn Pro Lys Lys Thr Thr Thr Leu Ser Tyr Asp Val Tyr
        770                 775                 780
Lys Asp Lys Arg Phe Ser Glu Asp Gln Tyr Glu Leu His Ile Pro Ile
785                 790                 795                 800
Ala Ile Asn Lys Cys Pro Lys Asn Ile Phe Lys Ile Asn Thr Glu Val
                805                 810                 815
Arg Val Leu Leu Lys His Asp Asp Asn Pro Tyr Val Ile Gly Ile Asp
            820                 825                 830
Arg Gly Glu Arg Asn Leu Leu Tyr Ile Val Val Asp Gly Lys Gly
        835                 840                 845
Asn Ile Val Glu Gln Tyr Ser Leu Asn Glu Ile Ile Asn Asn Phe Asn
        850                 855                 860
Gly Ile Arg Ile Lys Thr Asp Tyr His Ser Leu Leu Asp Lys Lys Glu
865                 870                 875                 880
Lys Glu Arg Phe Glu Ala Arg Gln Asn Trp Thr Ser Ile Glu Asn Ile
                885                 890                 895
Lys Glu Leu Lys Ala Gly Tyr Ile Ser Gln Val Val His Lys Ile Cys
            900                 905                 910
Glu Leu Val Glu Lys Tyr Asp Ala Val Ile Ala Leu Glu Asp Leu Asn
        915                 920                 925
```

Ser Gly Phe Lys Asn Ser Arg Val Lys Val Glu Lys Gln Val Tyr Gln
       930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu Thr Ser Lys Ile Asp Pro Ser Thr
        995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His Ser Arg Ala Asp Pro
    1220                1225                1230

Lys Lys Lys Arg Lys Val
    1235

<210> SEQ ID NO 77
<211> LENGTH: 1311
<212> TYPE: PRT
<213> ORGANISM: Artificial Sequence
<220> FEATURE:
<223> OTHER INFORMATION: Protein sequence of FnCpf1 (from Francisella
      novicida U112) including a C-terminal NLS

<400> SEQUENCE: 77

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys

-continued

```
             20                  25                  30
Ala Arg Gly Leu Ile Leu Asp Asp Glu Lys Arg Ala Lys Asp Tyr Lys
             35                  40                  45
Lys Ala Lys Gln Ile Ile Asp Lys Tyr His Gln Phe Phe Ile Glu Glu
 50                  55                  60
Ile Leu Ser Ser Val Cys Ile Ser Glu Asp Leu Leu Gln Asn Tyr Ser
 65                  70                  75                  80
Asp Val Tyr Phe Lys Leu Lys Lys Ser Asp Asp Asn Leu Gln Lys
                 85                  90                  95
Asp Phe Lys Ser Ala Lys Asp Thr Ile Lys Lys Gln Ile Ser Glu Tyr
                100                 105                 110
Ile Lys Asp Ser Glu Lys Phe Lys Asn Leu Phe Asn Gln Asn Leu Ile
                115                 120                 125
Asp Ala Lys Lys Gly Gln Glu Ser Asp Leu Ile Leu Trp Leu Lys Gln
                130                 135                 140
Ser Lys Asp Asn Gly Ile Glu Leu Phe Lys Ala Asn Ser Asp Ile Thr
145                 150                 155                 160
Asp Ile Asp Glu Ala Leu Glu Ile Ile Lys Ser Phe Lys Gly Trp Thr
                165                 170                 175
Thr Tyr Phe Lys Gly Phe His Glu Asn Arg Lys Asn Val Tyr Ser Ser
                180                 185                 190
Asn Asp Ile Pro Thr Ser Ile Ile Tyr Arg Ile Val Asp Asp Asn Leu
                195                 200                 205
Pro Lys Phe Leu Glu Asn Lys Ala Lys Tyr Glu Ser Leu Lys Asp Lys
                210                 215                 220
Ala Pro Glu Ala Ile Asn Tyr Glu Gln Ile Lys Lys Asp Leu Ala Glu
225                 230                 235                 240
Glu Leu Thr Phe Asp Ile Asp Tyr Lys Thr Ser Glu Val Asn Gln Arg
                245                 250                 255
Val Phe Ser Leu Asp Glu Val Phe Glu Ile Ala Asn Phe Asn Asn Tyr
                260                 265                 270
Leu Asn Gln Ser Gly Ile Thr Lys Phe Asn Thr Ile Ile Gly Gly Lys
                275                 280                 285
Phe Val Asn Gly Glu Asn Thr Lys Arg Lys Gly Ile Asn Glu Tyr Ile
                290                 295                 300
Asn Leu Tyr Ser Gln Gln Ile Asn Asp Lys Thr Leu Lys Lys Tyr Lys
305                 310                 315                 320
Met Ser Val Leu Phe Lys Gln Ile Leu Ser Asp Thr Glu Ser Lys Ser
                325                 330                 335
Phe Val Ile Asp Lys Leu Glu Asp Asp Ser Asp Val Val Thr Thr Met
                340                 345                 350
Gln Ser Phe Tyr Glu Gln Ile Ala Ala Phe Lys Thr Val Glu Glu Lys
                355                 360                 365
Ser Ile Lys Glu Thr Leu Ser Leu Leu Phe Asp Asp Leu Lys Ala Gln
                370                 375                 380
Lys Leu Asp Leu Ser Lys Ile Tyr Phe Lys Asn Asp Lys Ser Leu Thr
385                 390                 395                 400
Asp Leu Ser Gln Gln Val Phe Asp Asp Tyr Ser Val Ile Gly Thr Ala
                405                 410                 415
Val Leu Glu Tyr Ile Thr Gln Gln Ile Ala Pro Lys Asn Leu Asp Asn
                420                 425                 430
Pro Ser Lys Lys Glu Gln Glu Leu Ile Ala Lys Lys Thr Glu Lys Ala
                435                 440                 445
```

```
Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                    485                 490                 495

Asp Asn Leu Ala Gln Ile Ser Ile Lys Tyr Gln Asn Gln Gly Lys Lys
                500                 505                 510

Asp Leu Leu Gln Ala Ser Ala Glu Asp Val Lys Ala Ile Lys Asp
            515                 520                 525

Leu Leu Asp Gln Thr Asn Asn Leu Leu His Lys Leu Lys Ile Phe His
        530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
                580                 585                 590

Asp Glu Lys Phe Lys Leu Asn Phe Glu Asn Ser Thr Leu Ala Asn Gly
            595                 600                 605

Trp Asp Lys Asn Lys Glu Pro Asp Asn Thr Ala Ile Leu Phe Ile Lys
        610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
                660                 665                 670

Phe Phe Ser Ala Lys Ser Ile Lys Phe Tyr Asn Pro Ser Glu Asp Ile
            675                 680                 685

Leu Arg Ile Arg Asn His Ser Thr His Thr Lys Asn Gly Ser Pro Gln
        690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
                740                 745                 750

Phe Tyr Arg Glu Val Glu Asn Gln Gly Tyr Lys Leu Thr Phe Glu Asn
            755                 760                 765

Ile Ser Glu Ser Tyr Ile Asp Ser Val Val Asn Gln Gly Lys Leu Tyr
        770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
                820                 825                 830

Arg Lys Gln Ser Ile Pro Lys Lys Ile Thr His Pro Ala Lys Glu Ala
            835                 840                 845

Ile Ala Asn Lys Asn Lys Asp Asn Pro Lys Lys Glu Ser Val Phe Glu
850                 855                 860
```

```
Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
        995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
```

```
                1265                1270                1275
Gly Lys  Lys Leu Asn Leu Val  Ile Lys Asn Glu Glu  Tyr Phe Glu
            1280                1285                1290

Phe Val  Gln Asn Arg Asn Asn  Ser Arg Ala Asp Pro  Lys Lys Lys
            1295                1300                1305

Arg Lys  Val
            1310

<210> SEQ ID NO 78
<211> LENGTH: 3957
<212> TYPE: DNA
<213> ORGANISM: Artificial Sequence
<220> FEATURE:
<223> OTHER INFORMATION: Nucleotide sequence of codon pair optimized
      (CPO) AsCpf1 including a C-terminal NLS

<400> SEQUENCE: 78
atgacccaat tgaaggtttt cactaacttg taccaagttt ctaagacttt aagatttgaa    60
ttgattccac aaggtaagac tttgaagcat atccaagaac aaggtttcat cgaagaagac   120
aaggctagaa acgaccatta caaggaattg aagccaatta tcgatcgtat ttacaagacc   180
tacgctgacc aatgtttgca attggttcaa ttggactggg aaaacttatc tgctgctatt   240
gattcctaca gaaagaaaaa gactgaagaa actagaaacg ccttgattga agaacaagct   300
acctaccgta tgccattcca cgattatttc atcggtagaa ctgacaactt gactgatgct   360
atcaacaaac gtcacgctga aatctacaag ggtttgttca aggctgaatt gttcaacggt   420
aaagtcttga acaattggga tactgtcacc accactgaac acgaaaacgc cttattaaga   480
tcctttgaca gttcaccac ctacttctct ggtttctacg aaaacagaaa gaacgtcttc   540
tccgctgaag atatctctac cgctattcca cacagaattg ccaagataa cttcccaaag   600 tttaagaaaa actgtcacat tttcaccaga tgatcactg ctgttccatc tttgagagaa   660
cacttcgaaa acgtcaagaa ggccatcggt atttttcgtt tctacctctat tgaagaagtc   720 ttctcttttcc cattctacaa ccaattattg actcaaaccc aaattgattt gtacaaccaa   780
ctattgggtg gtatttccag agaagctggt actgaaaaga ttaagggttt gaacgaagtt   840
ttaaacttgg ctatccaaaa gaacgatgaa actgctcaca tcattgcttc tttgccacac   900
cgtttcattc cattgttcaa acaaattttg tccgacagaa cactttgtc cttcattttg   960 gaagaattca gtctgacga agaagtcatc caatctttct gtaaatacaa gactttgttg  1020
cgtaacgaaa acgttcttga aaccgctgaa gctttgttta tgaattgaa ctccatcgat  1080 ttgactcaca tcttcatctc ccacaagaag ttggaaacca tctcctctgc tttgtgtgat  1140
cattgggaca cctgagaaa cgcttttgtac gaaagaagaa tctctgaatt gactggtaag  1200
atcaccaagt ctgctaagga aaaggtccaa cgttccttga acacgaaga tatcaacttg  1260 caagaaatca tctctgctgc tggtaaggaa ttgtctgaag ccttcaagca aaagacttct  1320
gaaatcttat cccacgctca cgctgctttg gaccaaccat gccaaccac tttgaagaag  1380 caagaagaaa aagaaatctt gaaatctcaa ttggattctc tattgggttt gtaccatttg  1440
ttggactggt tcgctgtcga cgaatctaac gaagtcgacc agaattctc cgccagattg  1500 accggcatca gttggagat ggaaccatct tgtctttct acaacaaggc tcgtaactac  1560
gccaccaaga agccatactc tgttgaaaaa ttcaagttaa acttccaaat gccaactttg  1620
gcctctggtt gggacgtcaa caaggaaaag aacaacggtg ccatcttatt cgttaagaac  1680
ggtttatact acttgggtat tatgccaaag caaaagggta gatacaaggc tttatctttc  1740
```

```
gaacctaccg aaaagacctc cgaaggtttc gacaagatgt actacgatta ctttcctgat    1800
gctgctaaga tgatcccaaa gtgttctact caattaaagg ctgtcactgc tcacttccaa    1860
actcacacca ctccaatctt gttgtccaac aacttcatcg aaccattgga aattactaag    1920
gaaatttacg acttgaacaa cccagaaaag gaaccaaaga aattccaaac cgcttacgcc    1980
aagaagaccg gtgaccaaaa gggttacaga gaagccttgt gtaaatggat tgacttcacc    2040
agagacttct tgtccaaata caccaagact acttctatcg atttgtcttc tctaagacca    2100
tcctctcaat acaaggactt gggtgaatac tacgctgaat tgaatccatt attgtaccac    2160
atctccttcc aaagaatcgc tgaaaaagag attatgacg ctgttgaaac tggtaagttg    2220
tacttgttcc aaatttacaa caaagatttc gccaagggtc accacggtaa gccaaacttg    2280
cacactttgt actggaccgg tttgttctct ccagaaaacc tagctaagac ttctatcaag    2340
ttgaacggtc aagccgaatt gttctacaga ccaaagtcca gaatgaagag aatggctcac    2400
agattgggtg aaaagatgtt gaacaagaaa ttgaaggacc aaaagacccc aatcccagac    2460
actttatacc aagaattgta cgattatgtc aaccaccgtt tgtcccacga cttgtctgat    2520
gaagccagag ctttgttacc aaacgtcatc accaaggaag tttctcacga aatcattaag    2580
gacagaagat tcacctccga caattcttc ttccatgtcc caattacttt gaattaccaa    2640
gctgctaact ccccatctaa gttcaaccaa agagtcaacg cttacttgaa ggaacaccct    2700
gaaacccaa tcatcggtat cgatagaggt gaaagaaact tgatttacat tactgtcatc    2760
gattccaccg gtaagatctt ggaacaagga tccttgaaca ccattcaaca atttgattac    2820
caaaagaagc tagacaaccg tgaaaaggaa agagttgctg ccagacaagc ttggtccgtt    2880
gtcggtacta tcaaggattt gaagcaaggt tacttgtctc aagttatcca cgaaatcgtc    2940
gacttgatga tccactacca agccgtcgtc gttctagaaa acttaaactt cggttttaag    3000
tctaagagaa ccggtattgc tgagaaggct gtttaccaac aattcgaaaa gatgctaatt    3060
gacaaattga actgtttggt cttgaaggat tacccagccg aaaaggttgg tggtgttttg    3120
aacccatacc aattgaccga ccaattcacc tctttcgcta agatgggtac tcaatctggg    3180
ttcttgttct acgttccagc cccttacacc tccaagattg acccattgac cggtttcgtt    3240
gatccattcg tctggaagac catcaagaac cacgaatctc gtaaacattt cttggaaggt    3300
tttgacttct tgcactacga tgttaagact ggtgatttca tcttgcactt caagatgaac    3360
agaaacttgt ctttccaaag aggtttgcca ggtttcatgc cagcttggga tatcgttttc    3420
gagaagaacg aaactcaatt cgacgctaag ggtactccat ttatcgctgg taagagaatc    3480
gttccagtta tcgaaaacca cagattcacc ggtagatacc gtgacttgta cccagccaac    3540
gaattgattg ctttgttgga agaaaagggt attgttttca gagacggttc caacatctta    3600
ccaaaattgt tggaaaacga tgactctcac gctatcgaca ccatggttgc cttgattaga    3660
tccgtcttac aaatgagaaa ctctaacgct gctactggtg aggactacat taactctcca    3720
gttagagact tgaacggtgt tgtttcgac tccagattcc aaaacccaga atggccaatg    3780
gatgctgacg ctaacggtgc ttaccacatt gctttgaagg tcaattgtt gttgaaccat    3840
ttgaaggaat ctaaggactt gaagttgcaa aacggtatct ccaaccaaga ctggttggct    3900
tacatccaag aattaagaaa ctccagagct gacccaaaga agaagagaaa ggtataa      3957
```

<210> SEQ ID NO 79
<211> LENGTH: 3720
<212> TYPE: DNA

<213> ORGANISM: Artificial Sequence
<220> FEATURE:
<223> OTHER INFORMATION: Nucleotide sequence of CPO LbCpf1 including a C-terminal N

<400> SEQUENCE: 79

```
atgtctaagt tggaaaaatt caccaactgt tactctttgt ctaagacttt gagattcaag      60
gccatcccag ttggtaagac ccaagaaaac atcgacaaca agagactatt agttgaagat     120
gaaaagagag ctgaagacta caagggtgtc aagaaattgt tggacagata ctacttgtct     180
tttatcaacg acgttttgca ttccatcaag ctaaagaact tgaataacta catctctttg     240
ttcagaaaga agactagaac tgaaaaggaa aataaggaat tggaaaactt ggaaatcaac     300
ttgagaaagg aaattgctaa ggctttcaag ggtaatgaag ttacaagtc tttattcaag      360
aaagacatca ttgaaaccat tttgccagaa tttttggatg ataaggatga aattgctttg     420
gttaactctt tcaacggttt caccactgct ttcactggtt tcttcgacaa cagagaaaac     480
atgttctccg aggaagctaa atccacttct attgctttca gatgtatcaa cgaaaacttg     540
acccgttaca tctctaacat ggacattttt gaaaaggtcg acgccatctt tgacaagcac     600
gaagtccaag aaatcaagga aaagatctta aactccgact acgatgtcga agatttcttc     660
gaaggtgaat tcttcaactt tgttttaacc caagaaggta tcgatgtcta caacgccatt     720
atcggtggtt tgtcactga atctggtgaa aagatcaagg gtttgaacga atacattaac      780
ttgtacaacc aaaagaccaa acaaaaattg ccaaagttca gccattgta caagcaagtt     840
ttgtctgaca gagaatcttt gtctttttac ggtgaagggt acacctctga cgaagaagtc     900
ttggaagtct tcagaaacac tttgaacaag aactctgaaa tcttctcctc catcaagaag     960
ttagaaaagt tgttcaagaa cttcgatgaa tactcttctg ctggtatctt cgttaagaac    1020
ggtccagcca tctctaccat ttctaaggat atctttggtg aatggaacgt cattagagac    1080
aaatggaacg ctgaatacga tgacatccat ttgaagaaaa aggctgttgt caccgaaaag    1140
tacgaagacg acagaagaaa atccttcaag aagatcggtt ccttctcctt ggaacaatta    1200
caagaatacg ccgatgccga tttgtccgtt gtcgaaaaat tgaaggaaat tattattcaa    1260
aaggttgatg aaatttacaa agtttacggt tcctctgaaa agttattcga tgctgatttc    1320
gtcttggaaa agtctttgaa gaagaacgac gctgttgtcg ctatcatgaa ggacttgttg    1380
gactctgtca atctttcga aaactatatc aaggccttct tcggtgaagg taaggaaact    1440
aacagagatg aatccttcta cggtgacttt gtcttggctt acgatatttt gttgaaggtt    1500
gaccacatct acgatgccat cagaaactac gttactcaaa agccatactc taaggacaaa    1560
ttcaagttgt acttccaaaa cccacaattc atgggtggtt gggataagga caaggaaact    1620
gactacagag ctaccatttt gagatacggt tccaagtact acttggccat catggacaag    1680
aagtacgcca gtgtttgcaa aagattgac aaggacgatg tcaacggtaa ctacgaaaag    1740
attaactaca agttgttgcc aggtccaaac aagatgttgc caaaggtttt cttctccaaa    1800
aagtggatgg cttactacaa cccatctgaa gacatccaaa agatctacaa gaacggtact    1860
ttcaaaaagg gtgacatgtt caacttaaac gactgtcaca gttgatcga cttcttcaag    1920
gactccatct ctagataccc aaaatggtcc aacgcttacg atttcaactt ctctgaaact    1980
gaaaaataca aggatattgc tggtttctac cgtgaagtcg aggaacaagg ttataaggtt    2040
tctttcgaat ccgcttctaa gaagaagtt gacaaattag tcgaagaagg taagttgtac    2100
atgttccaaa tctacaacaa agatttctcc gacaagtctc acggtactcc aaacttgcac    2160
```

| | | | | |
|---|---|---|---|---|
| accatgtact | tcaagttgct | attcgatgaa | acaaccacg | gtcaaatcag attgtctggt | 2220 |
| ggtgctgaat | tgttcatgag | acgtgcttct | ctaaagaagg | aagaattagt cgtccaccca | 2280 |
| gctaactctc | caattgccaa | caagaaccca | gacaacccta | agaagaccac cactttgtcc | 2340 |
| tacgacgttt | acaaggacaa | gagattctcc | gaagaccaat | acgaattgca cattccaatt | 2400 |
| gctatcaaca | gtgtccaaa | gaacatcttc | aagatcaaca | ctgaagtcag agttttgtta | 2460 |
| aagcacgatg | acaacccta | cgttattggt | atcgaccgtg | gtgaaagaaa tttgttgtac | 2520 |
| attgttgttg | ttgacggtaa | gggtaacatc | gttgaacaat | actccttgaa cgaaatcatc | 2580 |
| aacaacttca | acggtattag | aatcaagact | gattaccact | ctttgttgga taagaaggaa | 2640 |
| aaggaacgtt | ttgaagctcg | tcaaaactgg | acctctattg | aaaacatcaa agaattgaag | 2700 |
| gctggttaca | tcagtcaagt | tgtccacaag | atctgtgaat | ggtcgagaa gtacgatgcc | 2760 |
| gttattgcct | tggaagattt | gaactctggt | tttaagaact | ctcgtgtcaa ggttgaaaag | 2820 |
| caagtctacc | aaaagttcga | aaagatgtta | atcgacaaat | tgaactacat ggttgacaag | 2880 |
| aaatccaacc | catgtgctac | cggtggtgct | ttgaaaggtt | accaaatcac caacaaattc | 2940 |
| gaatctttca | aatctatgtc | cactcaaaac | gggttcatct | tctacattcc agcttggttg | 3000 |
| acctccaaga | tcgacccatc | taccggttt | cgttaacttgt | tgaagaccaa gtacacttcc | 3060 |
| attgctgatt | ccaagaagtt | catctcttct | ttcgacagaa | tcatgtacgt tccagaagaa | 3120 |
| gacttgttcg | aattcgcctt | ggactataag | aacttctcca | gaaccgatgc tgactacatt | 3180 |
| aagaaatgga | aattgtactc | ctacggtaac | agaatcagaa | ttttcagaaa cccaagaaa | 3240 |
| aacaacgttt | tcgattggga | agaagtttgt | ttgacttctg | cctacaagga attattcaac | 3300 |
| aaatacggta | tcaactacca | caaggtgat | atcagagctt | tgttgtgtga acaatctgac | 3360 |
| aaggctttct | actcttcctt | catggctttg | atgtccttga | tgttgcaaat gagaaactcc | 3420 |
| atcactggta | gaactgatgt | cgacttcctc | atttctccag | ttaagaattc tgacggtatt | 3480 |
| ttctacgact | ctagaaatta | cgaagctcaa | gaaaacgcta | ttttgccaaa gaacgctgat | 3540 |
| gctaacggtg | cttacaatat | tgctagaaag | gttttgtggg | ctatcggtca attcaagaag | 3600 |
| gctgaagacg | aaaagctaga | caaggtcaag | attgctattt | ctaacaagga atggttggaa | 3660 |
| tacgctcaaa | cctccgtcaa | gcactccaga | gctgatccaa | agaagaagag aaaggtataa | 3720 |

<210> SEQ ID NO 80
<211> LENGTH: 3936
<212> TYPE: DNA
<213> ORGANISM: Artificial Sequence
<220> FEATURE:
<223> OTHER INFORMATION: Nucleotide sequence of CPO FnCpf1 including a
      C-terminal NLS

<400> SEQUENCE: 80

| | | | | |
|---|---|---|---|---|
| atgtccatct | accaagagtt | tgtcaacaaa | tactctttgt | ctaagacttt acgtttcgaa | 60 |
| ttgattccac | aaggtaagac | tttggaaaac | attaaggctc | gtggtttgat cttggacgac | 120 |
| gaaaagagag | ccaaggatta | caagaaggcc | aagcaaatca | tcgataagta ccaccaattc | 180 |
| ttcattgaag | aaatcttatc | ctctgtctgt | atctccgaag | atctattgca aaactactcc | 240 |
| gatgtctact | tcaagttgaa | aaagtctgac | gatgacaact | tgcaaaagga tttcaaatct | 300 |
| gccaaggaca | ccatcaagaa | acaaattct | gaatacataa | aggactctga aaaatttaag | 360 |
| aacttattca | accaaaactt | gatcgatgct | aagaagggtc | aagaatctga cttgatcttg | 420 |
| tggttgaagc | aatctaagga | caacggtatc | gaattgttca | aggctaactc tgatatcact | 480 |

```
gacattgacg aagctttgga aatcatcaag tctttcaaag gttggactac ctatttcaag    540
ggtttccacg aaaaccgtaa gaatgtctac tcttccaacg acatcccaac ttccatcatt    600
tacagaatcg ttgacgacaa tttgccaaag ttcctagaaa acaaggccaa atacgaatcc    660
ttgaaggaca aggctccaga agccattaac tacgaacaaa tcaagaagga cttggctgaa    720
gaattaactt tcgacattga ctacaagact tctgaagtta accaaagagt tttctctttg    780
gacgaagtct tcgagattgc taacttcaac aactacttga accaatctgg tatcaccaaa    840
ttcaacacca tcatcggtgg taagttcgtc aacggtgaaa acaccaagag aaagggtatc    900
aacgaataca ttaacttgta ctctcagcaa atcaacgaca agactttaaa gaaatacaag    960
atgtctgttt tgttcaagca aattttgtct gacactgaat ccaagtcttt tgtcattgat   1020
aagttggaag atgattccga cgtcgttacc accatgcaat cttttctacga gcaaatcgct   1080 gctttcaaga ccgttgaaga aaagtctatt aaggaaactt tgtctttgtt gttcgacgat   1140
ttgaaggctc aaaagttgga tttgtccaag atttacttca agaatgacaa gtctttgact   1200
gatttgtctc aacaagtttt cgatgactac tccgttattg gtactgctgt cttggaatac   1260
atcacccaac aaatcgctcc taagaacttg acaacccat ccaagaagga acaagaattg   1320
attgccaaga agaccgaaaa agctaaatac ttgtctttgg aaaccattaa attggcttta   1380
gaagagttca acaagcacag agatattgac aagcaatgta gattcgaaga aattttggct   1440
aacttcgctg ctatcccaat gatcttcgac gaaattgctc aaaacaagga taacttggct   1500
caaatctcca tcaagtacca aaaccagggt aagaaggatt tgttgcaagc ctccgctgaa   1560
gatgacgtca aggccatcaa agattattg gaccaaacta caacttgtt gcacaagcta   1620 aagatcttcc acatctctca atctgaagat aaagctaaca ttttggataa ggacgaacac   1680
ttctacttag ttttcgaaga atgttacttc gaactagcta acatcgtccc attgtacaac   1740
aagatcagaa actacattac tcaaaaacca tactctgatg aaaagttcaa gttaaacttc   1800
gaaaattcta ccttggctaa cggttgggac aagaacaaag aaccagacaa caccgccatc   1860
ttgttcatta aggacgacaa gtactacttg ggtgtcatga acaaaaagaa caataagatt   1920
ttcgacgaca aagctatcaa ggagaacaag ggtgaagggt acaagaagat tgtttataag   1980
ttgttgccag gtgctaacaa aatgttgcca aaggttttct tctccgctaa gtctatcaag   2040
ttctataacc cttctgaaga cattttgaga atcagaaacc actccaccca caccaagaac   2100
ggttctccac aaaagggtta cgaaaagttc gaattcaaca tcgaagactg tagaaagttc   2160
atcgatttct acaagcaatc catttccaag catccagaat ggaaggattt cggtttcaga   2220
ttctctgaca ctcaaagata caactccatt gatgaattct acagagaagt cgaaaaccaa   2280
ggttacaagt tgactttcga aaacatctct gaatcttaca ttgattccgt cgttaaccaa   2340
ggtaagttgt acttgttcca aatctacaac aaggacttct ccgcctactc caagggtaga   2400
ccaaacttgc acaccttgta ctggaaggct ttgtttgacg aaagaaactt gcaagatgtt   2460
gtctacaagc tgaacggtga agctgaattg ttttacagaa agcaaagtat tccaaagaaa   2520
atcactcacc cagctaagga agccattgcc aacaagaata aagacaaccc taagaaggaa   2580
tctgtttttg aatacgactt aatcaaggat aagagattca ccgaagacaa attcttcttc   2640
cattgtccaa tcaccatcaa cttcaagtcc tctggagcta acaagttcaa cgatgaaatc   2700
aacttgttat tgaaggaaaa ggctaacgat gttcacatct tgtctatcga tcgtggtgaa   2760
agacacttgg cttactacac ttttggttgat ggtaagggta acatcattaa gcaagacacc   2820
tttaacatta tcggtaacga cagaatgaag accaactacc acgacaaatt ggctgctatt   2880
```

```
gaaaaggaca gagactctgc tagaaaggac tggaaaaaga tcaataacat caaggaaatg    2940
aaggaaggtt acttgtctca agttgtccat gaaattgcta agttggttat cgaatacaat    3000
gctatcgttg tcttcgagga tttgaacttc ggttttaaga gaggtagatt caaggttgaa    3060
aagcaagttt accaaaaatt ggaaaagatg ttgattgaaa agttgaacta cttagtcttc    3120
aaggacaatg aatttgacaa gactggtggt gtcttgagag cttaccaatt gactgctcca    3180
ttcgaaactt caagaagat gggtaagcaa accggtatca tctactacgt tccagctggt    3240
ttcacttcta aaatctgtcc agttaccggt ttcgtcaacc aattgtaccc aaagtacgaa    3300
tccgttttca gtcccaaga atttttctcc aagttcgaca agatctgtta caacttagac    3360
aagggttatt tcgagttttc cttcgattac aaaaactttg gtgacaaagc cgctaagggt    3420
aaatggacta tcgcttcttt cggttctaga ttgatcaact tccgtaactc cgataagaac    3480
cacaactggg acactagaga agtttaccca accaaggaat tagaaaaatt gttgaaggac    3540
tactctattg aatacggtca cggtgaatgt atcaaggctg ccatctgtgg tgaatctgat    3600
aagaagttct tcgctaagct aacttccgtc ttgaacacca ttttgcaaat gagaaactcc    3660
aagaccggta ctgaattgga ctacttgatt tctccagttg ccgatgttaa cggtaacttc    3720
ttcgactcta gacaagctcc aaagaacatg ccacaagacg ctgatgctaa cggtgcctac    3780
cacattggtt tgaagggttt gatgttgttg ggtcgtatta agaacaacca agaaggtaag    3840
aagttgaacc tagtcattaa gaacgaagaa tacttcgaat tgttcaaaa cagaaacaac    3900 tccagagctg acccaaagaa gaagagaaaa gtctaa                              3936

<210> SEQ ID NO 81
<211> LENGTH: 69
<212> TYPE: DNA
<213> ORGANISM: Artificial Sequence
<220> FEATURE:
<223> OTHER INFORMATION: FW primer to amplify AsCpf1 expression cassette

<400> SEQUENCE: 81
cctcatagaa tattattctt cagtcactcg cttaaatact tatcaaaaat gacccaattt    60
gaaggtttc                                                            69

<210> SEQ ID NO 82
<211> LENGTH: 77
<212> TYPE: DNA
<213> ORGANISM: Artificial Sequence
<220> FEATURE:
<223> OTHER INFORMATION: REV primer to amplify AsCpf1 expression
      cassette

<400> SEQUENCE: 82
gtataattat ttgtgggaac ggctctagaa aagaaaactt tgcctttaac tcctttatac    60
ctttctcttc ttctttg                                                   77

<210> SEQ ID NO 83
<211> LENGTH: 69
<212> TYPE: DNA
<213> ORGANISM: Artificial Sequence
<220> FEATURE:
<223> OTHER INFORMATION: FW primer to amplify LbCpf1 expression cassette

<400> SEQUENCE: 83
cctcatagaa tattattctt cagtcactcg cttaaatact tatcaaaaat gtctaagttg    60
gaaaaattc                                                            69
```

<210> SEQ ID NO 84
<211> LENGTH: 74
<212> TYPE: DNA
<213> ORGANISM: Artificial Sequence
<220> FEATURE:
<223> OTHER INFORMATION: REV primer to amplify LbCpf1 expression
      cassette

<400> SEQUENCE: 84
cgtataatta tttgtgggaa cggctctaga aaagaaaact ttgcctttaa ctcctttata    60
cctttctctt cttc    74

<210> SEQ ID NO 85
<211> LENGTH: 70
<212> TYPE: DNA
<213> ORGANISM: Artificial Sequence
<220> FEATURE:
<223> OTHER INFORMATION: FW primer to amplify FnCpf1 expression cassette

<400> SEQUENCE: 85
cctcatagaa tattattctt cagtcactcg cttaaatact tatcaaaaat gtccatctac    60
caagagtttg    70

<210> SEQ ID NO 86
<211> LENGTH: 78
<212> TYPE: DNA
<213> ORGANISM: Artificial Sequence
<220> FEATURE:
<223> OTHER INFORMATION: REV primer to amplify FnCpf1 expression
      cassette

<400> SEQUENCE: 86
cgtataatta tttgtgggaa cggctctaga aaagaaaact ttgcctttaa ctcctttaga    60
cttttctctt cttctttg    78

<210> SEQ ID NO 87
<211> LENGTH: 11559
<212> TYPE: DNA
<213> ORGANISM: Artificial Sequence
<220> FEATURE:
<223> OTHER INFORMATION: Vector pCSN066 encoding AsCpf1

<400> SEQUENCE: 87
tcgcgcgttt cggtgatgac ggtgaaaacc tctgacacat gcagctcccg gagacggtca    60
cagcttgtct gtaagcggat gccgggagca gacaagcccg tcaggcgcgc tcagcgggtg   120
ttggcgggtg tcggggctgg cttaactatg cggcatcaga gcagattgta ctgagagtgc   180
accataaacg acattactat atatataata taggaagcat taatagaca gcatcgtaat    240 atatgtgtac tttgcagtta tgacgccaga tggcagtagt ggaagatatt ctttattgaa    300
aaatagcttg tcaccttacg tacaatcttg atccggagct tttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga agtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720

```
ttttggctct ggtcaatgat tacggcattg atatcgtcca actgcatgga gatgagtcgt      780
ggcaagaata ccaagagttc ctcggtttgc cagttattaa aagactcgta tttccaaaag      840
actgcaacat actactcagt gcagcttcac agaaacctca ttcgtttatt cccttgtttg      900
attcagaagc aggtgggaca ggtgaacttt tggattggaa ctcgatttct gactgggttg      960
gaaggcaaga gagccccgaa agcttacatt ttatgttagc tggtggactg acgccagaaa     1020
atgttggtga tgcgcttaga ttaaatggcg ttattggtgt tgatgtaagc ggaggtgtgg     1080
agacaaatgg tgtaaaagac tctaacaaaa tagcaaattt cgtcaaaaat gctaagaaat     1140
aggttattac tgagtagtat ttatttaagt attgtttgtg cacttgccta tgcggtgtga     1200
aataccgcac agatgcgtaa ggagaaaata ccgcatcagg aaattgtaaa cgttaatatt     1260
ttgttaaaat tcgcgttaaa ttttttgttaa atcagctcat tttttaaccca ataggccgaa     1320 atcggcaaaa tcccttataa atcaaaagaa tagaccgaga tagggttgag tgttgttcca     1380
gtttggaaca agagtccact attaaagaac gtggactcca acgtcaaagg gcgaaaaacc     1440
gtctatcagg gcgatggccc actacgtgaa ccatcaccct aatcaagttt ttgggggtcg     1500
aggtgccgta agcactaaa tcggaaccct aaagggagcc cccgatttag agcttgacgg     1560
ggaaagccgg cgaacgtggc gagaaaggaa gggaagaaag cgaaaggagc gggcgctagg     1620
gcgctggcaa gtgtagcggt cacgctgcgc gtaaccacca cacccgccgc gcttaatgcg     1680
ccgctacagg gcgcgtcgcg ccattcgcca ttcaggctgc gcaactgttg ggaagggcga     1740
tcggtgcggg cctcttcgct attacgccag ctggcgaaag ggggatgtgc tgcaaggcga     1800
ttaagttggg taacgccagg gttttcccag tcacgacgtt gtaaaacgac ggccagtgag     1860
cgcgcgtaat acgactcact ataggggcgaa ttgggtacct tttcttttttt tgcggtcacc     1920 cccatgtggc ggggaggcag aggagtaggt agagcaacga atcctactat ttatccaaat     1980
tagtctagga actcttttc tagattttt agattgagg gcaagcgctg ttaacgactc     2040
agaaatgtaa gcactacgga gtagaacgag aaatccgcca taggtggaaa tcctagcaaa     2100
atcttgctta ccctagctag cctcaggtaa gctagcctta gcctgtcaaa ttttttttcaa     2160 aatttggtaa gtttctacta gcaaagcaaa cacggttcaa caaaccgaaa actccactca     2220
ttatacgtgg aaaccgaaac aaaaaaacaa aaaccaaaat actcgccaat gagaaagttg     2280
ctgcgtttct actttcgagg aagaggaact gagaggattg actacgaaag gggcaaaaac     2340
gagtcgtatt ctcccattat tgtctgctac cacgcggtct agtagaataa gcaaccagtc     2400
aacgctaaga caggtaatca aaataccagt ctgctggcta cgggctagtt tttacctctt     2460
ttagaaccca ctgtaaaagt ccgttgtaaa gcccgttctc actgttggcg ttttttttt     2520 tttggtttag tttcttattt ttcatttttt tctttcatga ccaaaaacaa acaaatctcg     2580
cgatttgtac tgcggccact ggggcgtggc caaaaaaatg acaaatttag aaaccttagt     2640
ttctgatttt tcctgttatg aggagatatg ataaaaaata ttactgcttt attgttttt     2700 ttttatctac tgaaatagag aaacttaccc aaggaggagg caaaaaaag agtatatata     2760 cagcagctac cattcagatt ttaatatatt cttttctctt cttctacact attattataa     2820
taattttact atattcattt ttagcttaaa acctcataga atattattct tcagtcactc     2880
gcttaaatac ttatcaaaaa tgacccaatt tgaaggtttc actaacttgt accaagtttc     2940
taagacttta agatttgaat tgattccaca aggtaagact ttgaagcata tccaagaaca     3000
aggtttcatc gaagaagaca aggctagaaa cgaccattac aaggaattga agccaattat     3060
cgatcgtatt tacaagacct acgctgacca atgtttgcaa ttggttcaat tggactggga     3120
```

```
aaacttatct gctgctattg attcctacag aaaagaaaag actgaagaaa ctagaaacgc    3180
cttgattgaa gaacaagcta cctaccgtaa tgccattcac gattatttca tcggtagaac    3240
tgacaacttg actgatgcta tcaacaaacg tcacgctgaa atctacaagg gtttgttcaa    3300
ggctgaattg ttcaacggta aagtcttgaa acaattgggt actgtcacca ccactgaaca    3360
cgaaaacgcc ttattaagat cctttgacaa gttcaccacc tacttctctg gtttctacga    3420
aaacagaaag aacgtcttct ccgctgaaga tatctctacc gctattccac acagaattgt    3480
ccaagataac ttcccaaagt ttaaagaaaa ctgtcacatt ttcaccagat tgatcactgc    3540
tgttccatct ttgagagaac acttcgaaaa cgtcaagaag gccatcggta ttttcgtttc    3600
tacctctatt gaagaagtct tctctttccc attctacaac caattattga ctcaaaccca    3660
aattgatttg tacaaccaac tattgggtgg tatttccaga gaagctggta ctgaaaagat    3720
taagggtttg aacgaagttt taaacttggc tatccaaaag aacgatgaaa ctgctcacat    3780
cattgcttct ttgccacacc gtttcattcc attgttcaaa caattttgt ccgacagaaa     3840
cactttgtcc ttcatttggg aagaattcaa gtctgacgaa gaagtcatcc aatctttctg    3900
taaatacaag actttgttgc gtaacgaaaa cgttcttgaa accgctgaag ctttgtttaa    3960
tgaattgaac tccatcgatt tgactcacat cttcatctcc cacaagaagt tggaaaccat    4020
ctcctctgct ttgtgtgatc attgggacac cttgagaaac gctttgtacg aaagaagaat    4080
ctctgaattg actggtaaga tcaccaagtc tgctaaggaa aaggtccaac gttccttgaa    4140
acacgaagat atcaacttgc aagaaatcat ctctgctgct ggtaaggaat tgtctgaagc    4200
cttcaagcaa aagacttctg aaatcttatc ccacgctcac gctgctttgg accaaccatt    4260
gccaaccact ttgaagaagc aagaagaaaa agaaatcttg aaatctcaat tggattctct    4320
attgggtttg taccatttgt tggactggtt cgctgtcgac gaatctaacg aagtcgaccc    4380
agaattctcc gccagattga ccggcatcaa gttggagatg gaaccatctt tgtctttcta    4440
caacaaggct cgtaactacg ccaccaagaa gccatactct gttgaaaaat tcaagttaaa    4500
cttccaaatg ccaactttgg cctctggttg ggacgtcaac aaggaaaaga caacggtgc     4560
catcttattc gttaagaacg gtttatacta cttgggtatt atgccaaagc aaaagggtag    4620
atacaaggct ttatctttcg aacctaccga aaagacctcc gaaggtttcg acaagatgta    4680
ctacgattac tttcctgatg ctgctaagat gatcccaaag tgttctactc aattaaaggc    4740
tgtcactgct cacttccaaa ctcacaccac tccaatcttg ttgtccaaca acttcatcga    4800
accattggaa aattactaag aaatttacga cttgaacaac ccagaaaagg aaccaaagaa    4860
attccaaacc gcttacgcca agaagaccgg tgaccaaaag ggttacagag aagccttgtg    4920
taaatggatt gacttcacca gagacttctt gtccaaatac accaagacta cttctatcga    4980
tttgtcttct ctaagaccat cctctcaata caaggacttg ggtgaatact acgctgaatt    5040
gaatccatta ttgtaccaca tctccttcca agaatcgct gaaaagaga ttatggacgc      5100
tgttgaaact ggtaagttgt acttgttcca aatttacaac aaagatttcg ccaagggtca    5160
ccacggtaag ccaaacttgc acactttgta ctggaccggt ttgttctctc cagaaaacct    5220
agctaagact tctatcaagt tgaacggtca agccgaattg ttctacagac caaagtccag    5280
aatgaagaga atggctcaca gattgggtga aaagatgttg aacaagaaat tgaaggacca    5340
aaagaccccca atcccagaca ctttatacca agaattgtac gattatgtca accaccgttt    5400
gtcccacgac ttgtctgatg aagccagagc tttgttacca aacgtcatca ccaaggaagt    5460
```

```
ttctcacgaa atcattaagg acagaagatt cacctccgac aaattcttct tccatgtccc    5520
aattactttg aattaccaag ctgctaactc cccatctaag ttcaaccaaa gagtcaacgc    5580
ttacttgaag gaacaccctg aaacccccaat catcggtatc gatagaggtg aaagaaactt  5640
gatttacatt actgtcatcg attccaccgg taagatcttg aacaaagat ccttgaacac    5700 cattcaacaa tttgattacc aaaagaagct agacaaccgt gaaaaggaaa gagttgctgc   5760
cagacaagct tggtccgttg tcggtactat caaggatttg aagcaaggtt acttgtctca   5820
agttatccac gaaatcgtcg acttgatgat ccactaccaa gccgtcgtcg ttctagaaaa   5880
cttaaacttc ggttttaagt ctaagagaac cggtattgct gagaaggctg tttaccaaca   5940
attcgaaaag atgctaattg acaaattgaa ctgtttggtc ttgaaggatt acccagccga   6000
aaaggttggt ggtgttttga acccatacca attgaccgac caattcacct ctttcgctaa   6060
gatgggtact caatctgggt tcttgttcta cgttccagcc ccttacacct ccaagattga   6120
cccattgacc ggtttcgttg atccattcgt ctggaagacc atcaagaacc acgaatctcg   6180
taaacatttc ttggaaggtt ttgacttctt gcactacgg gttaagactg gtgatttcat    6240
cttgcacttc aagatgaaca gaaacttgtc tttccaaaga ggtttgccag gtttcatgcc   6300
agcttgggat atcgttttcg agaagaacga aactcaattc gacgctaagg gtactccatt   6360
tatcgctggt aagagaatcg ttccagttat cgaaaaccac agattcaccg gtagataccg   6420
tgacttgtac ccagccaacg aattgattgc tttgttggaa gaaagggta ttgttttcag    6480 agacggttcc aacatcttac caaaattgtt ggaaaacgat gactctcacg ctatcgacac   6540
catggttgcc ttgattagat ccgtcttaca aatgagaaac tctaacgctg ctactggtga   6600
ggactacatt aactctccag ttagagactt gaacggtgtt tgtttcgact ccagattcca   6660
aaacccagaa tggccaatgg atgctgacgc taacggtgct tacccacattg ctttgaaggg  6720 tcaattgttg ttgaaccatt tgaaggaatc taaggacttg aagttgcaaa acggtatctc   6780
caaccaagac tggttggctt acatccaaga attaagaaac tccagagctg acccaaagaa   6840
gaagagaaag gtataaagga gttaaaggca agttttctt ttctagagcc gttcccacaa    6900
ataattatac gtatatgctt ctttcgtttt actatatc tatatttaca agcctttatt     6960
cactgatgca atttgtttcc aaatactttt ttggagatct cataactaga tatcatgatg   7020
gcgcaacttg gcgctatctt aattactctg gctgccaggc ccgtgtagag ggccgcaaga   7080
ccttctgtac gccatatagt ctctaagaac ttgaacaagt ttctagacct attgccgcct   7140
ttcggatcgc tattgttgcg gccgccagct gaagcttcgt acgctgcagg tcgacgaatt   7200
ctaccgttcg tataatgtat gctatacgaa gttatagatc tgtttagctt gcctcgtccc   7260
cgccgggtca cccggccagc gacatggagg cccagaatac cctccttgac agtcttgacg   7320
tgcgcagctc aggggcatga tgtgactgtc gcccgtacat ttagcccata catccccatg   7380
tataatcatt tgcatccata cattttgatg gccgcacggc gcgaagcaaa aattacggct   7440
cctcgctgca gacctgcgag cagggaaacg ctcccctcac agacgcgttg aattgtcccc   7500
acgccgcgcc cctgtagaga aatataaaag gttaggattt gccactgagg ttcttctttc   7560
atatacttcc ttttaaaatc ttgctaggat acagttctca catcacatcc gaacataaac   7620
aaccatgggt aaggaaaaga ctcacgtttc gaggccgcga ttaaattcca acatggatgc   7680
tgatttatat gggtataaat gggctcgcga taatgtcggg caatcaggtg cgacaatcta   7740
tcgattgtat gggaagcccg atgcgccaga gttgtttctg aaacatggca aaggtagcgt   7800
tgccaatgat gttacagatg agatggtcag actaaactgg ctgacggaat ttatgcctct   7860
```

```
tccgaccatc aagcatttta tccgtactcc tgatgatgca tggttactca ccactgcgat    7920
ccccggcaaa acagcattcc aggtattaga agaatatcct gattcaggtg aaaatattgt    7980
tgatgcgctg gcagtgttcc tgcgccggtt gcattcgatt cctgtttgta attgtccttt    8040
taacagcgat cgcgtatttc gtctcgctca ggcgcaatca cgaatgaata acggtttggt    8100
tgatgcgagt gattttgatg acgagcgtaa tggctggcct gttgaacaag tctggaaaga    8160
aatgcataag cttttgccat tctcaccgga ttcagtcgtc actcatggtg atttctcact    8220
tgataacctt atttttgacg aggggaaatt aataggttgt attgatgttg acgagtcgg    8280 aatcgcagac cgataccagg atcttgccat cctatggaac tgcctcggtg agttttctcc    8340
ttcattacag aaacggcttt ttcaaaaata tggtattgat aatcctgata tgaataaatt    8400
gcagtttcat ttgatgctcg atgagttttt ctaatcagta ctgacaataa aaagattctt    8460
gttttcaaga acttgtcatt tgtatagttt ttttatattg tagttgttct attttaatca    8520
aatgttagcg tgatttatat ttttttttcgc ctcgacatca tctgcccaga tgcgaagtta    8580
agtgcgcaga aagtaatatc atgcgtcaat cgtatgtgaa tgctggtcgc tatactgctg    8640
tcgattcgat actaacgccg ccatccagtg tcgaaaacga gctcataact tcgtataatg    8700
tatgctatac gaacggtaga attcgaatca gatccactag tggcctatgc ggccgccacc    8760
gcggtggagc tccagctttt gttcccttta gtgagggtta attgcgcgct tggcgtaatc    8820
atggtcatag ctgtttcctg tgtgaaattg ttatccgctc acaattccac acaacatagg    8880
agccggaagc ataaagtgta aagcctgggg tgcctaatga gtgaggtaac tcacattaat    8940
tgcgttgcgc tcactgcccg ctttccagtc gggaaacctg tcgtgccagc tgcattaatg    9000
aatcggccaa cgcgcgggga gaggcggttt gcgtattggg cgctcttccg cttcctcgct    9060
cactgactcg ctgcgctcgg tcgttcggct gcggcgagcg gtatcagctc actcaaaggc    9120
ggtaatacgg ttatccacag aatcagggga taacgcagga agaacatgt gagcaaaagg    9180 ccagcaaaag gccaggaacc gtaaaaaggc cgcgttgctg gcgtttttcc ataggctccg    9240 ccccctgac gagcatcaca aaaatcgacg ctcaagtcag aggtggcgaa acccgacagg    9300
actataaaga taccaggcgt ttccccctgg aagctccctc gtgcgctctc ctgttccgac    9360
cctgccgctt accggatacc tgtccgcctt tctcccttcg ggaagcgtgg cgctttctca    9420
tagctcacgc tgtaggtatc tcagttcggt gtaggtcgtt cgctccaagc tgggctgtgt    9480
gcacgaaccc cccgttcagc ccgaccgctg cgccttatcc ggtaactatc gtcttgagtc    9540
caacccggta agacacgact tatcgccact ggcagcagcc actggtaaca ggattagcag    9600
agcgaggtat gtaggcggtg ctacagagtt cttgaagtgg tggcctaact acggctacac    9660
tagaaggaca gtatttggta tctgcgctct gctgaagcca gttaccttcg gaaaagagt    9720 tggtagctct tgatccggca acaaaccac cgctggtagc ggtggttttt ttgtttgcaa    9780
gcagcagatt acgcgcagaa aaaaaggatc tcaagaagat cctttgatct tttctacggg    9840
gtctgacgct cagtggaacg aaaactcacg ttaagggatt ttggtcatga gattatcaaa    9900
aaggatcttc acctagatcc ttttaaatta aaaatgaagt tttaaatcaa tctaaagtat    9960
atatgagtaa acttggtctg acagttacca atgcttaatc agtgaggcac ctatctcagc    10020
gatctgtcta tttcgttcat ccatagttgc ctgactcccc gtcgtgtaga taactacgat    10080
acgggagggc ttaccatctg gccccagtgc tgcaatgata ccgcgagacc cacgctcacc    10140
ggctccagat ttatcagcaa taaaccagcc agccggaagg gccgagcgca gaagtggtcc    10200
```

| | | | | |
|---|---|---|---|---|
| tgcaacttta | tccgcctcca | tccagtctat | taattgttgc | cgggaagcta gagtaagtag | 10260 |
| ttcgccagtt | aatagtttgc | gcaacgttgt | tgccattgct | acaggcatcg tggtgtcacg | 10320 |
| ctcgtcgttt | ggtatggctt | cattcagctc | cggttcccaa | cgatcaaggc gagttacatg | 10380 |
| atcccccatg | ttgtgcaaaa | aagcggttag | ctccttcggt | cctccgatcg ttgtcagaag | 10440 |
| taagttggcc | gcagtgttat | cactcatggt | tatggcagca | ctgcataatt ctcttactgt | 10500 |
| catgccatcc | gtaagatgct | tttctgtgac | tggtgagtac | tcaaccaagt cattctgaga | 10560 |
| atagtgtatg | cggcgaccga | gttgctcttg | cccggcgtca | atacgggata ataccgcgcc | 10620 |
| acatagcaga | actttaaaag | tgctcatcat | tggaaaacgt | tcttcggggc gaaaactctc | 10680 |
| aaggatctta | ccgctgttga | gatccagttc | gatgtaaccc | actcgtgcac ccaactgatc | 10740 |
| ttcagcatct | tttactttca | ccagcgtttc | tgggtgagca | aaaacaggaa ggcaaaatgc | 10800 |
| cgcaaaaaag | ggaataaggg | cgacacggaa | atgttgaata | ctcatactct tcctttttca | 10860 |
| atattattga | agcatttatc | agggttattg | tctcatgagc | ggatacatat ttgaatgtat | 10920 |
| ttagaaaaat | aaacaaatag | gggttccgcg | cacatttccc | cgaaaagtgc cacctgggtc | 10980 |
| cttttcatca | cgtgctataa | aaataattat | aatttaaatt | ttttaatata aatatataaa | 11040 |
| ttaaaatag | aaagtaaaaa | aagaaattaa | agaaaaaata | gttttgttt tccgaagatg | 11100 |
| taaaagactc | taggggatc | gccaacaaat | actaccttt | atcttgctct tcctgctctc | 11160 |
| aggtattaat | gccgaattgt | ttcatcttgt | ctgtgtagaa | gaccacacac gaaaatcctg | 11220 |
| tgatttaca | ttttacttat | cgttaatcga | atgtatatct | atttaatctg cttttcttgt | 11280 |
| ctaataaata | tatatgtaaa | gtacgctttt | tgttgaaatt | ttttaaacct tgtttattt | 11340 |
| tttttcttc | attccgtaac | tcttctacct | tctttattta | ctttctaaaa tccaaataca | 11400 |
| aaacataaaa | ataaataaac | acagagtaaa | ttcccaaatt | attccatcat taaaagatac | 11460 |
| gaggcgcgtg | taagttacag | gcaagcgatc | cgtcctaaga | aaccattatt atcatgacat | 11520 |
| taacctataa | aaataggcgt | atcacgaggc | cctttcgtc | | 11559 |

<210> SEQ ID NO 88
<211> LENGTH: 11322
<212> TYPE: DNA
<213> ORGANISM: Artificial Sequence
<220> FEATURE:
<223> OTHER INFORMATION: Vector pCSN067 encoding LbCpf1

<400> SEQUENCE: 88

| | | | | |
|---|---|---|---|---|
| tcgcgcgttt | cggtgatgac | ggtgaaaacc | tctgacacat | gcagctcccg gagacggtca | 60 |
| cagcttgtct | gtaagcggat | gccgggagca | gacaagcccg | tcagggcgcg tcagcgggtg | 120 |
| ttggcgggtg | tcgggctgg | cttaactatg | cggcatcaga | gcagattgta ctgagagtgc | 180 |
| accataaacg | acattactat | atatataata | taggaagcat | ttaatagaca gcatcgtaat | 240 |
| atatgtgtac | tttgcagtta | tgacgccaga | tggcagtagt | ggaagatatt ctttattgaa | 300 |
| aaatagcttg | tcaccttacg | tacaatcttg | atccggagct | tttctttttt tgccgattaa | 360 |
| gaattaattc | ggtcgaaaaa | agaaaaggag | agggccaaga | gggagggcat tggtgactat | 420 |
| tgagcacgtg | agtatacgtg | attaagcaca | caaaggcagc | ttggagtatg tctgttatta | 480 |
| atttcacagg | tagttctggt | ccattggtga | aagtttgcgg | cttgcagagc acagaggccg | 540 |
| cagaatgtgc | tctagattcc | gatgctgact | tgctgggtat | tatatgtgtg cccaatagaa | 600 |
| agagaacaat | tgacccggtt | attgcaagga | aaatttcaag | tcttgtaaaa gcatataaaa | 660 |
| atagttcagg | cactccgaaa | tacttggttg | gcgtgtttcg | taatcaacct aaggaggatg | 720 |

```
ttttggctct ggtcaatgat tacggcattg atatcgtcca actgcatgga gatgagtcgt    780
ggcaagaata ccaagagttc ctcggttttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttgttaa atcagctcat ttttttaacca ataggccgaa    1320
atcggcaaaa tcccttataa atcaaagaa tagaccgaga tagggttgag tgttgttcca    1380
gtttggaaca agagtccact attaaagaac gtggactcca acgtcaaagg gcgaaaaacc   1440
gtctatcagg gcgatggccc actacgtgaa ccatcaccct aatcaagttt ttggggtcg    1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact ataggggaa ttgggtacct tttcttttt tgcggtcacc    1920
cccatgtggc ggggaggcag aggagtaggt agagcaacga atcctactat ttatccaaat   1980
tagtctagga actcttttc tagattttt agattttgagg gcaagcgctg ttaacgactc    2040
agaaatgtaa gcactacgga gtagaacgag aaatccgcca taggtggaaa tcctagcaaa   2100
atcttgctta ccctagctag cctcaggtaa gctagcctta gcctgtcaaa ttttttttcaa   2160
aatttggtaa gtttctacta gcaaagcaaa cacggttcaa caaaccgaaa actccactca   2220
ttatacgtgg aaaccgaaac aaaaaaacaa aaaccaaaat actcgccaat gagaaagttg   2280
ctgcgtttct actttcgagg aagaggaact gagaggattg actacgaaag gggcaaaaac   2340
gagtcgtatt ctcccattat tgtctgctac cacgcggtct agtagaataa gcaaccagtc   2400
aacgctaaga caggtaatca aaataccagt ctgctggcta cgggctagtt tttacctctt   2460
ttagaaccca ctgtaaaagt ccgttgtaaa gcccgttctc actgttggcg ttttttttt   2520
tttggtttag tttcttattt ttcatttttt tctttcatga ccaaaaacaa acaaatctcg   2580
cgatttgtac tgcggccact ggggcgtggc caaaaaaatg acaaatttag aaaccttagt   2640
ttctgatttt tcctgttatg aggagatatg ataaaaaata ttactgcttt attgttttt    2700
ttttatctac tgaaatagag aaacttaccc aaggaggagg caaaaaaaag agtatatata   2760
cagcagctac cattcagatt ttaatatatt cttttctctt cttctacact attattataa   2820
taatttact atattcattt ttagcttaaa acctcataga atattattct tcagtcactc    2880
gcttaaatac ttatcaaaaa tgtctaagtt ggaaaaattc accaactgtt actctttgtc   2940
taagactttg agattcaagg ccatcccagt tggtaagacc caagaaaaca tcgcacaacaa   3000
gagactatta gttgaagatg aaaagagagc tgaagactac aagggtgtca agaaattgtt   3060
```

-continued

```
ggacagatac tacttgtctt ttatcaacga cgttttgcat tccatcaagc taaagaactt    3120
gaataactac atctctttgt tcagaaagaa gactagaact gaaaaggaaa ataaggaatt    3180
ggaaaacttg gaaatcaact tgagaaagga aattgctaag gctttcaagg gtaatgaagg    3240
ttacaagtct ttattcaaga aagacatcat tgaaaccatt ttgccagaat ttttggatga    3300
taaggatgaa attgctttgg ttaactcttt caacggtttc accactgctt tcactggttt    3360
cttcgacaac agagaaaaca tgttctccga ggaagctaaa tccacttcta ttgctttcag    3420
atgtatcaac gaaaacttga cccgttacat ctctaacatg acattttttg aaaaggtcga    3480
cgccatcttt gacaagcacg aagtccaaga aatcaaggaa aagatcttaa actccgacta    3540
cgatgtcgaa gatttcttcg aaggtgaatt cttcaacttt gttttaaccc aagaaggtat    3600
cgatgtctac aacgccatta tcggtggttt tgtcactgaa tctggtgaaa agatcaaggg    3660
tttgaacgaa tacattaact tgtacaacca aaagaccaaa caaaaattgc caaagttcaa    3720
gccattgtac aagcaagttt tgtctgacag agaatctttg tcttttttacg gtgaagggta    3780 cacctctgac gaagaagtct tggaagtctt cagaaacact ttgaacaaga actctgaaat    3840
cttctcctcc atcaagaagt tagaaaagtt gttcaagaac ttcgatgaat actcttctgc    3900
tggtatcttc gttaagaacg gtccagccat ctctaccatt tctaaggata tctttggtga    3960
atggaacgtc attagagaca aatggaacgc tgaatacgat gacatccatt tgaagaaaaa    4020
ggctgttgtc accgaaaagt acgaagacga cagaagaaaa tccttcaaga gatcggttc    4080 cttctccttg gaacaattac aagaatacgc cgatgccgat tgtccgttg tcgaaaaatt    4140 gaaggaaatt attattcaaa aggttgatga aatttacaaa gtttacggtt cctctgaaaa    4200
gttattcgat gctgatttcg tcttggaaaa gtctttgaag aagaacgacg ctgttgtcgc    4260
tatcatgaag gacttgttgg actctgtcaa atctttcgaa aactatatca aggccttctt    4320
cggtgaaggt aaggaaacta acagagatga atccttctac ggtgactttg tcttggctta    4380
cgatattttg ttgaaggttg accacatcta cgatgccatc agaaactacg ttactcaaaa    4440
gccatactct aaggacaaat tcaagttgta cttccaaaac ccacaattca tgggtggttg    4500
ggataaggac aaggaaactg actacagagc taccattttg agatacggtt ccaagtacta    4560
cttggccatc atggacaaga gtacgccaa gtgtttgcaa aagattgaca aggacgatgt    4620
caacggtaac tacgaaaaga ttaactacaa gttgttgcca ggtccaaaca agatgttgcc    4680 aaaggtttc ttctccaaaa agtggatggc ttactacaac ccatctgaag acatccaaaa    4740
gatctacaag aacggtactt tcaaaaaggg tgacatgttc aacttaaacg actgtcacaa    4800
gttgatcgac ttcttcaagg actccatctc tagatacca aaatggtcca acgcttacga    4860
tttcaacttc tctgaaactg aaaaatacaa ggatattgct ggtttctacc gtgaagtcga    4920
ggaacaaggt tataaggttt ctttcgaatc cgcttctaag aaagaagttg acaaattagt    4980
cgaagaaggt aagttgtaca tgttccaaat ctacaacaaa gatttctccg acaagtctca    5040
cggtactcca aacttgcaca ccatgtactt caagttgcta ttcgatgaaa acaaccacgg    5100
tcaaatcaga ttgtctggtg gtgctgaatt gttcatgaga cgtgcttctc taaagaagga    5160
agaattagtc gtccacccag ctaactctcc aattgccaac aagaacccag acaaccctaa    5220
gaagaccacc actttgtcct acgacgttta caaggacaag agattctccg aagaccaata    5280
cgaattgcac attccaattg ctatcaacaa gtgtccaaag aacatcttca agatcaacac    5340
tgaagtcaga gttttgttaa agcacgatga caacccttac gttattggta tcgaccgtgg    5400
tgaaagaaat ttgttgtaca ttgttgttgt tgacggtaag ggtaacatcg ttgaacaata    5460
```

```
ctccttgaac gaaatcatca acaacttcaa cggtattaga atcaagactg attaccactc    5520
tttgttggat aagaaggaaa aggaacgttt tgaagctcgt caaaactgga cctctattga    5580
aaacatcaaa gaattgaagg ctggttacat cagtcaagtt gtccacaaga tctgtgaatt    5640
ggtcgagaag tacgatgccg ttattgcctt ggaagatttg aactctggtt ttaagaactc    5700
tcgtgtcaag gttgaaaagc aagtctacca aaagttcgaa agatgttaa tcgacaaatt     5760 gaactacatg gttgacaaga atccaaccc atgtgctacc ggtggtgctt tgaaaggtta     5820
ccaaatcacc aacaaattcg aatctttcaa atctatgtcc actcaaaacg ggttcatctt    5880
ctacattcca gcttggttga cctccaagat cgacccatct accggtttcg ttaacttgtt    5940
gaagaccaag tacacttcca ttgctgattc caagaagttc atctcttctt tcgacagaat    6000
catgtacgtt ccagaagaag acttgttcga attcgccttg gactataaga acttctccag    6060
aaccgatgct gactacatta agaaatggaa attgtactcc tacggtaaca gaatcagaat    6120
tttcagaaac ccaaagaaaa acaacgtttt cgattgggaa gaagtttgtt tgacttctgc    6180
ctacaaggaa ttattcaaca aatacggtat caactaccaa caaggtgata tcagagcttt    6240
gttgtgtgaa caatctgaca aggctttcta ctcttccttc atggctttga tgtccttgat    6300
gttgcaaatg agaaactcca tcactggtag aactgatgtc gacttcctca tttctccagt    6360
taagaattct gacggtattt tctacgactc tagaaattac gaagctcaag aaaacgctat    6420
tttgccaaag aacgctgatg ctaacggtgc ttacaatatt gctagaaagg ttttgtgggc    6480
tatcggtcaa ttcaagaagg ctgaagacga aaagctagac aaggtcaaga ttgctatttc    6540
taacaaggaa tggttggaat acgctcaaac ctccgtcaag cactccagag ctgatccaaa    6600
gaagaagaga aaggtataaa ggagttaaag gcaaagtttt cttttctaga gccgttccca    6660
caaataatta tacgtatatg cttctttcg tttactatat atctatattt acaagccttt     6720
attcactgat gcaatttgtt tccaaatact tttttggaga tctcataact agatatcatg    6780
atggcgcaac ttggcgctat cttaattact ctggctgcca ggcccgtgta gagggccgca    6840
agaccttctg tacgccatat agtctctaag aacttgaaca agtttctaga cctattgccg    6900
cctttcggat cgctattgtt gcggccgcca gctgaagctt cgtacgctgc aggtcgacga    6960
attctaccgt tcgtataatg tatgctatac gaagttatag atctgtttag cttgcctcgt    7020
ccccgccggg tcacccggcc agcgacatgg aggcccagaa taccctcctt gacagtcttg    7080
acgtgcgcag ctcaggggca tgatgtgact gtcgcccgta catttagccc atacatcccc    7140
atgtataatc atttgcatcc atacattttg atggccgcac ggcgcgaagc aaaaattacg    7200
gctcctcgct gcagacctgc gagcagggaa acgctcccct cacagacgcg ttgaattgtc    7260
cccacgccgc gcccctgtag agaaatataa aggttaggaa tttgccactg aggttcttct    7320
ttcatatact ccttttttaaa atcttgctag gatacagttc tcacatcaca tccgaacata    7380
aacaaccatg ggtaaggaaa agactcacgt ttcgaggccg cgattaaatt ccaacatgga    7440
tgctgattta tatgggtata aatgggctcg cgataatgtc gggcaatcag gtgcgacaat    7500
ctatcgattg tatgggaagc ccgatgcgcc agagttgttt ctgaaacatg gcaaaggtag    7560
cgttgccaat gatgttacag atgagatggt cagactaaac tggctgacgg aatttatgcc    7620
tcttccgacc atcaagcatt ttatccgtac tcctgatgat gcatggttac tcaccactgc    7680
gatccccggg aaaacagcat tccaggtatt agaagaatat cctgattcag gtgaaaatat    7740
tgttgatgcg ctggcagtgt tcctgcgccg gttgcattcg attcctgttt gtaattgtcc    7800
```

```
ttttaacagc gatcgcgtat ttcgtctcgc tcaggcgcaa tcacgaatga ataacggttt    7860
ggttgatgcg agtgattttg atgacgagcg taatggctgg cctgttgaac aagtctggaa    7920
agaaatgcat aagcttttgc cattctcacc ggattcagtc gtcactcatg gtgatttctc    7980
acttgataac cttattttg acgagggaa attaataggt tgtattgatg ttggacgagt     8040
cggaatcgca gaccgatacc aggatcttgc catcctatgg aactgcctcg gtgagttttc    8100
tccttcatta cagaaacggc ttttcaaaa atatggtatt gataatcctg atatgaataa     8160
attgcagttt catttgatgc tcgatgagtt tttctaatca gtactgacaa taaaaagatt    8220
cttgttttca agaacttgtc atttgtatag tttttttata ttgtagttgt tctattttaa    8280
tcaaatgtta gcgtgattta tatttttttt cgcctcgaca tcatctgccc agatgcgaag    8340
ttaagtgcgc agaaagtaat atcatgcgtc aatcgtatgt gaatgctggt cgctatactg    8400
ctgtcgattc gatactaacg ccgccatcca gtgtcgaaaa cgagctcata acttcgtata    8460
atgtatgcta tacgaacggt agaattcgaa tcagatccac tagtggccta tgcggccgcc    8520
accgcggtgg agctccagct tttgttccct ttagtgaggg ttaattgcgc gcttggcgta    8580
atcatggtca tagctgtttc ctgtgtgaaa ttgttatccg ctcacaattc cacacaacat    8640
aggagccgga agcataaagt gtaaagcctg gggtgcctaa tgagtgaggt aactcacatt    8700
aattgcgttg cgctcactgc ccgctttcca gtcgggaaac ctgtcgtgcc agctgcatta    8760
atgaatcggc caacgcgcgg ggagaggcgg tttgcgtatt gggcgctctt ccgcttcctc    8820
gctcactgac tcgctgcgct cggtcgttcg gctgcggcga gcggtatcag ctcactcaaa    8880
ggcggtaata cggttatcca cagaatcagg ggataacgca ggaaagaaca tgtgagcaaa    8940
aggccagcaa aaggccagga accgtaaaaa ggccgcgttg ctggcgtttt tccataggct    9000
ccgcccccct gacgagcatc acaaaaatcg acgctcaagt cagaggtggc gaaacccgac    9060
aggactataa agataccagg cgtttccccc tggaagctcc ctcgtgcgct ctcctgttcc    9120
gaccctgccg cttaccggat acctgtccgc ctttctccct tcgggaagcg tggcgctttc    9180
tcatagctca cgctgtaggt atctcagttc ggtgtaggtc gttcgctcca agctgggctg    9240
tgtgcacgaa ccccccgttc agcccgaccg ctgcgcctta tccggtaact atcgtcttga    9300
gtccaacccg gtaagacacg acttatcgcc actggcagca gccactggta acaggattag    9360
cagagcgagg tatgtaggcg gtgctacaga gttcttgaag tggtggccta actacggcta    9420
cactagaagg acagtatttg gtatctgcgc tctgctgaag ccagttacct tcggaaaaag    9480
agttggtagc tcttgatccg gcaaacaaac caccgctggt agcggtggtt tttttgtttg    9540
caagcagcag attacgcgca gaaaaaaagg atctcaagaa gatcctttga tcttttctac    9600
ggggtctgac gctcagtgga acgaaaactc acgttaaggg attttggtca tgagattatc    9660
aaaaaggatc ttcacctaga tccttttaaa ttaaaaatga agttttaaat caatctaaag    9720
tatatatgag taaacttggt ctgacagtta ccaatgctta atcagtgagg cacctatctc    9780
agcgatctgt ctatttcgtt catccatagt tgcctgactc cccgtcgtgt agataactac    9840
gatacgggag ggcttaccat ctggccccag tgctgcaatg ataccgcgag acccacgctc    9900
accggctcca gatttatcag caataaacca gccagccgga agggccgagc gcagaagtgg    9960
tcctgcaact ttatccgcct ccatccagtc tattaattgt tgccgggaag ctagagtaag   10020
tagttcgcca gttaatagtt tgcgcaacgt tgttgccatt gctacaggca tcgtggtgtc   10080
acgctcgtcg tttggtatgg cttcattcag ctccggttcc caacgatcaa ggcgagttac   10140
atgatccccc atgttgtgca aaaaagcggt tagctccttc ggtcctccga tcgttgtcag   10200
```

```
aagtaagttg gccgcagtgt tatcactcat ggttatggca gcactgcata attctcttac    10260
tgtcatgcca tccgtaagat gcttttctgt gactggtgag tactcaacca agtcattctg    10320
agaatagtgt atgcggcgac cgagttgctc ttgcccggcg tcaatacggg ataataccgc    10380
gccacatagc agaactttaa aagtgctcat cattggaaaa cgttcttcgg ggcgaaaact    10440
ctcaaggatc ttaccgctgt tgagatccag ttcgatgtaa cccactcgtg cacccaactg    10500
atcttcagca tctttactt tcaccagcgt ttctgggtga gcaaaaacag gaaggcaaaa    10560
tgccgcaaaa aagggaataa gggcgacacg gaaatgttga atactcatac tcttcctttt    10620
tcaatattat tgaagcattt atcagggtta ttgtctcatg agcggataca tatttgaatg    10680
tatttagaaa aataaacaaa tagggggttcc gcgcacattt ccccgaaaag tgccacctgg    10740
gtccttttca tcacgtgcta taaaaataat tataatttaa attttttaat ataaatatat    10800
aaattaaaaa tagaaagtaa aaaaagaaat taaagaaaaa atagttttg ttttccgaag    10860 atgtaaaaga ctctaggggg atcgccaaca aatactacct tttatcttgc tcttcctgct    10920
ctcaggtatt aatgccgaat tgtttcatct tgtctgtgta gaagaccaca cacgaaaatc    10980
ctgtgatttt acattttact tatcgttaat cgaatgtata tctatttaat ctgcttttct    11040
tgtctaataa atatatatgt aaagtacgct ttttgttgaa attttttaaa cctttgttta    11100 ttttttttc ttcattccgt aactcttcta ccttctttat ttactttcta aaatccaaat    11160
acaaaacata aaaataaata aacacagagt aaattcccaa attattccat cattaaaaga    11220
tacgaggcgc gtgtaagtta caggcaagcg atccgtccta agaaaccatt attatcatga    11280
cattaaccta taaaaatagg cgtatcacga ggcccctttcg tc                     11322
```

<210> SEQ ID NO 89
<211> LENGTH: 11538
<212> TYPE: DNA
<213> ORGANISM: Artificial Sequence
<220> FEATURE:
<223> OTHER INFORMATION: Vector pCSN068 encoding FnCpf1

<400> SEQUENCE: 89

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accataaacg acattactat atatataata taggaagcat ttaatagaca gcatcgtaat     240
atatgtgtac tttgcagtta tgacgccaga tggcagtagt ggaagatatt ctttattgaa     300
aaatagcttg tcaccttacg tacaatcttg atccggagct tttctttttt tgccgattaa     360
gaattaattc ggtcgaaaaa agaaaaggag agggccaaga gggagggcat tggtgactat     420
tgagcacgtg agtatacgtg attaagcaca caaaggcagc ttggagtatg tctgttatta     480
atttcacagg tagttctggt ccattggtga agtttgcgg cttgcagagc acagaggccg     540
cagaatgtgc tctagattcc gatgctgact tgctgggtat tatatgtgtg cccaatagaa     600
agagaacaat tgacccggtt attgcaagga aaatttcaag tcttgtaaaa gcatataaaa     660
atagttcagg cactccgaaa tacttggttg gcgtgttcg taatcaacct aaggaggatg     720
ttttggctct ggtcaatgat tacggcattg atatcgtcca actgcatgga gatgagtcgt     780
ggcaagaata ccaagagttc ctcggtttgc cagttattaa aagactcgta tttccaaaag     840
actgcaacat actactcagt gcagcttcac agaaacctca ttcgtttatt cccttgtttg     900
```

```
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt ttgggttcg    1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg gaagggcga    1740
tcggtgcggg cctcttcgct attacgccag ctggcgaaag ggggatgtgc tgcaaggcga   1800
ttaagttggg taacgccagg ttttcccag tcacgacgtt gtaaaacgac ggccagtgag   1860
cgcgcgtaat acgactcact ataggggcgaa ttgggtaccc tttcttttt tgcggtcacc   1920
cccatgtggc ggggaggcag aggagtaggt agagcaacga atcctactat ttatccaaat   1980
tagtctagga actcttttc tagatttttt agatttgagg gcaagcgctg ttaacgactc   2040
agaaatgtaa gcactacgga gtagaacgag aaatccgcca taggtggaaa tcctagcaaa   2100
atcttgctta ccctagctag cctcaggtaa gctagcctta gcctgtcaaa tttttttcaa   2160
aatttggtaa gtttctacta gcaaagcaaa cacggttcaa caaaccgaaa actccactca   2220
ttatacgtgg aaaccgaaac aaaaaaacaa aaaccaaaat actcgccaat gagaaagttg   2280
ctgcgtttct actttcgagg aagaggaact gagaggattg actacgaaag gggcaaaaac   2340
gagtcgtatt ctcccattat tgtctgctac cacgcggtct agtagaataa gcaaccagtc   2400
aacgctaaga caggtaatca aaataccagt ctgctggcta cgggctagtt tttacctctt   2460
ttagaaccca ctgtaaaagt ccgttgtaaa gcccgttctc actgttggcg tttttttttt   2520
tttggtttag tttcttattt tcattttt tctttcatga ccaaaaacaa acaaatctcg   2580
cgatttgtac tgcggccact ggggcgtggc caaaaaaatg acaaatttag aaaccttagt   2640
ttctgatttt tcctgttatg aggagatatg ataaaaaata ttactgcttt attgttttt    2700
ttttatctac tgaaatagag aaacttaccc aaggaggagg caaaaaaaag agtatatata   2760
cagcagctac cattcagatt ttaatatatt cttttctctt cttctacact attattataa   2820
taatttact atattcattt ttagcttaaa acctcataga atattattct tcagtcactc   2880
gcttaaatac ttatcaaaaa tgtccatcta ccaagagttt gtcaacaaat actctttgtc   2940
taagacttta cgtttcgaat tgattccaca aggtaagact ttggaaaaca ttaaggctcg   3000
tggtttgatc ttggacgacg aaaagagagc caaggattac aagaaggcca agcaaatcat   3060
cgataagtac caccaattct tcattgaaga atcttatcc tctgtctgta tctccgaaga   3120
tctattgcaa aactactccg atgtctactt caagttgaaa agtctgacg atgacaactt   3180
gcaaaaggat ttcaaatctg ccaaggacac catcaagaaa caatttctg aatacataaa   3240
ggactctgaa aaatttaaga acttattcaa ccaaaacttg atcgatgcta agaagggtca   3300
```

```
agaatctgac ttgatcttgt ggttgaagca atctaaggac aacggtatcg aattgttcaa    3360
ggctaactct gatatcactg acattgacga agctttggaa atcatcaagt ctttcaaagg    3420
ttggactacc tatttcaagg gtttccacga aaaccgtaag aatgtctact cttccaacga    3480
catcccaact tccatcattt acagaatcgt tgacgacaat ttgccaaagt tcctagaaaa    3540
caaggccaaa tacgaatcct tgaaggacaa ggctccagaa gccattaact acgaacaaat    3600
caagaaggac ttggctgaag aattaacttt cgacattgac tacaagactt ctgaagttaa    3660
ccaaagagtt ttctctttgg acgaagtctt cgagattgct aacttcaaca actacttgaa    3720
ccaatctggt atcaccaaat tcaacaccat catcggtggt aagttcgtca acggtgaaaa    3780
caccaagaga aagggtatca acgaatacat taacttgtac tctcagcaaa tcaacgacaa    3840
gactttaaag aaatacaaga tgtctgtttt gttcaagcaa attttgtctg acactgaatc    3900
caagtctttt gtcattgata agttggaaga tgattccgac gtcgttacca ccatgcaatc    3960
tttctacgag caaatcgctg ctttcaagac cgttgaagaa aagtctatta aggaaacttt    4020
gtctttgttg ttcgacgatt tgaaggctca aaagttggat ttgtccaaga tttacttcaa    4080
gaatgacaag tctttgactg atttgtctca acaagttttc gatgactact ccgttattgg    4140
tactgctgtc ttggaataca tcacccaaca aatcgctcct aagaacttgg acaacccatc    4200
caagaaggaa caagaattga ttgccaagaa gaccgaaaaa gctaaatact tgtctttgga    4260
aaccattaaa ttggctttag aagagttcaa caagcacaga gatattgaca agcaatgtag    4320
attcgaagaa attttggcta acttcgctgc tatcccaatg atcttcgacg aaattgctca    4380
aaacaaggat aacttggctc aaatctccat caagtaccaa aaccagggta agaaggattt    4440
gttgcaagcc tccgctgaag atgacgtcaa ggccatcaaa gatttattgg accaaactaa    4500
caacttgttg cacaagctaa agatcttcca catctctcaa tctgaagata agctaacat    4560 tttggataag gacgaacact tctacttagt tttcgaagaa tgttacttcg aactagctaa    4620
catcgtccca ttgtacaaca agatcagaaa ctacattact caaaaaccat actctgatga    4680
aaagttcaag ttaaacttcg aaaattctac cttggctaac ggttgggaca agaacaaaga    4740
accagacaac accgccatct tgttcattaa ggacgacaag tactacttgg gtgtcatgaa    4800
caaaaagaac aataagattt tcgacgacaa agctatcaag gagaacaagg gtgaagggta    4860
caagaagatt gtttataagt tgttgccagg tgctaacaaa atgttgccaa ggtttttctt    4920
ctccgctaag tctatcaagt tctataaccc ttctgaagac attttgagaa tcagaaacca    4980 ctccaccca accaagaacg ttctccaca aagggttac gaaaagttcg aattcaacat    5040
cgaagactgt agaaagttca tcgatttcta caagcaatcc atttccaagc atccagaatg    5100
gaaggatttc ggtttcagat tctctgacac tcaaagatac aactccattg atgaattcta    5160
cagagaagtc gaaaaccaag gttacaagtt gactttcgaa aacatctctg aatcttacat    5220
tgattccgtc gttaaccaag gtaagttgta cttgttccaa atctacaaca aggacttctc    5280
cgcctactcc aagggtagac caaacttgca caccttgtac tggaaggctt tgtttgacga    5340
aagaaacttg caagatgttg tctacaagct gaacggtgaa gctgaattgt tttacagaaa    5400
gcaaagtatt ccaaagaaaa tcactcaccc agctaaggaa gccattgcca acaagaataa    5460
agacaaccct aagaaggaat ctgtttttga atacgactta atcaaggata agagattcac    5520
cgaagacaaa tccttcttcc attgtccaat caccatcaac ttcaagtcct ctggagctaa    5580
caagttcaac gatgaaatca acttgttatt gaaggaaaag gctaacgatg ttcacatctt    5640
```

```
gtctatcgat cgtggtgaaa gacacttggc ttactacact ttggttgatg gtaagggtaa    5700
catcattaag caagacacct ttaacattat cggtaacgac agaatgaaga ccaactacca    5760
cgacaaattg gctgctattg aaaaggacag agactctgct agaaaggact ggaaaaagat    5820
caataacatc aaggaaatga aggaaggtta cttgtctcaa gttgtccatg aaattgctaa    5880
gttggttatc gaatacaatg ctatcgttgt cttcgaggat ttgaacttcg ttttaagag    5940 aggtagattc aaggttgaaa agcaagttta ccaaaaattg gaaagatgt tgattgaaaa    6000 gttgaactac ttagtcttca aggacaatga atttgacaag actggtggtg tcttgagagc    6060
ttaccaattg actgctccat tcgaaacttt caagaagatg ggtaagcaaa ccggtatcat    6120
ctactacgtt ccagctggtt tcacttctaa atctgtcca gttaccggtt tcgtcaacca    6180
attgtaccca agtacgaat ccgttttccaa gtcccaagaa tttttctcca gttcgacaa    6240 gatctgttac aacttagaca agggttattt cgagttttcc ttcgattaca aaactttgg    6300 tgacaaagcc gctaagggta aatggactat cgcttctttc ggttctagat tgatcaactt    6360
ccgtaactcc gataagaacc acaactggga cactagagaa gtttacccaa ccaaggaatt    6420
agaaaaattg ttgaaggact actctattga atacggtcac ggtgaatgta tcaaggctgc    6480
catctgtggt gaatctgata gaagttctt cgctaagcta acttccgtct tgaacaccat    6540
tttgcaaatg agaaactcca agaccggtac tgaattggac tacttgattt ctccagttgc    6600
cgatgttaac ggtaacttct tcgactctag acaagctcca agaacatgc cacaagacgc    6660 tgatgctaac ggtgcctacc acattggttt gaagggtttg atgttgttgg gtcgtattaa    6720
gaacaaccaa gaaggtaaga agttgaacct agtcattaag aacgaagaat acttcgaatt    6780
tgttcaaaac agaaacaact ccagagctga cccaagaag agagaaaaag tctaaggag    6840 ttaaaggcaa agttttcttt tctagagccg ttcccacaaa taattatacg tatatgcttc    6900
ttttcgttta ctatatatct atatttacaa gcctttattc actgatgcaa tttgtttcca    6960 aatactttt tggagatctc ataactagat atcatgatgg cgcaacttgg cgctatctta    7020
attactctgg ctgccaggcc cgtgtagagg gccgcaagac cttctgtacg ccatatagtc    7080
tctaagaact tgaacaagtt tctagaccta ttgccgcctt tcggatcgct attgttgcgg    7140
ccgccagctg aagcttcgta cgctgcaggt cgacgaattc taccgttcgt ataatgtatg    7200
ctatacgaag ttatagatct gtttagcttg cctcgtcccc gccgggtcac ccggccagcg    7260
acatggaggc ccagaatacc ctccttgaca gtcttgacgt gcgcagctca ggggcatgat    7320
gtgactgtcg cccgtacatt tagcccatac atccccatgt ataatcattt gcatccatac    7380
attttgatgg ccgcacggcg cgaagcaaaa attacggctc ctcgctgcag acctgcgagc    7440
agggaaacgc tccccctcaca gacgcgttga attgtccca cgccgcgccc ctgtagagaa    7500
atataaaagg ttaggatttg ccactgaggt tcttctttca tatacttcct tttaaaatct    7560
tgctaggata cagttctcac atcacatccg aacataaaca accatgggta aggaaaagac    7620
tcacgtttcg aggccgcgat taaattccaa catggatgct gatttatatg gtataaatg    7680 ggctcgcgat aatgtcgggc aatcaggtgc gacaatctat cgattgtatg ggaagcccga    7740
tgcgccagag ttgtttctga acatggcaa aggtagcgtt gccaatgatg ttacagatga    7800
gatggtcaga ctaaactggc tgacggaatt tatgcctctt ccgaccatca agcattttat    7860
ccgtactcct gatgatgcat ggttactcac cactgcgatc cccggcaaaa cagcattcca    7920
ggtattagaa gaatatcctg attcaggtga aaatattgtt gatgcgctgg cagtgttcct    7980
gcgccggttg cattcgattc ctgtttgtaa ttgtcctttt aacagcgatc gcgtatttcg    8040
```

```
tctcgctcag gcgcaatcac gaatgaataa cggtttggtt gatgcgagtg attttgatga    8100
cgagcgtaat ggctggcctg ttgaacaagt ctggaaagaa atgcataagc ttttgccatt    8160
ctcaccggat tcagtcgtca ctcatggtga tttctcactt gataaccttg tttttgacga    8220
ggggaaatta ataggttgta ttgatgttgg acgagtcgga atcgcagacc gataccagga    8280
tcttgccatc ctatggaact gcctcggtga gttttctcct tcattacaga aacggctttt    8340
tcaaaaatat ggtattgata atcctgatat gaataaattg cagtttcatt tgatgctcga    8400 tgagttttc  taatcagtac tgacaataaa aagattcttg ttttcaagaa cttgtcattt    8460
gtatagtttt tttatattgt agttgttcta ttttaatcaa atgttagcgt gatttatatt    8520
ttttttcgcc tcgacatcat ctgcccagat gcgaagttaa gtgcgcagaa agtaatatca    8580
tgcgtcaatc gtatgtgaat gctggtcgct atactgctgt cgattcgata ctaacgccgc    8640
catccagtgt cgaaaacgag ctcataactt cgtataatgt atgctatacg aacggtagaa    8700
ttcgaatcag atccactagt ggcctatgcg gccgccaccg cggtggagct ccagcttttg    8760
ttccctttag tgagggttaa ttgcgcgctt ggcgtaatca tggtcatagc tgtttcctgt    8820
gtgaaattgt tatccgctca caattccaca acatagga  gccggaagca taaagtgtaa    8880
agcctggggt gcctaatgag tgaggtaact cacattaatt gcgttgcgct cactgcccgc    8940
tttccagtcg ggaaacctgt cgtgccagct gcattaatga atcggccaac gcgcggggag    9000
aggcggtttg cgtattgggc gctcttccgc ttcctcgctc actgactcgc tgcgctcggt    9060
cgttcggctg cggcgagcgg tatcagctca ctcaaaggcg gtaatacggt tatccacaga    9120
atcaggggat aacgcaggaa agaacatgtg agcaaaaggc cagcaaaagg ccaggaaccg    9180
taaaaaggcc gcgttgctgg cgttttttcca taggctccgc ccccctgacg agcatcacaa    9240
aaatcgacgc tcaagtcaga ggtggcgaaa cccgacagga ctataaagat accaggcgtt    9300
tccccctgga agctccctcg tgcgctctcc tgttccgacc ctgccgctta ccggatacct    9360
gtccgccttt ctcccttcgg gaagcgtggc gctttctcat agctcacgct gtaggtatct    9420
cagttcggtg taggtcgttc gctccaagct gggctgtgtg cacgaacccc ccgttcagcc    9480
cgaccgctgc gccttatccg gtaactatcg tcttgagtcc aacccggtaa gacacgactt    9540
atcgccactg gcagcagcca ctggtaacag gattagcaga gcgaggtatg taggcggtgc    9600
tacagagttc ttgaagtggt ggcctaacta cggctacact agaaggacag tatttggtat    9660
ctgcgctctg ctgaagccag ttaccttcgg aaaaagagtt ggtagctctt gatccggcaa    9720
acaaaccacc gctggtagcg gtggtttttt tgtttgcaag cagcagatta cgcgcagaaa    9780
aaaaggatct caagaagatc ctttgatctt ttctacgggg tctgacgctc agtggaacga    9840
aaactcacgt taagggattt tggtcatgag attatcaaaa aggatcttca cctagatcct    9900
tttaaattaa aaatgaagtt ttaaatcaat ctaaagtata tatgagtaaa cttggtctga    9960
cagttaccaa tgcttaatca gtgaggcacc tatctcagcg atctgtctat ttcgttcatc    10020
catagttgcc tgactccccg tcgtgtagat aactacgata cgggagggct taccatctgg    10080
ccccagtgct gcaatgatac cgcgagaccc acgctcaccg gctccagatt tatcagcaat    10140
aaaccagcca gccggaaggg ccgagcgcag aagtggtcct gcaactttat ccgcctccat    10200
ccagtctatt aattgttgcc gggaagctag agtaagtagt tcgccagtta atagtttgcg    10260
caacgttgtt gccattgcta caggcatcgt ggtgtcacgc tcgtcgtttg gtatggcttc    10320
attcagctcc ggttcccaac gatcaaggcg agttacatga tccccccatgt tgtgcaaaaa    10380
```

```
agcggttagc tccttcggtc ctccgatcgt tgtcagaagt aagttggccg cagtgttatc    10440
actcatggtt atggcagcac tgcataattc tcttactgtc atgccatccg taagatgctt    10500
ttctgtgact ggtgagtact caaccaagtc attctgagaa tagtgtatgc ggcgaccgag    10560
ttgctcttgc ccggcgtcaa tacgggataa taccgcgcca catagcagaa ctttaaaagt    10620
gctcatcatt ggaaaacgtt cttcggggcg aaaactctca aggatcttac cgctgttgag    10680
atccagttcg atgtaaccca ctcgtgcacc caactgatct tcagcatctt ttactttcac    10740
cagcgtttct gggtgagcaa aacaggaag gcaaaatgcc gcaaaaaagg gaataagggc     10800
gacacggaaa tgttgaatac tcatactctt ccttttcaa tattattgaa gcatttatca    10860
gggttattgt ctcatgagcg gatacatatt tgaatgtatt tagaaaaata aacaaatagg    10920
ggttccgcgc acatttcccc gaaaagtgcc acctgggtcc ttttcatcac gtgctataaa    10980
aataattata atttaaattt tttaatataa atatataaat taaaaataga aagtaaaaaa    11040
agaaattaaa gaaaaaatag tttttgtttt ccgaagatgt aaaagactct aggggggatcg    11100 ccaacaaata ctacctttta tcttgctctt cctgctctca ggtattaatg ccgaattgtt    11160
tcatcttgtc tgtgtagaag accacacacg aaaatcctgt gattttacat tttacttatc    11220
gttaatcgaa tgtatatcta tttaatctgc ttttcttgtc taataaatat atatgtaaag    11280
tacgcttttt gttgaaattt tttaaacctt tgtttatttt tttttcttca ttccgtaact    11340
cttctacctt ctttatttac tttctaaaat ccaaatacaa aacataaaaa taataaaca    11400 cagagtaaat tcccaaatta ttccatcatt aaaagatacg aggcgcgtgt aagttacagg    11460
caagcgatcc gtcctaagaa accattatta tcatgacatt aacctataaa aataggcgta    11520
tcacgaggcc ctttcgtc                                                  11538
```

<210> SEQ ID NO 90
<211> LENGTH: 2540
<212> TYPE: DNA
<213> ORGANISM: Artificial Sequence
<220> FEATURE:
<223> OTHER INFORMATION: CrtE expression cassette (con5-KlTDH2p-crtE-ScTDH3t-conA)

<400> SEQUENCE: 90

```
aagcgacttc caatcgcttt gcatatccag taccacaccc acaggcgttt gtgccgtaaa      60
aactaaaacg agcccccacc aaagaacaaa aagaaggtg ctgggccccc actttcttcc     120
cttgcacgtg ataggaagat ggctacagaa acaagaagat ggaaatcgaa ggaaagaggg     180
agactggaag ctgtaaaaac tgaaatgaaa aaaaaaaaa aaaaaaaaaa caagaagctg     240
aaaatggaag actgaaattt gaaaatggt aaaaaaaaa aagaaacacg aagctaaaaa      300
cctggattcc attttgagaa gaagcaagaa aggtaagtat ggtaacgacc gtacaggcaa     360
gcgcgaaggc aaatggaaaa gctggagtcc ggaagataat catttcatct tctttttgtta    420 gaacagaaca gtggatgtcc ctcatctcgg taacgtattg tccatgccct agaactctct     480
gtccctaaaa agaggacaaa aacccaatgg tttccccagc ttccagtgga gccaccgatc     540
ccactggaaa ccactggaca ggaagagaaa atcacggact tcctctattg aaggataatt     600
caacactttc accagatccc aaatgtcccg cccctattcc cgtgttccat cacgtaccat     660
aacttaccat ttcatcacgt tctctatggc acactggtac tgcttcgact gctttgcttc     720
atcttctcta tgggccaatg agctaatgag cacaatgtgc tgcgaaataa agggatatct     780
aatttatatt attacattat aatatgtact agtgtggtta ttgtaattg tacttaattt     840
```

```
tgatatataa agggtggatc ttttcattt tgaatcagaa ttggaattgc aacttgtctc      900
ttgtcactat tacttaatag taattatatt tcttattaac cttttttta agtcaaaaca      960 ccaaggacaa gaactactct tcaaaggtat ttcaagttat catacgtgtc acacacgctt    1020
cacagtttca gtaaaaaaa aagaatatta cacaatggac tacgctaaca tcttgactgc    1080
cattcctttg gaattcaccc cacaagatga cattgtcttg ttggaaccat accactactt   1140
aggtaagaac ccaggtaagg aaatcagatc tcaattgatt gaagctttca actactggtt    1200
agatgtcaag aaggaagact tggaagttat ccaaaatgtt gttggtatgt tgcacaccgc    1260
ttctttgttg atggatgatg ttgaagattc ttccgtcttg agaagaggtt ctccagttgc    1320
tcatttgatc tacggtattc cacaaaccat caacactgct aactacgttt acttcttggc    1380
ttaccaagaa atcttcaaat tgcgtccaac tccaattcca atgccagtta tcccaccatc    1440
ttctgcttct ttgcaatctt ctgtctcctc cgcctcctct tcctcttctg cctcctctga    1500
aaacggtggt acctccactc caaactccca aatcccattc tccaaggaca cctacttgga    1560
caaggttatc actgacgaaa tgttgtcttt gcaccgtggt caaggtttgg aattattctg    1620
gagagactct ttgacctgtc catctgaaga agaatacgtc aagatggtct tgggtaagac    1680
cggtggtttg ttcagaattg ctgtcagatt gatgatggcc aagtctgaat gtgacattga    1740
ctttgttcaa ttggttaact tgattccat ctacttccaa atcagagatg actacatgaa    1800
cttgcaatcc tctgaatacg ctcacaacaa gaacttcgct gaagacttga ctgaaggtaa    1860
gttctccttc ccaaccattc actccattca cgctaaccca tcttccagat tggttatcaa    1920
cactttacaa aagaagtcca cttctccaga aatcttacat cactgtgtca actacatgag    1980
aactgaaacc cactctttcg aatacactca agaagtcttg aacactttat ctggtgcttt    2040
ggaaagagaa ttgggtagat acaaggtga atttgctgaa gctaactcca agatcgattt    2100
gggtgacgtt gaatctgaag gtagaaccgg taagaacgtc aaattggaag ccatcttgaa    2160
gaaattggct gatatccctc tataaagtga atttacttta atcttgcat ttaaataaat    2220 tttcttttta tagctttatg acttagtttc aatttatata ctatttaat gacattttcg    2280 attcattgat tgaaagcttt gtgttttttc ttgatgcgct attgcattgt tcttgtcttt    2340
ttcgccacat gtaatatctg tagtagatac ctgatacatt gtggatgctg agtgaaattt    2400
tagttaataa tggaggcgct cttaataatt tggggatat tggcttttt ttttaaagtt    2460 tacaaatgaa ttttttccgc aggatcctc ttgcccatcg aacgtacaag tactcctctg    2520
ttctctcctt cctttgcttt                                                 2540

<210> SEQ ID NO 91
<211> LENGTH: 3431
<212> TYPE: DNA
<213> ORGANISM: Artificial Sequence
<220> FEATURE:
<223> OTHER INFORMATION: CrtYB expression cassette (conA-KlTDH2p-crtYB-
      ScPDC1t-conB)

<400> SEQUENCE: 91
ttgcccatcg aacgtacaag tactcctctg ttctctcctt cctttgcttt gtgcttttct      60
ttttttgcgg tcaccccat gtggcgggga ggcagaggag taggtagagc aacgaatcct     120
actatttatc caaattagtc taggaactct tttctagat tttttagatt tgagggcaag     180
cgctgttaac gactcagaaa tgtaagcact acggagtaga acgagaaatc cgccataggt     240
ggaaatccta gcaaaatctt gcttacccta gctagcctca ggtaagctag ccttagcctg     300
```

```
tcaaatttttt ttcaaaattt ggtaagtttc tactagcaaa gcaaacacgg ttcaacaaac    360
cgaaaactcc actcattata cgtggaaacc gaaacaaaaa aacaaaaacc aaaatactcg    420
ccaatgagaa agttgctgcg tttctacttt cgaggaagag gaactgagag gattgactac    480
gaaaggggca aaaacgagtc gtattctccc attattgtct gctaccacgc ggtctagtag    540
aataagcaac cagtcaacgc taagacaggt aatcaaaata ccagtctgct ggctacgggc    600 tagttttttac ctcttttaga acccactgta aaagtccgtt gtaaagcccg ttctcactgt    660
tggcgttttt ttttttttgg tttagtttct tattttttcat ttttttcttt catgaccaaa    720
aacaaacaaa tctcgcgatt tgtactgcgg ccactgggc gtggccaaaa aaatgacaaa    780
tttagaaacc ttagtttctg attttttcctg ttatgaggag atatgataaa aaatattact    840
gctttattgt ttttttttta tctactgaaa tagagaaact tacccaagga ggaggcaaaa    900
aaaagagtat atatacagca ggtaccattc agattttaat atattctttt ctcttcttct    960
acactattat tataataatt ttactatatt catttttagc ttaaaacctc atagaatatt   1020
attcttcagt cactcgctta aatacttatc aaaaatgacc gctttggctt actaccaaat   1080
ccacttgatc tacactttgc caatcttagg tttgctaggt tgttgacttt ctccaattttt   1140 gaccaaattc gacatctaca agatttctat cttagtcttt attgctttct ctgctaccac   1200
tccatgggac tcctggatca tcagaaacgg tgcctggacc tacccatctg ctgaatctgg   1260
tcaaggtgtt ttcggtacct ttttggatgt cccatacgaa gaatacgcct tctttgttat   1320
ccaaaccgtc atcaccggtt tggtttacgt tttggctacc agacatttgt tgccatcttt   1380
ggctctacca aagacccgtt cttctgcctt gtctctagct ttgaaggctt taatcccatt   1440
gccaatcatc tatttgttca ccgctcatcc atctccatcc ccagatcctt tggttactga   1500
ccactacttc tacatgagag ctttgtcttt gttgatcacc ccaccaacca tgttgttggc   1560
tgctttatct ggtgaatacg ctttcgactg gaaatctggt agagctaagt ccaccattgc   1620
tgccatcatg atcccaactg tctacttgat ctgggttgac tacgttgccg ttggtcaaga   1680
ctcctggtcc atcaacgatg aaaagattgt cggttggaga ttaggtggtg tcttgccaat   1740
tgaagaagct atgttcttct tattgaccaa cttgatgatc gttttgggtt tgtctgcctg   1800
tgaccacact caagccttgt acttgttgca cggtagaact atctacggta caagaagat   1860 gccatcttct ttcccattaa tcactccacc agttttgtcc ttgttcttct cctccagacc   1920
atactcctcc caaccaaaga gagatttgga attggctgtc aagttgttgg aaaagaagtc   1980
cagatctttc ttcgttgctt ctgccggttt cccatctgaa gtcagagaaa gattggttgg   2040
tttgtacgct ttctgtcgtg tcaccgatga cttgattgac tctccagaag tttcctccaa   2100
cccacacgct accattgaca tggtttccga tttcttgact ttattattcg gtcctccatt   2160
gcacccatct caaccagaca agattttgtc ttctccatta ttaccacctt cccacccatc   2220
cagaccaact ggtatgtacc cattaccacc acctccatct ttgtctccag ctgaattggt   2280
ccaattcttg actgaacgtg tcccagttca ataccacttc gctttcagat tgttggccaa   2340
attgcaaggt ttgattccaa gatacccatt ggatgaatta ttgagaggtt acaccactga   2400
cttgatcttc ccattgtcca ctgaagccgt ccaagctaga aagacccaa ttgaaactac   2460 tgctgacttg ttggactacg gtttgtgtgt tgccggttct gttgctgaat gttggtcta   2520 cgtttcctgg gcttccgctc catcccaagt tccagctact attgaagaaa gagaagctgt   2580
tttggtcgcc tctcgtgaaa tgggtaccgc tttgcaattg gtcaacattg ccagagatat   2640
caagggtgac gctactgaag gtagattcta cttgccattg tctttctttg gtttgagaga   2700
```

```
tgaatccaaa ttggccattc caactgactg gactgaacca agacctcaag atttcgacaa    2760
attgttgtct ctatctccat cttccacttt accatcctct aacgcttctg aatccttcag    2820
attcgaatgg aagacctact ctttgccatt ggttgcttac gctgaagatt tggctaagca    2880
ctcttacaag ggtattgaca gattaccaac tgaagtccaa gctggtatga gagctgcttg    2940
tgcttcttac ttgttgattg gtcgtgaaat caaggttgtc tggaagggtg atgtcggtga    3000
aagaagaacc gttgctggtt ggagaagagt cagaaaggtt ttgtctgttg tcatgtccgg    3060
ttgggaaggt caataaagcg atttaatctc taattattag ttaaagtttt ataagcattt    3120
ttatgtaacg aaaaataaat tggttcatat tattactgca ctgtcactta ccatggaaag    3180
accagacaag aagttgccga cagtctgttg aattggcctg gttaggctta agtctgggtc    3240
cgcttcttta caaatttgga gaatttctct taaacgatat gtatattctt ttcgttggaa    3300
aagatgtctt ccaaaaaaaa aaccgatgaa ttagtggaac caaggaaaaa aaaagaggta    3360
tccttgatta aggaacacct ccggatcgat gtacacaacc gactgcaccc aaacgaacac    3420
aaatcttagc a                                                         3431

<210> SEQ ID NO 92
<211> LENGTH: 2758
<212> TYPE: DNA
<213> ORGANISM: Artificial Sequence
<220> FEATURE:
<223> OTHER INFORMATION: CrtI expression cassette (conB-ScPRE3p-crtI-
      ScTAL1t-con3)

<400> SEQUENCE: 92
cggatcgatg tacacaaccg actgcaccca acgaacacaca atcttagca gtgccaaaca      60 ttaatttgtt ctgcatactt tgaacctttc agaaaataaa aaacattacg cgcatactta     120
ccctgctcgc gaagaagagt aacactaacg cattctatgg gcaattgaag acagtattca     180
gtacaagaca tagtccgttt ccttgagtca attcctatag cattatgaac tagccgcctt     240
taagagtgcc aagctgttca acaccgatca ttttgatga tttggcgttt tgttatatt      300 gatagatttc tttgaattt tgtcattttc actttccac tcgcaacgga atccggtggc      360
aaaaagggga aaagcattga atgcaatct ttaacagtat ttaaacaag ttgcgacacg      420 gtgtacaatt acgataagaa ttgctacttc aaagtacaca cagaaagtta acatgaatgg     480
aattcaagtg gacatcaatc gtttgaaaaa gggcgaagtc agtttaggta cctcaatgta     540
tgtatataag aatttttcct cccacttat tgtttctaaa agttcaatga agtaaagtct     600
caattggcct tattactaac taataggtat cttataatca cctaataaaa tagaatgggt     660
aaggaacaag accaagacaa gccaactgcc atcatcgttg gttgtggtat cggtggtatt     720
gctaccgctg ccagattagc taaggaaggt ttccaagtta ccgtctttga aaagaacgac     780
tactccggtg gtagatgttc tttgattgaa agagatggtt acagattcga ccaaggtcca     840
tctttgttgc tattaccaga cttgttcaag caaaccttcg aagatttggg tgaaaagatg     900
gaagactggg ttgatttgat caagtgtgaa ccaaactacg tttgtcacttccatgatgaa     960 gaaactttca ccttctccac tgacatggct ttattgaaga gaagtcga aagatttgaa    1020 ggtaaagatg gtttcgacag attcttgtct ttcatccaag aagctcacag acattacgaa    1080
ttggctgttg tccacgtctt gcaaaagaac ttcccaggtt tcgctgcttt cttgagatta    1140
caattcatcg gtcaaatctt agcctttgcac ccatttgaat ccatctggac cagagtttgt    1200
cgttacttca agactgacag attgagaaga gtcttctcct tgccgttat gtacatgggt    1260
```

```
caatctccat actctgctcc aggtacctac tccttgttgc aatacactga attgactgaa     1320
ggtatctggt acccaagagg tggtttctgg caagttccaa acactttgtt gcaaatcgtc     1380
aagagaaaca acccatctgc taagttcaac ttcaacgctc cagtttctca agttttgttg     1440
tctccagcta aggacagagc taccggtgtc agattagaat ctggtgaaga acaccacgct     1500
gatgttgtca ttgtcaatgc tgacttggtc tacgcttctg aacatttgat tccagatgat     1560
gctagaaaca agatcggtca attaggtgaa gttaagcgtt cctggtgggc tgatttggtt     1620
ggtggtaaga agttgaaggg ttcttgttct tctttgtctt tctactggtc tatggacaga     1680
atcgttgacg gtttgggtgg tcacaacatc ttccttggctg aagacttcaa gggttccttc     1740
gacaccattt tcgaagaatt gggtttgcca gctgacccat ctttctatgt taacgttcca     1800
tccagaattg acccttctgc tgctccagaa ggtaaggatg ccattgtcat cttagtccca     1860
tgtggtcaca tcgatgcttc caaccctcaa gactacaaca aattggttgc cagagccaga     1920
aagttcgtca tccaaaacctt gtctgccaag ttgggtctac cagatttcga aaagatgatt     1980
gttgctgaaa aggttcacga tgctccatcc tgggaaaagg aattcaactt gaaggacggt     2040 tccatttttgg gtttggctca aacttcatg caagtcttgg gtttcagacc atccaccaga     2100
cacccaaagt acgacaaatt gttctttgtc ggtgcttcta cccacccagg tactggtgtt     2160
ccaattgtct tggctggtgc caaattgact gctaaccaag ttttggaatc cttcgatcgt     2220
tctccagctc cagatcctaa catgtctttg tctgttccat acggtaagcc attgaaatcc     2280
aacggtactg gtattgactc tcaagtccaa ttgaaattca tggacttgga acgttgggtt     2340
tacctattag tcttgttgat tggtgctgtt atcgccagat ccgtcggtgt cttggccttt     2400
taaaggaagt atctcggaaa tattaattta ggccatgtcc ttatgcacgt ttcttttgat     2460
acttacgggt acatgtacac aagtatatct atatatataa attaatgaaa atcccctatt     2520
tatatatatg actttaacga gacagaacag ttttttatttt tttatcctat ttgatgaatg     2580
atacagtttc ttattcacgt gttatacccca caccaaatcc aatagcaata ccggccatca     2640
caatcactgt ttcggcagcc cctaagatca gacaaaacat ccggaaccac cttaaatcaa     2700
cgtccctcag aaagcctgta tgcgaagcca caatccttttc aacagacca tactaagt       2758
```

<210> SEQ ID NO 93
<211> LENGTH: 577
<212> TYPE: DNA
<213> ORGANISM: Artificial Sequence
<220> FEATURE:
<223> OTHER INFORMATION: INT1 5' flank-Con5

<400> SEQUENCE: 93

```
cactatagca atctggctat atgatatgca gaaaatagtg attactgtgc tctttgctgc       60
atcatgcatc atatgtttgg cattctgtcc tgtcagatga atgggcgaaa caattcgggg      120
agctttgttg cgacttggta cccggcaagc cgcgacctat attttgcatt aaacgagttc      180
atcgtggatt tatcgccatg agccttagct tatcaagcct ctcacagaca attaagcaat      240
gaaaaaggta taccatcggc gcagaatggt taactagtgg gttcatactg ctgtgttata      300
gattgttacc taagtgatca ccaaaaaaaa gtgcaaaaag gaaaaaaaaa taagagacag      360
gtaacttcca caagcttatt cttccaaaaa tcaatcttat cttcatgcca gcaatagttg      420
cgtgctgagc tcaacagtgc ccaacccttg tgcaccgtag aattgtagaa tacaaataca      480
taaataagtg tgttcccgaa ggactaagga atgacggcag aggagtcaag cgacttccaa      540
```
tcgctttgca tatccagtac cacacccaca ggcgttt 577

<210> SEQ ID NO 94
<211> LENGTH: 581
<212> TYPE: DNA
<213> ORGANISM: Artificial Sequence
<220> FEATURE:
<223> OTHER INFORMATION: Con3-INT1 3' flank

<400> SEQUENCE: 94
agaaagcctg tatgcgaagc cacaatcctt tccaacagac catactaagt aagcgttgaa 60
gtttcctctt tgtatatttg agatcttcat tttatcggat tctttgtcat cagacaactt 120
gttgagtggt actaaaggag tgcttttcat catcctttg gtgaacgatt tcaaatacgt 180
tagtgttttc tgagctagtt ttgatcaatt caggtgattc gttatcagaa ctctcaggtt 240
tgtattcgtg tccagttgtg tagcattcgc ctaacgtgta agcacggatt tcttcctcag 300
aaatttcact gtatggaatc atgcccttct ttctcgcttc ttcgtcggta aatgcaccat 360
agtaatcttt gtcatcatgt ctaacagtaa ttttgaatgg gaagaagaca catagccccc 420
agtaaacgaa aaaagaaatc aaaaaggaga agaaagaatc accataaaag aatttaacaa 480
tacctgagtc gtggaaatag ttattgttga cttcccaagc gataccaggt agaccgggag 540
ccataccaca cacccaggca acgatagctc tccagttgac a 581

<210> SEQ ID NO 95
<211> LENGTH: 22
<212> TYPE: DNA
<213> ORGANISM: Artificial Sequence
<220> FEATURE:
<223> OTHER INFORMATION: Con5 FW

<400> SEQUENCE: 95
aagcgacttc caatcgcttt gc 22

<210> SEQ ID NO 96
<211> LENGTH: 21
<212> TYPE: DNA
<213> ORGANISM: Artificial Sequence
<220> FEATURE:
<223> OTHER INFORMATION: ConA REV

<400> SEQUENCE: 96
aaagcaaagg aaggagagaa c 21

<210> SEQ ID NO 97
<211> LENGTH: 20
<212> TYPE: DNA
<213> ORGANISM: Artificial Sequence
<220> FEATURE:
<223> OTHER INFORMATION: ConA FW

<400> SEQUENCE: 97
ttgcccatcg aacgtacaag 20

<210> SEQ ID NO 98
<211> LENGTH: 23
<212> TYPE: DNA
<213> ORGANISM: Artificial Sequence
<220> FEATURE:
<223> OTHER INFORMATION: ConB REV

<400> SEQUENCE: 98
tgctaagatt tgtgttcgtt tgg 23

<210> SEQ ID NO 99
<211> LENGTH: 20
<212> TYPE: DNA
<213> ORGANISM: Artificial Sequence
<220> FEATURE:
<223> OTHER INFORMATION: ConB FW

<400> SEQUENCE: 99
cggatcgatg tacacaaccg                                                    20

<210> SEQ ID NO 100
<211> LENGTH: 72
<212> TYPE: DNA
<213> ORGANISM: Artificial Sequence
<220> FEATURE:
<223> OTHER INFORMATION: Con3-ScTAL1t REV

<400> SEQUENCE: 100
acttagtatg gtctgttgga aaggattgtg gcttcgcata caggctttct gagggacgtt        60
gatttaaggt gg                                                            72

<210> SEQ ID NO 101
<211> LENGTH: 23
<212> TYPE: DNA
<213> ORGANISM: Artificial Sequence
<220> FEATURE:
<223> OTHER INFORMATION: 5' flank FW 1 kb deletion

<400> SEQUENCE: 101
cactatagca atctggctat atg                                                23

<210> SEQ ID NO 102
<211> LENGTH: 70
<212> TYPE: DNA
<213> ORGANISM: Artificial Sequence
<220> FEATURE:
<223> OTHER INFORMATION: 5' flank REV 1 kb deletion - connector 5 tail

<400> SEQUENCE: 102
aaacgcctgt gggtgtggta ctggatatgc aaagcgattg gaagtcgctt gactcctctg        60
ccgtcattcc                                                               70

<210> SEQ ID NO 103
<211> LENGTH: 72
<212> TYPE: DNA
<213> ORGANISM: Artificial Sequence
<220> FEATURE:
<223> OTHER INFORMATION: 3' flank FW 1 kb deletion - connector 3 tail

<400> SEQUENCE: 103
agaaagcctg tatgcgaagc cacaatcctt tccaacagac catactaagt aagcgttgaa        60
gtttcctctt tg                                                            72

<210> SEQ ID NO 104
<211> LENGTH: 20
<212> TYPE: DNA
<213> ORGANISM: Artificial Sequence
<220> FEATURE:
<223> OTHER INFORMATION: 3' flank REV 1 kb deltion

<400> SEQUENCE: 104
tgtcaactgg agagctatcg                                                    20

<210> SEQ ID NO 105
<211> LENGTH: 269
<212> TYPE: DNA
<213> ORGANISM: Artificial Sequence
<220> FEATURE:
<223> OTHER INFORMATION: SNR52 promoter

<400> SEQUENCE: 105
tctttgaaaa gataatgtat gattatgctt tcactcatat ttatacagaa acttgatgtt     60
ttctttcgag tatatacaag gtgattacat gtacgtttga agtacaactc tagattttgt    120
agtgccctct tgggctagcg gtaaaggtgc gcatttttc acaccctaca atgttctgtt     180
caaaagattt tggtcaaacg ctgtagaagt gaaagttggt gcgcatgttt cggcgttcga    240
aacttctccg cagtgaaaga taaatgatc                                      269

<210> SEQ ID NO 106
<211> LENGTH: 20
<212> TYPE: DNA
<213> ORGANISM: Artificial Sequence
<220> FEATURE:
<223> OTHER INFORMATION: AsCpf1 crRNA direct repeat

<400> SEQUENCE: 106
taatttctac tcttgtagat                                                 20

<210> SEQ ID NO 107
<211> LENGTH: 21
<212> TYPE: DNA
<213> ORGANISM: Artificial Sequence
<220> FEATURE:
<223> OTHER INFORMATION: LbCpf1 crRNA direct repeat

<400> SEQUENCE: 107
taatttctac taagtgtaga t                                               21

<210> SEQ ID NO 108
<211> LENGTH: 20
<212> TYPE: DNA
<213> ORGANISM: Artificial Sequence
<220> FEATURE:
<223> OTHER INFORMATION: FnCpf1 crRNA direct repeat

<400> SEQUENCE: 108
taatttctac tgttgtagat                                                 20

<210> SEQ ID NO 109
<211> LENGTH: 20
<212> TYPE: DNA
<213> ORGANISM: Artificial Sequence
<220> FEATURE:
<223> OTHER INFORMATION: Nucleotide sequence of the INT1 genomic DNA
    position A spacer sequence comprising the guide-sequence or
    genomic target sequence, specific for Cpf1

<400> SEQUENCE: 109
ctggtgggag agaaagctta                                                 20

<210> SEQ ID NO 110
<211> LENGTH: 20
<212> TYPE: DNA
<213> ORGANISM: Artificial Sequence
<220> FEATURE:
<223> OTHER INFORMATION: Nucleotide sequence of the INT1 genomic DNA
    position B spacer sequence comprising the guide-sequence or
    genomic target sequence, specific for Cpf1

<400> SEQUENCE: 110
tctcccacca gcaaagcctg                                          20

<210> SEQ ID NO 111
<211> LENGTH: 20
<212> TYPE: DNA
<213> ORGANISM: Artificial Sequence
<220> FEATURE:
<223> OTHER INFORMATION: Nucleotide sequence of the INT1 genomic DNA
      position C spacer sequence comprising the guide-sequence or
      genomic target sequence, specific for SpCas9

<400> SEQUENCE: 111
ctggtgggag agaaagctta                                          20

<210> SEQ ID NO 112
<211> LENGTH: 20
<212> TYPE: DNA
<213> ORGANISM: Artificial Sequence
<220> FEATURE:
<223> OTHER INFORMATION: SUP4 terminator

<400> SEQUENCE: 112
tattagaacc agggaggtcc                                          20

<210> SEQ ID NO 113
<211> LENGTH: 494
<212> TYPE: DNA
<213> ORGANISM: Artificial Sequence
<220> FEATURE:
<223> OTHER INFORMATION: AsCpf1 crRNA expression cassette, genomic DNA
      INT1 position A

<400> SEQUENCE: 113
catgtttgac agcttatcat cgataatccg gagctagcat gcggccgctc tagaactagt    60 ggatccccg gctgcagtc tttgaaaaga taatgtatga ttatgctttc actcatattt   120
atacagaaac ttgatgtttt ctttcgagta tatacaaggt gattacatgt acgtttgaag   180
tacaactcta gattttgtag tgccctcttg ggctagcggt aaaggtgcgc attttttcac   240
accctacaat gttctgttca aaagattttg gtcaaacgct gtagaagtga agttggtgc    300 gcatgtttcg gcgttcgaaa cttctccgca gtgaaagata aatgatctaa tttctactct   360
tgtagatctg gtgggagaga agcttatttt ttttgttttt tatgtctggg gggcccggta   420
cccagctttt gttccctta gtgagggtta attccgagct tggcgtaatc atggtcatag   480
ctgtttcctg tgtg                                                    494

<210> SEQ ID NO 114
<211> LENGTH: 495
<212> TYPE: DNA
<213> ORGANISM: Artificial Sequence
<220> FEATURE:
<223> OTHER INFORMATION: LbCpf1 crRNA expression cassette, genomic DNA
      INT1 position B

<400> SEQUENCE: 114
catgtttgac agcttatcat cgataatccg gagctagcat gcggccgctc tagaactagt    60 ggatccccg gctgcagtc tttgaaaaga taatgtatga ttatgctttc actcatattt   120
atacagaaac ttgatgtttt ctttcgagta tatacaaggt gattacatgt acgtttgaag   180
tacaactcta gattttgtag tgccctcttg ggctagcggt aaaggtgcgc attttttcac   240

```
accctacaat gttctgttca aaagattttg gtcaaacgct gtagaagtga aagttggtgc    300
gcatgtttcg gcgttcgaaa cttctccgca gtgaaagata aatgatctaa tttctactaa    360
gtgtagattc tcccaccagc aaagcctgtt tttttgtttt ttatgtctgg ggggcccggt    420
acccagcttt tgttcccttt agtgagggtt aattccgagc ttggcgtaat catggtcata    480
gctgtttcct gtgtg                                                     495
```

<210> SEQ ID NO 115
<211> LENGTH: 494
<212> TYPE: DNA
<213> ORGANISM: Artificial Sequence
<220> FEATURE:
<223> OTHER INFORMATION: FnCpf1 crRNA expression cassette, genomic DNA
      INT1 position A

<400> SEQUENCE: 115

```
catgtttgac agcttatcat cgataatccg gagctagcat gcggccgctc tagaactagt    60 ggatccccg gctgcagtc tttgaaaaga taatgtatga ttatgctttc actcatattt      120
atacagaaac ttgatgtttt ctttcgagta tatacaaggt gattacatgt acgtttgaag    180
tacaactcta gattttgtag tgccctcttg ggctagcggt aaaggtgcgc attttttcac    240
accctacaat gttctgttca aaagattttg gtcaaacgct gtagaagtga aagttggtgc    300
gcatgtttcg gcgttcgaaa cttctccgca gtgaaagata aatgatctaa tttctactgt    360
tgtagatctg gtgggagaga aagcttattt ttttgttttt tatgtctggg gggcccggta    420
cccagctttt gttcccttta gtgagggtta attccgagct tggcgtaatc atggtcatag    480
ctgtttcctg tgtg                                                      494
```

<210> SEQ ID NO 116
<211> LENGTH: 553
<212> TYPE: DNA
<213> ORGANISM: Artificial Sequence
<220> FEATURE:
<223> OTHER INFORMATION: Nucleotide sequence of the SpCAS9 gRNA
      expression cassette, genomic DNA INT1 position C

<400> SEQUENCE: 116

```
catgtttgac agcttatcat cgataatccg gagctagcat gcggccgctc tagaactagt    60 ggatccccg gctgcagtc tttgaaaaga taatgtatga ttatgctttc actcatattt      120
atacagaaac ttgatgtttt ctttcgagta tatacaaggt gattacatgt acgtttgaag    180
tacaactcta gattttgtag tgccctcttg ggctagcggt aaaggtgcgc attttttcac    240
accctacaat gttctgttca aaagattttg gtcaaacgct gtagaagtga aagttggtgc    300
gcatgtttcg gcgttcgaaa cttctccgca gtgaaagata aatgatctat tagaaccagg    360
gaggtccgtt ttagagctag aaatagcaag ttaaaataag gctagtccgt tatcaacttg    420
aaaaagtggc accgagtcgg tggtgctttt tttgtttttt atgtctgggg ggcccggtac    480
ccagcttttg ttccctttag tgagggttaa ttccgagctt ggcgtaatca tggtcatagc    540
tgtttcctgt gtg                                                       553
```

<210> SEQ ID NO 117
<211> LENGTH: 21
<212> TYPE: DNA
<213> ORGANISM: Artificial Sequence
<220> FEATURE:
<223> OTHER INFORMATION: FW primer guide RNA cassette with pRN1120
      overlap

<400> SEQUENCE: 117
catgtttgac agcttatcat c    21

<210> SEQ ID NO 118
<211> LENGTH: 21
<212> TYPE: DNA
<213> ORGANISM: Artificial Sequence
<220> FEATURE:
<223> OTHER INFORMATION: REV primer guide RNA cassette with pRN1120
      overlap

<400> SEQUENCE: 118
cacacaggaa acagctatga c    21

<210> SEQ ID NO 119
<211> LENGTH: 1141
<212> TYPE: DNA
<213> ORGANISM: Artificial Sequence
<220> FEATURE:
<223> OTHER INFORMATION: The nucleotide sequence of the Anid_TEF
      promoter

<400> SEQUENCE: 119
ggtctcggtg cttgcaccaa tcgccgttta ggtgttcatt aggttgtatt ttggctattt    60
attgcgatat ttaagcgagg cgaacatggg ataaaacgtt tgctgttagt gtttgtgtat   120
atgctagcga cttagagtgc acgctcaaaa gatacccta acttctgatt tgatagcatt   180
tgtatatggc atatagtacg cctgaagcat aaaaaaaaaa acagaattat tatagtttat   240
taatacgaga cagcagaatc accgcccaag ttaagccttt gtgctgatca tgctctcgaa   300
cgggccaagt tcgggaaaag caaaggagcg tttagtgagg ggcaatttga ctcacctccc   360
aggcaacaga tgaggggggc aaaaagaaag aaattttcgt gagtcaatat ggattccgag   420
catcattttc ttgcggtcta tcttgctacg tatgttgatc ttgacgctgt ggatcaagca   480
acgccactcg ctcgctccat cgcaggctgg tcgcagacaa attaaaaggc ggcaaactcg   540
tacagccgcg gggttgtccg ctgcaaagta cagagtgata aaagccgcca tgcgaccatc   600
aacgcgttga tgcccagctt tttcgatccg agaatccacc gtagaggcga tagcaagtaa   660
agaaaagcta acaaaaaaaa aatttctgcc cctaagccat gaaaacgaga tggggtggag   720
cagaaccaag gaaagagtcg cgctgggctg ccgttccgga aggtgttgta aaggctcgac   780
gcccaaggtg ggagtctagg agaagaattt gcatcgggag tggggcgggt taccccctcca   840
tatccaatga cagatatcta ccagccaagg gtttgagccc gcccgcttag tcgtcgtcct   900
cgcttgcccc tccataaaag gatttcccct ccccctccca caaaatttc tttcccttcc    960
tctccttgtc cgcttcagta cgtatatctt cccttccctc gcttctctcc tccatccttc   1020
tttcatccat ctcctgctaa cttctctgct cagcacctct acgcattact agccgtagta   1080
tctgagcact ctcccctttt atattccaca aaacataaca ccaccgtcaa aatgggagac   1140
c                                                                   1141

<210> SEQ ID NO 120
<211> LENGTH: 733
<212> TYPE: DNA
<213> ORGANISM: Artificial Sequence
<220> FEATURE:
<223> OTHER INFORMATION: The nucleotide sequence of the GFP ORF

<400> SEQUENCE: 120
ggtctccttt atttgtacag ctcatccatt ccgtgggtga taccagcagc agtgacgaac    60

```
tcgaggagga ccatgtggtc acgcttctcg ttggggtcct tggagagagc agactggtag      120
gacaggtagt ggttgtcggg gagcaacaca ggtccatcac cgatggggt gttctgctgg       180 tagtggtccg ccagctgcac accaccatcc tcaatgttgt ggcggatctt gaagttggcc      240
ttgatgccgt tcttctgctt gtcggcggtg atgtagacgt tgtgagagtt gtagttgtat      300
tccagcttgt ggccaaggat gttgccatct tccttgaagt cgatacccct cagctcaatg      360
cggttgacga gggtgtcacc ctcgaacttg acctcggcac gggtcttgta gttgccgtca      420
tccttgaaga agatggtgcg ctcctgcacg tagccctcgg gcatggcgga cttgaagaag      480
tcgtgctgct tcatgtggtc ggggtaacga gcgaagcact gcagaccgta tccgagggtg      540
gtgacgaggg tgggccaagg aacaggaagc ttgccagtgg tgcagatcag cttgagagtc      600
aacttgccgt aggtggcatc accctcgccc tcaccgctga cggagaactt gtggccgttg      660
acatcaccgt caagctcaac aagaatggga acaacaccag tgaagagttc ttcacccttg      720
ctcattcgag acc                                                         733
```

<210> SEQ ID NO 121
<211> LENGTH: 321
<212> TYPE: DNA
<213> ORGANISM: Artificial Sequence
<220> FEATURE:
<223> OTHER INFORMATION: The nucleotide sequence of the RE_FT016
      terminator

<400> SEQUENCE: 121

```
ggtctcgtaa aggtttccag acccaggata ctgcatgatt gatgagatct gcatgtgtgt      60
acattaatta aagctttacg cctacgaaat attattgatt gtacaggacg gtgcggtgta     120
ccaggaacca tctattatct tatgaaaaca taaaagaaa agaaaagagc accatactgc      180
ggatgcagag acagtatctc gtcctccgcc atagtccgcc gcctccgccg tagtggaacc     240
ttggcggaag cggagcggaa tatatagccc caaagtaaag aagactcgaa ctgtacactt     300
tttatcgctt cctcggagac c                                               321
```

<210> SEQ ID NO 122
<211> LENGTH: 3506
<212> TYPE: DNA
<213> ORGANISM: Artificial Sequence
<220> FEATURE:
<223> OTHER INFORMATION: The nucleotide sequence of the receiving CD
      backbone vector used to assemble the GFP expression cassette

<400> SEQUENCE: 122

```
tagaaaaact catcgagcat caaatgaaac tgcaatttat tcatatcagg attatcaata      60 ccatatttt gaaaaagccg tttctgtaat gaaggagaaa actcaccgag gcagttccat      120
aggatggcaa gatcctggta tcggtctgcg attccgactc gtccaacatc aatacaacct     180
attaatttcc cctcgtcaaa ataaggtta tcaagtgaga atcaccatg agtgacgact      240 gaatccggtg agaatggcaa aagtttatgc atttctttcc agacttgttc aacaggccag     300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat     480
tcttctaata cctggaacgc tgttttccg gggatcgcag tggtgagtaa ccatgcatca     540
tcaggagtac ggataaaatg cttgatggtc ggaagtggca taaattccgt cagccagttt     600
```

```
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc    1020
tgaccccatg ccgaactcag aagtgaaacg ccgtagcgcc gatggtagtg tggggactcc    1080
ccatgcgaga gtagggaact gccaggcatc aaataaaacg aaaggctcag tcgaaagact    1140
gggcctttcg cccgggctaa ttaggggggt tcgcccttat tcgactctat agtgaagttc    1200
ctattctcta gaaagtatag gaacttctga agtggggacg ctttccggca tcttccagac    1260
cacagtatat ccatccgcct cctgttggtg cggagaccgg cttactaaaa gccagataac    1320
agtatgcata tttgcgcgct gattttgcg gtataagaat atatactgat atgtataccc    1380
gaagtatgtc aaaagaggt atgctatgaa gcagcgtatt acagtgacag ttgacagcga    1440
cagctatcag ttgctcaagg catatatgat gtcaatatct ccggtctggt aagcacaacc    1500
atgcagaatg aagcccgtcg tctgcgtgcc gaacgctgga aagcggaaaa tcaggaaggg    1560
atggctgagg tcgcccggtt tattgaaatg aacggctctt tgctgacga aacaggggc    1620 tggtgaaatg cagtttaagg tttacaccta aaaagagag agccgttatc gtctgttggt    1680
ggatgtacag agtgatatta ttgacacgcc cgggcgacgg atggtgatcc ccctggccag    1740
tgcacgtctg ctgtcagata aagtctcccg tgaactttac ccggtggtgc atatcgggga    1800
tgaaagctgg cgcatgatga ccaccgatat ggccagtgtg ccggtttccg ttatcgggga    1860
agaagtggct gatctcagcc accgcgaaaa tgacatcaaa aacgccatta acctgatgtt    1920
ctggggaata taaggtctcg cctcaacgtt gtccaggttt gtatccacgt gtgtccgttc    1980
cgccaatatt ccgcaaaatg aagtgaagtt cctatacttt ctagagaata ggaacttcta    2040
tagtgagtcg aataagggcg cacaaaatt tattctaaat gcataataaa tactgataac    2100
atcttatagt ttgtattata ttttgtatta tcgttgacat gtataatttt gatatcaaaa    2160
actgattttc cctttattat tttcgagatt tattttctta attctcttta acaaactaga    2220
aatattgtat atacaaaaaa tcataaataa tagatgaata gtttaattat aggtgttcat    2280
caatcgaaaa agcaacgtat cttatttaaa gtgcgttgct tttttctcat ttataaggtt    2340
aaataattct catatatcaa gcaaagtgac aggcgccctt aaatattctg acaaatgctc    2400
tttccctaaa ctccccccat aaaaaaaccc gccgaagcgg ttttttacgt tatttgcgga    2460
ttaacgatta ctcgttatca gaaccgccca gggggcccga gcttaagact ggccgtcgtt    2520
ttacaacaca gaaagagttt gtagaaacgc aaaaaggcca tccgtcaggg gccttctgct    2580
tagtttgatg cctggcagtt ccctactctc gccttccgct tcctcgctca ctgactcgct    2640
gcgctcggtc gttcggctgc ggcgagcggt atcagctcac tcaaaggcgg taatacggtt    2700
atccacagaa tcagggata acgcaggaaa gaacatgtga gcaaaaggcc agcaaaaggc    2760
caggaaccgt aaaaaggccg cgttgctggc gttttccat aggctccgcc cccctgacga    2820
gcatcacaaa aatcgacgct caagtcagag gtggcgaaac ccgacaggac tataagata    2880 ccaggcgttt cccctggaa gctccctcgt gcgctctcct gttccgaccc tgccgcttac    2940
cggatacctg tccgcctttc tcccttcggg aagcgtggcg ctttctcata gctcacgctg    3000
```

```
taggtatctc agttcggtgt aggtcgttcg ctccaagctg ggctgtgtgc acgaaccccc    3060
cgttcagccc gaccgctgcg ccttatccgg taactatcgt cttgagtcca acccggtaag    3120
acacgactta tcgccactgg cagcagccac tggtaacagg attagcagag cgaggtatgt    3180
aggcggtgct acagagttct tgaagtggtg ggctaactac ggctacacta agaacagt     3240 atttggtatc tgcgctctgc tgaagccagt taccttcgga aaaagagttg gtagctcttg    3300
atccggcaaa caaccaccg ctggtagcgg tggttttttt gtttgcaagc agcagattac     3360
gcgcagaaaa aaaggatctc aagaagatcc tttgatcttt tctacggggt ctgacgctca    3420
gtggaacgac gcgcgcgtaa ctcacgttaa gggattttgg tcatgagctt gcgccgtccc    3480
gtcaagtcag cgtaatgctc tgcttt                                         3506

<210> SEQ ID NO 123
<211> LENGTH: 4994
<212> TYPE: DNA
<213> ORGANISM: Artificial Sequence
<220> FEATURE:
<223> OTHER INFORMATION: The nucleotide sequence of the GFP expression
      cassette vector, containing a functional GFP expression cassette

<400> SEQUENCE: 123
tagaaaaact catcgagcat caaatgaaac tgcaatttat tcatatcagg attatcaata      60
ccatattttt gaaaaagccg tttctgtaat gaaggagaaa actcaccgag gcagttccat     120
aggatggcaa gatcctggta tcggtctgcg attccgactc gtccaacatc aatacaacct    180
attaatttcc cctcgtcaaa aataaggtta tcaagtgaga atcaccatg agtgacgact     240 gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900 atagggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaagact    1140 gggcctttcg cccgggctaa ttagggggtg tcgcccttat tcgactctat agtgaagttc   1200
ctattctcta gaaagtatag gaacttctga agtggggacg ctttccggca tcttccagac   1260
cacagtatat ccatccgcct cctgttggtg cttgcaccaa tcgccgttta ggtgttcatt   1320
aggttgtatt ttggctattt attgcgatat ttaagcgagg cgaacatggg ataaaacgtt   1380
tgctgttagt gtttgtgtat atgctagcga cttagagtgc acgctcaaaa gatacccta   1440 acttctgatt tgatagcatt tgtatatggc atatagtacg cctgaagcat aaaaaaaaaa   1500
```

```
acagaattat tatagtttat taatacgaga cagcagaatc accgcccaag ttaagccttt    1560
gtgctgatca tgctctcgaa cgggccaagt tcgggaaaag caaaggagcg tttagtgagg    1620
ggcaatttga ctcacctccc aggcaacaga tgagggggc aaaaagaaag aaatttcgt     1680
gagtcaatat ggattccgag catcattttc ttgcggtcta tcttgctacg tatgttgatc    1740
ttgacgctgt ggatcaagca acgccactcg ctcgctccat cgcaggctgg tcgcagacaa    1800
attaaaaggc ggcaaactcg tacagccgcg gggttgtccg ctgcaaagta cagagtgata    1860
aaagccgcca tgcgaccatc aacgcgttga tgcccagctt tttcgatccg agaatccacc    1920
gtagaggcga tagcaagtaa agaaaagcta aacaaaaaaa aatttctgcc cctaagccat    1980
gaaaacgaga tggggtggag cagaaccaag gaaagagtcg cgctgggctg ccgttccgga    2040
aggtgttgta aaggctcgac gcccaaggtg ggagtctagg agaagaattt gcatcgggag    2100
tggggcgggt taccctccca tatccaatga cagatatcta ccagccaagg gtttgagccc    2160
gcccgcttag tcgtcgtcct cgcttgcccc tccataaaag gatttcccct ccccctccca    2220
caaaatttc tttcccttcc tctccttgtc cgcttcagta cgtatatctt cccttccctc    2280
gcttctctcc tccatccttc tttcatccat ctcctgctaa cttctctgct cagcacctct    2340
acgcattact agccgtagta tctgagcact tctcccttt atattccaca aaacataaca     2400
ccaccgtcaa aatgagcaag ggtgaagaac tcttcactgg tgttgttccc attcttgttg    2460
agcttgacgg tgatgtcaac ggccacaagt tctccgtcag cggtgagggc gagggtgatg    2520
ccacctacgg caagttgact ctcaagctga tctgcaccac tggcaagctt cctgttcctt    2580
ggcccaccct cgtcaccacc ctcggatacg gtctgcagtg cttcgctcgt taccccgacc    2640
acatgaagca gcacgacttc ttcaagtccg ccatgcccga gggctacgtg caggagcgca    2700
ccatcttctt caaggatgac ggcaactaca agacccgtgc cgaggtcaag ttcgagggtg    2760
acacccgtcgt caaccgcatt gagctgaagg gtatcgactt caaggaagat ggcaacatcc    2820
ttggccacaa gctggaatac aactacaact ctcacaacgt ctacatcacc gccgacaagc    2880
agaagaacgg catcaaggcc aacttcaaga tccgccacaa cattgaggat ggtggtgtgc    2940
agctggcgga ccactaccag cagaacaccc ccatcggtga tggacctgtg ttgctccccg    3000
acaaccacta cctgtcctac cagtctgctc tctccaagga ccccaacgag aagcgtgacc    3060
acatggtcct cctcgagttc gtcactgctg ctggtatcac ccacggaatg gatgagctgt    3120
acaaataaag gtttccagac ccaggatact gcatgattga tgagatctgc atgtgtgtac    3180
attaattaaa gctttacgcc tacgaaatat tattgattgt acaggacggt gcggtgtacc    3240
aggaaccatc tattatctta tgaaaacata aaagaaaag aaaagagcac catactgcgg     3300
atgcagagac agtatctcgt cctccgccat agtccgccgc ctccgccgta gtggaacctt    3360
ggcggaagcg gagcggaata tatagcccca agtaaagaa gactcgaact gtacactttt     3420
tatcgcttcc tcaacgttgt ccaggtttgt atccacgtgt gtccgttccg ccaatattcc    3480
gcaaaatgaa gtgaagttcc tatactttct agagaatagg aacttctata gtgagtcgaa    3540
taagggcgac acaaaattta ttctaaatgc ataataaata ctgataacat cttatagttt    3600
gtattatatt ttgtattatc gttgacatgt ataatttga tatcaaaaac tgattttccc     3660
tttattattt tcgagattta ttttcttaat tctctttaac aaactagaaa tattgtatat    3720
acaaaaaatc ataataata gatgaatagt ttaattatag gtgttcatca atcgaaaaag    3780
caacgtatct tatttaaagt gcgttgcttt tttctcattt ataaggttaa ataattctca    3840
```

```
tatatcaagc aaagtgacag gcgcccttaa atattctgac aaatgctctt tccctaaact    3900
cccccataa aaaaacccgc cgaagcgggt ttttacgtta tttgcggatt aacgattact    3960
cgttatcaga accgcccagg gggcccgagc ttaagactgg ccgtcgtttt acaacacaga    4020
aagagtttgt agaaacgcaa aaaggccatc cgtcaggggc cttctgctta gtttgatgcc    4080
tggcagttcc ctactctcgc cttccgcttc ctcgctcact gactcgctgc gctcggtcgt    4140
tcggctgcgg cgagcggtat cagctcactc aaaggcggta atacggttat ccacagaatc    4200
aggggataac gcaggaaaga acatgtgagc aaaaggccag caaaaggcca ggaaccgtaa    4260
aaaggccgcg ttgctggcgt ttttccatag gctccgcccc cctgacgagc atcacaaaaa    4320
tcgacgctca agtcagaggt ggcgaaaccc gacaggacta taaagatacc aggcgtttcc    4380
ccctggaagc tccctcgtgc gctctcctgt tccgaccctg ccgcttaccg gatacctgtc    4440
cgcctttctc ccttcgggaa gcgtggcgct ttctcatagc tcacgctgta ggtatctcag    4500
ttcggtgtag tcgttcgct ccaagctggg ctgtgtgcac gaaccccccg ttcagcccga    4560
ccgctgcgcc ttatccggta actatcgtct tgagtccaac ccggtaagac acgacttatc    4620
gccactggca gcagccactg gtaacaggat tagcagagcg aggtatgtag gcggtgctac    4680
agagttcttg aagtggtggg ctaactacgg ctacactaga agaacagtat ttggtatctg    4740
cgctctgctg aagccagtta ccttcggaaa aagagttggt agctcttgat ccggcaaaca    4800
aaccaccgct ggtagcggtg gttttttgt ttgcaagcag cagattacgc gcagaaaaaa    4860
aggatctcaa gaagatcctt tgatctttc tacggggtct gacgctcagt ggaacgacgc    4920
gcgcgtaact cacgttaagg gattttggtc atgagcttgc gccgtcccgt caagtcagcg    4980
taatgctctg cttt                                                     4994
```

<210> SEQ ID NO 124
<211> LENGTH: 21
<212> TYPE: DNA
<213> ORGANISM: Artificial Sequence
<220> FEATURE:
<223> OTHER INFORMATION: The nucleotide sequence of the forward primer
      to amplify the GFP expression cassette

<400> SEQUENCE: 124
acgctttccg gcatcttcca g                                              21

<210> SEQ ID NO 125
<211> LENGTH: 20
<212> TYPE: DNA
<213> ORGANISM: Artificial Sequence
<220> FEATURE:
<223> OTHER INFORMATION: The nucleotide sequence of out the reverse
      primer to amplify the GFP expression cassette

<400> SEQUENCE: 125
gcggaatatt ggcggaacgg                                                20

<210> SEQ ID NO 126
<211> LENGTH: 101
<212> TYPE: DNA
<213> ORGANISM: Artificial Sequence
<220> FEATURE:
<223> OTHER INFORMATION: The nucleotide sequence of the ssODN 5' end of
      the fnwA6 locus upper strand

<400> SEQUENCE: 126
ctgcgacagc ggattgggcg gagaagaaga caacccttca gatatattca gacgctttcc    60

```
ggcatcttcc agaccacagt atatccatcc gcctcctgtt g                          101
```

<210> SEQ ID NO 127
<211> LENGTH: 101
<212> TYPE: DNA
<213> ORGANISM: Artificial Sequence
<220> FEATURE:
<223> OTHER INFORMATION: The nucleotide sequence of the ssODN 5' end of
      the fnwA6 locus lower strand

<400> SEQUENCE: 127

```
caacaggagg cggatggata tactgtggtc tggaagatgc cggaaagcgt ctgaatatat       60
ctgaagggtt gtcttcttct ccgcccaatc cgctgtcgca g                         101
```

<210> SEQ ID NO 128
<211> LENGTH: 100
<212> TYPE: DNA
<213> ORGANISM: Artificial Sequence
<220> FEATURE:
<223> OTHER INFORMATION: The nucleotide sequence of the ssODN 3' end of
      the fnwA6 locus upper strand

<400> SEQUENCE: 128

```
aacgttgtcc aggtttgtat ccacgtgtgt ccgttccgcc aatattccgc gggaagaaga       60
cggctgacca cgcaacttgc actgtccgat tctttgactg                           100
```

<210> SEQ ID NO 129
<211> LENGTH: 100
<212> TYPE: DNA
<213> ORGANISM: Artificial Sequence
<220> FEATURE:
<223> OTHER INFORMATION: The nucleotide sequence of the ssODN 3' end of
      the fnwA6 locus lower strand

<400> SEQUENCE: 129

```
cagtcaaaga tcggacagt gcaagttgcg tggtcagccg tcttcttccc gcggaatatt        60
ggcggaacgg acacgtgg atacaaacct ggacaacgtt                             100
```

<210> SEQ ID NO 130
<211> LENGTH: 20
<212> TYPE: DNA
<213> ORGANISM: Artificial Sequence
<220> FEATURE:
<223> OTHER INFORMATION: The nucleotide sequence of the fwnA6 guide-
      polynucleotide

<400> SEQUENCE: 130

```
tcagatatat tcagtcactg                                                  20
```

<210> SEQ ID NO 131
<211> LENGTH: 14317
<212> TYPE: DNA
<213> ORGANISM: Artificial Sequence
<220> FEATURE:
<223> OTHER INFORMATION: The nucleotide sequence of vector BG-AMA8

<400> SEQUENCE: 131

```
ggtaccttgc ccatcgaacg tacaagtact cctctgttct ctccttcctt tgctttgtgc       60
ggagaccggc ttactaaaag ccagataaca gtatgcatat ttgcgcgctg atttttgcgg      120
tataagaata tatactgata tgtatacccg aagtatgtca aaaagaggta tgctatgaag      180
cagcgtatta cagtgacagt tgacagcgac agctatcagt tgctcaaggc atatatgatg      240
tcaatatctc cggtctggta agcacaacca tgcagaatga agcccgtcgt ctgcgtgccg      300
```

-continued

```
aacgctggaa agcggaaaat caggaaggga tggctgaggt cgcccggttt attgaaatga     360
acggctcttt tgctgacgag aacaggggct ggtgaaatgc agtttaaggt ttacacctat     420
aaaagagaga gccgttatcg tctgtttgtg gatgtacaga gtgatattat tgacacgccc     480
gggcgacgga tggtgatccc cctggccagt gcacgtctgc tgtcagataa agtctcccgt     540
gaactttacc cggtggtgca tatcggggat gaaagctggc gcatgatgac caccgatatg     600
gccagtgtgc cggtttccgt tatcggggaa gaagtggctg atctcagcca ccgcgaaaat     660
gacatcaaaa acgccattaa cctgatgttc tggggaatat aaggtctcgc ctccggatcg     720
atgtacacaa ccgactgcac ccaaacgaac acaaatctta gcagtgccct cgccggatag     780
cttggactgt cctttaccgt cgccagcaca agaagggtat ctctgaggtc cgtaccgcct     840
tttctttacc actggattcg attttcgcag ttggaatgat acatctgggg actgcgaatg     900
gtttacccct cggccgatac tatgggtcgt gaagagatgg aacattccga agtgttttg     960
cggataacat tggtggcatc gaaaacagaa tgctgaccat tgatttcaac acgaacagga    1020
ggttgccaag aagcgtaccc gccgtgtcgt caagtcccag cgtgccatcg tcggtgcttc    1080
cctcgacgtg atcaaggagc gccgctccca gcgccccgag gcccgtgccg ccgcccgcca    1140
gcaggccatc aaggacgcca aggagaagaa ggctgccgct gagtccaaga agaaggctga    1200
gaaggctaag aacgccgctg ctggtgccaa gggtgctgct cagcgcatcc agagcaagca    1260
gggtgctaag ggttctgctc caaggtcgc tgccaagtct cgttaaggaa tgaataacgg    1320
ttcggcttgg gattgggtgc ggaaggcaag agtttcatgg acgaattttg ggaggttact    1380
ggagctggaa tatgtgtttt ccctaccacc aaaaatgaaa tgttccaaaa ctatcggcgt    1440
gcaagacggc ctcttacggg tttaacggct ctcagataag ctctatcaat cgcgccacgg    1500
atgcatgaat gaagatccag atggccgcgg gatatatcgt gctagtgtaa ttcctacatg    1560
atcttgctgt tcactccatg cgcatccaga tattccaggg gtcgactgtt aattgatatg    1620
cctgggcttg agactccgta gacgcccagt caatgtgcaa ttaatacgag ggtgctgtta    1680
tcggcagcaa ccttgtactt ctccataaga tgggggaatg ccatggacct gagtgatcaa    1740
ttgacgcaag tctcccataa cgcggcggct tgacctaaaa tccatatacc gccccgttga    1800
gcctccgcgc tccagagtcc tgtcccggaa tagggcacaa acctaggcta acctaattcg    1860
tcgtccgcgt ctgagttcag acaaaagaac ttccaagtat cagcagagta cgctgatatt    1920
gataagtagg caaacataag accaataagc aagtagaata aaaaattata aggacactgc    1980
ctccataaag cgccctccca agacctcagg gacaaaactt ccaagtggc aattcactgc    2040
ctcaggccgt gtccagtgaa gtgacgaagc gacactgttg cctgctgact cagccgcttt    2100
ccgccctgcc gaatttgcca tctcgcttac aggtcagcac tagcgcgatt cgcccacaga    2160
tgctcagcgc aaagtggtga ctcagtcaaa ccccccctac aagattccac ctcgattttt    2220
caacttccca tctcgatccg acaagttcta catccaccgt caaaatggcc tccagcgaag    2280
atgtcatcaa ggagttcatg cgcttcaagg tccgcatgga aggatccgtc aacggccacg    2340
agttcgagat tgagggtgag ggtgagggcc gcccctacga aggcacccag actgccaagc    2400
tcaaggtcac caagggtggt cctctcccct tcgctgggga tatcctgtct cctcagttcc    2460
agtacggctc caaggtctac gtcaagcacc ccgccgacat ccccgactac aagaagcttt    2520
cttttccccga gggtttcaag tgggagcgtg tcatgaactt cgaggatggt ggtgttgtga    2580
ccgttactca ggacagcagc ttgcaggatg gctctttcat ctacaaggtc aagttcattg    2640
```

```
gtgtcaacatt cccctccgac ggccctgtca tgcagaagaa gaccatgggc tgggaagcgt    2700
cgactgagcg tctgtacccc cgtgacggtg ttctcaaggg tgagatccac aaggctctca    2760
agctcaagga cggtggtcac taccttgttg agttcaagtc catctacatg gccaagaagc    2820
ctgtgcagct gcccggatac tactacgtgg actccaagct tgacatcacc tcccacaacg    2880
aagactacac cattgttgag cagtacgagc gtgctgaggg ccgccaccac ctcttcctga    2940
cccacggaat ggatgagctg tacaagtcga actataaat aaatggtttg cgttgcgatt    3000
gactgaaacg aaaaaaagcg aaaatgattc tgggaatgaa ttgataaagc gcgggctctg    3060
cggtacggtt acggttgcgg tcgcggacga atggactggg ctgagctggg ctggaggaag    3120
tccatcgaac aaggacaagg ggtggaatat ggcacgggtc gattttgtta tacatacccct   3180
accatccatc tatccatta aataccaaat gagttgttga atggattcgc ggtcttctcg    3240
gtttattttt gcttgcttgc gtgcttaagg gatagtgtgc ctcacgcttt ccggcatctt    3300
ccagaccaca gtatatccat ccgcctcctg ttgaagctta ttttttgtat actgttttgt    3360
gatagcacga agttttcca cggtatcttg ttaaaaatat atatttgtgg cgggcttacc    3420
tacatcaaat taataagaga ctaattataa actaaacaca caagcaagct actttagggt    3480
aaaagttat aaatgctttt gacgtataaa cgttgcttgt atttattatt acaattaaag    3540
gtggatagaa aacctagaga ctagttagaa actaatctca ggtttgcgtt aaactaaatc    3600
agagcccgag aggttaacag aacctagaag gggactagat atccgggtag ggaaacaaaa    3660
aaaaaaaaca agacagccac atattaggga gactagttag aagctagttc caggactagg    3720
aaaataaaag acaatgatac cacagtctag ttgacaacta gatagattct agattgaggc    3780
caaagtctct gagatccagg ttagttgcaa ctaatactag ttagtatcta gtctcctata    3840
actctgaagc tagaataact tactactatt atcctcacca ctgttcagct gcgcaaacgg    3900
agtgattgca aggtgttcag agactagtta ttgactagtc agtgactagc aataactaac    3960
aaggtattaa cctaccatgt ctgccatcac cctgcacttc ctcgggctca gcagcctttt    4020
cctcctcatt ttcatgctca ttttccttgt ttaagactgt gactagtcaa agactagtcc    4080
agaaccacaa aggagaaatg tcttaccact ttcttcattg cttgtctctt ttgcattatc    4140
catgtctgca actagttaga gtctagttag tgactagtcc gacgaggact tgcttgtctc    4200
cggattgttg gaggaactct ccagggcctc aagatccaca acagagcctt ctagaagact    4260
ggtcaataac tagttggtct ttgtctgagt ctgacttacg aggttgcata ctcgctccct    4320
ttgcctcgtc aatcgatgag aaaaagcgcc aaaactcgca atatggcttt gaaccacacg    4380
gtgctgagac tagttagaat ctagtcccaa actagcttgg atagcttacc tttgcccttt    4440
gcgttgcgac aggtcttgca gggtatggtt cctttctcac cagctgattt agctgccttg    4500
ctaccctcac ggcggatctg cataaagagt ggctagaggt tataaattag cactgatcct    4560
aggtacgggg ctgaatgtaa cttgcctttc ctttctcatc gcgcggcaag acaggcttgc    4620
tcaaattcct accagtcaca ggggtatgca cggcgtacgg accacttgaa ctagtcacag    4680
attagttagc aactagtctg cattgaatgg ctgtacttac gggccctcgc cattgtcctg    4740
atcatttcca gcttcaccct cgttgctgca aagtagttag tgactagtca aggactagtt    4800
gaaatgggag aagaaactca cgaattctcg acacccttag tattgtggtc cttggacttg    4860
gtgctgctat atattagcta atacactagt tagactcaca gaaacttacg cagctcgctt    4920
gcgcttcttg gtaggagtcg gggttgggag aacagtgcct tcaaacaagc cttcatacca    4980
tgctacttga ctagtcaggg actagtcacc aagtaatcta gataggactt gcctttggcc    5040
```

```
tccatcagtt ccttcatagt gggaggtcca ttgtgcaatg taaactccat gccgtgggag      5100
ttcttgtcct tcaagtgctt gaccaatatg tttctgttgg cagagggaac ctgtcaacta      5160
gttaataact agtcagaaac tagtatagca gtagactcac tgtacgcttg aggcatccct      5220
tcactcggca gtagacttca tatggatgga tatcaggcac gccattgtcg tcctgtggac      5280
tagtcagtaa ctaggcttaa agctagtcgg gtcggcttac tatcttgaaa tccggcagcg      5340
taagctcccc gtccttaact gcctcgagat agtgacagta ctctgggac tttcggagat      5400 cgttatcgcg aatgctcggc atactaatcg ttgactagtc ttggactagt cccgagcaaa      5460
aaggattgga ggaggaggag gaaggtgaga gtgagacaaa gagcgaaata agagcttcaa      5520
aggctatctc taagcagtat gaaggttaag tatctagttc ttgactagat ttaaaagaga      5580
tttcgactag ttatgtacct ggagtttgga tataggaatg tgttgtggta acgaaatgta      5640
agggggagga agaaaaagt cggtcaagag gtaactctaa gtcggccatt cctttttggg       5700
aggcgctaac cataaacggc atggtcgact tagagttagc tcaggaatt tagggagtta       5760 tctgcgacca ccgaggaacg gcggaatgcc aaagaatccc gatggagctc tagctggcgg      5820
ttgacaaccc caccttttgg cgtttctgcg gcgttgcagg cgggactgga tacttcgtag      5880
aaccagaaag gcaaggcaga acgcgctcag caagagtgtt ggaagtgata gcatgatgtg      5940
ccttgttaac taggtcaaaa tctgcagtat gcttgatgtt atccaaagtg tgagagagga      6000
aggtccaaac atacacgatt gggagagggc ctaggtataa gagttttttga gtagaacgca    6060 tgtgagccca gccatctcga ggagattaaa cacgggccgg catttgatgg ctatgttagt      6120
accccaatgg aaagcctgag agtccagtgg tcgcagataa ctccctaaat tccctgagct      6180
aactctaagt cgaccatgcc gtttatggtt agcgcctccc aaaaaggaat ggccgactta      6240
gagttacctc ttgaccgact ttttctttcc tccccttac atttcgttac cacaacacat       6300
tcctatatcc aaactccagg tacataacta gtcgaaatct cttttaaatc tagtcaagaa      6360
ctagatactt aaccttcata ctgcttagag atagcctttg aagctcttat ttcgctcttt      6420
gtctcactct caccttcctc ctcctcctcc aatccttttt gctcgggact agtccaagac      6480
tagtcaacga ttagtatgcc gagcattcgc gataacgatc tccgaaagtc cccagagtac      6540
tgtcactatc tcgaggcagt taaggacggg gagcttacgc tgccggattt caagatagta      6600
agccgacccg actagcttta agcctagtta ctgactagtc caggacga caatggcgtg        6660 cctgatatcc atccatatga agtctactgc cgagtgaagg gatgcctcaa gcgtacagtg      6720
agtctactgc tatactagtt tctgactagt tattaactag ttgacaggtt ccctctgcca      6780
acagaaacat attggtcaag cacttgaagg acaagaactc ccacggcatg gagtttacat      6840
tgcacaatgg acctcccact atgaaggaac tgatggaggc caaaggcaag tcctatctag      6900
attacttggt gactagtccc tgactagtca gtagcatgg tatgaaggct tgtttgaagg       6960
cactgttctc ccaaccccga ctcctaccaa gaagcgcaag cgagctgcgt aagtttctgt      7020
gagtctaact agtgtattag ctaatatata gcagcaccaa gtccaaggac cacaatacta     7080
agggtgtcga gaattcgtga gtttcttctc ccatttcaac tagtccttga ctagtcacta     7140
actactttgc agcaacgagg gtgaagctgg aaatgatcag gacaatggcg agggcccgta    7200
agtacagcca ttcaatgcag actagttgct aactaatctg tgactagttc aagtggtccg     7260
tacgccgtgc ataccctgt gactggtagg aatttgagca agcctgtctt gccgcgcgat      7320
gagaaaggaa aggcaagtta cattcagccc cgtacctagg atcagtgcta atttataacc     7380
```

```
tctagccact ctttatgcag atccgccgtg agggtagcaa ggcagctaaa tcagctggtg    7440
agaaaggaac catacccctgc aagacctgtc gcaacgcaaa gggcaaaggt aagctatcca    7500
agctagtttg ggactagatt ctaactagtc tcagcaccgt gtggttcaaa gccatattgc    7560
gagttttggc gcttttttctc atcgattgac gaggcaaagg gagcgagtat gcaacctcgt    7620
aagtcagact cagacaaaga ccaactagtt attgaccagt cttctagaag gctctgttgt    7680
ggatcttgag gccctggaga gttcctccaa caatccggag acaagcaagt cctcgtcgga    7740
ctagtcacta actagactct aactagttgc agacatggat aatgcaaaag agacaagcaa    7800
tgaagaaagt ggtaagacat ttctcctttg tggttctgga ctagtctttg actagtcaca    7860
gtcttaaaca aggaaaatga gcatgaaaat gaggaggaaa aggctgctga gcccgaggaa    7920
gtgcagggtg atggcagaca tggtaggtta ataccttgtt agttattgct agtcactgac    7980
tagtcaataa ctagtctctg aacaccttgc aatcactccg tttgcgcagc tgaacagtgg    8040
tgaggataat agtagtaagt tattctagct tcagagttat aggagactag atactaacta    8100
gtattagttg caactaacct ggatctcaga gactttggcc tcaatctaga atctatctag    8160
ttgtcaacta gactgtggta tcattgtctt ttattttcct agtcctggaa ctagcttcta    8220
actagtctcc ctaatatgtg gctgtcttgt tttttttttt tgtttcccta cccggatatc    8280
tagtcccctt ctaggttctg ttaacctctc gggctctgat ttagtttaac gcaaacctga    8340
gattagtttc taactagtct ctaggttttc tatccaccct taattgtaat aataaataca    8400
agcaacgttt atacgtcaaa agcatttata aacttttacc ctaaagtagc ttgcttgtgt    8460
gtttagttta taattagtct cttattaatt tgatgtaggt aagcccgcca caaatatata    8520 ttttttaacaa gataccgtgg aaaaacttcg tgctatcaca aaacagtata caaaaaataa    8580
gctatcgaat tcctgcagag atcatcctgt cttcagtctt aagacttctc tcctatatca    8640
cccgcactta ccctagagtg ccgcttaggt gctaagggca cattgagtat tggccgtgta    8700
gaatatatag cttaagtacg gccaagcaga cgggaagccc tgttctccac accctatggt    8760
cgtatatatc aggcttctac cgggaaacga ttaagagtgt ataatggact gaaaatcaat    8820
atgaacggga caatgctcaa gttaaattag ttaggcatcc taatctctac taaatgttct    8880
atctagagat cggggtacta taggcccgta cgttaatcac tctacgcttc tctcccttag    8940
gtatagtgta ggtaggggct agacatttat atgagtcaga tggtacaaac ggtaggcagt    9000
gcgggcgaag aagtgaagac ggagtcggtt gaagctacat acaaaagatg cattggctcg    9060
tcatgaagag cctcccgggt ttattccttt gccctcggac gagtgctggg gcgtcggttt    9120
ccactatcgg cgagtacttc tacacagcca tcggtccaga cggccgcgct tctgcgggcg    9180
atttgtgtac gcccgacagt cccggctccg gatcggacga ttgcgtcgca tcgaccctgc    9240
gcccaagctg catcatcgaa attgccgtca accaagctct gatagagttg gtcaagacca    9300
atgcggagca tatacgcccg gagccgcggc gatcctgcaa gctccggatg cctccgctcg    9360
aagtagcgcg tctgctgctc catacaagcc aaccacggcc tccagaagaa gatgttggcg    9420
acctcgtatt gggaatcccc gaacatcgcc tcgctccagt caatgaccgc tgttatgcgg    9480
ccattgtccg tcaggacatt gttggagccg aaatccgcgt gcacgaggtg ccggacttcg    9540
gggcagtcct cggcccaaag catcagctca tcgagagcct gcgcgacgga cgcactgacg    9600
gtgtcgtcca tcacagtttg ccagtgatac acatggggat cagcaatcgc gcatatgaaa    9660
tcacgccatg tagtgtattg accgattcct tgcggtccga atgggccgaa cccgctcgtc    9720
tggctaagat cggccgcagc gatcgcatcc atggcctccg cgaccggctg cagaacagcg    9780
```

```
ggcagttcgg tttcaggcag gtcttgcaac gtgacaccct gtgcacggcg ggagatgcaa    9840
taggtcaggc tctcgctgaa ttccccaatg tcaagcactt ccggaatcgg gagcgcggcc    9900
gatgcaaagt gccgataaac ataacgatct ttgtagaaac catcggcgca gctatttacc    9960
cgcaggacat atccacgccc tcctacatcg aagctgaaag cacagagattc ttcgccctcc   10020
gagagctgca tcaggtcgga gacgctgtcg aacttttcga tcagaaactt ctcgacagac   10080
gtcgcggtga gttcaggcat tttgacggtg ggatcctgtg atgtctgctc aagcggggta   10140
gctgttagtc aagctgcgat gaagtgggaa agctcgaact gaaaggttca aggaataag    10200
ggatgggaag gatggagtat ggatgtagca aagtacttac ttaggggaaa taaaggttct   10260
tggatgggaa gatgaatata ctgaagatgg gaaagaaag agaaagaaa agagcagctg     10320
gtggggagag caggaaaata tggcaacaaa tgttggactg acgcaacgac cttgtcaacc   10380
ccgccgacac accgggcgga cagacggggc aaagctgcct accagggact gagggacctc   10440
agcaggtcga gtgcagagca ccggatgggt cgactgccag cttgtgttcc cggtctgcgc   10500
cgctggccag ctcctgagcg gccttttcgg tttcatacac cgggcaaagc aggagaggca   10560
cgatatttgg acgccctaca gatgccggat gggccaatta gggagcttac gcgccgggta   10620
ctcgctctac ctacttcgga gaaggtacta tctcgtgaat cttttaccag atcggaagca   10680
attggacttc tgtacctagg ttaatggcat gctatttcgc cgacggctat acaccctgg    10740
cttcacattc tccttcgctt actgccggtg attcgatgaa gctccatatt ctccgatgat   10800
gcaatagatt cttggtcaac gaggggcaca ccagcctttc cacttcgggg cggaggggcg   10860
gccggtcccg gattaataat catccactgc acctcagagc cgccagagct gtctggcgca   10920
gtggcgctta ttactcagcc cttctctctg cgtccgtccg tctctccgca tgccagaaag   10980
agtcaccggt cactgtacag agcggccgcc accgcgtgg agctccaatt cgccctatag    11040
tgagtcgtat tacgcgcgct cactggccgt cgttttacaa cgtcgtgact gggaaaaccc   11100
tggcgttacc caacttaatc gccttgcagc acatccccct ttcgccagct ggcgtaatag   11160
cgaagaggcc cgcaccgatc gcccttccca acagttgcgc agcctgaatg gcgaatggga   11220
cgcgccctgt agcggcgcat taagcgcggc gggtgtggtg gttacgcgca gcgtgaccgc   11280
tacacttgcc agcgccctag cgcccgctcc tttcgctttc ttcccttcct ttctcgccac   11340
gttcgccggc tttccccgtc aagctctaaa tcggggggctc cctttagggt tccgatttag   11400
tgctttacgg cacctcgacc ccaaaaaact tgattagggt gatggttcac gtagtgggcc   11460
atcgccctga tagacggttt ttcgcccttt gacgttggag tccacgttct ttaatagtgg   11520
actcttgttc caaactggaa caacactcaa ccctatctcg gtctattctt tgatttata    11580
agggattttg ccgatttcgg cctattggtt aaaaaatgag ctgatttaac aaaaatttaa   11640
cgcgaatttt aacaaaatat taacgcttac aatttaggtg cacttttcg gggaaatgtg    11700
cgcggaaccc ctatttgttt attttttctaa atacattcaa atatgtatcc gctcatgaga   11760
caataaccct gataaatgct tcaataatat tgaaaaagga agagtatgag tattcaacat   11820
ttccgtgtcg cccttattcc cttttttgcg cattttgcc ttcctgtttt tgctcaccca    11880
gaaacgctgg tgaaagtaaa agatgctgaa gatcagttgg gtgcacgagt gggttacatc   11940
gaactggatc tcaacagcgg taagatcctt gagagttttc gccccgaaga acgttttcca   12000
atgatgagca cttttcgacc gaataaatac ctgtgacgga agatcacttc gcagaataaa   12060
taaatcctgg tgtccctgtt gataccggga agccctgggc caacttttgg cgaaaatgag   12120
```

```
acgttgatcg gcacgtaaga ggttccaact ttcaccataa tgaaataaga tcactaccgg    12180
gcgtattttt tgagttgtcg agattttcag gagctaagga agctaaaatg gagaaaaaaa    12240
tcactggata taccaccgtt gatatatccc aatggcatcg taaagaacat tttgaggcat    12300
ttcagtcagt tgctcaatgt acctataacc agaccgttca gctggatatt acggccttt    12360 taaagaccgt aaagaaaaat aagcacaagt tttatccggc ctttattcac attcttgccc    12420
gcctgatgaa tgctcatccg gaattacgta tggcaatgaa agacggtgag ctggtgtatat    12480 gggatagtgt tcacccttgt tacaccgttt tccatgagca aactgaaacg ttttcatcgc    12540
tctggagtga ataccacgac gatttccggc agtttctaca catatattcg caagatgtgg    12600
cgtgttacgg tgaaaacctg gcctatttcc ctaaagggtt tattgagaat atgttttcg    12660 tctcagccaa tccctgggtg agtttcacca gttttgattt aaacgtggcc aatatggaca    12720
acttcttcgc ccccgttttc accatgggca aatattatac gcaaggcgac aaggtgctga    12780
tgccgctggc gattcaggtt catcatgccg tttgtgatgg cttccatgtc ggcagaatgc    12840
ttaatgaatt acaacagtac tgcgatgagt ggcagggcgg ggcgtaattt ttttaaggca    12900
gttattggtg cccttaaacg cctggttgct acgcctgaat aagtgataat aagcggatga    12960
atggcagaaa ttcgaaagca aattcgaccc ggtcgtcggt tcagggcagg gtcgttaaat    13020
agccgcttat gtctattgct ggtttaccgg tttattgact accggaagca gtgtgaccgt    13080
gtgcttctca aatgcctgag gccagtttgc tcaggctctc cccgtggagg taataattga    13140
cgatatgatc cttttttct gatcaaaaag gatctaggtg aagatccttt tgataatct    13200 catgaccaaa atcccttaac gtgagttttc gttccactga gcgtcagacc ccgtagaaaa    13260
gatcaaagga tcttcttgag atccttttt tctgcgcgta atctgctgct tgcaaacaaa    13320
aaaaccaccg ctaccagcgg tggtttgttt gccggatcaa gagctaccaa ctcttttcc    13380 gaaggtaact ggcttcagca gagcgcagat accaaatact gttcttctag tgtagccgta    13440
gttaggccac cacttcaaga actctgtagc accgcctaca tacctcgctc tgctaatcct    13500
gttaccagtg gctgctgcca gtggcgataa gtcgtgtctt accgggttgg actcaagacg    13560
atagttaccg gataaggcgc agcggtcggg ctgaacgggg ggttcgtgca cacagcccag    13620
cttggagcga acgacctaca ccgaactgag atacctacag cgtgagctat gagaaagcgc    13680
cacgcttccc gaagggagaa aggcggacag gtatccggta agcggcaggg tcggaacagg    13740
agagcgcacg agggagcttc cagggggaaa cgcctggtat ctttatagtc ctgtcgggtt    13800
tcgccacctc tgacttgagc gtcgattttt gtgatgctcg tcaggggggc ggagcctatg    13860
gaaaaacgcc agcaacgcgg cctttttacg gttcctggcc ttttgctggc cttttgctca    13920
catgttcttt cctgcgttat cccctgattc tgtggataac cgtattaccg cctttgagtg    13980
agctgatacc gctcgccgca gccgaacgac cgagcgcagc gagtcagtga gcgaggaagc    14040
ggaagagcgc ccaatacgca aaccgcctct ccccgcgcgt tggccgattc attaatgcag    14100
ctggcacgac aggtttcccg actggaaagc gggcagtgag cgcaacgcaa ttaatgtgag    14160
ttagctcact cattaggcac cccaggcttt acactttatg ctcccggctc gtatgttgtg    14220
tggaattgtg agcggataac aatttcacac aggaaacagc tatgaccatg attacgccaa    14280
gcgcgcaatt aaccctcact aaagggaaca aaagctg                              14317
```

<210> SEQ ID NO 132
<211> LENGTH: 21
<212> TYPE: DNA
<213> ORGANISM: Artificial Sequence

```
<220> FEATURE:
<223> OTHER INFORMATION: The nucleotide sequence of the forward primer
      colony /sequence PCR to determine correct integration of the 5
      part of GFP expression cassette at the fwnA6 locus

<400> SEQUENCE: 132
acagtcttgc gagccttcat c                                              21

<210> SEQ ID NO 133
<211> LENGTH: 23
<212> TYPE: DNA
<213> ORGANISM: Artificial Sequence
<220> FEATURE:
<223> OTHER INFORMATION: The nucleotide sequence of the reverse primer
      colony /sequence PCR to determine correct integration of the 3
      part of GFP expression cassette at the fwnA6 locus.

<400> SEQUENCE: 133
caactggagg taggaccgta tcg                                            23

<210> SEQ ID NO 134
<211> LENGTH: 21
<212> TYPE: DNA
<213> ORGANISM: Artificial Sequence
<220> FEATURE:
<223> OTHER INFORMATION: The nucleotide sequence of the reverse primer
      used in the colony PCR to determine correct integration of the 5
      part of GFP expression cassette at the fwnA6 locus

<400> SEQUENCE: 134
cttgccagtg gtgcagatca g                                              21

<210> SEQ ID NO 135
<211> LENGTH: 21
<212> TYPE: DNA
<213> ORGANISM: Artificial Sequence
<220> FEATURE:
<223> OTHER INFORMATION: The nucleotide sequence of the forward primer
      used in the colony PCR to determine correct integration of the 3
      part of GFP expression cassette at the fwnA6 locus

<400> SEQUENCE: 135
tgccacctac ggcaagttga c                                              21

<210> SEQ ID NO 136
<211> LENGTH: 79
<212> TYPE: DNA
<213> ORGANISM: Artificial Sequence
<220> FEATURE:
<223> OTHER INFORMATION: The guide RNA structural component sequence
      specific for CAS9.

<400> SEQUENCE: 136
gttttagagc tagaaatagc aagttaaaat aaggctagtc cgttatcaac ttgaaaaagt   60
ggcaccgagt cggtggtgc                                                 79
```

The invention claimed is:

1. A method for assembly within a cell of at least two double-stranded nucleic acid molecules into a single double-stranded nucleic acid construct of pre-determined sequence, wherein the assembly is mediated by at least a first and a second single-stranded oligonucleotide, wherein the first and second single-stranded oligonucleotide are at least about 80% complementary to each other over their full length and wherein the first and second single-stranded oligonucleotides are not annealed to each other prior to introduction into the cell, wherein a first of the at least two double-stranded nucleic acid molecules integrates into a second of the at least two double stranded nucleic acid molecules to result into a single double-stranded nucleic acid construct, wherein a part of the first single-stranded oligonucleotide has sequence identity with the first of the at least two double-stranded nucleic acid molecules and wherein a part of the first single-stranded oligonucleotide has sequence identity with the second of the at least two double-stranded nucleic acid molecules, wherein the sequence identity is sufficient for assembly of the double-stranded nucleic acid construct, said method comprising contacting the cell with the single-stranded oligonucleotides and at least one of the double-stranded nucleic acid molecules such that the single-stranded oligonucleotides and at least one of the double-stranded nucleic acid molecules are introduced into the cell and wherein the second of the at least two double-stranded nucleic acid molecule is a genome locus.

2. The method according to claim 1, wherein the at least two-double-stranded nucleic acid molecules are not capable of recombining with each other via homology-mediated recombination.

3. The method according to claim 1, wherein the cell is a eukaryotic cell, optionally a fungus (yeast or filamentous fungus) and/or wherein the cell is deficient in an NHEJ (non-homologous end joining) component.

4. The method according to claim 1 wherein integration occurs within proximity of a break in the second of the at least two double-stranded nucleic acid molecules, wherein the break is one selected from the group consisting of a single-stranded break (nick), an induced single-stranded break, a double-stranded break and an induced double-stranded break.

5. The method according to claim 1, wherein at least a first, second, third and fourth single-stranded oligonucleotide are used, wherein the first and second single-stranded oligonucleotide are essentially complementary to each other, and wherein the third and fourth single-stranded oligonucleotide are essentially complementary to each other, and wherein the third and fourth single-stranded oligonucleotides are not annealed to each other prior to introduction into the cell.

6. The method according to claim 5, wherein:
a part of the first and second essentially complementary single-stranded oligonucleotides has sequence identity with the first of the at least two double-stranded nucleic acid molecules and wherein a part of the first and second essentially complementary single-stranded oligonucleotides has sequence identity with the second of the at least two double-stranded nucleic acid molecules; and
wherein a part of the third and fourth essentially complementary single-stranded oligonucleotides has sequence identity with the first of the at least two double-stranded nucleic acid molecules and wherein a part of the third and fourth essentially complementary single-stranded oligonucleotides has sequence identity with the second of the at least two double-stranded nucleic acid molecules.

7. The method according to claim 1, wherein the method is a multiplex method of assembly within a cell of multiple double-stranded nucleic acid molecules assembled into single or multiple double-stranded nucleic acid constructs.

8. The method according to claim 1, wherein integration occurs within proximity of an induced single-stranded or double-stranded break in the second of the at least two double-stranded nucleic acid molecules, and wherein the break is induced by a functional genome editing system, optionally TALENs, CRISPR/Cas, CRISPR/Cpf1, I-SceI and NgAgo.

9. The method according to claim 1, wherein the cell expresses a functional heterologous genome editing enzyme, optionally a Cas enzyme, optionally Cas9 or Cas9 nickase; Cpf1; I-SceI; NgAgo, or wherein in the cell a heterologous genome editing enzyme, optionally a Cas enzyme, optionally Cas9 or Cas9 nickase; Cpf1; I-SceI; NgAgo, is present.

10. The method according to claim 1, wherein in the cell a guide-polynucleotide is present.

11. The method according to claim 10, wherein the guide-polynucleotide in the cell is expressed from a vector, and wherein the vector is introduced into the cell together with the single-stranded oligonucleotide and at least one of the double-stranded nucleic acid molecules.

12. The method according to claim 11, wherein the plasmid from which the guide-polynucleotide is expressed, is assembled within the cell by integration of a single-stranded or double-stranded oligonucleotide comprising the target sequence of the guide-polynucleotide into the plasmid, wherein in the single-stranded or double-stranded oligonucleotide comprising the target sequence of the guide-polynucleotide and the plasmid are introduced into the cell either simultaneously or consecutively with the single-stranded oligonucleotide and at least one of the double-stranded nucleic acid molecules.

13. The method according to claim 12, wherein assembly of the single-stranded or double-stranded oligonucleotide comprising the target sequence of the guide-polynucleotide into the plasmid and assembly of at least two double-stranded nucleic acid molecules into a single double-stranded nucleic acid construct occur essentially simultaneously within the cell.

* * * * *